(12) United States Patent
Chu et al.

(10) Patent No.: US 6,818,663 B2
(45) Date of Patent: Nov. 16, 2004

(54) DIAMINOTHIAZOLES

(75) Inventors: Xin-Jie Chu, Livingston, NJ (US); Qingjie Ding, Bridgewater, NJ (US); Nan Jiang, Fairfield, NJ (US); Kyungjin Kim, Livingston, NJ (US); Allen John Lovey, North Caldwell, NJ (US); Warren William McComas, Denville, NJ (US); John Guifoyle Mullin, Jr., Hawthorne, NJ (US); Jefferson Wright Tilley, North Caldwell, NJ (US)

(73) Assignee: Hoffmann-La Roches, Nutley, NY (US)

( * ) Notice: Subject to any disclaimer, the term of this patent is extended or adjusted under 35 U.S.C. 154(b) by 0 days.

(21) Appl. No.: 10/429,551

(22) Filed: May 5, 2003

(65) Prior Publication Data

US 2004/0006058 A1 Jan. 8, 2004

Related U.S. Application Data

(60) Provisional application No. 60/381,513, filed on May 17, 2002.

(51) Int. Cl.⁷ ..................... C07D 277/42; A61K 31/426
(52) U.S. Cl. ........................................ 514/370; 548/191
(58) Field of Search ........................... 548/191; 514/370

(56) References Cited

U.S. PATENT DOCUMENTS 6,569,878 B1 * 5/2003 Chong et al. ................ 514/370

FOREIGN PATENT DOCUMENTS

WO  WO 02 057261   7/2002

* cited by examiner

Primary Examiner—Kamal Saeed
(74) Attorney, Agent, or Firm—George W. Johnston; Patricia S. Rocha-Tramaioni

(57) ABSTRACT

The present invention is directed to novel diaminothiazoles of formula

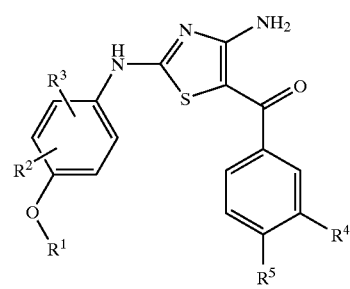

I

These compounds inhibit cyclin-dependent kinase 4 (Cdk4) and are selective against Cdk2 and Cdk1. These compounds and their pharmaceutically acceptable salts and esters have antiproliferative activity and are useful in the treatment or control of cancer, in particular solid tumors. This invention is also directed to pharmaceutical compositions containing such compounds and to methods of treating or controlling cancer, most particularly the treatment or control of breast, lung and colon and prostate tumors.

63 Claims, No Drawings

DIAMINOTHIAZOLES

CONTINUITY INFORMATION

This application claims priority of U.S. Provisional application Ser. No. 60/381,513, filed May 17, 2002.

FIELD OF THE INVENTION

The present invention is directed to novel diaminothiazoles of formulas

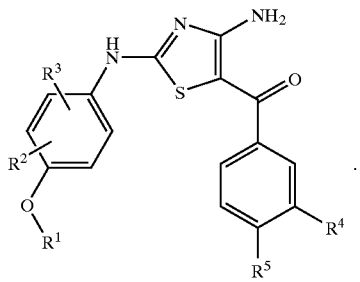

I

These compounds inhibit cyclin-dependent kinase 4 (Cdk4) and are selective against Cdk2 and Cdk1. These compounds and their pharmaceutically acceptable salts and esters have antiproliferative activity and are useful in the treatment or control of cancer, in particular solid tumors. This invention is also directed to pharmaceutical compositions containing such compounds and to methods of treating or controlling cancer, most particularly the treatment or control of breast, lung and colon and prostate tumors.

BACKGROUND OF THE INVENTION

Uncontrolled cell proliferation is the hallmark of cancer. Cancerous tumor cells typically have some form of damage to the genes that directly or indirectly regulate the cell-division cycle.

The progression of cells-through the various phases of the cell cycle is regulated by a series of multienzyme complexes consisting of a regulatory protein, a cyclin, and a kinase. These kinases are called cyclin-dependent kinases (Cdks). The Cdks are expressed throughout the cell cycle, while the levels of the cyclins vary depending on the stage of the cell cycle.

The transition from $G_1$ phase into S phase is regulated by the complex of Cdk4 with cyclin D. This complex phosphorylates the tumor suppressor protein Retinoblastoma (pRb), releasing the transcription factor E2F and allowing the expression of genes required in S phase (Nevins, J. R. Science 1992, 258, 424–429). Blocking the activity of the Cdk4/cyclin D complex arrests the cell cycle in $G_1$ phase. For example, the proteins of the INK4 family, including $p16^{INK4a}$, which block the kinase activity of the Cdk4/cyclin D complex, cause arrest in G, (Sherr, C. J. Science 1996, 274, 1672–1677).

Recent experiments show that the complex of Cdk4 with cyclin D3 also plays a role in cell cycle progression through $G_2$ phase. Inhibition of this complex, either by p16 or using a dominant negative Cdk4, results in arrest in $G_2$ phase in cells that do not express pRb (Gabrielli B. G. et al. J. Biol. Chem. 1999, 274, 13961–13969).

Numerous defects in the pRb pathway have been shown to be involved in various cancers. For example, overexpression of Cdk4 has been observed in cases of hereditary melanoma (Webster, K. R. Exp. Opin. Invest. Drugs 1998, 7, 865–887); cyclin D is overexpressed in many human cancers (Sherr, C. J. Science 1996, 274, 1672–1677); p16 is mutated or deleted in many tumors (Webster, K. R. Exp. Opin. Invest Drugs 1998, 7, 865–887); and pRb function is lost through mutation or deletion in many human cancers (Weinberg, R. A. Cell 1995, 81, 323–330). Defects in this pathway have also been shown to have an effect on prognosis. For example, loss of p16 is correlated with poor prognosis in non-small-cell lung carcinoma (NSCLC) and malignant melanoma (Tsihlias, J. et al. Annu. Rev. Med. 1999, 50, 401–423).

Because of the involvement of the Cdk4/cyclin D/pRb pathway in human cancer through its role in regulating progression of the cell cycle from $G_1$ to S phase, and the potential therapeutic benefit from modulating this pathway, there has been considerable interest in agents that inhibit or, promote elements of this pathway. For example, effects on cancer cells have been shown using antibodies, antisense oligonucleotides and overexpression or addition of proteins involved in the pathway. See, e.g., Lukas, J. et al. Nature 1995, 79, 573–582; Nevins, J. R. Science 1992, 258, 424429; Lim, I. K. et al. Molecular Carcinogenesis 1998, 23, 25–35; Tam, S. W. et al. Oncogene 1994, 9, 2663–2674; Driscoll, B. et al. Am. J. Physiol. 1997, 273 (Lung Cell. Mol. Physiol.), L941–L949; and Sang, J. et al. Chin. Sci. Bull. 1999, 44, 541–544). There is thus an extensive body of literature validating the use of compounds inhibiting targets in the Cdk4 pathway as anti-proliferative therapeutic agents.

Several small molecules have been identified as Cdk inhibitors and have been the subject of recent reviews (Webster, Exp. Opin. Invest. Drugs, vol. 7, pp. 865–887 (1988), Stover, et al., Curr. Opin. In Drug Discov. and Devel., vol. 2, pp. 274–285 (1999) and Toogood, Med. Res. Rev., vol. 6, pp 487–498 (2001).

It is thus desirable to identify chemical inhibitors of Cdk4 kinase activity. It is particularly desirable to identify small molecule compounds that may be readily synthesized and are effective in inhibiting Cdk4 or Cdk4/cyclin complexes, for treating one or more types of tumors.

There are several examples of small molecule inhibitors of the cyclin-dependent kinases, including Cdk4 (Rosania, G. R. et al. Exp. Opin. Ther. Patents 2000, 10, 215–230). Several of these compounds inhibit multiple targets.

For example, Flavopiridol (Aventis)

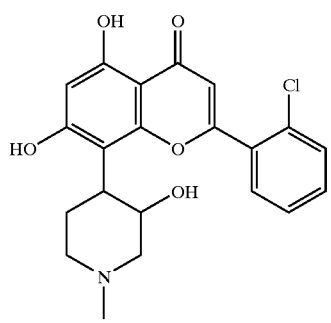

is in Phase II clinical trials for lymphoma and multiple myeloma and also for the treatment of solid tumors. It inhibits Cdk1, Cdk2 and Cdk4 and it blocks cells in both G1 and G2 phases. It is also a weaker inhibitor of PKC and EGFR (Senderowicz, A. M. et al. J. Natl. Cancer Inst. 2000, 92, 376–387).-

WO9716447 (Mitotix) discloses the following compounds related to flavopiridol

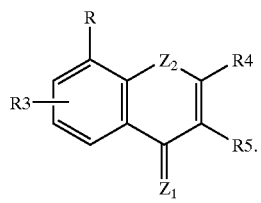

Some of these compounds are stated to inhibit Cdk4.

WO9943675 and WO9943676 (Hoechst) disclose the following purine derivatives

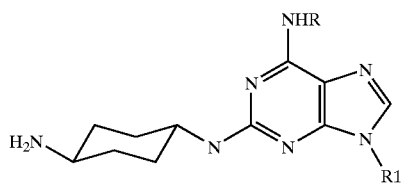

which are stated to inhibit Cdk2 and Cdk4.

WO9833798 (Warner-Lambert) discloses the following pyridopyrimidines

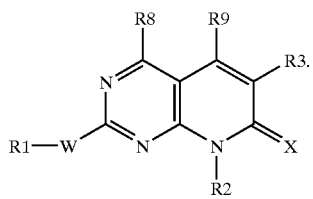

These compounds are stated to inhibit the cyclin dependent kinases Cdk1, Cdk2, and Cdk4. Some of these compounds also inhibit the receptor tyrosine kinases PDGFR and EGFR, and the cellular Src protein kinase, c-Src.

WO9909030 (Warner-Lambert) discloses naphthyridinones

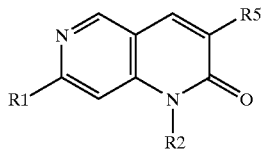

that inhibit PDGFR, FGFR, c-Src, and the cyclin dependent kinases Cdk1, Cdk2, and Cdk4.

WO0039101 (AstraZeneca) discloses diaminopyrimidines

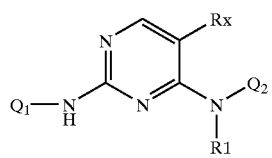

that inhibit Cdk4 and FAK3.

WO0012485 (Zeneca) discloses diaminopyrimidines

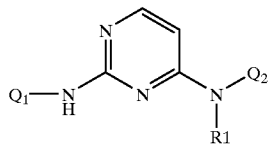

that inhibit Cdk4 and FAK3.

WO9924416 (Bristol-Myers Squibb) discloses aminothiazole inhibitors of formula

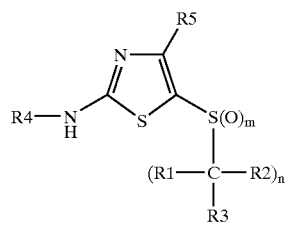

The compounds inhibit $Cdk_1$, Cdk2 and Cdk4.

WO9921845 (Agouron) discloses diaminothiazole inhibitors of Cdk1, Cdk2 and Cdk4, having the following structure

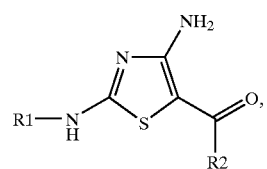

where R1 and R2 are ring systems. This patent application indicates that in cases where the $R^2$ ring system does not bear an ortho substituent, the compounds lack potency and selectivity as inhibitors of Cdk4.

WO0075120 (Agouron) discloses diaminothiazole inhibitors of protein kinases including VEGF-R, FGF-R, CDK complexes, TEK, CHK1, LCK, and FAK, having the following structure

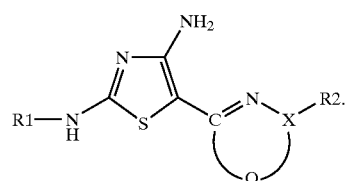

WO0026202 (Pharmacia & Upjohn S.p.A., Italy) discloses 2-amino-thiazole derivatives of formula

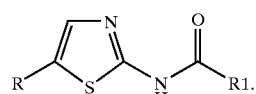

These compounds are asserted to be antitumor agents operating by a kinase dependent mechanism.

WO01056567 (Novo Nordisk) discloses diaminothiazoles of formula

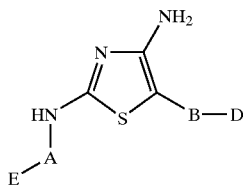

as GSK-3 inhibitors. These compounds are stated to be useful in treating type 2 diabetes.

WO0160816 (Amgen) discloses pyrimidines of formula.

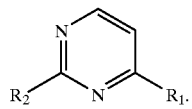

These compounds are asserted to modulate kinase activity.

WO0179198 (Agouron) discloses amino-pyrazoles of formula

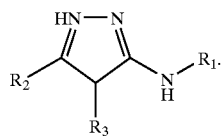

These compounds are asserted to mediate/inhibit Cdks, VEGF, and CHK1, and to be useful in treating cancer.

WO 02/12250 A2 (Agouron) discloses pyrazole-thiazole compounds of formula

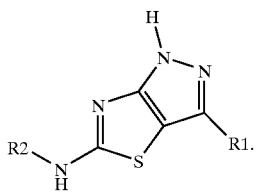

These compounds are asserted to be Cdk4/Cdk2 inhibitors.

It is desirable to provide small molecule inhibitors of Cdk4 that are selective against other Cdks. That is, the small molecule is selectively more inhibitory (at least about five times) of Cdk4 than Cdk1 and Cdk2. This parameter is desirable because of the potential concomitant toxicity and other undesirable complications that may follow from inhibiting multiple targets. Thus, for purposes of this invention, the inhibition of Cdk2 and Cdk1 are monitored to determine the selectivity of the inhibition of Cdk4. A compound that exhibits selectivity against Cdk2 and Cdk1 is expected to have a better safety profile than a compound that is not selective between, Cdk4, Cdk2 and Cdk1.

There continues to be a need for easily synthesized, small molecule compounds that are specific inhibitors of Cdk4 for the treatment or control of one or more types of solid tumors. It is an object of this invention to provide such compounds, compositions containing such compounds, and methods of using such compounds in the treatment or control of breast, colon, lung and prostate tumors.

SUMMARY OF THE INVENTION

The present invention is directed to novel diaminothiazoles capable of selectively inhibiting the activity of Cdk4. These compounds are useful in the treatment or control of cancer, in particular the treatment or control of solid tumors. In particular this invention is directed to a compound of formula

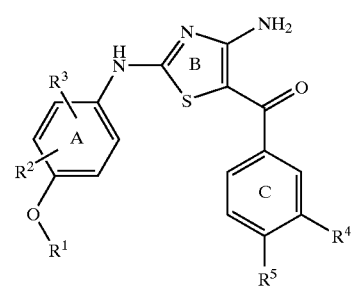

I wherein,
O—$R^1$ represents a group selected from

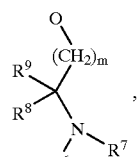

II

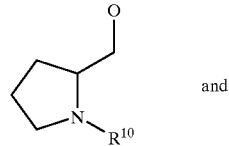

and

III

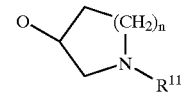

IV $R^2$ and $R^3$ are independently selected from the group consisting of
H,
lower alkyl, and
halogen;
$R^4$ is selected from the group consisting of
lower alkyl,
lower alkyl-cycloalkyl,
cycloalkyl,
O-lower alkyl,
halogen,
$NO_2$,
S-lower alkyl
$CF_3$, and
CN;
$R^5$ is selected from the group consisting of
H,
O-lower alkyl,
lower alkyl,
halogen, and
OH,
or alternatively, $R^4$ and $R^5$ together with the two carbon atoms and bond between them from the benzene ring (C) to which $R^4$ and $R^5$ are attached can form a ring having 5–7 atoms, said 5–7 atom ring optionally including one or two heteroatoms and being optionally substituted by $C_1$–$C_4$-alkyl;

$R^6$ and $R^7$ are each independently selected from the group consisting of
H,
lower alkyl,
lower alkyl substituted by OH, and
$COOR^{12}$,
or, alternatively, the group —$NR^6R^7$ can be a ring having 5–7 atoms, said ring optionally including one or two additional heteroatoms and being optionally substituted by lower alkyl;
$R^8$ and $R^9$ are each independently selected from the group consisting of
H, and
lower alkyl;
$R^{10}$ is selected from the group consisting of
H,
lower alkyl,
lower alkyl substituted by OH, and
$COOR^{12}$;
$R^{11}$ is selected from the group consisting of
H,
lower alkyl, and
lower alkyl substituted by OH; and
$COOR^{12}$;
$R^{12}$ is lower alkyl;
m is 1 or 2; and
n is 0, 1 or 2;
provided that when m is 2 and $R^4$ is F, $R^5$ is not H, and provided further that when m is 2 and $R^4$ is lower alkyl, $R^5$ is not OH;

or the pharmaceutically acceptable salts or esters thereof.

The present invention is also directed to pharmaceutical compositions comprising a therapeutically effective amount of one or more compounds of formula I and a pharmaceutically acceptable carrier or excipient.

The present invention is further directed to a method for treating solid tumors, in particular breast or colon tumors, by administering to a human patient in need of such therapy an effective amount of a compound of formula I, its salt and/or ester.

DETAILED DESCRIPTION OF THE INVENTION

Definitions

As used herein, the following terms shall have the following definitions.

"Cycloalkyl" means a non-aromatic, partially or completely saturated cyclic aliphatic hydrocarbon group containing 3 to 8 atoms. Examples of cycloalkyl groups include cyclopropyl, cyclopentyl and cyclohexyl.

"Effective amount" means an amount that is effective to prevent, alleviate or ameliorate symptoms of disease or prolong the survival of the subject being treated.

"Halogen" means fluorine, chlorine, bromine or iodine.

"Heteroatom" means an atom selected from N, O and S. Preferred heteroatoms are N and O.

"$IC_{50}$" refers to the concentration of a particular compound according to the invention required to inhibit 50% of a specific measured activity. $IC_{50}$ can be measured, inter alia, as is described in Example 149, infra.

"Lower alkyl" denotes a straight-chain or branched saturated aliphatic hydrocarbon having 1 to 6, preferably 1 to 4, carbon atoms. Typical lower alkyl groups include methyl, ethyl, propyl, isopropyl, butyl, t-butyl, 2-butyl, pentyl, hexyl and the like.

"Pharmaceutically acceptable ester" refers to a conventionally esterified compound of formula I having a carboxyl group, which esters retain the biological effectiveness and properties of the compounds of formula I and are cleaved in vivo (in the organism) to the corresponding active carboxylic acid. Examples of ester groups which are cleaved (in this case hydrolyzed) in vivo, to the corresponding carboxylic acids ($R^{24}C(=O)OH$) are lower alkyl esters which may be substituted with $NR^{25}R^{26}$ where $R^{25}$ and $R^{26}$ are lower alkyl, or where $NR^{25}R^{26}$ taken together form a monocyclic aliphatic heterocycle, such as pyrrolidine, piperidine, morpholine, N-methylpiperazine, etc.; acyloxyalkyl esters of the formula $R^{24}C(=O)OCHR^{27}OC(=O)R^{28}$ where $R^{27}$ is hydrogen or methyl, and $R^{28}$ is lower alkyl or cycloalkyl; carbonate esters of the formula $R^{24}C(=O)OCHR^{27}OC(=O))R^{29}$ where $R^{27}$ is hydrogen or methyl, and $R^{29}$ is lower alkyl or cycloalkyl; or aminocarbonylmethyl esters of the formula $R^{24}C(=O)OCH_2C(=O)NR^{25}R^{26}$ where $R^{25}$ and $R^25$ are hydrogen or lower alkyl, or where $NR^{25}R^{26}$ taken together form a monocyclic aliphatic heterocycle, such as pyrrolidine, piperidine, morpholine, N-methylpiperazine, etc.

Examples of lower alkyl esters are the methyl, ethyl, and n-propyl esters, and the like. Examples of lower alkyl esters substituted with $NR^{25}R^{25}$ are the diethylaminoethyl, 2-(4-morpholinyl)ethyl, 2-(4-methylpiperazin-1-yl)ethyl esters, and the like. Examples of acyloxyalkyl esters are the pivaloxymethyl, 1-acetoxyethyl, and acetoxymethyl esters. Examples of carbonate esters are the 1-(ethoxycarbonyloxy) ethyl and 1-(cyclohexyloxycarbonyloxy)ethyl esters. Examples of aminocarbbnylmethyl esters are the N,N-dimethylcarbamoylmethyl and carbamoylmethyl esters.

Further information concerning examples of and the use of esters for the delivery of pharmaceutical compounds is available in Design of Prodrugs. Bundgaard H. ed. (Elsevier, 1985). See also, H. Ansel et. al., Pharmaceutical Dosage Forms and Drug Delivery Systems (6th Ed. 1995) at pp. 108–109; Krogsgaard-Larsen, et. al., Textbook of Drug Design and Development (2d Ed. 1996) at pp. 152–191.

"Pharmaceutically acceptable salt" refers to conventional acid-addition salts or base-addition salts that retain the biological effectiveness and properties of the compounds of formula I and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. The chemical modification of a pharmaceutical compound(i.e. drug) into a salt is a technique well known to pharmaceutical chemists to obtain improved physical and chemical stability, hygroscopicity, flowability and solubility of compounds. See, e.g., H. Ansel et. al., Pharmaceutical Dosage Forms and Drug Delivery Systems (6th Ed. 1995) at pp. 196 and 1456–1457.

"Pharmaceutically acceptable," such as pharmaceutically acceptable carrier, excipient, etc., means pharmacologically acceptable and substantially non-toxic to the subject to which the particular compound is administered.

"Ring", when describing a chemical ring, unless otherwise indicated, may be saturated or unsaturated.

"Substituted," as in "lower alkyl substituted by" means that the substitution can occur at one or more positions and, unless otherwise indicated, that the substituents at each substitution site are independently selected from the specified options.

"Therapeutically effective amount" means an amount of at least one compound of Formula I, or a pharmaceutically acceptable salt or ester thereof, that significantly inhibits proliferation and/or prevents differentiation of a human tumor cell, including human tumor cell lines.

In one embodiment, the present invention is directed to a, compound of formula

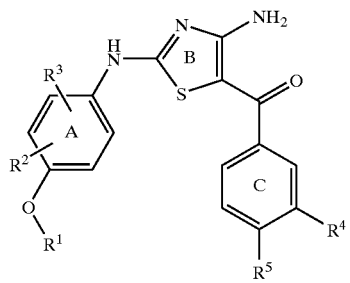

I wherein,
O—$R^1$ represents a group selected from

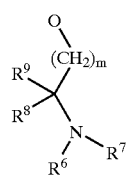

II

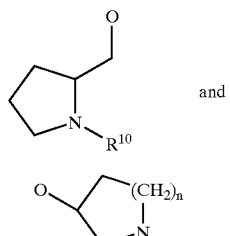

III and

IV $R^2$ and $R^3$ are independently selected from the group consisting of
  H,
  lower alkyl, and
  halogen;
$R^4$ is selected from the group consisting of
  lower alkyl,
  lower alkyl-cycloalkyl,
  cycloalkyl,
  O-lower alkyl,
  halogen,
  $NO_2$,
  S-lower alkyl
  $CF_3$, and
  CN;
$R^5$ is selected from the group consisting of
  H,
  O-lower alkyl,
  lower alkyl,
  halogen, and
  OH,
or alternatively, $R^4$ and $R^5$ together with the two carbon atoms and bond between them from the benzene ring (C) to which $R^4$ and $R^5$ are attached can form a ring having 5–7 atoms, said 5–7 atom ring optionally including one or two heteroatoms and being optionally substituted by $C_1$–$C_4$-alkyl;
$R^6$ and $R^7$ are each independently selected from the group consisting of
  H,
  lower alkyl,
  lower alkyl substituted by OH, and
  $COOR^{12}$,
or, alternatively, the group —$NR^6R^7$ can be a ring having 5–7 atoms, said ring optionally including one or two additional heteroatoms; and being optionally substituted by lower alkyl;
$R^8$ and $R^9$ are each independently selected from the group consisting of
  H, and
  lower alkyl;
$R^{10}$ is selected from the group consisting of
  H,
  lower alkyl,
  lower alkyl substituted by OH, and
  $COOR^{12}$;
$R^{11}$ is selected from the group consisting of
  H,
  lower alkyl, and
  lower alkyl substituted by OH; and
  $COOR^{12}$;
$R^{12}$ is lower alkyl;
m is 1 or 2;
n is 0, 1 or 2;
provided that when m is 2 and $R^4$ is F, $R^5$ is not H, and provided further that when m is 2 and $R^4$ is lower alkyl, $R^5$ is not OH;
or the pharmaceutically acceptable salts or esters thereof.

In a preferred embodiment of the compounds of formula I, $R^2$ is lower alkyl, preferably methyl.

In another preferred embodiment of the compounds of formula I, $R^2$ is halogen, preferably F.

In another preferred embodiment of the compounds of formula I, $R^3$ is H.

In another preferred embodiment of the compounds of formula I, $R^4$ is halogen, preferably F. In another preferred embodiment, $R^4$ is lower alkyl, preferably methyl.

In another preferred embodiment of the compounds of formula I, $R^5$ is halogen, preferably F. In another preferred embodiment, $R^5$ is H. In another preferred embodiment, $R^5$ is O-lower alkyl, mostly preferably O-methyl.

In a most preferred embodiment, $R^4$ is F and $R^5$ is O-methyl.

In another preferred embodiment of the compounds of the invention, the group —$NR^6R^7$ is a saturated 5- or 6-membered ring.

In another preferred embodiment of the compounds of formula I, the group —$NR^6R^7$ is a saturated 5 or 6-membered ring.

In another preferred embodiment of the compounds of formula I, $R^8$ and $R^9$ are independently lower alkyl, preferably methyl, or H.

In another preferred embodiment of the compounds of formula I, $R^{10}$ is lower alkyl, preferably methyl, or H.

In another preferred embodiment of the compounds of formula I, $R^{11}$ is lower alkyl, preferably ethyl, or H, and n is 1 or 2, preferably 1.

In another preferred embodiment R$^{12}$ is methyl.
In another preferred embodiment m is 1.
In a particularly preferred embodiment, the invention is directed to a compound of formula

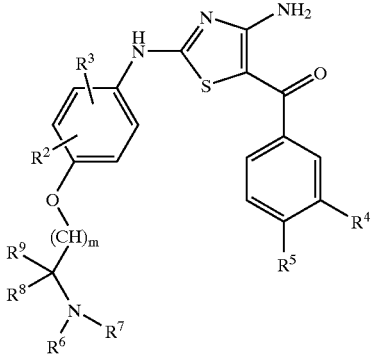

Ia or the pharmaceutically acceptable salts or esters thereof. Especially preferred are compounds of formula Ia wherein m is 1.

Examples of such compounds include:
[4-Amino-2-[4-(2-pyrrolidin-1-yl-ethoxy)-phenylamino]-thiazol-5-yl]-(4-ethyl-3-fluoro-phenyl)-methanone; compound with trifluoroacetic acid (Example 6);
[4-Amino-2-[4-(2-pyrrolidin-1-yl-ethoxy)-phenylamino]-thiazol-5-yl]-(3-fluoro-phenyl)-methanone (Example 36);
[4-Amino-2-[4-(2-dimethylamino-ethoxy)-phenylamino]-thiazol-5-yl]-(3-fluoro-phenyl)-methanone (Example 37);
[4-Amino-2-[4(2-dimethylamino-propoxy)-phenylamino]-thiazol-5-yl]-(3-fluoro-phenyl)-methanone (Example 38);
[4-Amino-2-[4-(2-dimethylamino-2-methyl-propoxy)-phenylamino]-thiazol-5-yl]-(3-fluoro-phenyl)-methanone (Example 39);
(R)-[4-Amino-2-[4-(2-dimethylamino-propoxy)-phenylamino]-thiazol-5-yl]-(3-fluoro-phenyl)-methanone (Example 40);
(R)-[4-Amino-2-[4-(2-pyrrolidin-1-yl-propoxy)-phenylamino]-thiazol-5-yl]-(3-fluoro-phenyl)-methanone (Example 41);
[4-Amino-2-[4-(2-morpholin-4-yl-ethoxy)-phenylamino]-thiazol-5-yl]-(3-fluoro-phenyl)-methanone (Example 47);
[4-Amino-2-[4-(2-pyrrolidin-1-yl-ethoxy)-phenylamino]-thiazol-5-yl]-(4-methoxy-3-nitro-phenyl)-methanone (Example 48);
[4-Amino-2-[4-(2-dimethylamino-ethoxy)-phenylamino]-thiazol-5-yl]-(4-methoxy-3-nitro-phenyl)-methanone (Example 49);
[4-Amino-2-[4-(2-dimethylamino-ethoxy)-phenylamino]-thiazol-5-yl]-m-tolyl-methanone (Example 50);
[4-Amino-2-[4-(2-pyrrolidin-1-yl-ethoxy)-phenylamino]-thiazol-5-yl]-m-tolyl-methanone (Example 51);
[4-Amino-2-[4-(2-dimethylamino-ethoxy)-phenylamino]-thiazol-5-yl]-(3-ethyl-phenyl)-methanone (Example 52);
[4-Amino-2-[4-(2-pyrrolidin-1-yl-ethoxy)-phenylamino]-thiazol-5-yl]-(3-ethyl-phenyl)-methanone (Example 53);
[4-Amino-2-[4-(2-dimethylamino-ethoxy)-phenylamino]-thiazol-5-yl]-(3-nitro-phenyl)-methanone (Example 54);
[4-Amino-2-[4-(2-morpholin-4-yl-ethoxy)-phenylamino]-thiazol-5-yl]-(2,3-dihydro-benzo[1,4]dioxin-6-yl)-methanone (Example 55);
[4-Amino-2-[4-(2-morpholin-4-yl-ethoxy)-phenylamino]-thiazol-5-yl]-benzo[1,3]dioxol-5-yl-methanone (Example 56);
[4-Amino-2-[4-(2-pyrrolidin-1-yl-ethoxy)-phenylamino]-thiazol-5-yl]-benzo[1,3]dioxol-5-yl-methanone (Example 57);
[4-Amino-2-[4-(2-dimethylamino-ethoxy)-phenylamino]-thiazol-5-yl]-(2,3-dihydro-benzo[1,4]dioxin-6-yl)-methanone (Example 58);
[4-Amino-2-[4-(2-dimethylamino-ethoxy)-phenylamino]-thiazol-5-yl]-benzo[1,3]dioxol-5-yl-methanone (Example 59);
3-[4-Amino-2-[4-(2-dimethylamino-ethoxy)-phenylamino]-thiazole-5-carbonyl]-benzonitrile (Example 60);
[4-Amino-2-[4-(2-dimethylaminb-2-methyl-propoxy)-phenylamino]-thiazol-5-yl]-(3-ethyl-phenyl)-methanone (Example 61);
[4-Amino-2-[4-(2-pyrrolidin-1-yl-ethoxy)-phenylamino]-thiazol-5-yl]-(3-ethoxy-phenyl)-methanone (Example 62);
(R)-[4-Amino-2-[4-(2-dimethylamino-propoxy)-phenylamino]-thiazol-5-yl]-(3-ethyl-phenyl)-methanone (Example 63);
[4-Amino-2-[4-(2-dimethylamino-ethoxy)-phenylamino]-thiazol-5-yl]-(3-bromo-phenyl)-methanone (Example 65);
(R)-[4-Amino-2-[4-(2-pyrrolidin-1-yl-propoxy)-phenylamino]-thiazol-5-yl]-(3-ethyl-phenyl)-methanone (Example 67);
(R)-[4-Amino-2-[4-(2-pyrrolidin-1-yl-propoxy)-phenylamino]-thiazol-5-yl]-(3-cyclopropyl-phenyl)-methanone (Example 68);
[4-Amino-2-[4-(2-dimethylamino-ethoxy)-phenylamino]-thiazol-5-yl]-(3-cyclopropyl-phenyl)-methanone (Example 69);
(R)-[4-Amino-2-[4-(2-dimethylamino-propoxy)-phenylamino]-thiazol-5-yl]-(3-cyclopropyl-phenyl)-methanone (Example 70);
[4-Amino-2-[4-(2-dimethylamino-2-methyl-propoxy)-phenylamino]-thiazol-5-yl]-(3-cyclopropyl-phenyl)-methanone (Example 71);
[4-Amino-2-[4-(2-pyrrolidin-1-yl-ethoxy)-phenylamino]-thiazol-5-yl]-(3-cyclopropyl-phenyl)-methanone (Example 72);
[4-Amino-2-[4-(2-dimethylamino-ethoxy)-phenylamino]-thiazol-5-yl]-(3-fluoro-4-methyl-phenyl)-methanone (Example 73);
(R)-[4-Amino-2-[4-(2-dimethylamino-propoxy)-phenylamino]-thiazol-5-yl]-(3-fluoro-4-methyl-phenyl)-methanone (Example 74);
[4-Amino-2-[4-(2-dimethylamino-2-methyl-propoxy)-phenylamino]-thiazol-5-yl]-(3-fluoro-4-methyl-phenyl)-methanone (Example 75);
[4-Amino-2-[4-(2-pyrrolidin-1-yl-ethoxy)-phenylamino]-thiazol-5-yl]-(3-ethyl-4-fluoro-phenyl)-methanone (Example 76);

(R)-[4-Amino-2-[4-(2-dimethylamino-propoxy)-phenylamino]-thiazol-5-yl]-(3-ethyl-4-fluoro-phenyl)-methanone (Example 77);

[4-Amino-2-[4-(2-ethylamino-ethoxy)-phenylamino]-thiazol-5-yl]-m-tolyl-methanone; compound with acetic acid (Example 100);

[4-Amino-2-[4-(2-ethylamino-ethoxy)-phenylamino]-thiazol-5-yl]-(3-ethyl-phenyl)-methanone; compound with acetic acid (Example 101);

[4-Amino-2-[4-(2ethylamino-ethoxy)-phenylamino]-thiazol-5-yl]-(3-cyclopropyl-phenyl)-methanone; compound with acetic acid (Example 102);

[4-Amino-2-[4-(2-ethylamino-ethoxy)-phenylamino]-thiazol-5-yl]-(3-fluoro-4-methyl-phenyl)-methanone; compound with acetic acid (Example 103);

[4-Amino-2-[4-(2-ethylamino-ethoxy)-phenylamino]-thiazol-5-yl]-(3-ethyl-4-fluoro-phenyl)-methanone; compound with acetic acid (Example 104);

[4-Amino-2-[4-(2-ethylamino-ethoxy)-phenylamino]-thiazol-5-yl]-(4-hydroxy-3-propyl-phenyl)-methanone; compound with acetic acid (Example 105);

[4-Amino-2-[4-(2-dimethylamino-ethoxy)-phenylamino]-thiazol-5-yl]-(4-hydroxy-3-propyl-phenyl)-methanone; compound with acetic acid (Example 106);

(R)-[4-Amino-2-[4-(2-dimethylamino-propoxy)-phenylamino]-thiazol-5-yl]-(4-hydroxy-3-propyl-phenyl)-methanone; compound with acetic acid (Example 107);

[4-Amino-2-[4-(2-dimethylamino-2-methyl-propoxy)-phenylamino]-thiazol-5-yl]-(4-hydroxy-3-propyl-phenyl)-methanone; compound with acetic acid (Example 108);

[4-Amino-2-[4-(2-pyrrolidin-1-yl-ethoxy)-phenylamino]-thiazol-5-yl]-(4-hydroxy-3-propyl-phenyl)-methanone; compound with acetic acid (Example 109);

(R)-[4-Amino-2-[4-(2-pyrrolidin-1-yl-propoxy)-phenylamino]-thiazol-5-yl]-(4-hydroxy-3-propyl-phenyl)-methanone; compound with acetic acid (Example 110);

[4-Amino-2-[4-(2-pyrrolidin-1-yl-ethoxy)-phenylamino]-thiazol-5-yl]-(3-fluoro-phenyl)-methanone; compound with acetic acid (Example 118);

[4-Amino-2-[4-(2-pyrrolidin-1-yl-ethoxy)-phenylamino]-thiazol-5-yl]-(3-fluoro-4-hydroxy-phenyl)-methanone; compound with acetic acid (Example 120);

[R]-[4-Amino-2-[4-(2-pyrrolidin-1-yl-propoxy)-phenylamino]-thiazol-5-yl]-(3-methoxy-phenyl)-methanone; compound with acetic acid (Example 121);

[4-Amino-2-[4-(2-diethylamino-ethoxy)-phenylamino]-thiazol-5-yl]-(3-fluoro-4-hydroxy-phenyl)-methanone (Example 123);

[4-Amino-2-[4-(2-diethylamino-ethoxy)-phenylamino]-thiazol-5-yl]-(3-fluoro-4-methoxy-phenyl)-methanone (Example 125);

[4-Amino-2-[4-(2-diethylamino-ethoxy)-phenylamino]-thiazol-5-yl]-(3-methylsulfanyl-phenyl)-methanone (Example 126);

[4-Amino-2-[4-(2-pyrrolidin-1-yl-ethoxy)-phenylamino]-thiazol-5-yl]-(3-trifluoromethyl-phenyl)-methanone (Example 128);

[4-Amino-2-[4-(2-ethylamino-ethoxy)-phenylamino]-thiazol-5-yl]-(3-methoxy-phenyl)-methanone (Example 130);

[4-Amino-2-[4-(2-ethylamino-ethoxy)-phenylamino]-thiazol-5-yl]-(3-fluoro-phenyl)-methanone (Example 131);

[4-Amino-2-[4-(2-ethylamino-ethoxy)-phenylamino]-thiazol-5-yl]-benzo[1,3]dioxol-5-yl-methanone (Example 133);

[4-Amino-2-[4-(2-ethylamino-ethoxy)-phenylamino]-thiazol-5-yl]-(2,3-dihydro-benzo[1,4]dioxin-6-yl)-methanone (Example 134);

[4-Amino-2-[4-(2-isopropylamino-ethoxy)-phenylamino]-thiazol-5-yl]-(2,3-dihydro-benzo[1,4]dioxin-6-yl)-methanone (Example 136);

1-(1,3-Benzodioxol-5-yl)-2-bromoethanone (Example 137);

[4-Amino-2-[4-(2-diethylamino-ethoxy)-phenylamino]-thiazol-5-yl]-(3-methyl-2,3-dihydro-benzofuran-5-yl)-methanone (Example 139);

[4-Amino-2-[4-(2-pyrrolidin-1-yl-ethoxy)-phenylamino]-thiazol-5-yl]-(3-methyl-2,3-dihydro-benzofuran-5-yl)-methanone (Example 140);

[4-Amino-2-[4-(2-diethylamino-ethoxy)-phenylamino]-thiazol-5-yl]-(2,3-dihydro-benzofuran-5-yl)-methanone (Example 142);

[4-Amino-2-[4-(2-ethylamino-ethoxy)-phenylamino]-thiazol-5-yl]-(2,3-dihydro-benzofuran-5-yl)-methanone (Example 143);

[4-Amino-2-[4-(2-dimethylaminoethoxy)-phenylamino]-thiazol-5-yl]-(3-methoxy-phenyl)-methanone (Example 144);

[4-Amino-2-[4-(2-diethylaminoethoxy)-phenylamino]-thiazol-5-yl](3-methoxy-phenyl)-methanone (Example 145); and

[4-Amino-2-[4-(2-imidazol-1-yl-ethoxy)-phenylamino]-thiazol-5-yl]-(3-methoxy-phenyl)-methanone (Example 146).

Examples of compounds of formula Ia wherein m is 2 are:

[4-Amino-2-[4-(3-amino-propoxy)-phenylamino]-thiazol-5-yl]-(3-fluoro-4-methoxy-phenyl)-methanone (Example 147); and

[4-Amino-2-[4-(3-ethylamino-propoxy)-phenylamino]-thiazol-5-yl]-(3-fluoro-4-methoxy-phenyl)methanone (Example 148).

In another preferred embodiment, the invention is directed to a compound of formula

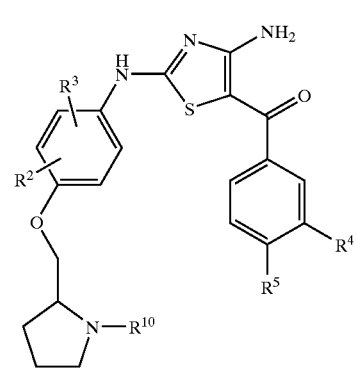

or the pharmaceutically acceptable salts or esters thereof.

Examples of such compounds include:

[4-Amino-2-[4-(pyrrolidin-2-ylmethoxy)-phenylamino]-thiazol-5-yl]-(3-fluoro-phenyl)-methanone (Example 3);

(S)-[4-Amino-2-[4-(1-methyl-pyrrolidin-2-ylmethoxy)-phenylamino]-thiazol-5-yl]-(3-fluoro-phenyl)-methanone (Example 44);
(S)-[4-Amino-2-[4-(1-methyl-pyrrolidin-2-ylmethoxy)-phenylamino]-thiazol-5-yl]-m-tolyl-methanone (Example 111);
(S)-[4-Amino-2-[4-(1-methyl-pyrrolidin-2-ylmethoxy)-phenylamino]-thiazol-5-yl]-(3-ethyl-phenyl)-methanone (Example 112);
(S)-[4-Amino-2-[4-(1-methyl-pyrrolidin-2-ylmethoxy)-phenylamino]-thiazol-5-yl]-(3-cyclopropyl-phenyl)-methanone (Example 113);
(S)-[4-Amino-2-[4-(1-methyl-pyrrolidin-2-ylmethoxy)-phenylamino]-thiazol-5-yl]-(3-fluoro-4-methyl-phenyl)-methanone (Example 114); and
(S)-[4-Amino-2-[4-(1-methyl-pyrrolidin-2-ylmethoxy)-phenylamino]-thiazol-5-yl]-(4-hydroxy-3-propyl-phenyl)-methanone acetate (Example 115).

In another preferred embodiment, the invention is directed to a compound of formula

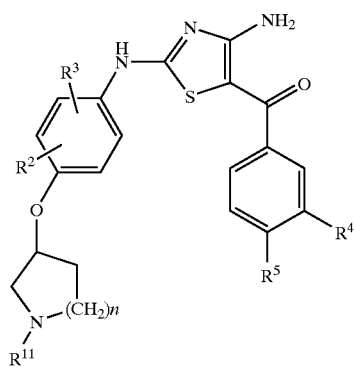

Ic or the pharmaceutically acceptable salts or esters thereof.
Examples of such compounds include:
[4-Amino-2-[4-(1-ethyl-pyrrolidin-3-yloxy)-phenylamino]-thiazol-5-yl]-(3-fluoro-phenyl)-methanone (Example 42);
[4-Amino-2-[4-(1-ethyl-piperidin-3-yloxy)-phenylamino]-thiazol-5-yl]-(3-fluoro-phenyl)-methanone (Example 43);
[4-Amino-2-[4-(pyrrolidin-3-yloxy)-phenylamino]-thiazol-5-yl]-(3-fluoro-phenyl)-methanone (Example 45);
[4-Amino-2-[4-(piperidin-3-yloxy)-phenylamino]-thiazol-5-yl]-(3-fluoro-phenyl)-methanone (Example 46);
[4-Amino-2-[4-(1-ethyl-piperidin-3-yloxy)-phenylamino]-thiazol-5-yl]-m-tolyl-methanone (Example 78);
[4-Amino-2-[4-(1-ethyl-piperidin-3-yloxy)-phenylamino]-thiazol-5-yl]-(3-ethyl-phenyl)-methanone (Example 79);
[4-Amino-2-[4-(1-ethyl-piperidin-3-yloxy)-phenylamino]-thiazol-5-yl]-(3-cyclopropyl-phenyl)-methanone (Example 80);
[4-Amino-2-[4-(1-ethyl-piperidin-3-yloxy)-phenylamino]-thiazol-5-yl]-(3-ethyl-4-fluoro-phenyl)-methanone (Example 81);
[4-Amino-2-[4-(1-ethyl-piperidin-3-yloxy)-phenylamino]-thiazol-5-yl]-(3-fluoro-4-hydroxy-phenyl)-methanone (Example 82);
[4-Amino-2-[4-(1-ethyl-pyrrolidin-3-yloxy)-phenylamino]-thiazol-5-yl]-m-tolyl-methanone (Example 83);
[4-Amino-2-[4-(1-ethyl-pyrrolidin-3-yloxy)-phenylamino]-thiazol-5-yl]-(3-ethyl-phenyl)-methanone (Example 84);
[4-Amino-2-[4-(1-ethyl-pyrrolidin-3-yloxy)-phenylamino]-thiazol-5-yl]-(3-cyclopropyl-phenyl)-methanone (Example 85);
[4-Amino-2-[4-(1-ethyl-pyrrolidin-3-yloxy)-phenylamino]-thiazol-5-yl]-(3-fluoro-4-methyl-phenyl)-methanone (Example 86);
[4-Amino-2-[4-(1-ethyl-piperidin-3-yloxy)-phenylamino]-thiazol-5-yl]-(3-fluoro-4-methyl-phenyl)-methanone (Example 87);
[4-Amino-2-[4-(1-ethyl-piperidin-3-yloxy)-phenylamino]-thiazol-5-yl]-(4-hydroxy-3-propyl-phenyl)-methanone; compound with acetic acid (Example 88);
[4-Amino-2-[4-(1-ethyl-pyrrolidin-3-yloxy)-phenylamino]-thiazol-5-yl]-(4-hydroxy-3-propyl-phenyl)-methanone; compound with acetic acid (Example 89);
[4-Amino-2-[4-(pyrrolidin-3-yloxy)-phenylamino]-thiazol-5-yl]-(4-hydroxy-3-propyl-phenyl)-methanone; compound with acetic acid (Example 90);
[4-Amino-2-[4-(pyrrolidin-3-yloxy)-phenylamino]-thiazol-5-yl]-m-tolyl-methanone; compound with acetic acid (Example 91);
[4-Amino-2-[4-(pyrrolidin-3-yloxy)-phenylamino]-thiazol-5-yl]-(3-ethyl-phenyl)-methanone; compound with acetic acid (Example 92).
[4-Amino-2-[4-(pyrrolidin-3-yloxy)-phenylamino]-thiazol-5-yl]-(3-cyclopropyl-phenyl)-methanone; compound with acetic acid (Example 93);
[4-Amino-2-[4-(pyrrolidin-3-yloxy)-phenylamino]-thiazol-5-yl]-(3-fluoro-4-methyl-phenyl)-methanone; compound with acetic acid (Example 94);
[4-Amino-2-[4-(pyrrolidin-3-yloxy)-phenylamino]-thiazol-5-yl]-(3-fluoro-4-methoxy-phenyl)-methanone (Example 96);
[4-Amino-2-[4-(piperidin-3-yloxy)-phenylamino]-thiazol-5-yl]-(3-fluoro-4-methoxy-phenyl)-methanone (Example 97);
[4-Amino-2-[4-(piperidin-3-yloxy)-phenylamino]-thiazol-5-yl]-(3-ethyl-phenyl)-methanone (Example 98);
[4-Amino-2-[4-(piperidin-3-yloxy)-phenylamino]-thiazol-5-yl]-(4-hydroxy-3-propyl-phenyl)-methanone (Example 99);
3-[4-[4-Amino-5-(3-fluoro-benzoyl)-thiazol-2-ylamino]-phenoxy]-azetidine-1-carboxylic acid tert-butyl ester (Example 116); and
[4-Amino-2-[4-(azetidin-3-yloxy)-phenylamino]-thiazol-5-yl]-(3-fluoro-phenyl)-methanone (Example 117).

The compounds disclosed herein and covered by formula I above may exhibit tautomerism or structural isomerism. It is intended that the invention encompasses any tautomeric or structural isomeric form of these compounds, or mixtures of such forms, and is not limited to any one tautomeric or structural isomeric form depicted in the formula above.

General Synthesis of Compounds According to the Invention

The compounds of the present invention can be prepared by any conventional means. Suitable processes for synthesizing these compounds are provided in the examples. Generally, compounds of formula I can be prepared according to one of the below described synthetic routes.

A. Ring Formation

Compounds of the invention can be prepared by the alkylation and cyclization of a number of thiourea derivatives, as shown in Scheme I, using reactions that are known. Among the thiourea derivatives that can be used are nitroamidinothioureas (Binu, R. et al. *Org. Prep. Proced. Int.* 1998, 30, 93–96); 1-[(arylthiocarbamoyl)amino]-3,5-dimethylpyrazoles (Jenardanan, G. C. et al. *Synth. Commun.* 1997, 27, 3457–3462); and N-(aminoiminomethyl)-N'-phenylthioureas (Rajasekharan, K. N. et al. *Synthesis* 1986, 353–355).

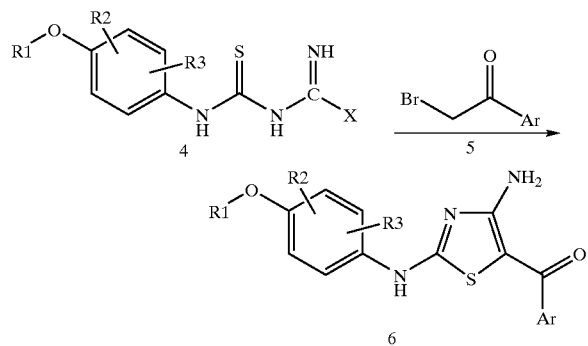

Another thiourea derivative that can be used for the preparation of compounds of the invention by alkylation and cyclization is N-cyanothiourea (Gewald, K. et al. *J. Prakt. Chem.* 1967, 97–104). For example, pursuant to Scheme IA below, an N-cyanothiourea of formula 4A can be reacted with a halomethylketone, such as a bromomethylketone of formula 5, at a temperature between around room temperature and around 65° C., to give a compound of formula 6.

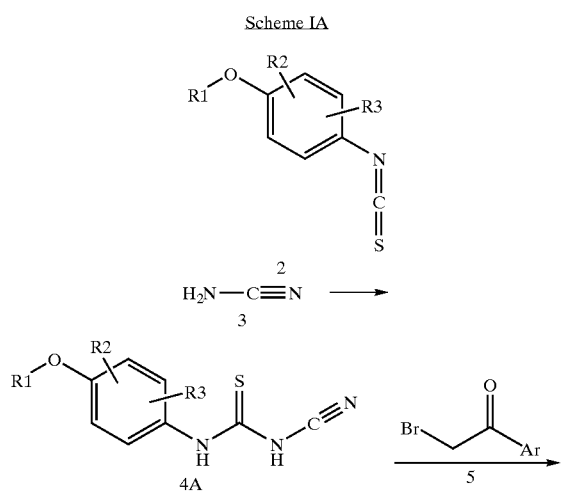

Alternatively, the compounds of the invention are also conveniently prepared by reaction of a resin-bound substituted (aminothioxomethyl) carbamimidothioic acid methyl ester of formula 8 with a bromomethyl aryl ketone of formula 5 as shown in Scheme II below.

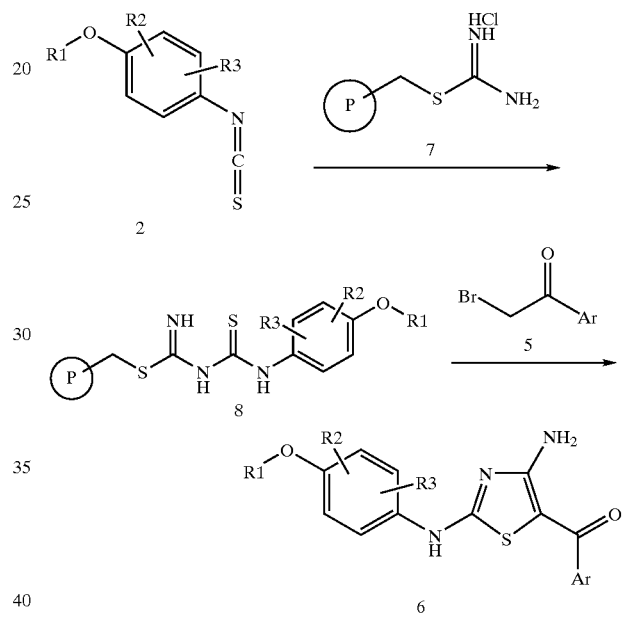

The resin-bound thiourea derivative of formula 8 can be made by any conventional procedure known to one skilled in the art of organic synthesis. For example, it can be conveniently prepared by the reaction of a resin-bound thiouronium salt of formula 7 with an isothiocyanate of formula 2 in the presence of a base, such as a tertiary amine (e.g., triethylamine or diisopropylethylamine) in an inert solvent, such as a polar aprotic solvent (e.g., N,N-dimethylformamide). The reaction is conveniently carried out at a temperature around room temperature. The resin-bound thiourea derivative of formula 8 is then converted to the product of formula 6 by treatment with a halomethylketone (for example, a bromomethylketone of formula 5) in a suitable inert solvent such as a polar aprotic solvent (e.g., N,N-dimethylformamide) at a temperature around room temperature.

B. Separating a Mixture of Stereoisomers Into the Optically Pure Stereoisomers (When Compound of Formula I is Chiral)

The optional separation of isomeric structures of formula I can be carried out according to known methods such as for example resolution or chiral high pressure liquid chromatography (also known as chiral HPLC). Resolution methods are well known, and are summarized in "Enantiomers, Racemates, and Resolutions" (Jacques, J. et al. John Wiley and Sons, NY, 1981).

Methods for chiral HPLC are also well known, and are summarized in "Separation of Enantiomers by Liquid Chromatographic Methods" (Pirkle, W. H. and Finn, J. in "Asymmetric Synthesis", Vol. 1, Morrison, J. D., Ed., Academic Press, Inc., NY 1983, pp. 87–124).

C. Converting a Compound of Formula I That Bears a Basic Nitrogen Into a Pharmaceutically Acceptable Acid Addition Salt The optional conversion of a compound of formula I that bears a basic nitrogen into a pharmaceutically acceptable acid addition salt can be effected by conventional means. For example, the compound can be treated with an inorganic acid such as for example hydrochloric acid, hydrobromic acid, sulfuric acid, nitric acid, phosphoric acid, or with an appropriate organic acid such as acetic acid, citric acid, tartaric acid, methanesulfonic acid, p-toluenesulfonic acid, or the like.

D. Converting a Compound of Formula I That Bears a Carboxylic Acid Group Into a Pharmaceutically Acceptable Alkali Metal Salt The optional conversion of a compound of formula I that bears a carboxylic acid group into a pharmaceutically acceptable alkali metal salt can be effected by conventional means. For example, the compound can be treated with an inorganic base such as lithium hydroxide, sodium hydroxide, potassium hydroxide, or the like.

E. Converting a Compound of Formula I That Bears a Carboxylic Acid Group Into a Pharmaceutically Acceptable Ester The optional conversion of a compound of formula I that bears a carboxylic acid group into a pharmaceutically acceptable ester can be effected by conventional means. The conditions for the formation of the ester will depend on the stability of the other functional groups in the molecule to the reaction conditions. If the other moieties in the molecule are stable to acidic conditions, the ester may be conveniently prepared by heating in a solution of a mineral acid (e.g., sulfuric acid) in an alcohol. Other methods of preparing the ester, which may be convenient if the molecule is not stable to acidic conditions include treating the compound with an alcohol in the presence of a coupling agent and in the optional presence of additional agents that may accelerate the reaction. Many such coupling agents are known to one skilled in the art of organic chemistry. Two examples are dicyclohexylcarbodiimide and triphenylphosphine/diethyl azodicarboxylate. In the case where dicyclohexylcarbodiimide is used as the coupling agent, the reaction is conveniently carried out by treating the acid with the alcohol, dicyclohexylcarbodiimide, and the optional presence of a catalytic amount (0–10 mole %) of N,N-dimethylaminopyridine, in an inert solvent such as a halogenated hydrocarbon (e.g., dichloromethane) at a temperature between about 0 degrees and about room temperature, preferably at about room temperature. In the case where triphenylphosphine/diethyl azodicarboxylate is used as the coupling agent, the reaction is conveniently carried out by treating the acid with the alcohol, triphenylphosphine and diethyl azodicarboxylate, in an inert solvent such as an ether (e.g., tetrahydrofuran) or an aromatic hydrocarbon (e.g., benzene) at a temperature between about 0 degrees and about room temperature, preferably at about 0 degrees.

Turning to the intermediates, isothiocyanate intermediates of formula 2 used to make compounds of the invention can be made by any conventional means. For example, they may be made by the route shown in Scheme III below.

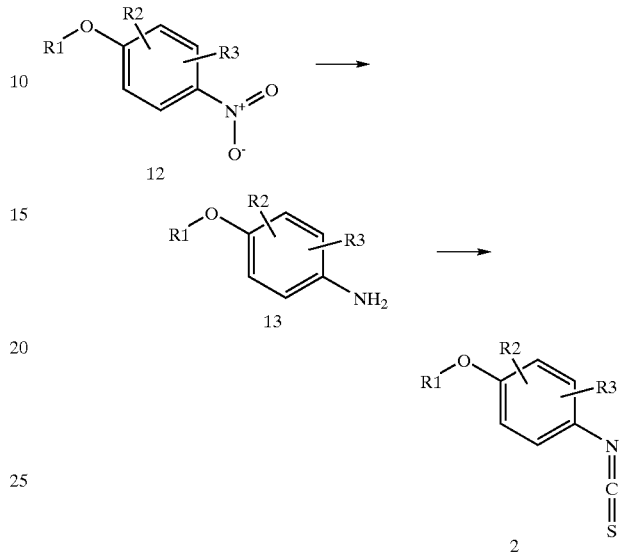

Scheme III

The nitro group in a compound of formula 12 can be reduced to give an aniline of formula 13 using a number of methods familiar to one skilled in the art. These methods include (1) treatment of the nitro compound of formula 12 with iron/acetic acid, with tin(II) chloride/hydrochloric acid, or with zinc and ammonium chloride; and (2) hydrogenation in the presence of a noble metal catalyst such as palladium-on-carbon.

The isothiocyanates of formula 2 may be made from anilines of formula 13 using any one of a number of reagents known to those skilled in organic synthesis to be useful for the transformation of an aniline of formula 13 into an isothiocyanate of formula 2. Among these reagents are carbon disulfide, thiophosgene, 1,1'-thiocarbonylbis(2-pyridone), and thiocarbonyl diimidazole. The reaction can be carried out by treating an aniline of formula 13 with thiocarbonyl diimidazole in a suitable inert solvent such as a polar aprotic solvent (e.g., N,N-dimethylformamide) at a temperature between about –20 degrees and about 0 degrees, preferably at about –15 degrees.

Nitro compounds of formula 12 can be made by a variety of methods that are known in the field of organic synthesis. For example, they may be made by the nucleophilic substitution of a nitrobenzene derivative that bears a leaving group at the position para to the nitro group in accordance with Scheme IV below:

Scheme IV

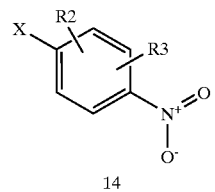

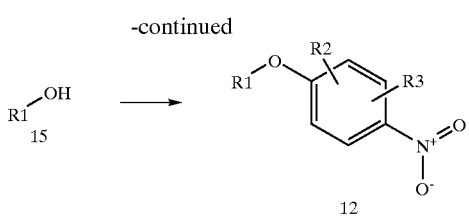

The nucleophilic substitution reaction between an alcohol of formula 15 and a nitrobenzene of formula 14 (wherein X is a leaving group) to give the substituted product of formula 12 can be conveniently carried out by heating these materials together with an appropriate base at a temperature between about 50 and about 100 degrees, preferably at about 80 degrees, in the optional presence of an inert solvent such as acetonitrile (Scheme IV). Suitable leaving groups of formula X include chloride and fluoride. By way of example and not as a limitation, the following compounds of formula 14 are available commercially from the noted vendors:

| | Supplier |
|---|---|
| Cl-C6H4-NO2 | Aldrich |
| Cl,Cl-C6H3-NO2 | Aldrich |
| F,F-C6H3-NO2 | Aldrich |
| Cl,CH3-C6H3-NO2 | Lancaster Synthesis |
| F,CH3-C6H3-NO2 | Aldrich |

Bromomethylketone intermediates 5 used to make compounds of the invention are available commercially or can be made using one of a number of methods known to those skilled in the art of organic synthesis, for example: Friedel-Crafts reactions of an arene with bromoacetyl bromide or bromoacetyl chloride; oxidation of a 2-bromo-1-phenethyl alcohol; reaction of a diazomethyl ketone with HBr; reduction of a dibromomethyl ketone (see Scheme V) below; or reaction of a methyl ketone with a brominating agent (see Scheme VI) such as bromine, copper(II) bromide, tetrabutylammonium tribromide, or 5,5-dibromobarbituric acid.

According to the method of Diwu et al. (Tetrahedron Lett. 1998, 39, 4987–4990), methyl ketones of formula 19 can be converted into the corresponding dibromomethyl ketones of formula 20 by treatment with bromine in neat sulfuric acid. The dibromomethyl ketones of formula 20 can then be converted into the desired bromomethyl ketones of formula 5 by reduction with diethylphosphite.

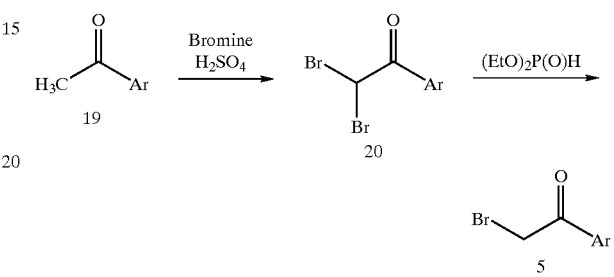

Scheme V

Bromomethyl ketones of formula 5 can also be prepared directly from methyl ketones of formula 19 using a variety of reagents well known to those of ordinary skill in the art of organic synthesis, such as those mentioned above. For example, the reaction may be conveniently carried out by treating the methyl ketone of formula 19 with bromine in a suitable inert solvent such as a halogenated hydrocarbon (e.g., carbon tetrachloride) in the optional presence of other agents that facilitate the reaction, such as a Bronsted or Lewis acid catalyst (e.g., aluminum chloride or acetic acid). The optimal reaction temperature depends on whether or not a catalyst is used. In the case where aluminum chloride is used, the reaction is conveniently carried out at about 0 degrees. In the cases where acetic acid is added, or where no catalyst is used, the reaction is conveniently carried out at a temperature between about room temperature and about 80 degrees, preferably at about room temperature. Alternatively, a methyl ketone of formula 19 may be converted to a bromomethylketone of formula 5 by treatment with copper(II) bromide in a suitable unreactive solvent such as ethyl acetate, preferably at the reflux temperature.

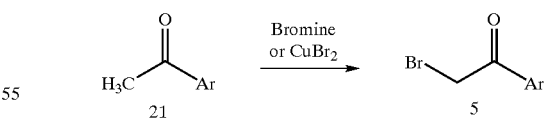

Scheme VI

Compositions/Formulations

In an alternative embodiment, the present invention is directed to pharmaceutical compositions comprising at least one compound of formula I, or a pharmaceutically acceptable salt or ester thereof.

These pharmaceutical compositions can be administered orally, for example in the form of tablets, coated tablets, dragees, hard or soft gelatin capsules, solutions, emulsions or suspensions. They can also be administered rectally, for example, in the form of suppositories, or parenterally, for example, in the form of injection solutions.

The pharmaceutical compositions of the present invention comprising compounds of formula I, and/or the salts or esters thereof, may be manufactured in a manner that is known in the art, e.g. by means of conventional mixing, encapsulating, dissolving, granulating, emulsifying, entrapping, dragee-making, or lyophilizing processes. These pharmaceutical preparations can be formulated with therapeutically inert, inorganic or organic carriers. Lactose, corn starch or derivatives thereof, talc, steric acid or its salts can be used as such carriers for tablets, coated tablets, dragees and hard gelatin capsules. Suitable carriers for soft gelatin capsules include vegetable oils, waxes and fats. Depending on the nature of the active substance, no carriers are generally required in the case of soft gelatin capsules. Suitable carriers for the manufacture of solutions and syrups are water, polyols, saccharose, invert sugar and glucose. Suitable carriers for injection are water, alcohols, polyols, glycerine, vegetable oils, phospholipids and surfactants. Suitable carriers for suppositories are natural or hardened oils, waxes, fats and semi-liquid polyols.

The pharmaceutical preparations can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain other therapeutically valuable substances, including additional active ingredients other than those of formula I.

Dosages

As mentioned above, the compounds of the present invention are useful in the treatment or control of cell proliferative disorders, in particular oncological disorders. These compounds and formulations containing said compounds are particularly useful in the treatment or control of solid tumors, such as, for example, breast, colon, lung and prostate tumors.

A therapeutically effective amount of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as continuous infusion.

EXAMPLES

The following examples illustrate preferred methods for synthesizing the compounds and formulations of the present invention.

Example 1

(S)-2-(4-Isothiocyanato-phenoxymethyl)-pyrrolidine-1-carboxylic Acid tert-Butyl Ester A. (S)-2-(4-Nitro-phenoxymethyl)-pyrrolidine-1-carboxylic Acid tert-Butyl Ester

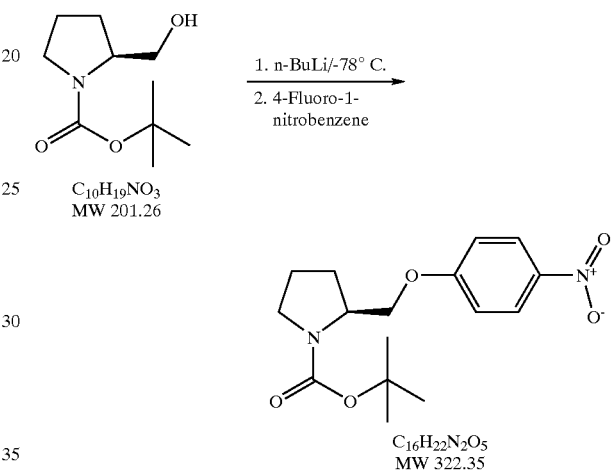

To a stirred solution of (S)-2-hydroxymethyl-pyrrolidine-1-carboxylic acid tert-butyl ester (Aldrich, 2.01 g, 10 mmol) in tetrahydrofura n (15 mL) at —78° C., n-BuLi (2.5 M in hexanes, 11 mmol, 4.4 mL) was added dropwise. After the addition, 4-fluoro nitrobenzene (1.41 g, 10 mmol) was added and the solution was gradually warmed to room temperature and stirred for 2 hours. The solution was poured into water and the mixture was extracted with ether. The extract was dried ($Na_2SO_4$) and concentrated to give the crude which was chromatographed (20% ethyl acetate/hexanes) to yield a pale yellow oil. 1.34 g.

B. (S)-2-(4-Amino-phenoxymethyl)-pyrrolidine-1-carboxylic Acid tert-Butyl Ester

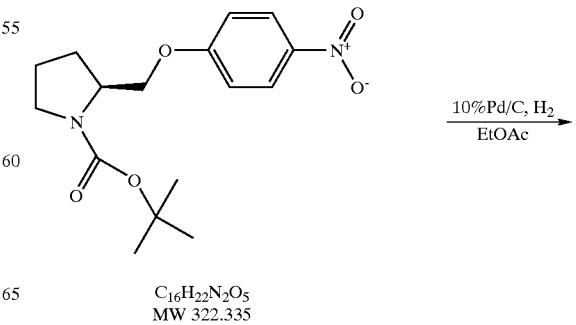

-continued

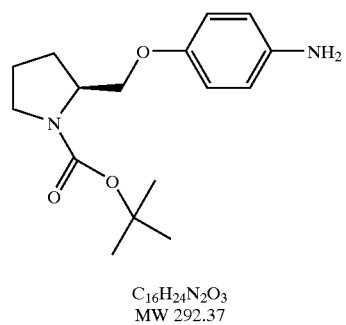

C₁₆H₂₄N₂O₃
MW 292.37

(S)-2-(4-Nitro-phenoxymethyl)-pyrrolidine-1-carboxylic acid tert-butyl ester obtained above (1.34 g, 4.16 mmol) was dissolved in ethyl acetate (50 mL). Palladium-on-carbon (10%, 250 mg) was added and the mixture was hydrogenated under 50 psi for 2 hours. The mixture was filtered and the solvent was removed to give the amine as a solid. 1.20 g, 98%. MS (ES) MH⁺=293.

C. (S)-2-(4-Isothiocyanato-phenoxymethyl)-pyrrolidine-1-carboxylic Acid tert-Butyl Ester

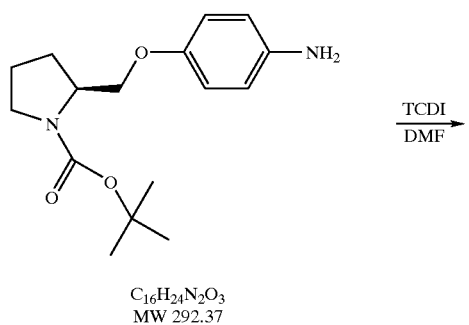

C₁₆H₂₄N₂O₃
MW 292.37

TCDI / DMF

C₁₇H₂₂N₂O₃S
MW 334.43

The amine (1.28 g, 4.38 mmol) was dissolved in N,N-dimethylformamide (7 mL) and 1,1'-thiocarbonyldiimidazole (TCDI, Aldrich, 904 mg, 90%, 4.57 mmol) was added and the mixture was stirred at room temperature for 1 hour. Then, the mixture was poured into water and extracted with diethyl ether. The extract was dried (Na₂SO₄) and concentrated to give the product. 1.20 g, 82%. MS (ES) MH⁺=335.

Example 2

(S)-2-[4-[4-Amino-5-(3-fluoro-benzoyl)-thiazol-2-ylamino]-phenoxymethyl]-pyrrolidine-1-carboxylic Acid tert-Butyl Ester

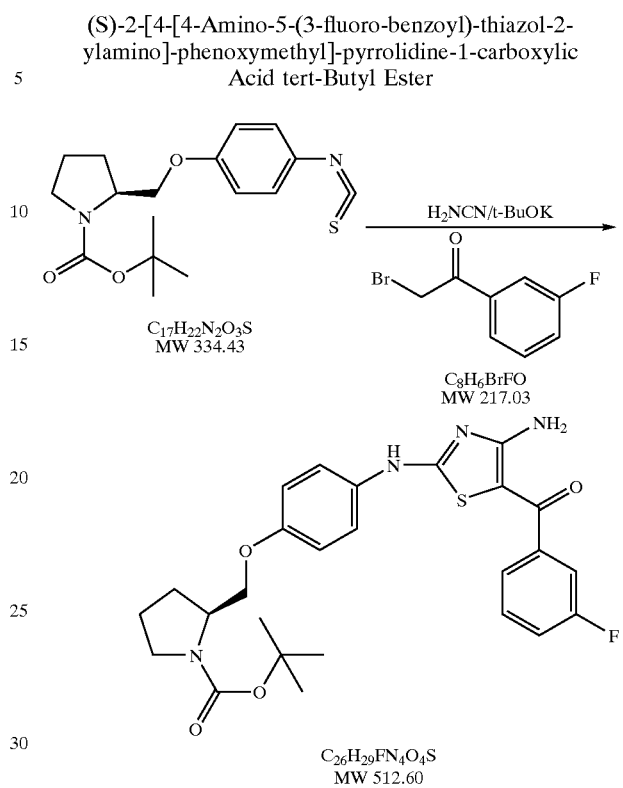

C₁₇H₂₂N₂O₃S
MW 334.43

H₂NCN/t-BuOK

C₈H₆BrFO
MW 217.03

C₂₆H₂₉FN₄O₄S
MW 512.60

Cyanamide (46.2 mg, 1.1 mmol) was suspended in acetonitrile (5 mL). To the stirred suspension, potassium tert-butoxide (123 mg, 1.1 mmol) in 2 mL of tert-butanol was added followed by isothiocyanate (Example 1, 334 mg, 1 mmol). The mixture was stirred for 30 minutes at room temperature followed by the addition of 2-bromo-1-(3-fluoro-phenyl)-ethanone (TCI, 261 mg, 1 mmol). After being stirred for 2 hours at room temperature, the mixture was poured into water and the new mixture was extracted with ether. The extract was dried(Na₂SO₄) and concentrated to give the desired product as a yellow solid, 510 mg, 99%. MS (ES) MH⁺=513.

Example 3

[4-Amino-2-[4-(pyrrolidin-2-ylmethoxy)-phenylamino]-thiazol-5-yl]-(3-fluoro-phenyl)-methanone

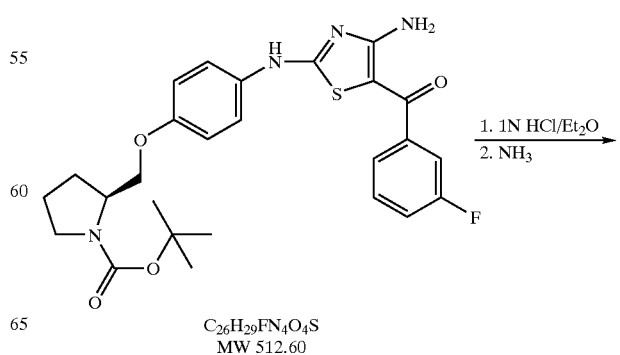

1. 1N HCl/Et₂O
2. NH₃

C₂₆H₂₉FN₄O₄S
MW 512.60

-continued

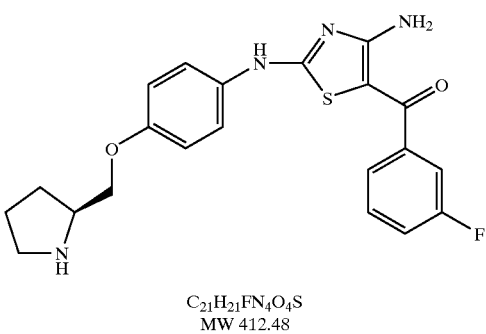

C$_{21}$H$_{21}$FN$_4$O$_4$S
MW 412.48

(S)-2-[4-[4-Amino-5-(3fluoro-benzoyl)-thiazol-2-ylamino]-phenoxymethyl]-pyrrolidine-1-carboxylic acid tert-butyl ester (Example 2, 200 mg, 0.39 mmol) was suspended in 1N HCl in diethyl ether and the mixture was stirred at room temperature overnight. The solid was filtered and passed through a C18 column eluting with aqueous ammonia in acetonitrile. The mixture was concentrated and the solid was filtered and dried to give a yellow solid. 120 mg, 75%. MS (ES) MH$^+$=413.

Example 4

[2-(4-Isothiocyanato-phenoxy)-ethyl]-dimethyl-amine

A. Dimethyl-[2-(4-nitro-phenoxy)-ethyl]-amine

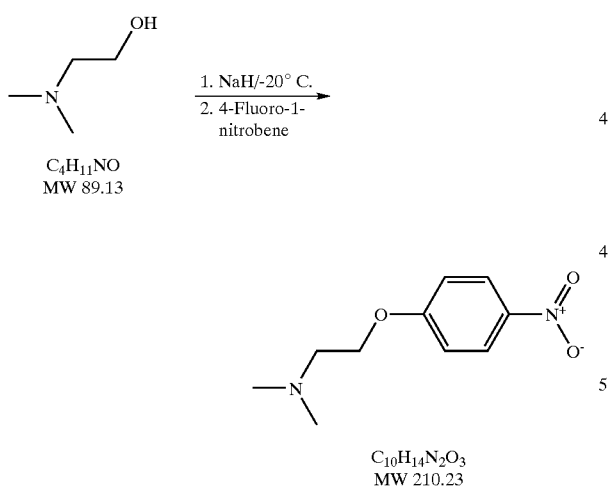

Sodium hydride (60% in oil, 1.04 g, 26 mmol) was placed in a round bottom flask and washed with hexanes and then was suspended in tetrahydrofuran and cooled to 0° C. A solution of 2-dimethylamino-ethanol (Aldrich, 1.78g, 20 mmol) in tetrahydrofuran was added and the suspension was stirred at 0° C. for 30 minutes and at room temperature for 1 hour. Then, the suspension was cooled to −20° C. and a solution of 4-fluoro nitrobenzene (Aldrich, 3.95g, 28 mmol) in tetrahydrofuran was added. The mixture was stirred for 2 hours by gradually increasing the temperature to around 5° C. The reaction was quenched by addition of 1N HCl and the mixture was washed with ether and basified with 1 N NaOH and extracted with diethyl ether. The extract was dried (Na$_2$SO$_4$) and concentrated to give a light yellow oil. 2.8 g, 66%. MS (ES) MH$^+$=211.

B. 4-(2-Dimethylamino-ethoxy)-phenylamine

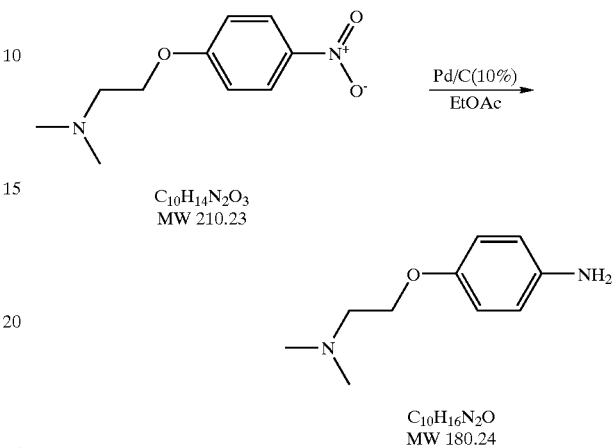

The nitro compound (2.80 g) was dissolved in ethanol (40 mL) and palladium-on-carbon (10%, 100 mg) was added and the mixture was hydrogenated under 20 psi for 1 hour. The mixture was filtered and the filtrate was concentrated to give a brown oil. 2.36g, 98%.

C. [2-(4-Isothiocyanato-phenoxy)-ethyl]-dimethyl-amine

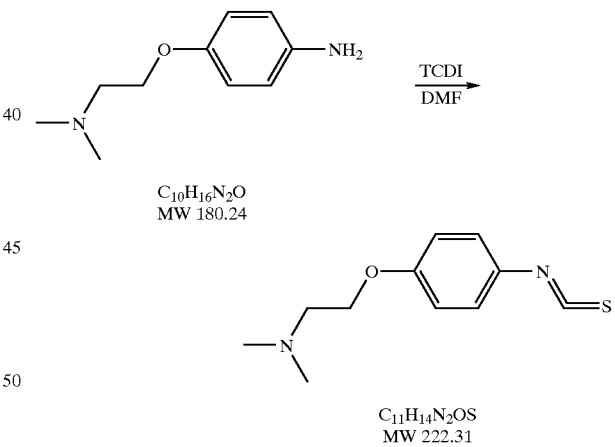

The brown oil in N,N-dimethylformamide (5 ml) was added to a stirred solution of TCDI (2.72g, 90%, 13.74 mmol) in N,N-dimethylformamide (5 mL) at −15° C. and the mixture was stirred for 30 minutes at this temperature and then at room temperature for 1.5 hours. The reaction was quenched with water and the solid precipitate was collected by filtration and dissolved in ethyl acetate. The filtrate was extracted with ethyl acetate and the combined organic solutions were dried (Na$_2$SO$_4$). Removal of solvent on a rotary evaporator gave a pale brown oil. 2.8 g, 96%. MS (ES) MH$^+$=223.

Example 5

1-[2-(4-Isothiocyanato-phenoxy)-ethyl]-pyrrolidine

A. 1-[2-(4-Nitro-phenoxy)-ethyl]-pyrrolidine

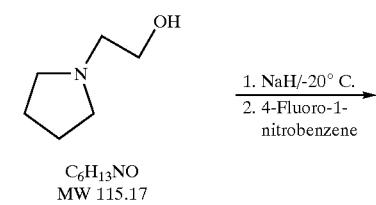

C$_6$H$_{13}$NO
MW 115.17

1. NaH/-20° C.
2. 4-Fluoro-1-nitrobenzene

C$_{12}$H$_{16}$N$_2$O$_3$
MW 236.26

B. 4-(2-Pyrrolidin-1-yl-ethoxy)-phenylamine

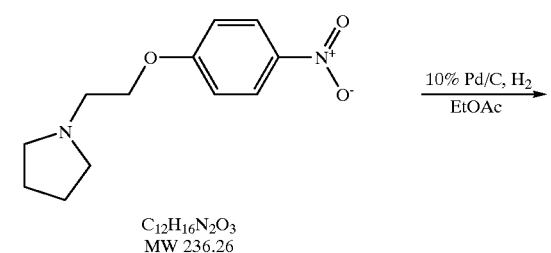

C$_{12}$H$_{16}$N$_2$O$_3$
MW 236.26

10% Pd/C, H$_2$ / EtOAc

C$_{12}$H$_{18}$N$_2$O
MW 206.28

C. 1-[2-(4-Isothiocyanato-phenoxy)-ethyl]-pyrrolidine

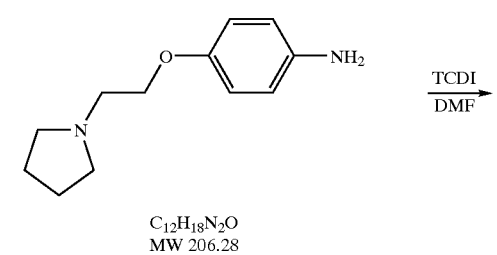

C$_{12}$H$_{18}$N$_2$O
MW 206.28

TCDI / DMF

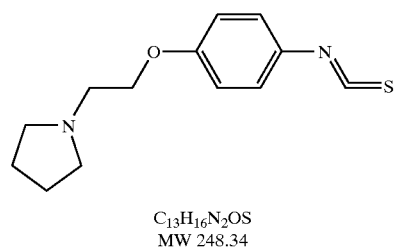

C$_{13}$H$_{16}$N$_2$OS
MW 248.34

This compound was made from 2-pyrrolidin-1-yl-ethanol (Aldrich) by the procedure described in Example 4. MS (ES) MH$^+$=249.

Example 6

[4-Amino-2-[4-(2-pyrrolidin-1-yl-ethoxy)-phenylamino]-thiazol-5-yl]-(4-ethyl-3-fluoro-phenyl)-methanone; Compound With Trifluoroacetic Acid

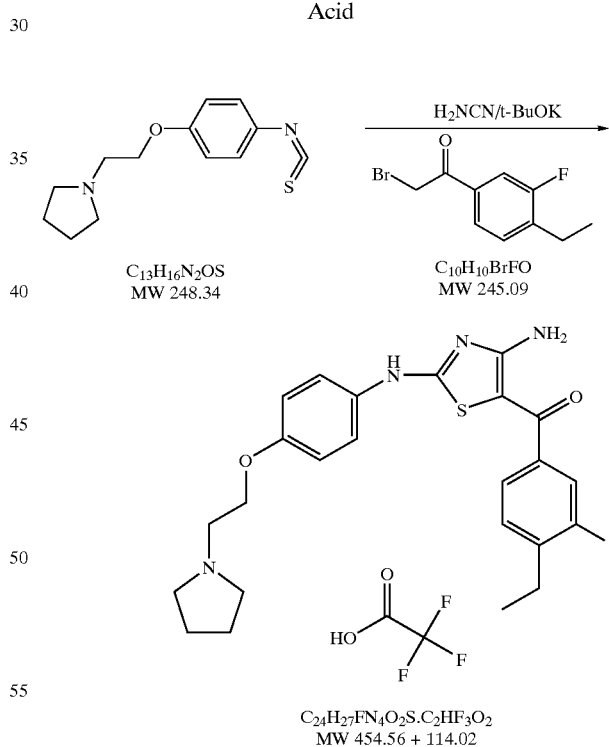

C$_{13}$H$_{16}$N$_2$OS
MW 248.34

H$_2$NCN/t-BuOK

C$_{10}$H$_{10}$BrFO
MW 245.09

C$_{24}$H$_{27}$FN$_4$O$_2$S·C$_2$HF$_3$O$_2$
MW 454.56 + 114.02

The named compound was made from the compound of Example 5 and 2-bromo-1-(4-ethyl-3-fluoro-phenyl)-ethanone (Example 17) by the procedure described in Example 2. Purification by reverse phase HPLC gave the trifluoroacetic acid salt. MS (ES) MH$^+$=455.

Example 7

4-[2-(4-Isothiocyanato-phenoxy)-ethyl]-morpholine

A. 4-[2-(4-Nitro-phenoxy)-ethyl]-morpholine

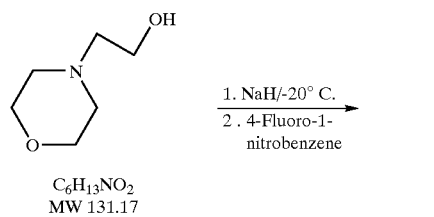

B. 4-(2-Morpholin-4-yl-ethoxy)-phenylamine

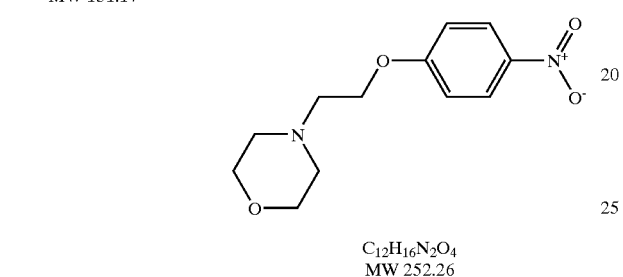

C. 4-[2-(4-Isothiocyanato-phenoxy)-ethyl]-morpholine

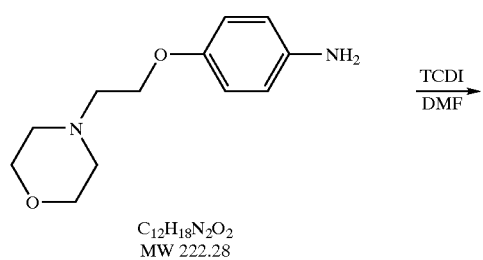

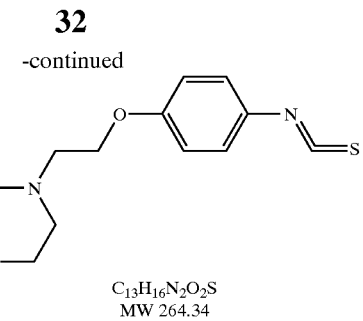

This compound was made from 2-morpholin-4-yl-ethanol (Aldrich) by the procedure described in Example 4. MS (ES) MH$^+$=265.

Example 8

[2-(4-Isothiocyanato-phenoxy)-1,1-dimethylethyl]-dimethyl-amine

A. [1,1-Dimethyl-2-(4-nitro-phenoxy)-ethyl]-dimethyl-amine

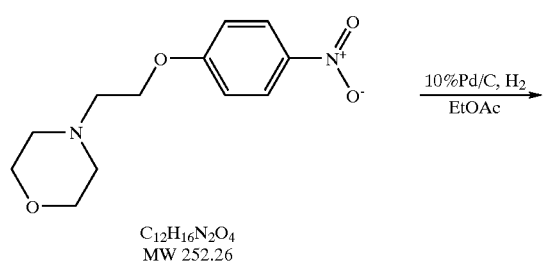

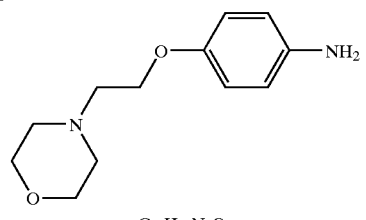

B. 4-(2-Dimethylamino-2-methyl-propoxy)-phenylamine

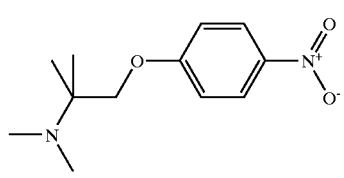

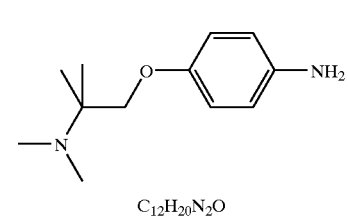

C. [2-(4-Isothiocyanato-phenoxy)-1,1-dimethyl-ethyl]-dimethyl-amine

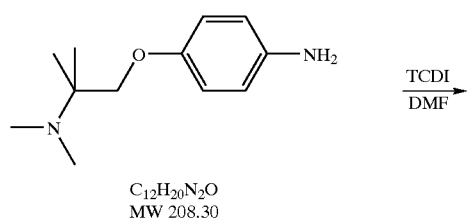

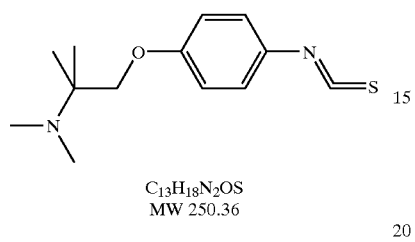

This compound was made from 2-dimethylamino-2-methyl-propan-1-ol (TCI) by the procedure described in Example 4. MS (ES) MH$^+$=251.

Example 9

[2-(4-Isothiocyanato-phenoxy)-1-methyl-ethyl]-dimethyl-amine

A. Dimethyl-[1-methyl-2-(4-nitro-phenoxy)-ethyl]-amine

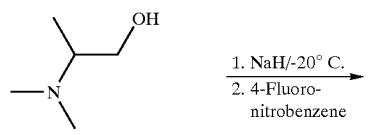

B. 4-(2-Dimethylamino-propoxy)-phenylamine

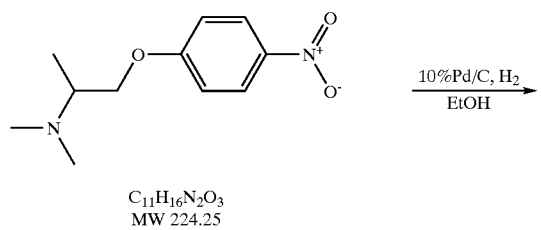

C. [2-(4-Isothiocyanato-phenoxy)-1-methyl-ethyl]-dimethyl-amine

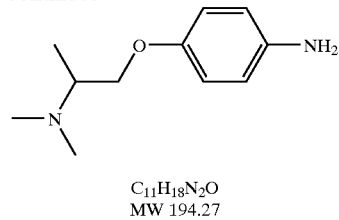

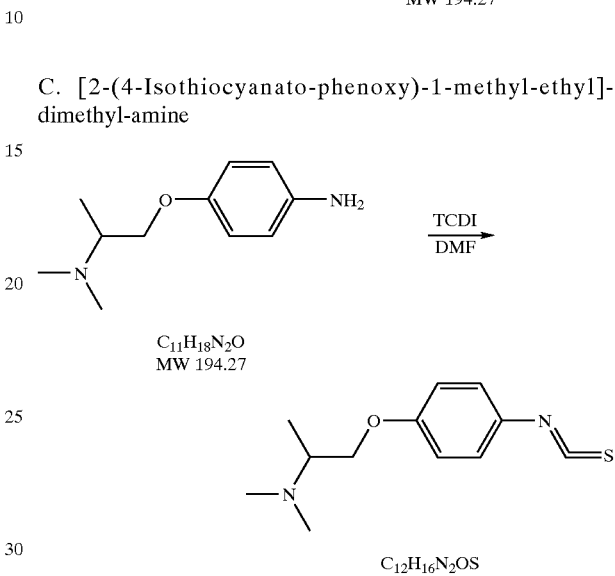

This compound was made from 2-dimethylamino-propan-1-ol (prepared by the procedure of Bhattacharyya, *Synthetic Commun.* 25 (14), 2061, 1995) by the procedure described in Example 4. MS (ES) MH$^+$=237.

Example 10

(R)-[2-(4-Isothiocyanato-phenoxy)-1-methyl-ethyl]-methyl-amine

A. (R)-Dimethyl-[1-methyl-2-(4-nitro-phenoxy)-ethyl]-amine

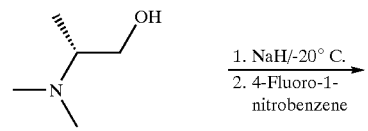

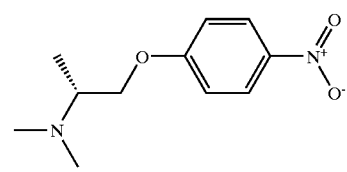

B. (R)-4-(2-Dimethylamino-propoxy)-phenylamine

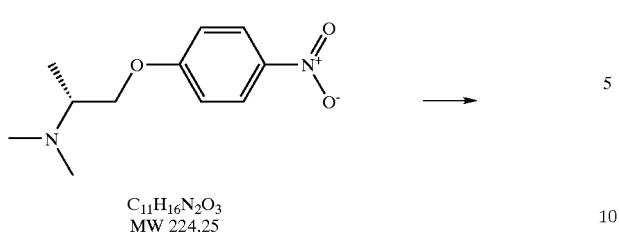

C. (R)-[2-(4-Isothiocyanato-phenoxy)-1-methyl-ethyl]-dimethyl-amine

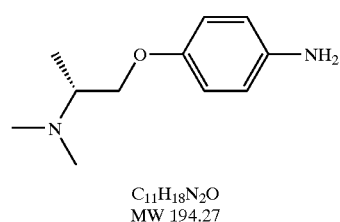

The named compound was made from (R)-2-dimethylamino-propan-1-ol (prepared by the procedure of Bhattacharyya, *Synthetic Commun.* 25 (14), 2061, 1995) by the procedure described in Example 4. MS (ES) MH$^+$=237.

Example 11

(R)-1-[2-(4-Isothiocyanato-phenoxy)-1-methyl-ethyl]-pyrrolidine

A. (R)-1-[1-Methyl-2-(4-nitro-phenoxy)-ethyl]-pyrrolidine

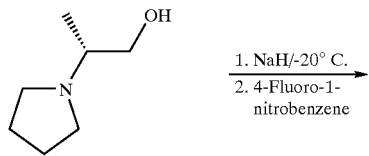

B. (R)-4-(2-Pyrrolidin-1-yl-propoxy)-phenylamine

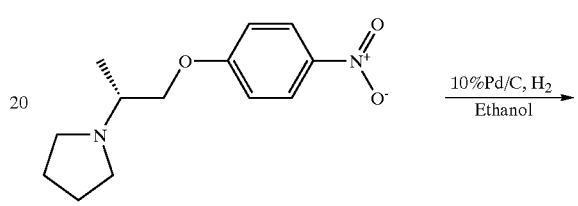

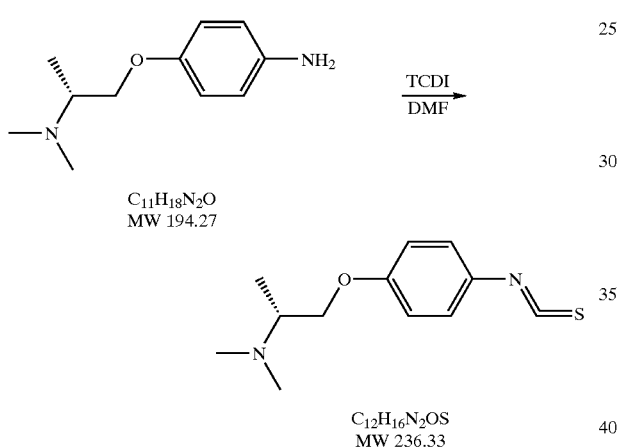

C. (R)-1-[2-(4-Isothiocyanato-phenoxy)-1-methyl-ethyl]-pyrrolidine

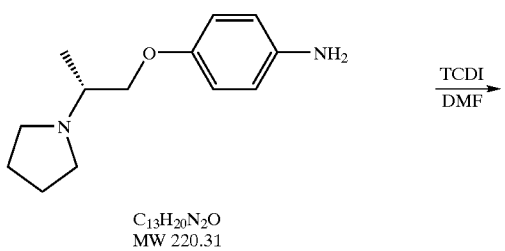

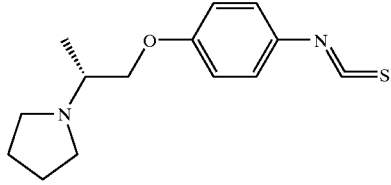

The named compound was made from (R)-2-pyrrolidin-1-yl-propan-1-ol (prepared by the procedure of Bhattacharyya, *Synthetic Commun.* 25 (14), 2061, 1995) by the procedure described in Example 4. MS (ES) MH$^+$=263.

Example 12

(S)-2-(4-Isothiocyanato-phenoxymethyl)-1-methyl-pyrrolidine

A. (S)-1-Methyl-2-(4-nitro-phenoxymethyl)-pyrrolidine

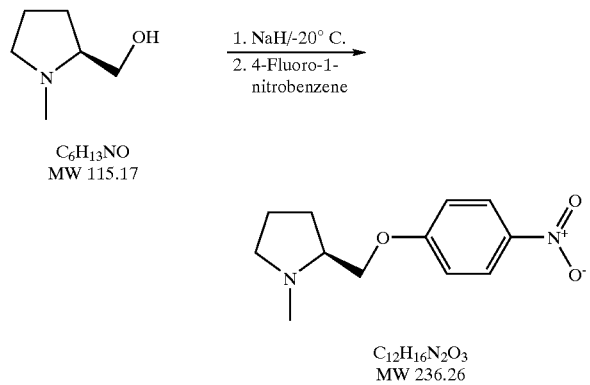

B. (S)4-(1-Methyl-pyrrolidin-2-ylmethoxy)-phenylamine

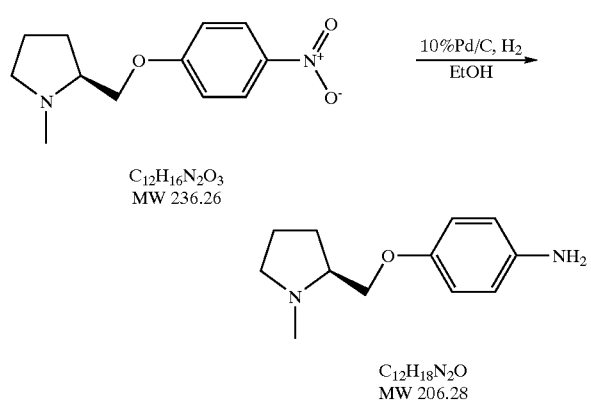

C. (S)-2-(4-Isothiocyanato-phenoxymethyl)-1-methyl-pyrrolidine

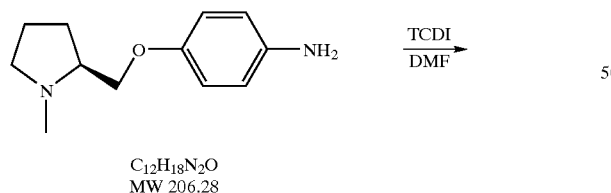

The named compound was made from (S)-(1-methyl-pyrrolidin-2-yl)-methanol (Aldrich) by the procedure described in Example 4. MS (ES) MH$^+$=249.

Example 13

1-Ethyl-3-(4-isothiocyanato-phenoxy)-piperidine

A. 1-Ethyl-3-(4-nitro-phenoxy)-piperidine

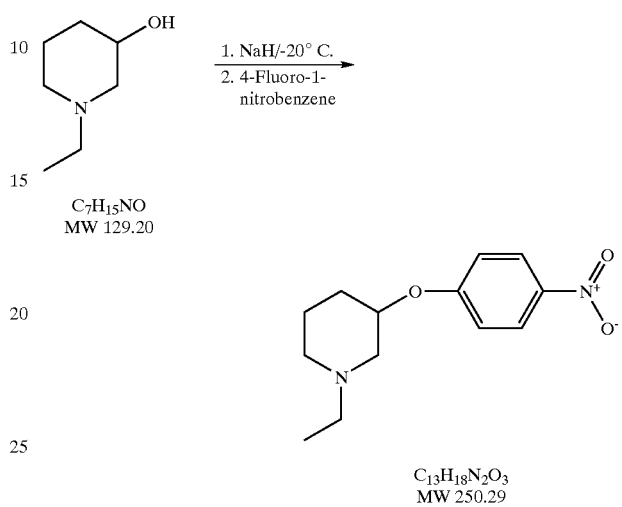

B. 4-(1-Ethyl-piperidin-3-yloxy)-phenylamine

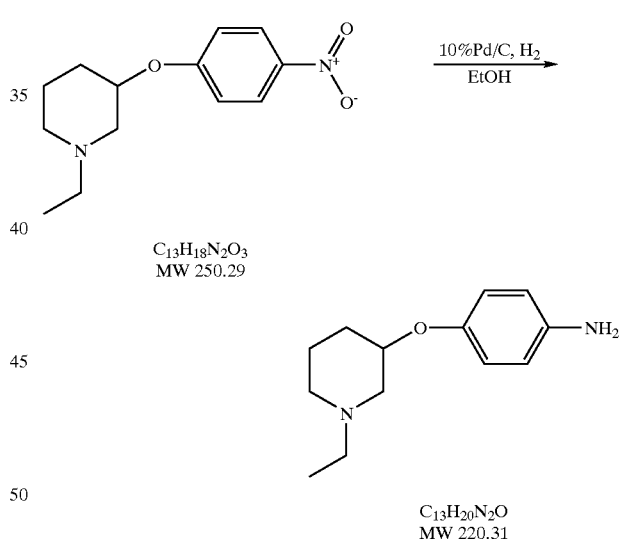

C. 1-Ethyl-3-(4-isothiocyanato-phenoxy)-piperidine

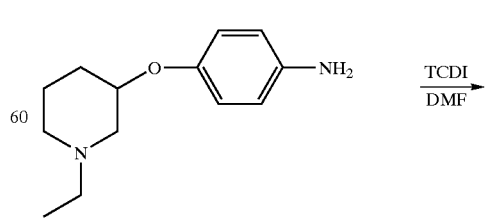

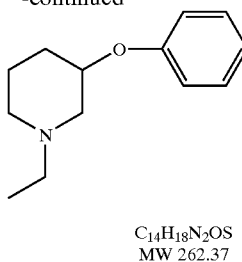

C₁₄H₁₈N₂OS
MW 262.37

The named compound was made from 1-ethyl-piperidin-3-ol (Aldrich) by the procedure described in Example 4. MS (ES) MH⁺=263.

Example 14

1-Ethyl-3-(4-isothiocyanato-phenoxy)-pyrrolidine

A. 1-Ethyl-3-(4-nitro-phenoxy)-pyrrolidine

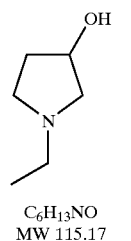

C₆H₁₃NO
MW 115.17

1. NaH/-20° C.
2. 4-Fluoro-1-nitrobenzene

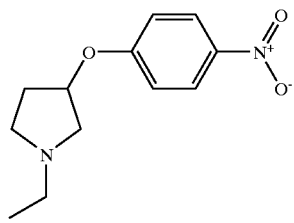

C₁₂H₁₆N₂O₃
MW 236.26

B. 4-(1-Ethyl-pyrrolidin-3-yloxy)-phenylamine

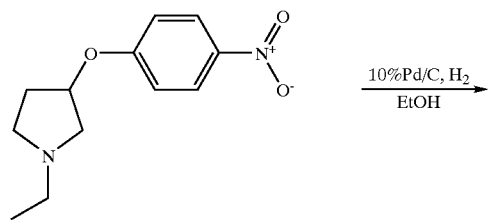

C₁₂H₁₆N₂O₃
MW 236.26

10%Pd/C, H₂ / EtOH

C₁₂H₁₈N₂O
MW 206.28

C. 1-Ethyl-3-(4-isothiocyanato-phenoxy)-pyrrolidine

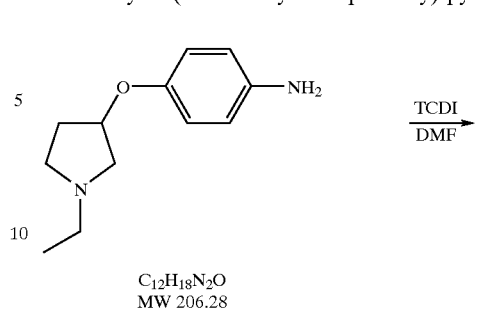

C₁₂H₁₈N₂O
MW 206.28

TCDI / DMF

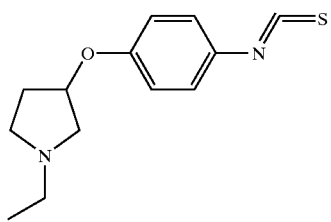

C₁₃H₁₆N₂OS
MW 248.34

The named compound was made from 1-ethyl-pyrolidin-3-ol (Aldrich) by procedure described in Example 4. MS (ES) MH⁺=249.

Example 15

3-(4-Isothiocyanato-phenoxy)-pyrrolidine-1-carboxylic Acid tert-Butyl Ester

A. 3-(4-Nitro-phenoxy)-pyrrolidine-1-carboxylic Acid tert-Butyl Ester

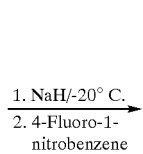

C₉H₁₇NO₃
MW 187.23

1. NaH/-20° C.
2. 4-Fluoro-1-nitrobenzene

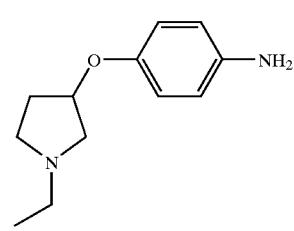

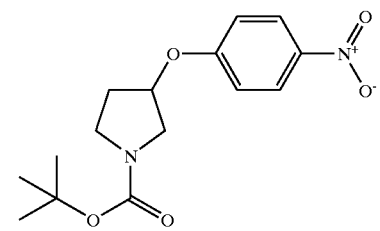

C₁₅H₂₀N₂O₅
MW 308.33

B. 3-(4-Amino-phenoxy)-pyrrolidine-1-carboxylic Acid tert-Butyl Ester

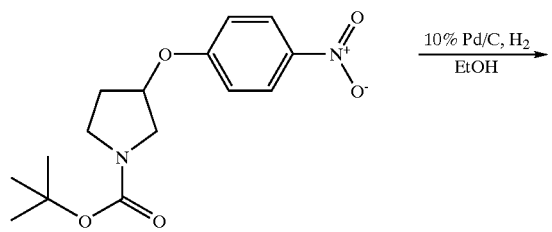

$C_{15}H_{20}N_2O_5$
MW 308.33

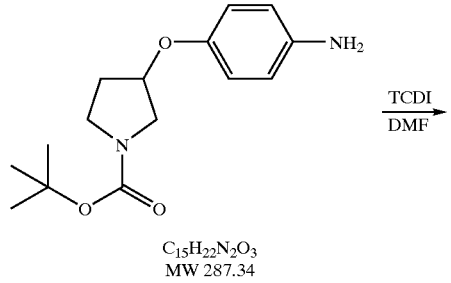

$C_{15}H_{22}N_2O_3$
MW 278.34

C. 3-(4-Isothiocyanato-phenoxy)-pyrrolidine-1-carboxylic Acid tert-Butyl Ester

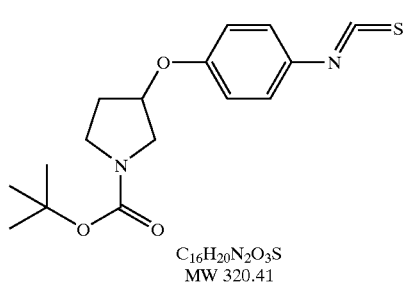

$C_{15}H_{22}N_2O_3$
MW 287.34

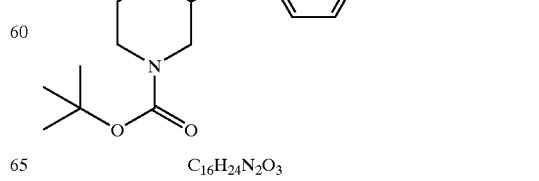

$C_{16}H_{20}N_2O_3S$
MW 320.41

The named compound was made from 3-hydroxy-pyrrolidine-1-carboxylic acid tert-butyl ester(Aldrich) by the procedure described in Example 4. MS (ES) MH$^+$=321.

Example 16

3-(4-Isothiocyanato-phenoxy)-piperidine-1-carboxylic Acid tert-Butyl Ester

A. 3-(4-Nitro-phenoxy)-piperidine-1-carboxylic Acid tert-Butyl Ester

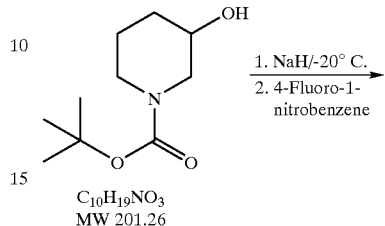

$C_{10}H_{19}NO_3$
MW 201.26

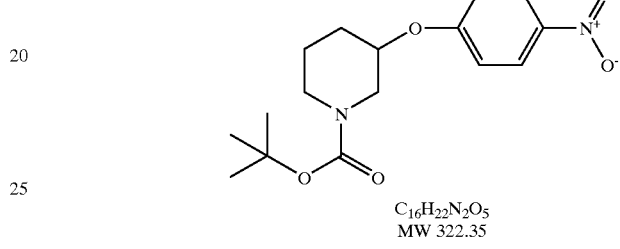

$C_{16}H_{22}N_2O_5$
MW 322.35

B. 3-(4-Amino-phenoxy)-piperidine-1-carboxylic Acid tert-Butyl Ester

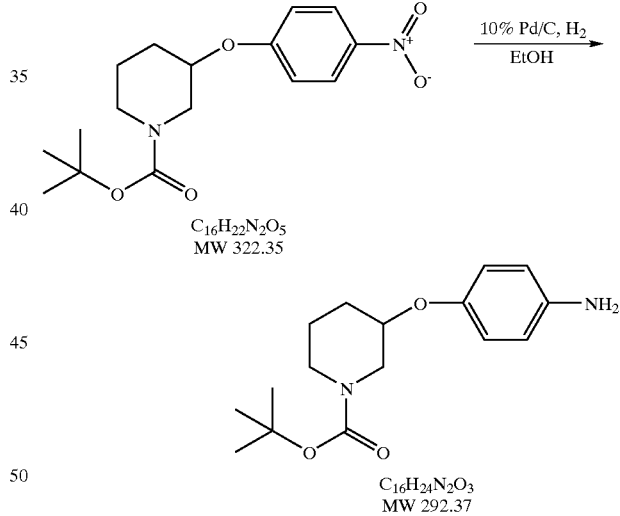

$C_{16}H_{22}N_2O_5$
MW 322.35

$C_{16}H_{24}N_2O_3$
MW 292.37

C. 3-(4-Isothiocyanato-phenoxy)-piperidine-1-carboxylic Acid tert-Butyl Ester $C_{16}H_{24}N_2O_3$
MW 292.37

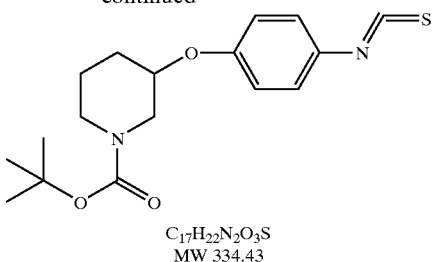

C₁₇H₂₂N₂O₃S
MW 334.43

The named compound was made from 3-Hydroxy-piperidine-1-carboxylic acid tert-butyl ester (Aldrich) by the procedure described in Example 4. MS (ES) MH⁺=335.

Example 17

2-Bromo-1-(4-ethyl-3-fluoro-phenyl)-ethanone

A. 4-Bromo-2-fluoro-1-vinyl-benzene

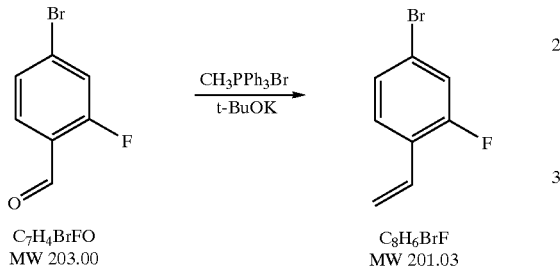

C₇H₄BrFO          C₈H₆BrF
MW 203.00         MW 201.03

To a stirred suspension of 4-bromo-2-fluoro-benzaldehyde (Aldrich, 2.30 g, 11.3 mmol) and methyltriphenylphosphonium bromide(Aldrich, 4.93 g, 13.6 mmol) in ether (50 mL), potassium tert-butoxide(1.52 g, 13.6 mmol) was added and the mixture was stirred at room temperature for 1 hour. The solid was filtered off and the filtrate was concentrated. The residue was treated with 30% ethyl acetate/hexanes (3 mL) and the solid was removed by filtration. The filtrate was filtered through a silica gel pad eluting with 30% ethyl acetate/hexanes to give a yellow oil. 1.54 g, 68%.

B. 4-Bromo-1-ethyl-2-fluoro-benzene

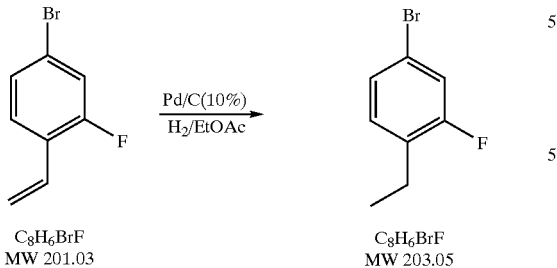

C₈H₆BrF           C₈H₆BrF
MW 201.03         MW 203.05

4-Bromo-2-fluoro-1-vinyl-benzene (1.80 g, 8.96 mmol) was dissolved in ethyl acetate (50 mL) and palladium-on-carbon (10%, 70 mg) was added and the mixture was hydrogenated under 1 atmosphere overnight. The mixture was filtered and the filtrate was concentrated to give the crude, 1.80 g, which was used directly for the next step.

C. (4-Ethyl-3-fluoro-phenylethynyl)-trimethyl-silane

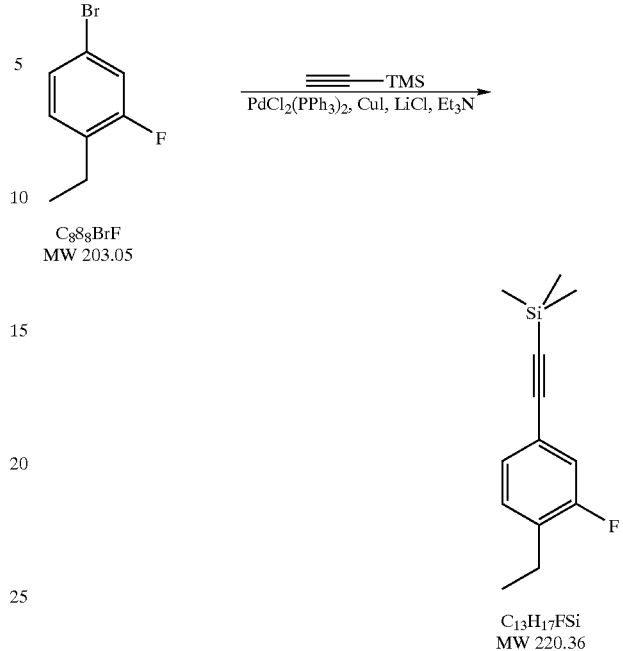

C₈H₈BrF
MW 203.05

C₁₃H₁₇FSi
MW 220.36

To a stirred solution of 4-bromo-1-ethyl-2-fluoro-benzene (1.80 g, 8.86 mmol) in N,N-dimethylformamide (20 mL), under a nitrogen atmosphere was added PdCl₂(PPh₃)₂, CuI, and LiCl. The mixture was stirred at 60° C. for 3 hours, then poured into water and extracted with ether (3×20 mL). The extract was dried (Na₂SO₄) and concentrated. The residue was filtered through a pad of silica gel eluting with hexanes. Removal of solvent gave the crude, 1.67 g, which was used for the next step.

D. 1-(4-Ethyl-3-fluoro-phenyl)-ethanone

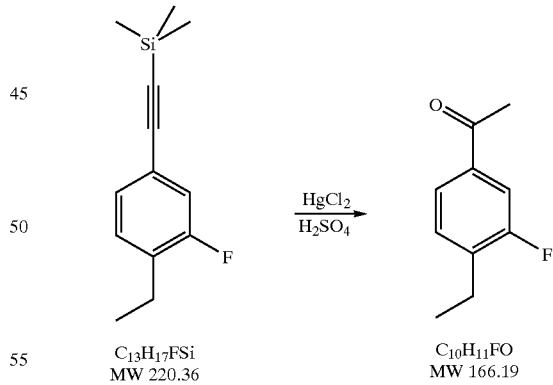

C₁₃H₁₇FSi         C₁₀H₁₁FO
MW 220.36         MW 166.19

To a stirred mixture of (4-ethyl-3-fluoro-phenylethynyl)-trimethyl-silane (1.43 g, 6.5 mmol), HgCl₂ (250 mg, 0.92 mmol) in aqueous tetrahydrofuran (tetrahydrofuran, 10 mL, H₂O, 3 mL), concentrated sulfuric acid (98%, 0.70 mL) was added and the mixture stirred for 6 hours. The mixture was poured into water (50 mL) and extracted with ether (3×20 mL). Removal of solvent gave a solid that was chromatographed (20% thyl acetate/hexanes) to give the desired product. 560 mg, 52%.

E. 2-Bromo-1-(4-ethyl-3-fluoro-phenyl)-ethanone

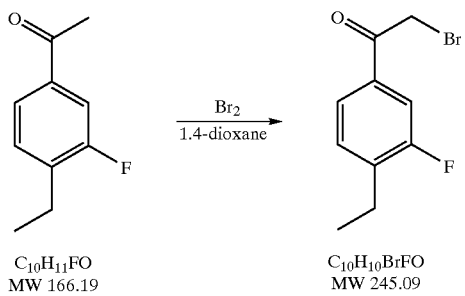

To a stirred solution of 1-(4-ethyl-3-fluoro-phenyl)-ethanone (166 mg, 1 mmol) in 1,4-dioxane (5 mL), bromine was added dropwise at room temperature. After the addition, the solvent was removed and the residue was chromatographed (dichloromethane/hexanes) to give a solid. 77 mg, 31%. $^1$H NMR(CDCl$_3$, 300MHz), σ 1.22 (t, 3H), 2.73 (q, 2H), 4.40 (s, 2H), 7.735 (t, 1H), 7.56–7.75 (dd, 2H).

Example 18

3-Hydroxy-cyclobutanecarboxylic Acid tert-Butyl Ester

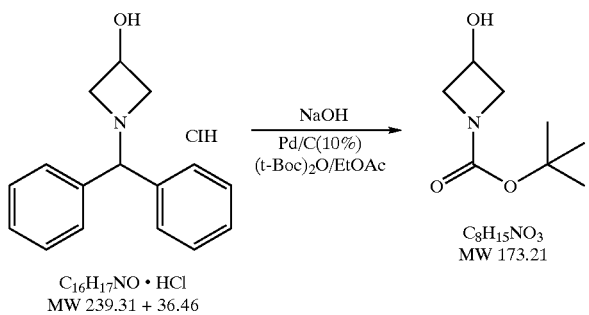

1-Benzhydryl-azetidin-3-ol (2.0 g, 7.53 mmol) (Maybridge Chemical) was suspended in ethyl acetate (50 mL) and treated with 2N sodium hydroxide solution (20 mL) and the mixture was thoroughly shaken and the layers were allowed to separate. The organic layer was dried (Na$_2$SO$_4$) and transferred to a hydrogenation bottle and treated with palladium-on-carbon (10%, 320 mg) and (Boc)$_2$O (7.91 mmol). The mixture was hydrogenated under 50 psi for 9 hours and filtered. Removal of solvent gave the crude that was chromatographed (hexanes first, then 50% ethyl acetate/hexanes) to yield a colorless solid. 1.13 g. $^1$H NMR(d$^6$-DMSO, 400 MHz), σ 1.32 (s, 9H), 3.55 (q, 2H), 3.96 (t, 2H), 4.34 (m, 1H), 5.61 (d, 1H, OH).

Example 19

3-(4-Isothiocyanato-phenoxy)-cyclobutanecarboxylic Acid tert-Butyl Ester

A. 3-(4-Nitro-phenoxy)-azetidine-1-carboxylic Acid tert-Butyl Ester

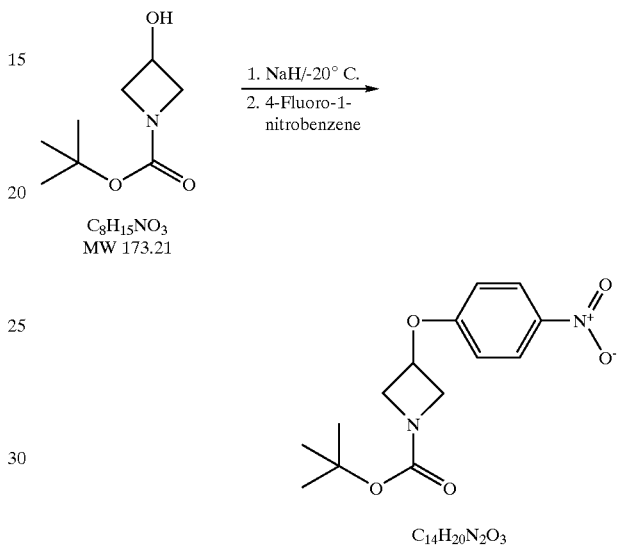

B. 3-(4-Amino-phenoxy)-azetidine-1-carboxylic Acid tert-Butyl Ester

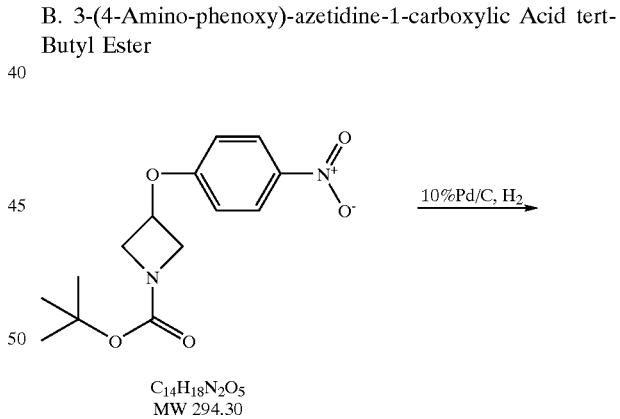

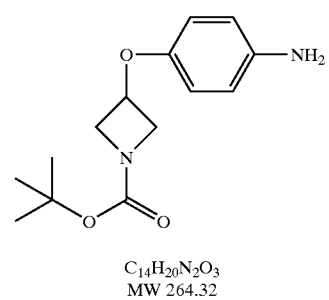

C. 3-(4-Isothiocyanato-phenoxy)-azetidine-1-carboxylic Acid tert-Butyl Ester

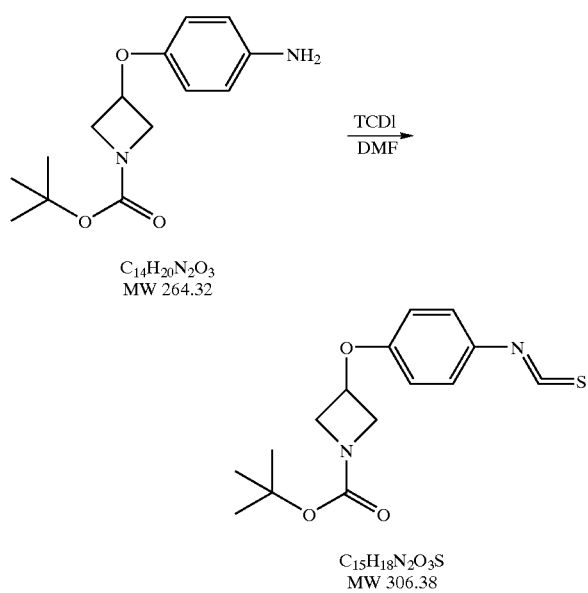

This compound was made from 3-hydroxy-cyclobutanecarboxylic acid tert-butyl ester (from Example 18) by the procedure described in Example 4. MS (ES) MH+=307.

Example 20

2-Bromo-1-(3-cyclopropyl-phenyl)-ethanone

A. 2-(3-Bromo-phenyl)-2-methyl-[1,3]dioxolane

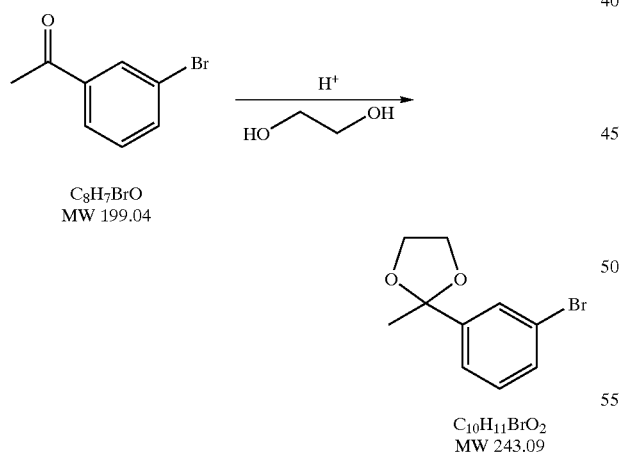

A mixture of 3-bromo-acetophenone (Aldrich, 8.0 g, 40 mmol), ethylene glycol (3.72 g, 60 mmol) and 4-toluenesulfonic acid (10 mg) was heated in toluene (130 mL) with azotropic removal of water for 24 hours. The mixture was washed with water, dried (Na₂SO₄) and concentrated to give the desired product as an oil, which was distilled at reduced pressure to give a pale yellow liquid. 7.58 g, 93%.

B. 3-Cyclopropyl-acetylphenone

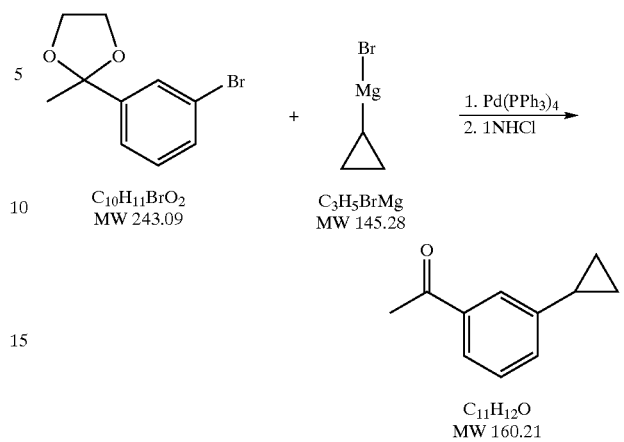

To a stirred solution of bromocyclopropane (Aldrich, 4.2 g, 35 mmol) in tetrahydrofuran (15 mL), magnesium turnings (Aldrich, 0.795 g, 33.1 mmol) were added in three equal portions at room temperature while the reaction was controlled with a water bath so that slight boiling of the solvent was maintained. When the magnesium was dissolved, Pd(PPh₃)₄ (640 mg) was added followed by the addition of 2-(3-bromo-phenyl)-2-methyl-[1,3]dioxolane (5.05 g, 20.87 mmol) in 80 mL of tetrahydrofuran. The mixture was refluxed for 5 hours and another portion of cyclopropyl magnesium bromide (made from 2 g of bromocyclopropane and 0.4 g magnesium turnings in 15 mL of tetrahydrofuran) was added and the mixture was again refluxed for 5 hours. The solution was poured into 1N HCl (150 mL) and stirred at room temperature for 1.5 hours and the mixture was extracted with diethyl ether. The extract was dried (Na₂SO₄) and concentrated. The residue was chromatographed (30% ethyl, acetate/hexanes) to give 3-cyclopropyl-acetylphenone as an oil, 4.05 g, 72%.

C. 2-Bromo-1-(3-cyclopropyl-phenyl)-ethanone

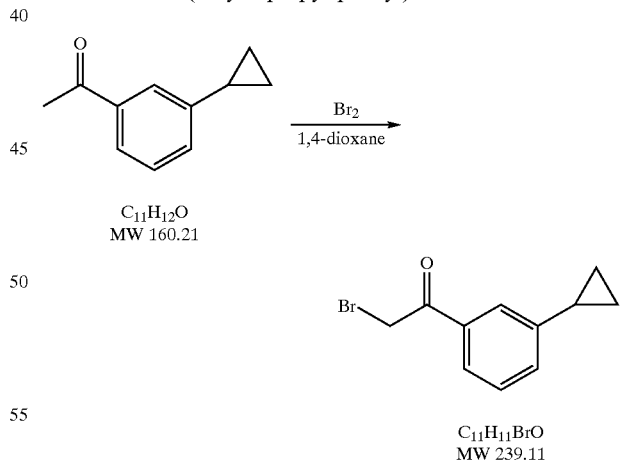

3-Cyclopropyl-acetylphenone (2.04 g, 12.75 mmol) was dissolved in 1,4-dioxane (15 mL) and bromine (2.08 g, 13 mmol) was added dropwise. After the addition, the solution was stirred at room temperature for 30 minute and the solvent was removed on a rotary evaporator. The residue was chromatographed (30% ethyl acetate/hexanes) to give a pale yellow solid. 2.0 g, 66%. $^1$H NMR(CDCl₃, 300 MHz), σ 0.65–0.70 (s, 2H), 0.95–1.10(m, 2H), 1.87–2.05 (m, 1H), 4.45 (s, 2H), 7.24–7.43 (m, 2H), 7.65–7.80 (m, 2H).

Example 21

2-Chloro-1-(3-fluoro-4-methyl-phenyl)-ethanone

A. 3-Fluoro-4-methyl-benzoyl chloride

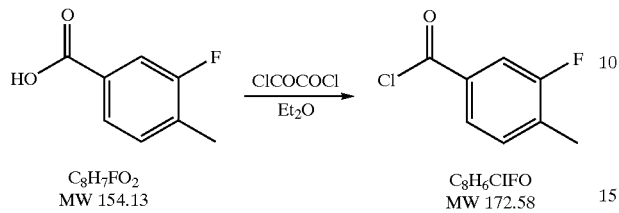

To a stirred solution of 3-fluoro-4-methyl-benzoic acid (Aldrich, 3.08 g, 20 mmol) in diethyl ether (30 mL), oxalyl chloride (2.85 mL, 30 mmol) was added slowly followed by a drop of N,N-dimethylformamide. The mixture was stirred at room temperature overnight and the solvent was removed under reduced pressure to give 3-fluoro-4-methyl-benzoyl chloride that was used directly for the next step.

B. 2-Chloro-1-(3-fluoro-4-methyl-phenyl)-ethanone

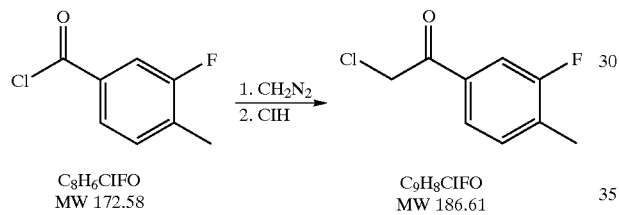

3-Fluoro-4-methyl-benzoyl chloride (1.72 g, 10 mmol) was dissolved in diethyl ether (10 mL) and the solution was cooled to 0° C., $CH_2N_2$ (10 eq, Organic Synth., Coll. II, 165) in diethyl ether was added and the mixture was stirred for 20 minute. The solvent was removed at reduced pressure and the residue was treated with 1 N HCl in 1,4-dioxane (4 mL). After the bubbles ceased, the solvent was removed on a rotary evaporator and the residue was chromatographed (30% Ethyl acetate/hexanes) to give a solid. 1.78 g, 96%. $^1$H NMR(CDCl$_3$, 300 MHz), σ 2.37 (d, 3H), 4.67 (s, 2H), 7.23–7.40 (t, 1H), 4.45 (s, 2H), 7.58–7.70 (m, 2H).

Example 22

2-Bromo-1-(3-ethyl-4-fluoro-phenyl)-ethanone

A. 4-Bromo-1-fluoro-2-vinyl-benzene

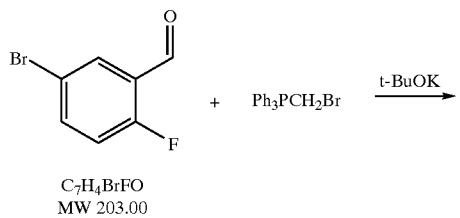

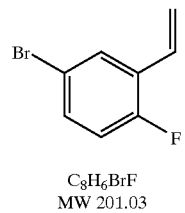

3-Bromo-2-fluorobenzaldehyde (Aldrich, 3.3 g, 16.26 mmol) was dissolved in diethyl ether and the solution was cooled to 0° C. To the stirred solution, Ph$_3$PCH$_2$Br (6.97 g, 19.51 mmol) and potassium tert-butoxide(2.19 g, 19.51 mmol) were added. Then, the ice bath was removed and the mixture was stirred at room temperature for 2 hours. The mixture was filtered and the solid was washed with diethyl ether and ethyl acetate successively. The filtrate was concentrated and the residue was chromatographed (loaded with a mixture of methylene chloride and hexanes, eluted with hexanes) to give a yellow oil. 2.8 g. 86%.

B. 4-Bromo-2-ethyl-1-fluoro-benzene

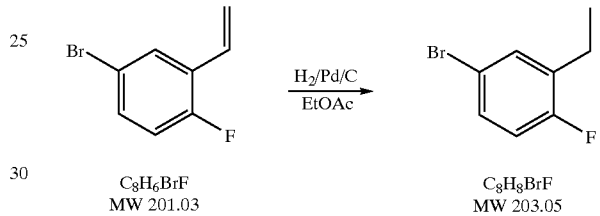

The yellow oil from step A (2.8 g, 10 mmol) was dissolved in Ethyl acetate (200 mL). Palladium-on-carbon (10%, 250 mg) was added and the mixture was hydrogenated under 1 atmosphere until TLC showed complete reaction. The mixture was filtered and the filtrate was concentrated to give an oil. 2.4 g, 87%.

C. (3-Ethyl-4-fluoro-phenylethynyl)-trimethyl-silane

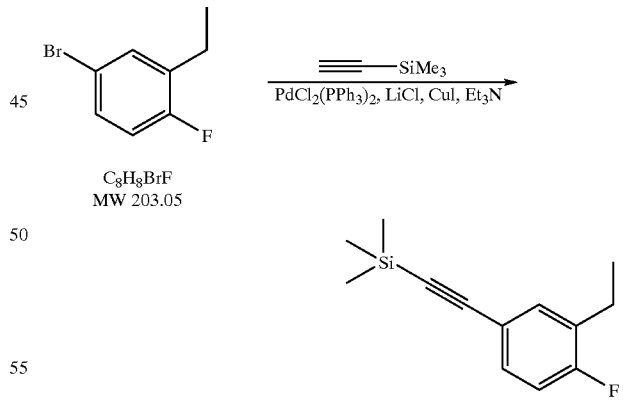

To a stirred solution of 4-bromo-2-ethyl-1-fluoro-benzene (2.4 g, 11.82 mmol) in N,N-dimethylformamide (100 mL), trimethylsilyl acetylene (2.0 mL, 14.19 mmol), PdCl$_2$(PPh$_3$)$_2$ (500 mg, 0.72 mmol), LiCl (1 g, 23.64 mmol), CuI (25 mg, 0.1 mmol) and triethylamine (3 mL) were added and the mixture was stirred at 80° C. for 3 hours. The reaction mixture was poured into water and extracted with diethyl ether. The extract was dried (Na$_2$SO$_4$) and concentrated. The residue was chromatographed on silica gel (hexanes) to give a brown oil. 1.58 g, 61%.

D. 1-(3-Ethyl-4-fluoro-phenyl)-ethanone

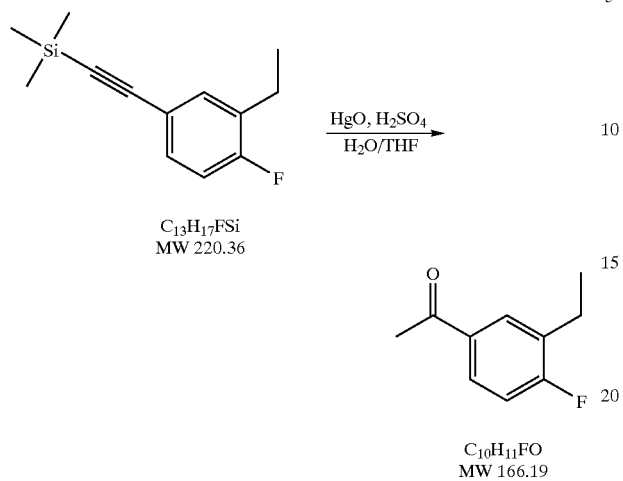

To a stirred solution of H$_2$SO$_4$ (0.25 mL) in H$_2$O (3 mL), HgO (154 mg, 0.712 mmol) was added. Another portion of H$_2$SO$_4$ (0.5 mL) was added so that all of the mercury oxide dissolved. Then the mixture was warmed to 60° C. and (3-ethyl-4-fluoro-phenylethynyl)-trimethyl-silane (1.57 g, 7.12 mmol) was added with tetrahydrofuran (2 mL) during 20 minutes. After the addition, the mixture was stirred for an additional 30 minutes and then cooled and extracted with ether. The extract was passed through a celite pad, washed with saturated brine and dried (Na$_2$SO$_4$). Removal of solvent on a rotary evaporator gave a brown oil, which was chromatographed (25%, dichloromethane/hexanes) to give a yellow oil. 404 mg, 34%.

E. 2-Bromo-1-(3-ethyl-4-fluoro-phenyl)-ethanone

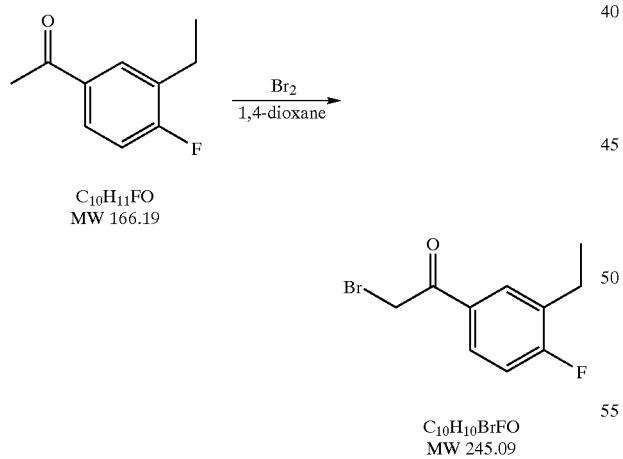

To a stirred solution of 1-(3-ethyl-4-fluoro-phenyl)-ethanone (400 mg, 2.41 mmol) (from Step D) in 1,4-dioxane, bromine (124 μL, 2.41 mmol) was added and the mixture was stirred for 30 minute. at room temperature. The solvent was removed and the residue was chromatographed (5% dichloromethane/hexanes) to give an oil. 317 mg, 54%. $^1$H NMR(CDCl$_3$, 300 MHz), σ 1.2–1.35 (t, 3H), 2.67–2.80 (q, 2H), 4.42 (s, 2H), 7.03–7.0 (t, 1H), 4.45 (s, 2H), 7.75–7.92 (m, 2H).

Example 23

2-Bromo-1-(4-hydroxy-3-propyl-phenyl)-ethanone

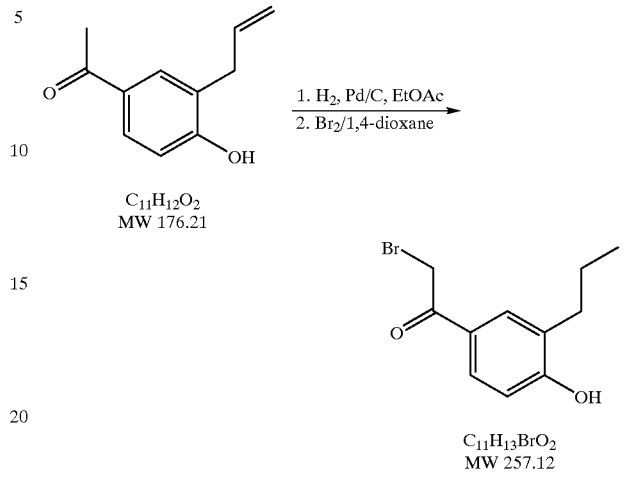

1-(3-Allyl-4-hydroxy-phenyl)-ethanone (Crescent Chemical Co., Inc. Islandia, N.Y. 11749. 2.0 g, 11.35 mmol) was dissolved in ethyl acetate (50 mL) and hydrogenated at 1 atmosphere of hydrogen using palladium-on-carbon(10%, 200mg) as catalyst for 1.5 hours. The mixture was filtered and the filtrate was concentrated to give a white solid 2.0 g, 99%.

The solid (2.0 g, 11.35 mmol) was dissolved in 1,4-dioxane (100 mL). To the stirred solution, bromine (583 μL, 11.35 mmol) was added and the solution was stirred for 30 minute. TLC indicted incomplete reaction. An additional portion of bromine (100 μL) was added and the mixture was stirred for another 30 minute. The solvent was removed on a rotary evaporator and the residue was chromatographed on a Foxy machine (ethyl acetate/dichloromethane, 0% ethyl acetate for 6 minutes.; then 2% for 6–20 minutes) to give a light pink solid after evaporation. 1.574 g, 54%. σ 0.9–1.1.50–1.80 (m, 2H), 2.55–2.70 (t, 2H), 4.40(s, 2H), 6.80–6.90 (d, 1H), 7.70–7.82 (m, 2H).

Example 24

A. Resin-bound Thiouronium Salt

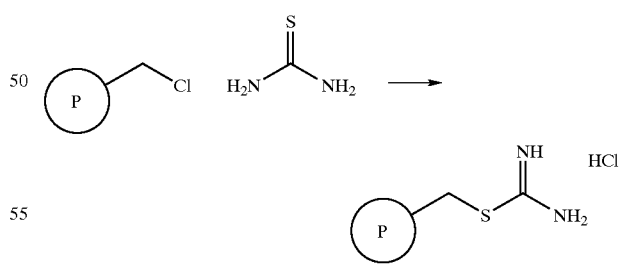

Following the procedure of Obrecht et al. (Helv. Chim. Acta. 1997, 80, 65–72), a mixture of Merrifield resin (77 g, 331 mmol: Cl load of 4.3 mmol/g) (Fluka) and thiourea (126 g, 1650 mmol) in dioxane/ethanol (4/1) (750 mL) was heated at 85° C. for 5 days. The reaction mixture was filtered and the resin was successively washed with hot ethanol (2×500 mL), ethanol (500 mL), dioxane (2×500 mL), hexanes (2×500 mL) and diethyl ether (2×500 mL). The pale yellow resin was dried in vacuo to afford 115 g of the title resin. The loading of the. resin was determined by nitrogen and sulfur analysis: N, (7.78), S, (9.77).

B.

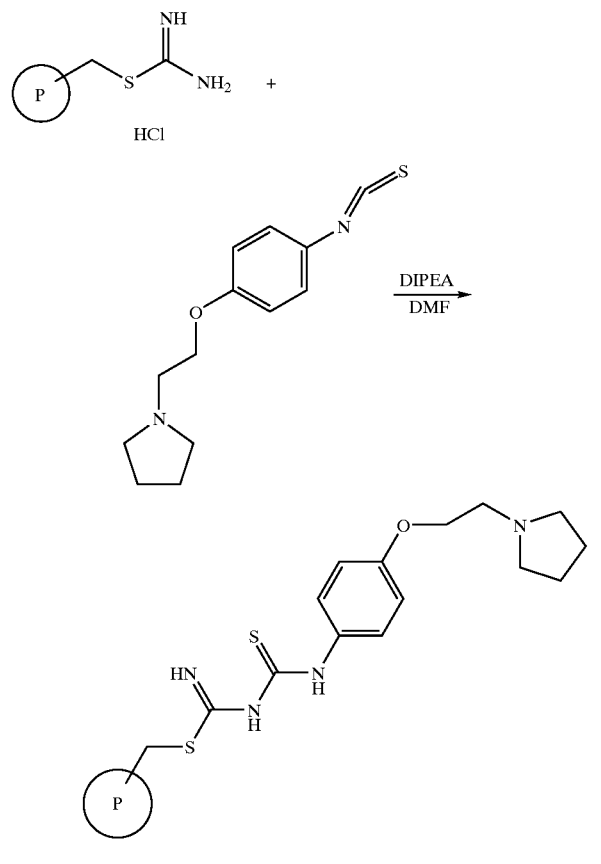

A mixture of resin-bound thiourea salt (from Step A above) 1.0 g, 3.26 mmol, loading: 1.60 mmol/g), isothiocyanate (Example 5, 950 mg, 3.60 mmol), N,N-diisopropylethylamine (3.40 mL, 20 mmol) in N,N-dimethylformamide (10 mL) was shaken gently overnight. The resin was filtered and washed successively with N,N-dimethylformamide, ethyl ether, and dried under vacuum. 1.65 g (loading, 1.6 mmol/g), which was used for the next step.

The following Examples were made from the indicated isothiocyanate using the general procedure described in Example 24.

Example 25

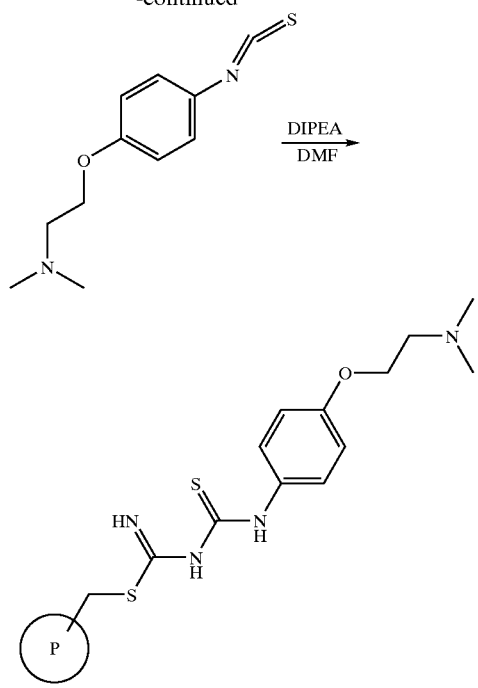

Prepared as in Example 24 from the isothiocyanate prepared in Example 4.

Example 26

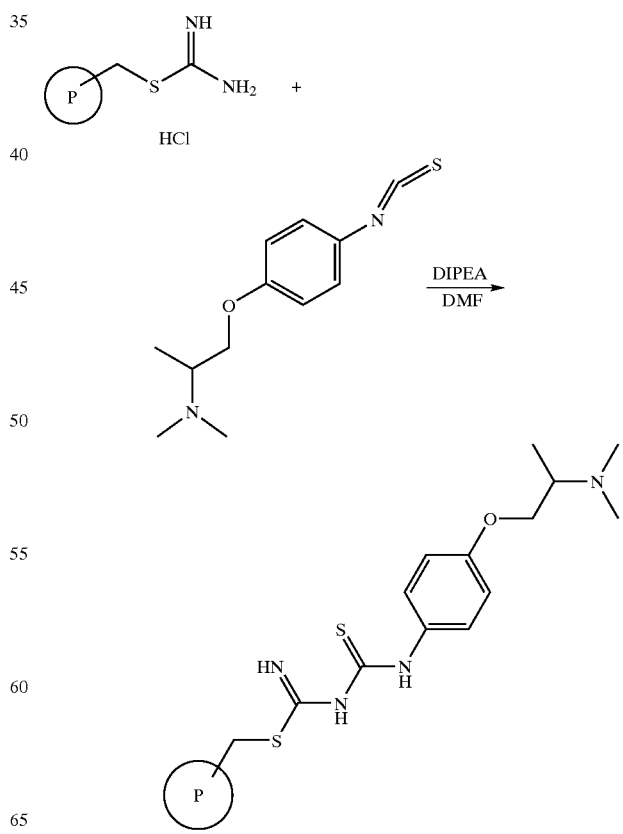

Prepared as in Example 24 from the isothiocyanate prepared in Example 9.
Example 27
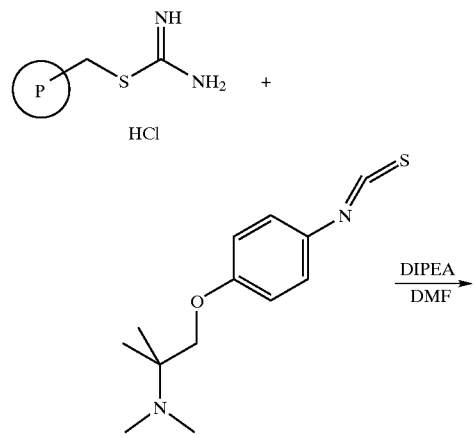
Prepared as in Example 24 from the isothiocyanate prepared in Example 8.
Example 28
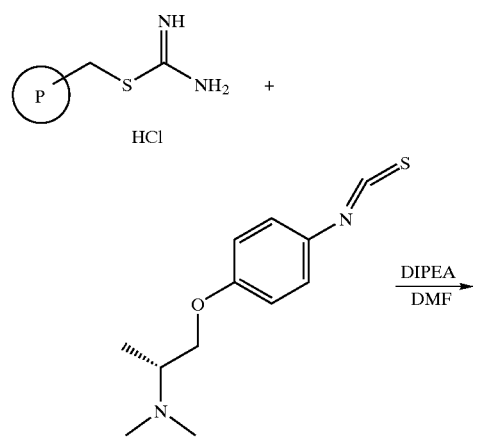
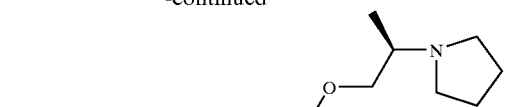
Prepared as in Example 24 from the isothiocyanate prepared in Example 10.
Example 29
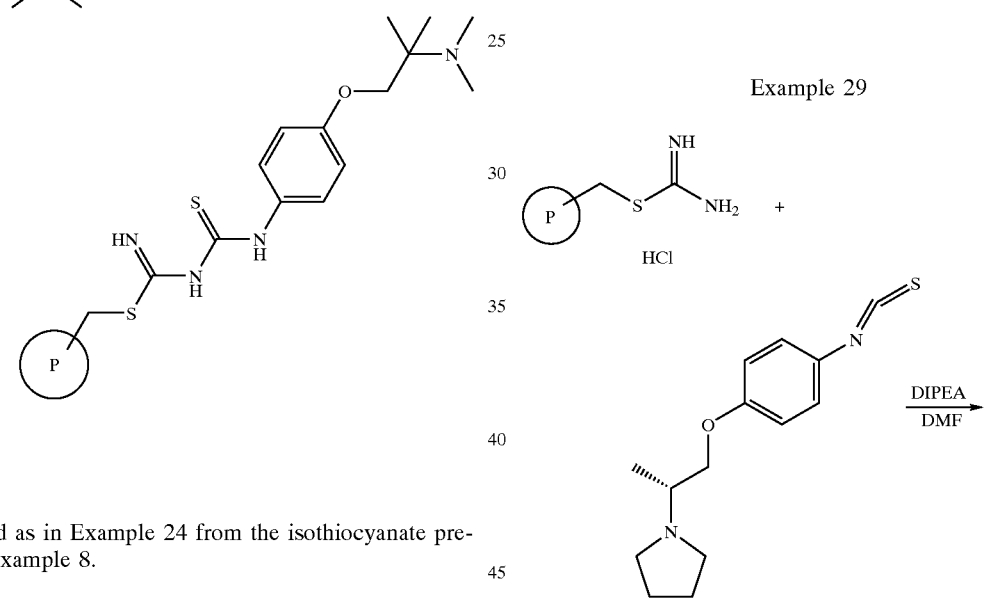
Prepared as in Example 24 from the isothiocyanate prepared in Example 11.

Example 30
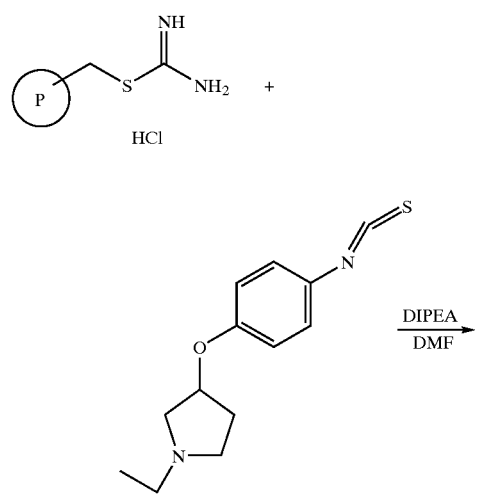
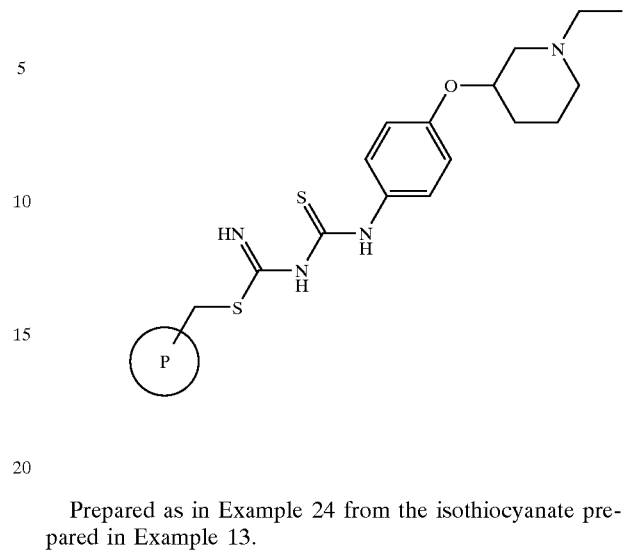
Prepared as in Example 24 from the isothiocyanate prepared in Example 14.
Example 31
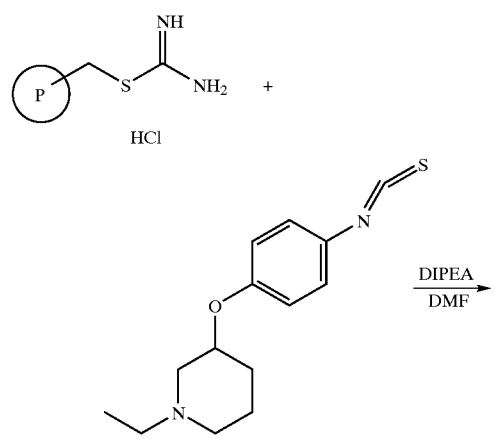
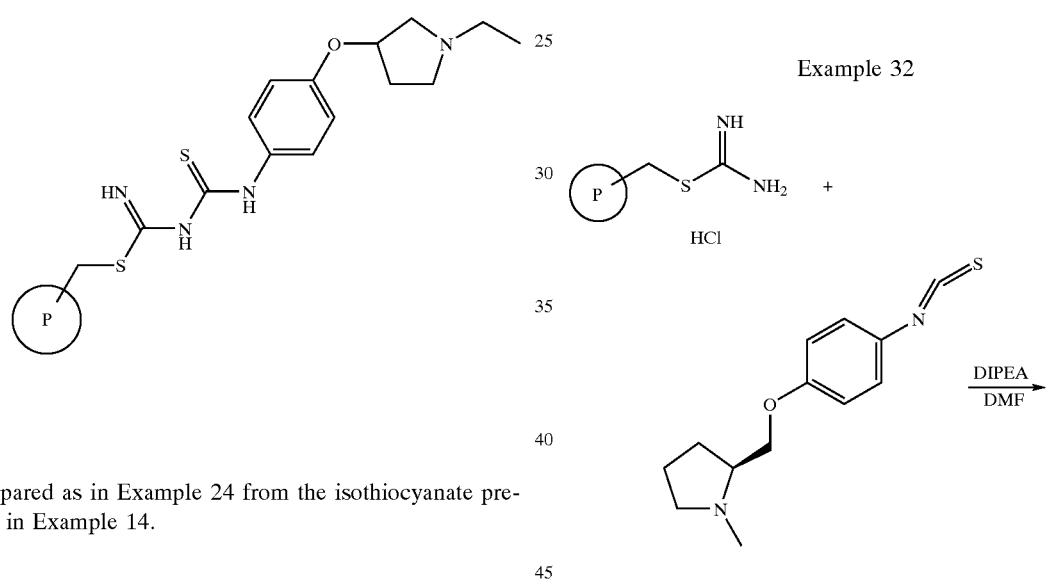
Prepared as in Example 24 from the isothiocyanate prepared in Example 13.
Example 32
Prepared as in Example 24 from the isothiocyanate prepared in Example 12.

Example 33
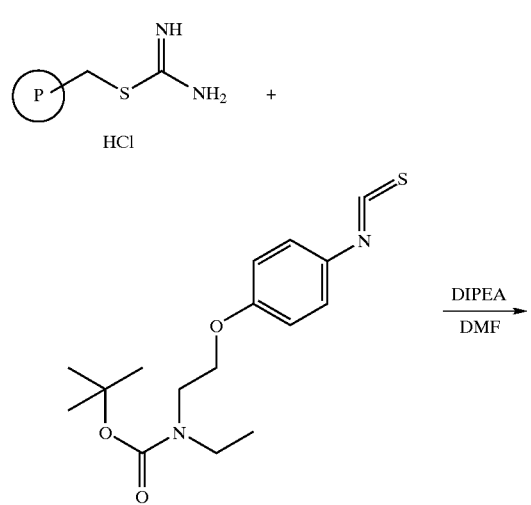
Prepared as in Example 24 from the isothiocyanate prepared in Example 129D.
Example 34
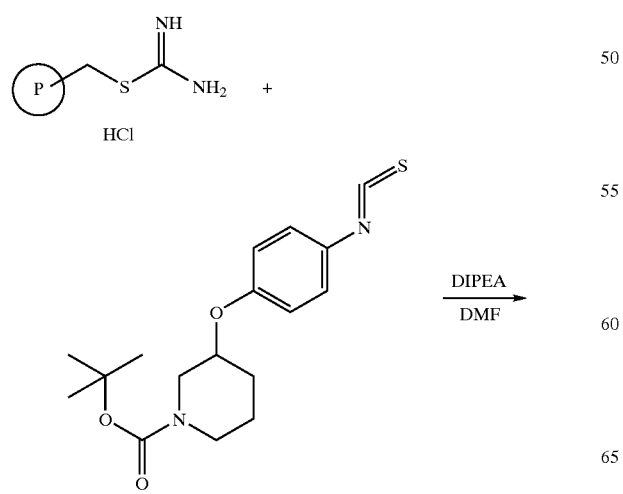
Prepared as in Example 24 from the isothiocyanate prepared in Example 16.
Example 35
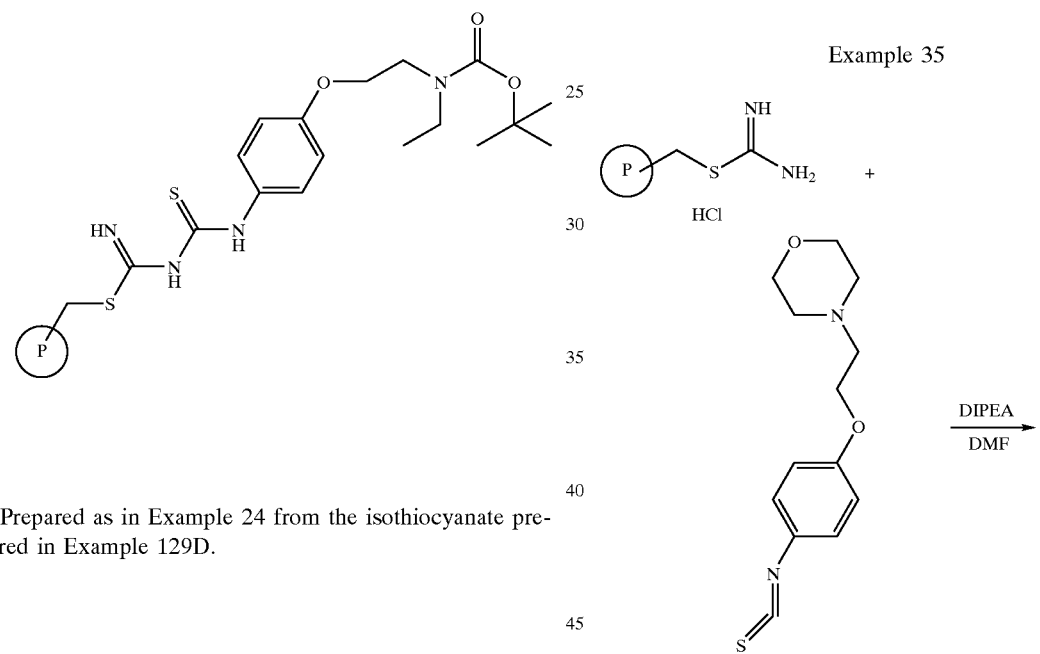

Prepared as in Example 24 from the isothiocyanate prepared in Example 7.

Example 36

[4-Amino-2-[4-(2-pyrrolidin-1-yl-ethoxy)-phenylamino]-thiazol-5-yl]-(3-fluoro-phenyl)-methanone

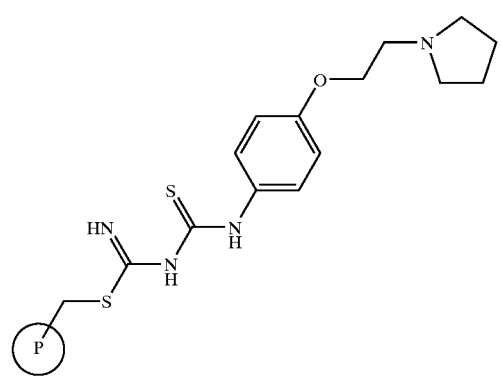

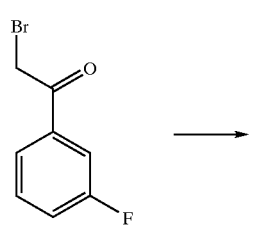

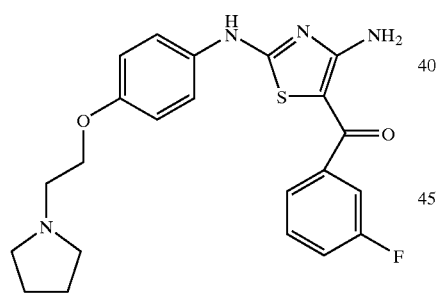

C$_{22}$H$_{23}$FN$_4$O$_2$S
MW 426.51

The resin (60 mg, 0.10 mmol, loading 1.6 mmol/g) (from Example 24) and 2-bromo-1-(3-fluoro-phenyl)-ethanone (Maybridge Chemical) (41 mg, 0.19 mmol) were gently shaken in N,N-dimethylformamide (2 mL) for 3 days. Polymer supported trisamine (Argonaut Technologies, 3.45 mmol/g, 80 mg) was added and the mixture was stirred for 2 hours. The resin was filtered and washed with N,N-dimethylformamide and dichloromethane. The filtrate was concentrated under vacuum to give the crude material, (48 mg), which was purified by reverse phase HPLC to give the trifluoroacetic acid salt. The salt was treated with 4N NaOH and the mixture was extracted with ethyl acetate/tetrahydrofuran. The extract was dried (Na$_2$SO$_4$) and concentrated to a yellow solid. 24 mg, 56%. MS (ES) MH$^+$= 427.

Example 37

[4-Amino-2-[4-(2-dimethylamino-ethoxy)-phenylamino]-thiazol-5-yl]-(3-fluoro-phenyl)-methanone

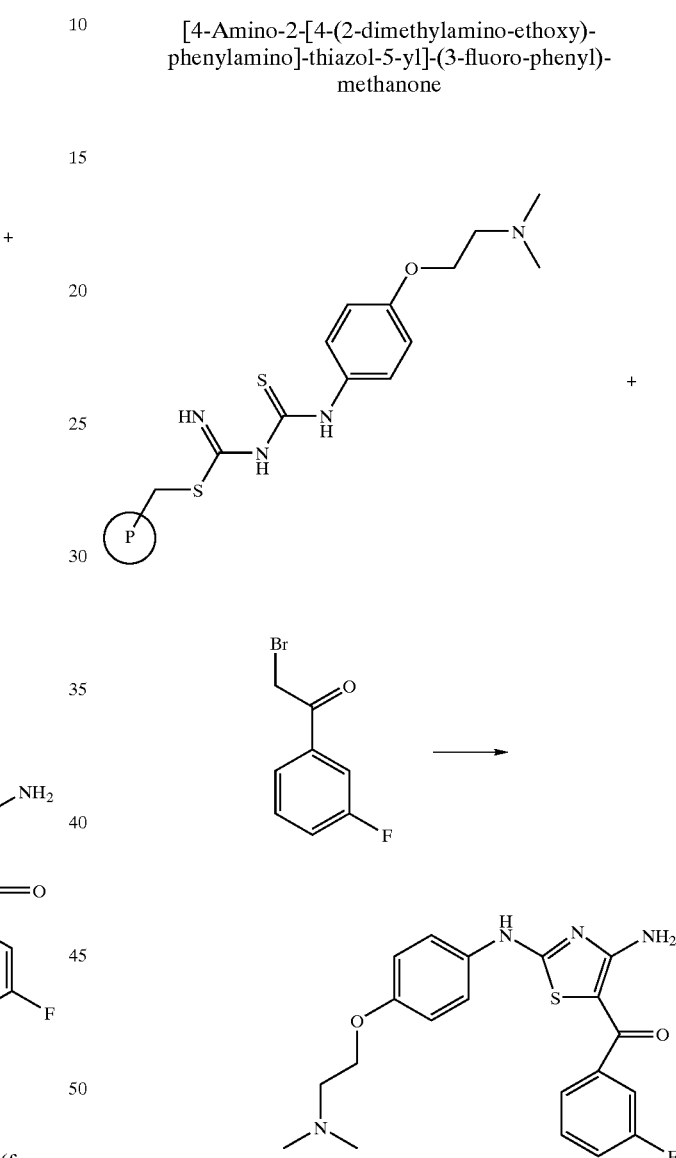

C$_{20}$H$_{21}$FN$_4$O$_2$S
MW 400.47

The named compound was prepared from resin-bound thiourea of Example 25 and 2-bromo-1-(3-fluoro-phenyl)-ethanone (Maybridge Chemical) by the procedure used in Example 36. MS (ES) MH$^+$=401.

Example 38

[4-Amino-2-[4-(2-dimethylamino-propoxy)-phenylamino]-thiazol-5-yl]-(3-fluoro-phenyl)-methanone

Example 39

[4-Amino-2-[4-(2-dimethylamino-2-methyl-propoxy)-phenylamino]-thiazol-5-yl]-(3-fluoro-phenyl)-methanone

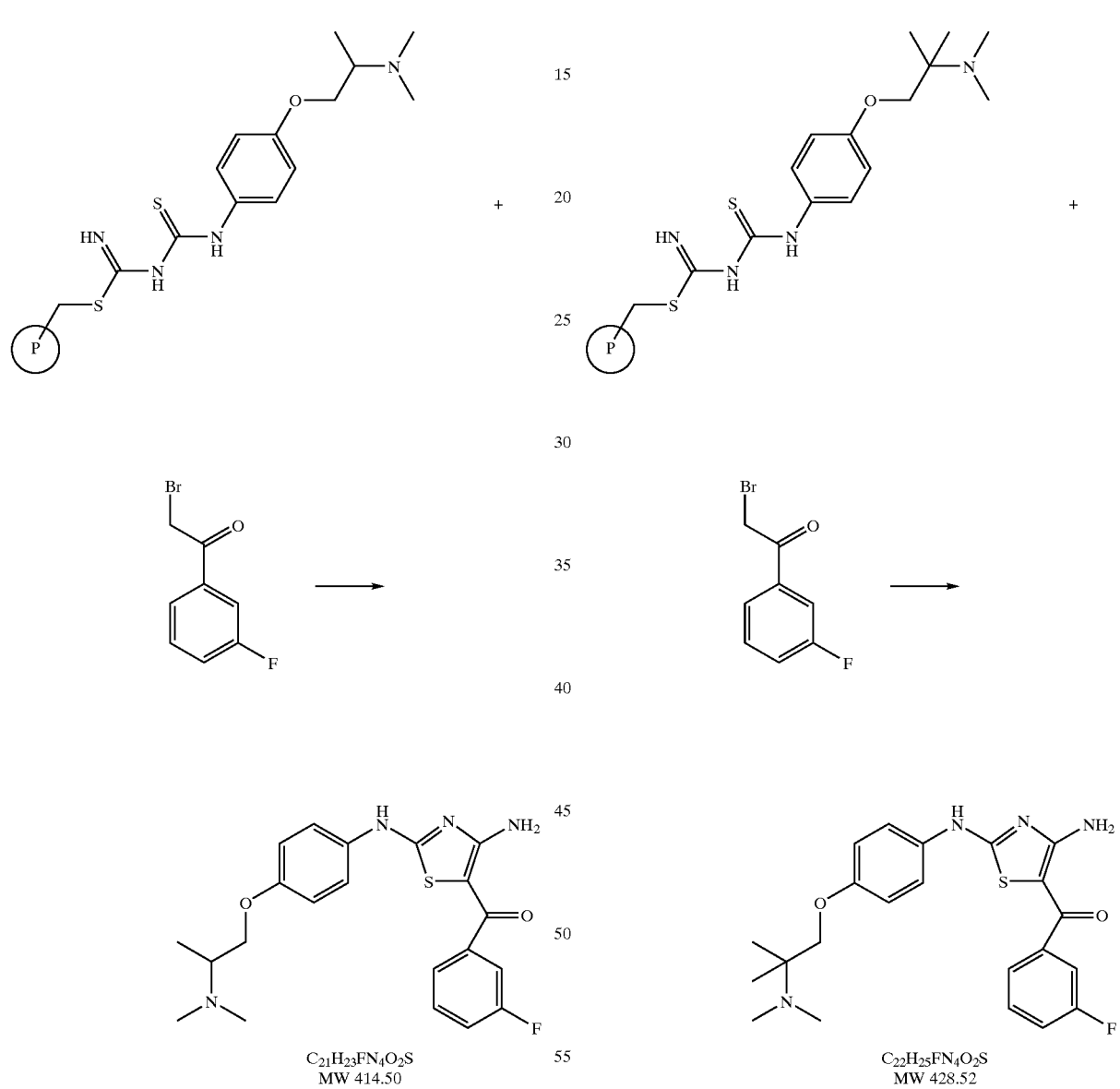

$C_{21}H_{23}FN_4O_2S$
MW 414.50

$C_{22}H_{25}FN_4O_2S$
MW 428.52

The named compound was prepared from resin-bound thiourea of Example 26 and 2-bromo-1-(3-fluoro-phenyl)-ethanone (Maybridge Chemical) by the procedure used in Example 36. MS (ES) MH$^+$=415.

This compound was prepared from resin-bound thiourea of Example 27 and 2-bromo-1-(3-fluoro-phenyl)-ethanone (Maybridge Chemical) by the procedure used in Example 36. MS (ES) MH$^+$=429.

Example 40

(R)-[4-Amino-2-[4-(2-dimethylamino-propoxy)-phenylamino]-thiazol-5-yl]-(3-fluoro-phenyl)-methanone

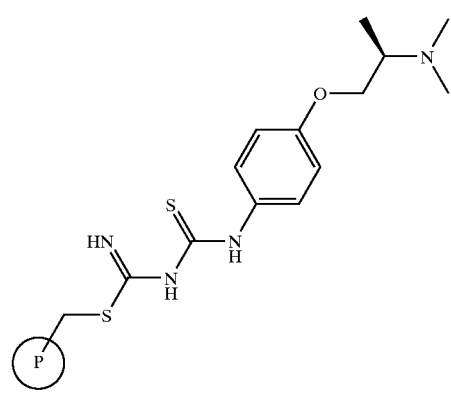

This compound was prepared from resin-bound thiourea of Example 28 and 2-bromo-1-(3-fluoro-phenyl)-ethanone (Maybridge Chemical) by the procedure used in Example 36. MS (ES) MH⁺=415.

Example 41

(R)-[4-Amino-2-[4-(2-pyrrolidin-1-yl-propoxy)-phenylamino]-thiazol-5-yl]-(3-fluoro-phenyl)-methanone This compound was prepared from resin-bound thiourea of Example 29 and 2-bromo-1-(3-fluorophenyl)-ethanone (Maybridge Chemical) by the procedure used in Example 36. MS (ES) MH⁺=441.

Example 42

[4-Amino-2-[4-(1-ethyl-pyrrolidin-3-yloxy)-phenylamino]-thiazol-5-yl]-(3-fluoro-phenyl)-methanone -continued

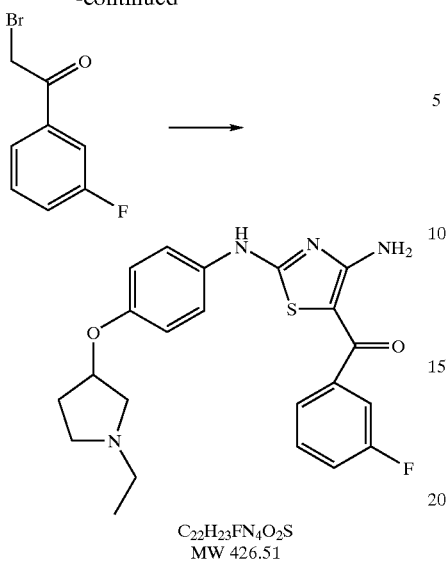

C₂₂H₂₃FN₄O₂S
MW 426.51

This compound was prepared from resin-bound thiourea of Example 30 and 2-bromo-1-(3-fluoro-phenyl)-ethanone (Maybridge Chemical) by the procedure used in Example 36. MS (ES) MH⁺=427.

Example 43

[4-Amino-2-[4-(1-ethyl-piperidin-3-yloxy)-phenylamino]-thiazol-5-yl]-(3-fluoro-phenyl)-methanone

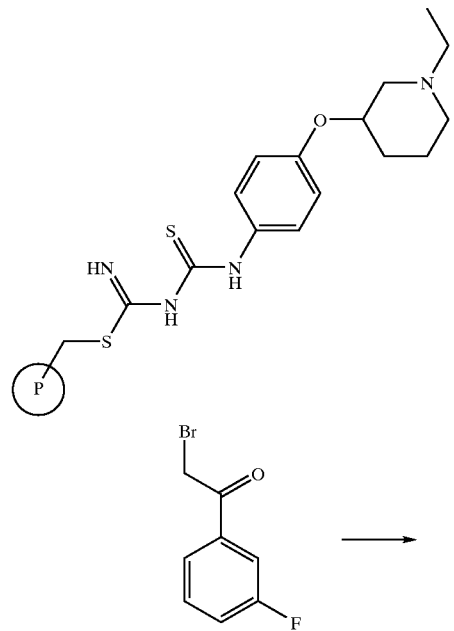

-continued

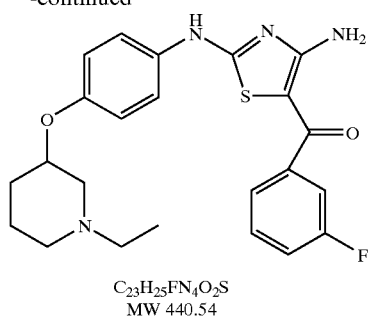

C₂₃H₂₅FN₄O₂S
MW 440.54

The named compound was prepared from resin-bound thiourea of Example 31 and 2-bromo-1-(3-fluoro-phenyl)-ethanone (Maybridge Chemical) by the procedure used in Example 36. MS (ES) MH⁺=440.

Example 44

(S)-[4-Amino-2-[4-(1-methyl-pyrrolidin-2-ylmethoxy)-phenylamino]-thiazol-5-yl]-(3-fluoro-phenyl)-methanone

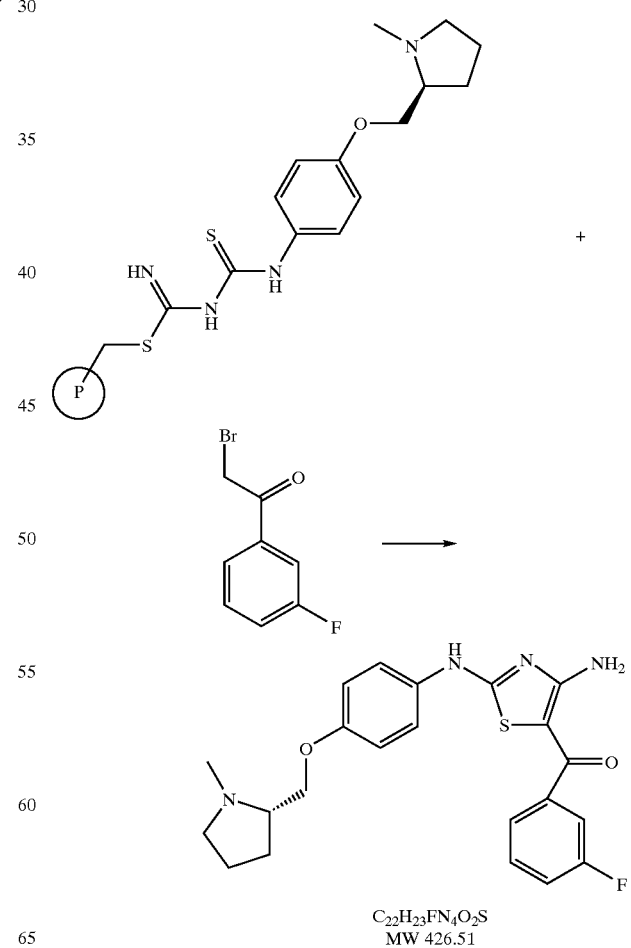

C₂₂H₂₃FN₄O₂S
MW 426.51

The named compound was prepared from resin-bound thiourea of Example 32 and 2-bromo-(3-fluorophenyl)ethanone (Maybridge Chemical) by the procedure used in Example 36. MS (ES) MH$^+$=427.

Example 45

[4-Amino-2-[4-(pyrrolidin-3-yloxy)-phenylamino]-thiazol-5-yl]-(3-fluoro-phenyl)-methanone

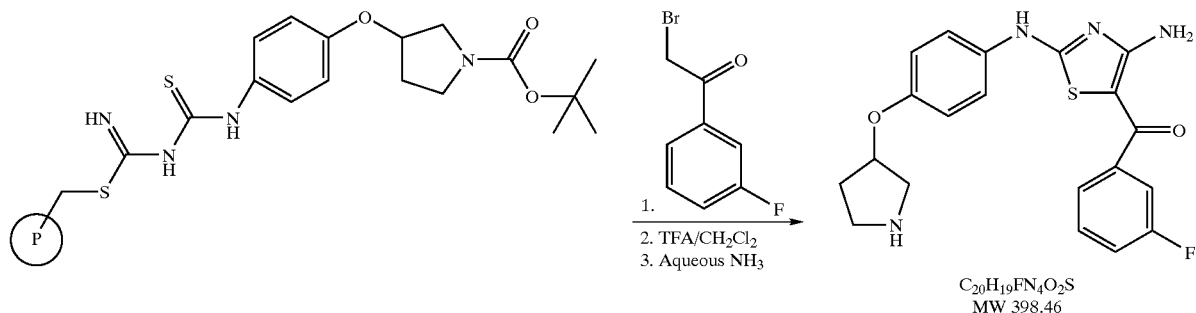

The crude tert-butyl ester (prepared from resin-bound thiourea of Example 95, 120 mg, loading 1.6 mmol/g, 0.19 mmol) and 2-bromo-1-(3-fluoro-phenyl)-ethanone (62.5 mg, 0.29 mmol) by the procedure used in Example 36) was dissolved in trifluoroacetic acid/dichloro-methane (30%, 3 mL) and shaken for 1 hour. The solvent was removed under reduced pressure to give the trifluoroacetic acid salt, 52 mg, which was purified on a reversed phase column eluting with concentrated aqueous ammonia and acetonitrile. Lyophilization gave a yellow powder. 27 mg, 35%. MS (ES) MH$^+$= 399.

Example 46

[4-Amino-2-[4-(piperidin-3-yloxy)-phenylarino]-thiazol-5-yl]-(3-fluoro-phenyl)-methanone

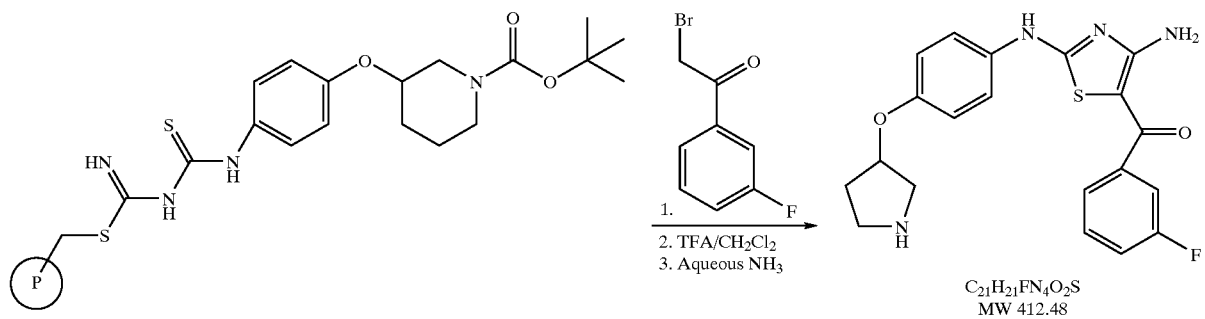

The named compound was prepared from resin-bound thiourea of Example 34 and 2-bromo-1-(3-fluoro-phenyl)-ethanone (Maybridge Chemical) by the procedure used in Example 45. MS (ES) MH$^+$=413.

Example 47

[4-Amino-2-[4-(2-morpholin-4-yl-ethoxy)-phenylamino]-thiazol-5-yl]-(3-fluoro-phenyl)-methanone

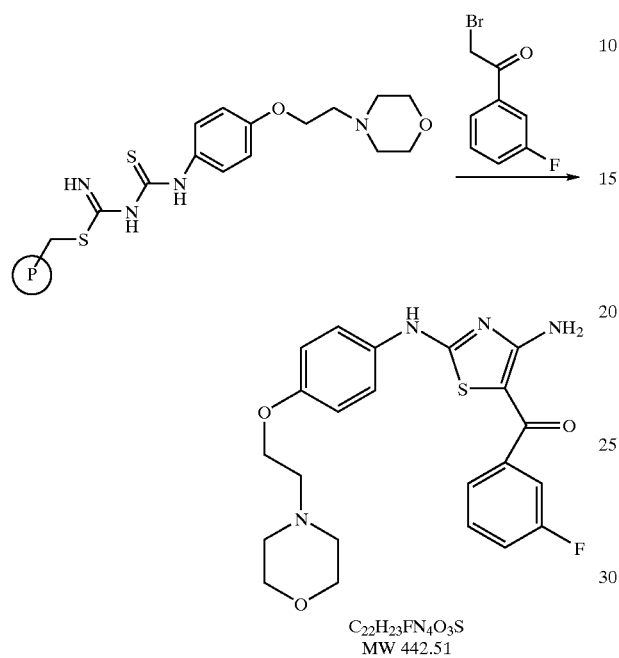

$C_{22}H_{23}FN_4O_3S$
MW 442.51

This compound was prepared from resin-bound thiourea of Example 35 and 2-bromo-1-(3-fluoro-phenyl)-ethanone (Maybridge Chemical) by the procedure used in Example 36. MS (ES) MH⁺=443.

Example 48

[4-Amino-2-[4-(2-pyrrolidin-1-yl-ethoxy)-phenylamino]-thiazol-5-yl]-(4-methoxy-3-nitro-phenyl)-methanone $C_{23}H_{25}N_5O_5S$
MW 483.54

This compound was prepared from resin-bound thiourea of Example 24 and 2-bromo-1-(4-methoxy-3-nitro-phenyl)-ethanone by the procedure used in Example 36. MS (ES) MH⁺=484. The 2-bromo-1-(4-methoxy-3-nitro-phenyl)-ethanone was prepared by treating 4-methoxy-3-nitro-acetophenone (Lancaster) with bromine as in Example 20C.

Example 49

[4-Amino-2-[4-(2-dimethylamino-ethoxy)-phenylamino]-thiazol-5-yl]-(4-methoxy-3-nitro-phenyl)-methanone

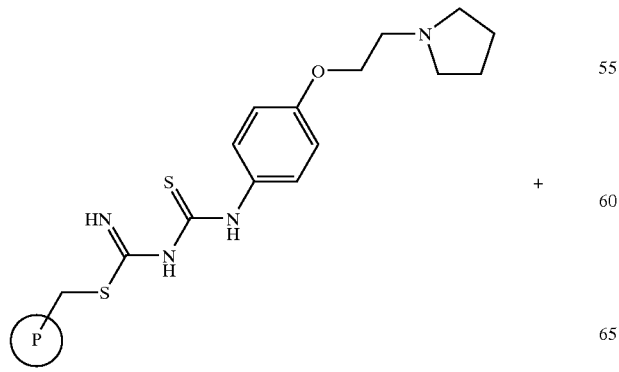

-continued

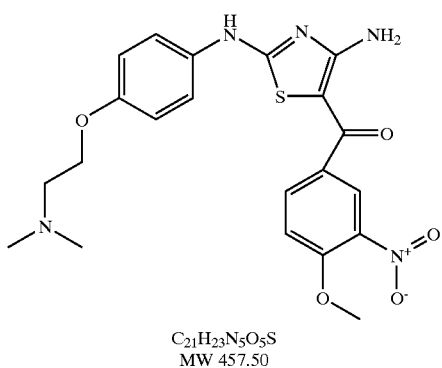

C₂₁H₂₃N₅O₅S
MW 457.50

This compound was prepared from resin-bound thiourea of Example 25 and 2-bromo-1-(4-methoxy-3-nitro-phenyl)-ethanone by the procedure used in Example 36. MS (ES) MH⁺=458. The 2-bromo-1-(4-methoxy-3-nitro-phenyl)-ethanone was prepared as described in Example 48.

Example 50
[4-Amino-2-[4-(2-dimethylamino-ethoxy)-phenylamino]-thiazol-5-yl]-m-tolyl-methanone

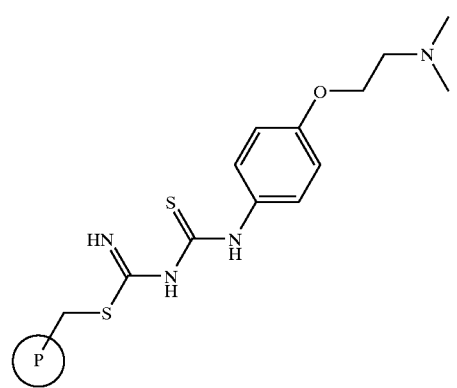

+

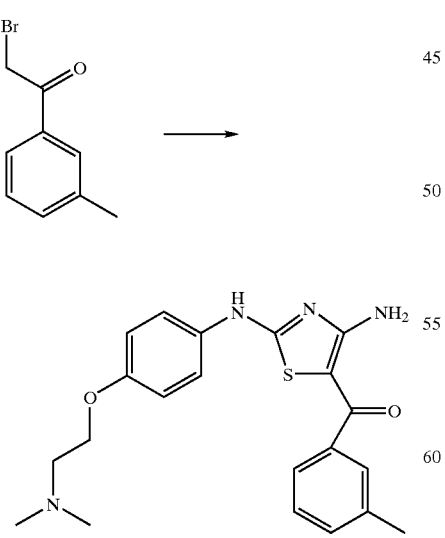

C₂₁H₂₄N₄O₂S
MW 396.51

This compound was prepared from resin-bound thiourea of Example 25 and 2-bromo-1-(3-methyl-phenyl)-ethanone by the procedure used in Example 36. MS (ES) MH⁺=397. The 2-bromo-1-(3-methyl-phenyl)-ethanone is prepared by treating 3'-methylacetophenone (Aldrich) with bromine as in Example 20C.

Example 51

[4-Amino-2-[4-(2-pyrrolidin-1-yl-ethoxy)-phenylamino]-thiazol-5-yl]-m-tolyl-methanone

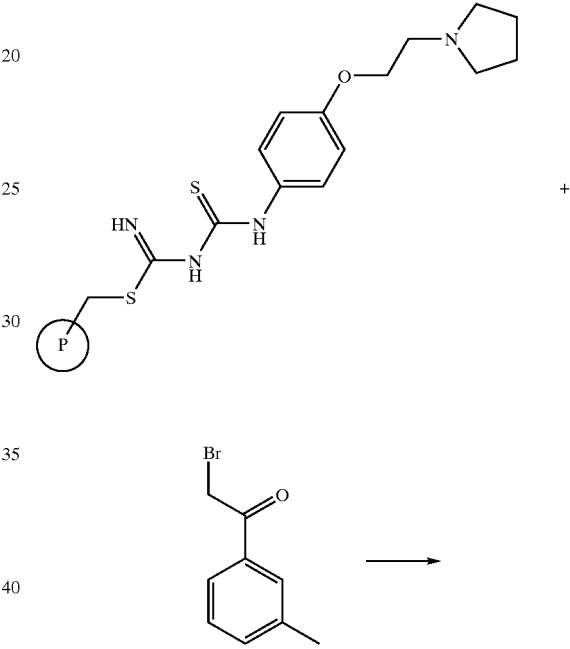

+

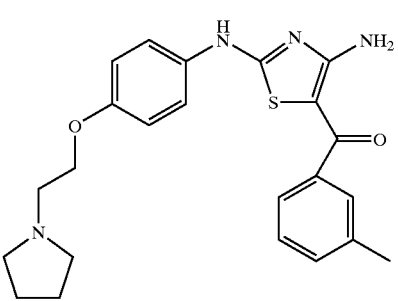

C₂₃H₂₆N₄O₂S
MW 422.55

This compound was prepared from resin-bound thiourea of Example 24 and 2-bromo-1-(3-methyl-phenyl)-ethanone by the procedure used in Example 36. MS (ES) MH⁺=423. The 2-bromo-1-(3-methyl-phenyl)-ethanone was prepared as described in Example 50.

Example 52

[4-Amino-2-[4-(2-dimethylamino-ethoxy)-phenylamino]-thiazol-5-yl]-(3-ethyl-phenyl)-methanone

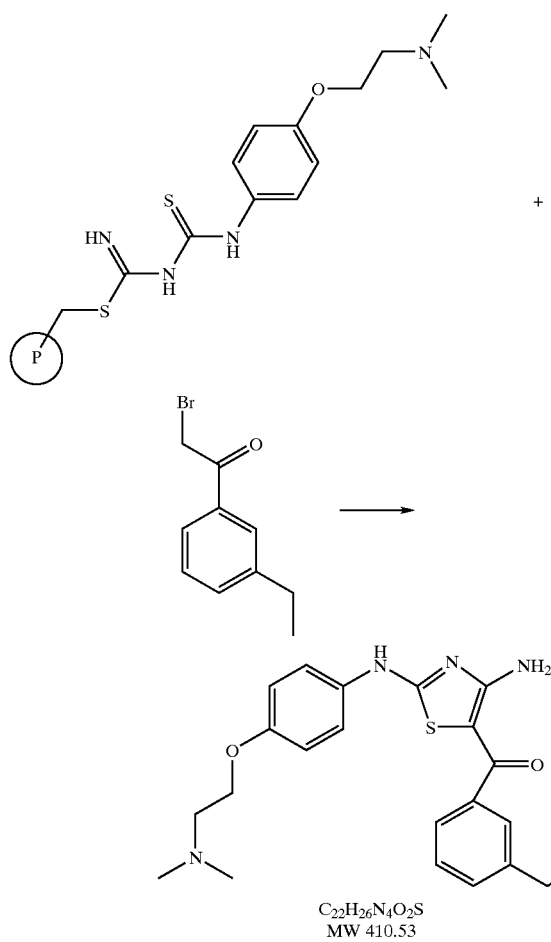

A. 2-Bromo-1-(3-ethylphenyl)ethanone

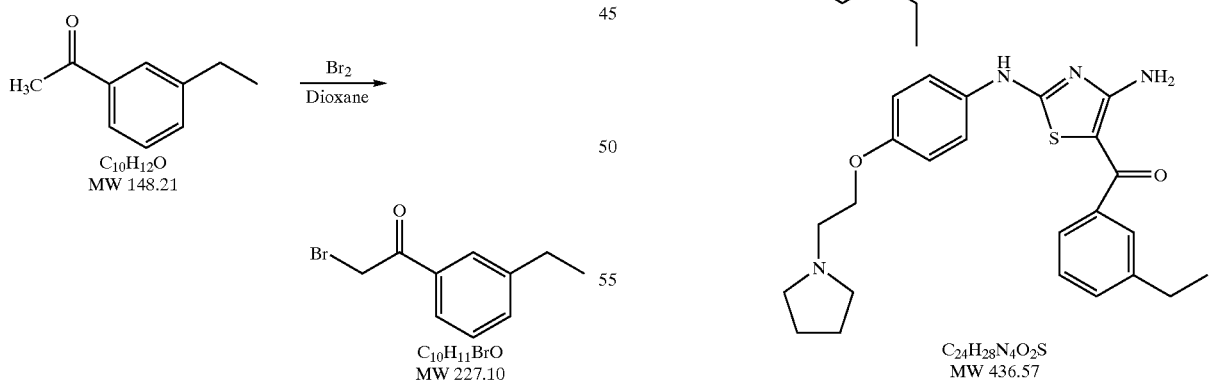

To a stirred solution of 3-ethylacetophenone (Maybridge Chemical; 1.103 g, 7.44 mmol) in dry 1,4-dioxane (15 mL) was added bromine (383 μL, 7.44 mmol). The solution was stirred at room temperature for 30 min. and then the solvent was removed on a rotary evaporator. The residue was chromatographed on a Foxy 200 machine (Isco, Inc., P.O. Box 82531, Lincoln, Nebr. 68501, USA.; eluent, 5%CH$_2$Cl$_2$/Hexane, 0–2 min. then 20–30% CH$_2$Cl$_2$/Hexane, 2–20 min.) to give 2-bromo-1-(3-ethylphenyl)ethanone (1.15 g, 68%) as a clear oil.

B.

The title compound was then prepared from resin-bound thiourea of Example 25 and the 2-bromo-1-(3-ethyl-phenyl)-ethanone of step A by the procedure used in Example 36. MS (ES) MH$^+$=411.

Example 53

[4-Amino-2-[4-(2-pyrrolidin-1-yl-ethoxy)-phenylamino]-thiazol-5-yl]-(3-ethyl-phenyl)-methanone

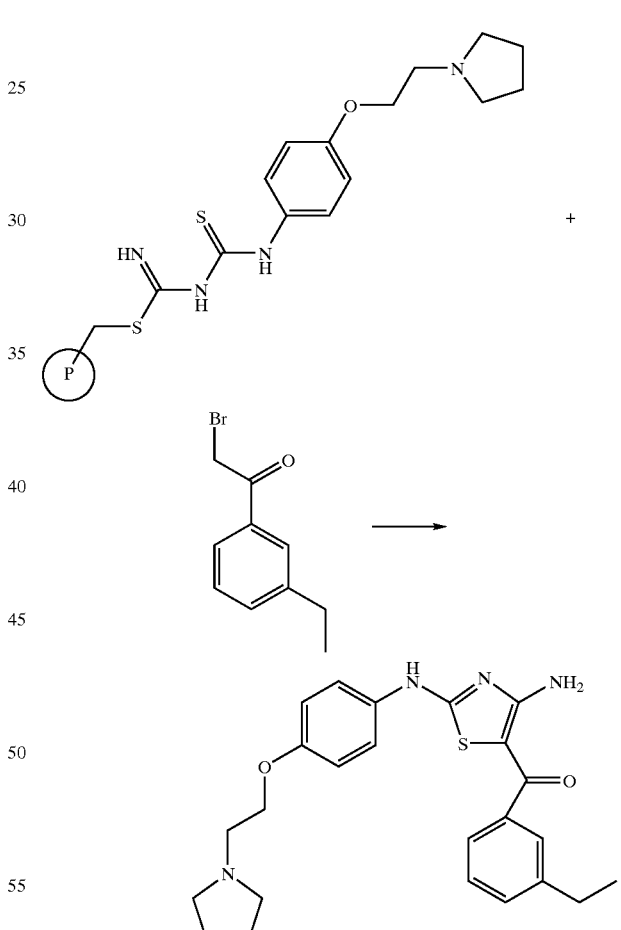

This compound was prepared from resin-bound thiourea of Example 24 and 2-bromo-1-(3-ethyl-phenyl)-ethanone (from Example 52 step A) by the procedure used in Example 36. MS (ES) MH$^+$=437.

Example 54

[4-Amino-2-[4-(2-dimethylamino-ethoxy)-phenylamino]-thiazol-5-yl]-(3-nitro-phenyl)-methanone

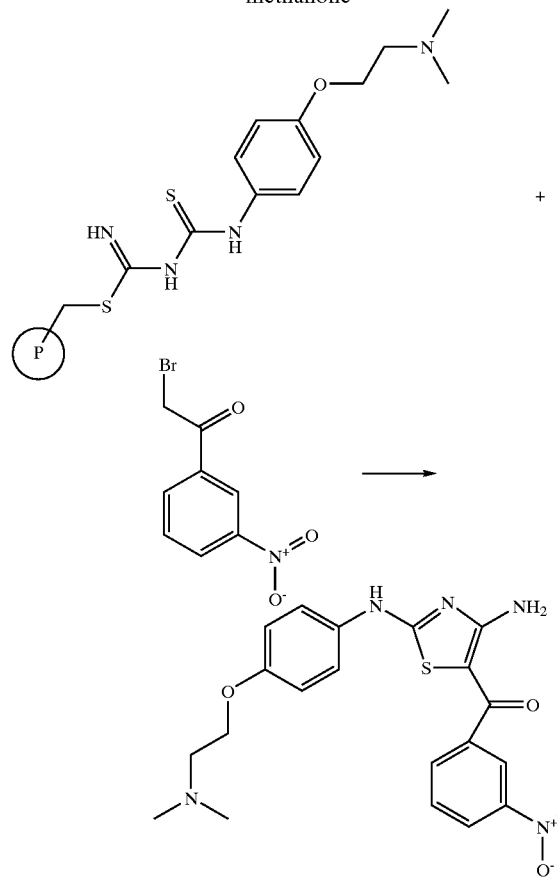

This compound was prepared from resin-bound thiourea of Example 25 and 2-bromo-1-(3-nitro-phenyl)-ethanone (Aldrich) by the procedure used in Example 36. MS (ES) MH+=428.

Example 55

[4-Amino-2-[4-(2-morpholin-4-yl-ethoxy)-phenylamino]-thiazol-5-yl]-(2,3-dihydro-benzo[1,4]dioxin-6-yl)-methanone

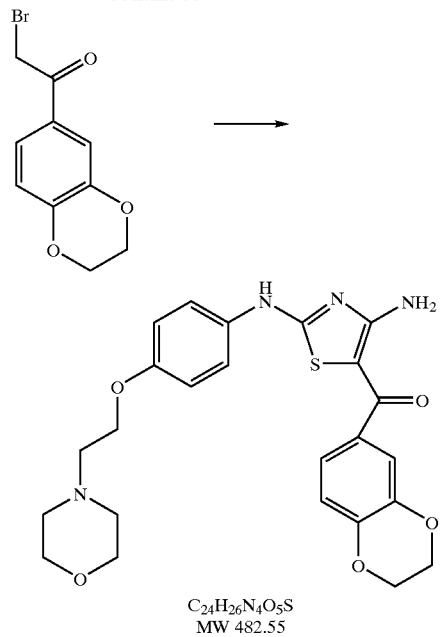

This compound was prepared from resin-bound thiourea of Example 35 and 2-bromo-1-(2,3-dihydro-benzo[1,4]dioxin-6-yl)-ethanone (Maybridge Chemical) by the procedure used in Example 36. MS (ES) MH+=483.

Example 56

[4-Amino-2-[4-(2-morpholin-4-yl-ethoxy)-phenylamino]-thiazol-5-yl]-benzo[1,3]dioxol-5-yl-methanone

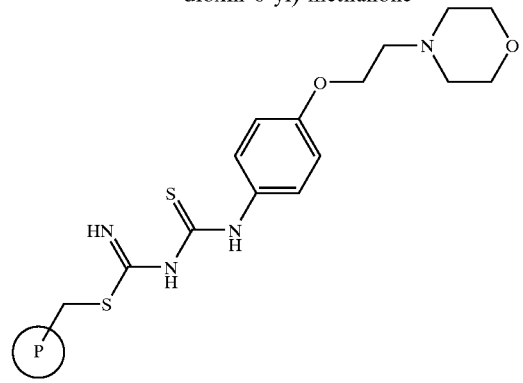

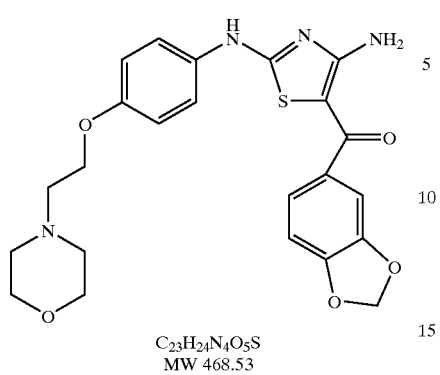

C₂₃H₂₄N₄O₅S
MW 468.53

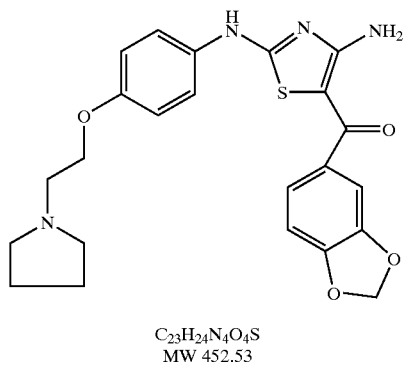

C₂₃H₂₄N₄O₄S
MW 452.53

This compound was prepared from resin-bound thiourea of Example 35 and 1-benzo[1,3]dioxol-5-yl-2-bromo-ethanone (from Example 132) by the procedure used in Example 36. MS (ES) MH⁺=469.

This compound was prepared from resin-bound thiourea of Example 24 and 1-benzo[1,3]dioxol-5-yl-2-bromo-ethanone (from Example 132) by the procedure used in Example 36. MS (ES) MH⁺=453.

Example 57

[4-Amino-2-[4-(2-pyrrolidin-1-yl-ethoxy)-phenylamino]-thiazol-5-yl]-benzo[1,3]dioxol-5-yl-methanone Example 58

[4-Amino-2-[4-(2-dimethylamino-ethoxy)-phenylamino]-thiazol-5-yl]-(2,3-dihydro-benzo[1,4]dioxin-6-yl)-methanone

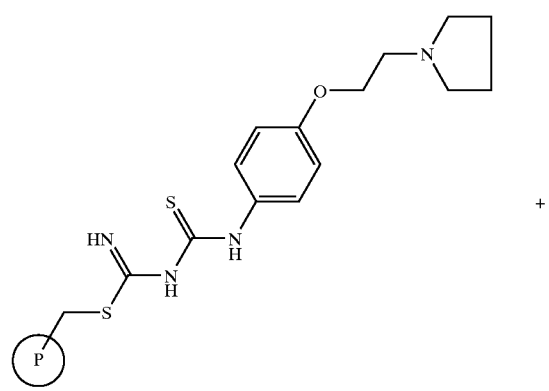

+

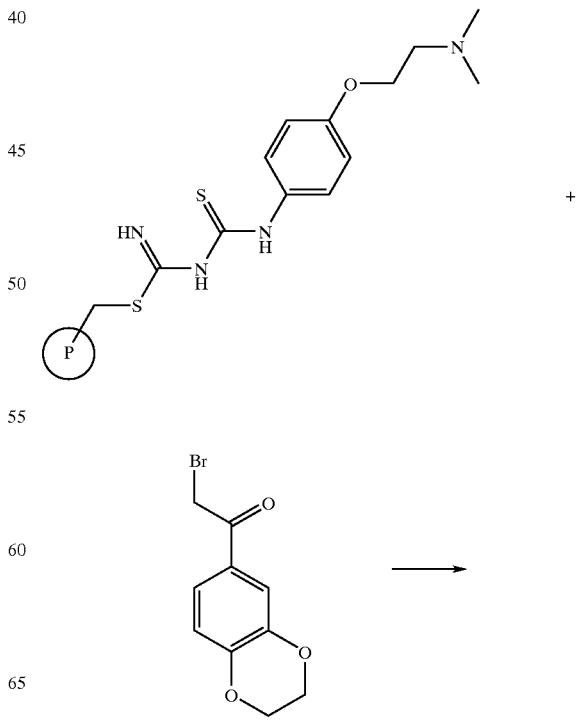

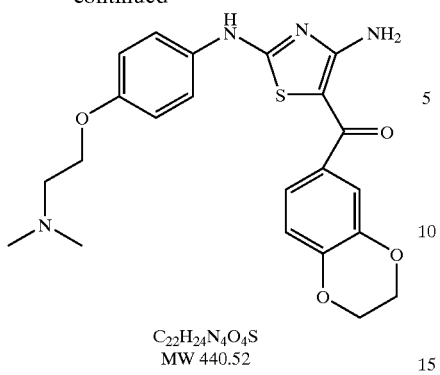

C₂₂H₂₄N₄O₄S
MW 440.52

This compound was prepared from resin-bound thiourea of Example 25 and 2-bromo-1-(2,3-dihydro-benzo[1,4]dioxin-6-yl)-ethanone (Maybridge Chemical) by the procedure used in Example 36. MS (ES) MH$^+$=441.

Example 59

[4-Amino-2-[4-(2-dimethylamino-ethoxy)-phenylamino]-thiazol-5-yl]-benzo[1,3]dioxol-5-yl-methanone This compound was prepared from resin-bound thiourea of Example 25 and 1-benzo[1,3]dioxol-5-yl-2-bromo-ethanone (from Example 132) by the procedure used in Example 36. MS (ES) MH$^+$=427.

Example 60

3-[4-Amino-2-[4-(2-dimethylamino-ethoxy)-phenylamino]-thiazole-5-carbonyl]-benzonitrile

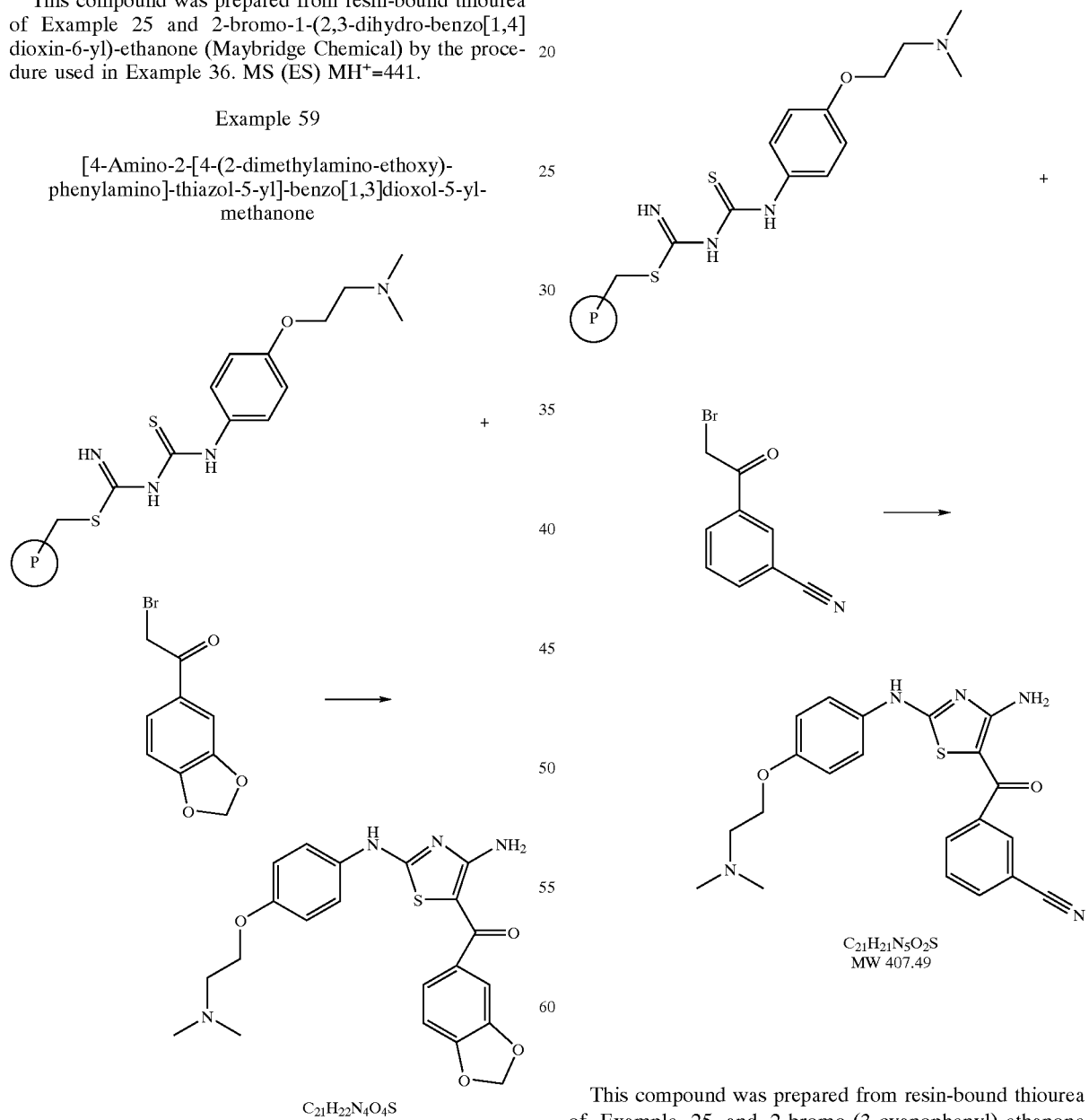

C₂₁H₂₂N₄O₄S
MW 426.49

C₂₁H₂₁N₅O₂S
MW 407.49

This compound was prepared from resin-bound thiourea of Example 25 and 2-bromo-(3-cyanophenyl)-ethanone (Maybridge Chemical) by the procedure used in Example 36. MS (ES). MH$^+$=408.

Example 61

[4-Amino-2-[4-(2-dimethylamino-2-methyl-propoxy)-phenylamino]-thiazol-5-yl]-(3-ethyl-phenyl)-methanone

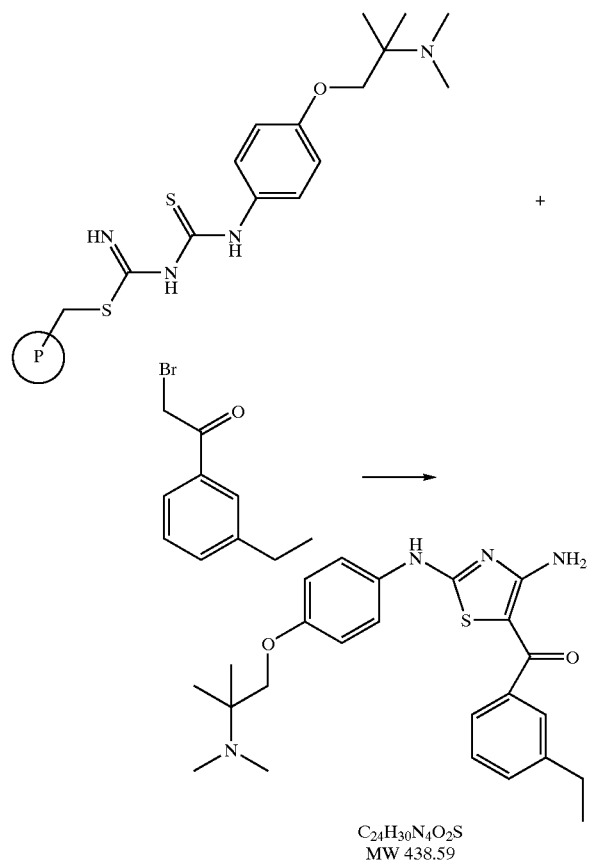

$C_{24}H_{30}N_4O_2S$
MW 438.59

This compound was prepared from resin-bound thiourea of Example 27 and 2-bromo-(3-ethylphenyl)-ethanone (from Example 52 Step A) by the procedure used in Example 36. MS (ES) MH$^+$=439.

Example 62

[4-Amino-2-[4-(2-pyrrolidin-1-yl-ethoxy)-phenylamino]-thiazol-5-yl]-(3-ethoxy-phenyl)-methanone

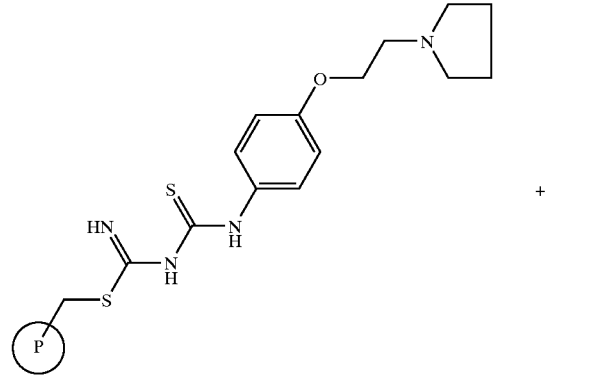

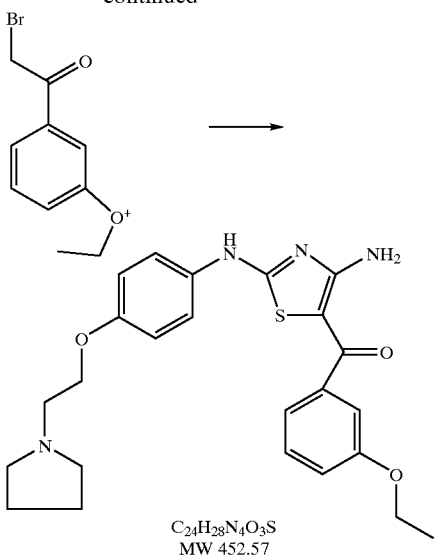

$C_{24}H_{28}N_4O_3S$
MW 452.57

This compound was prepared from resin-bound thiourea of Example 24 and 2-bromo-(3-ethoxyphehyl)-ethanone by the procedure used in Example 36. MS (ES) MH$^+$=453. The 2-bromo-(3-ethoxyphenyl)-ethanone was prepared by treating 1-(3-ethoxy-phenyl)-ethanone (prepared in accordance with the procedure in J. Chem. Soc. Perkin Trans. 2:1996, 755–760) with bromine as in Example 20C.

Example 63

(R)-[4-Amino-2-[4-(2-dimethylamino-propoxy)-phenylamino]-thiazol-5-yl]-(3-ethyl-phenyl)-methanone

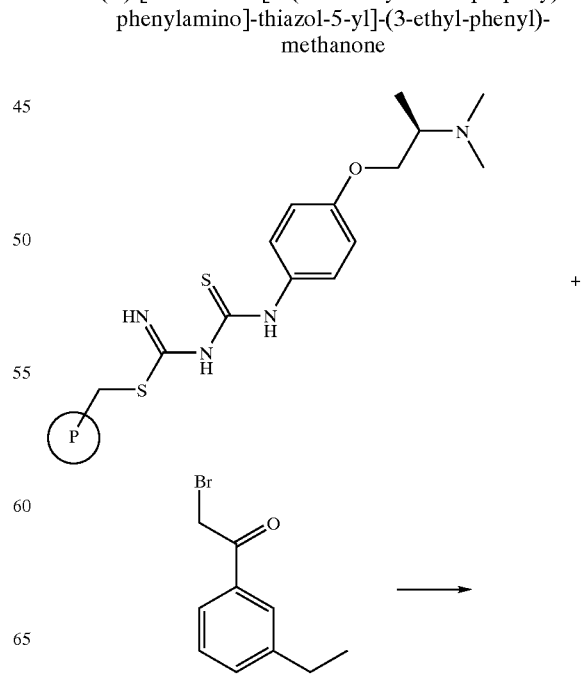

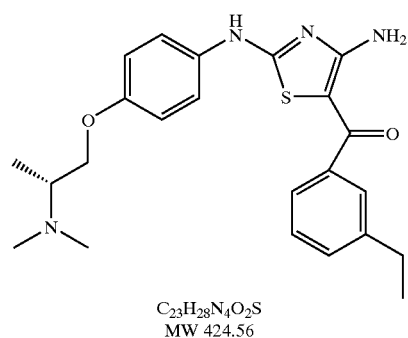

This compound was prepared from resin-bound thiourea of Example 28 and 2-bromo-(3-ethylphenyl)-ethanone (from Example 52A) by the procedure used in Example 36. MS (ES) MH+=425.

Example 64

[3-(4-Isothiocyanatophenoxy)propyl]carbamic Acid tert-Butyl Ester

A. [3-(4-Nitrophenoxy)propyl]carbamic Acid tert-Butyl Ester

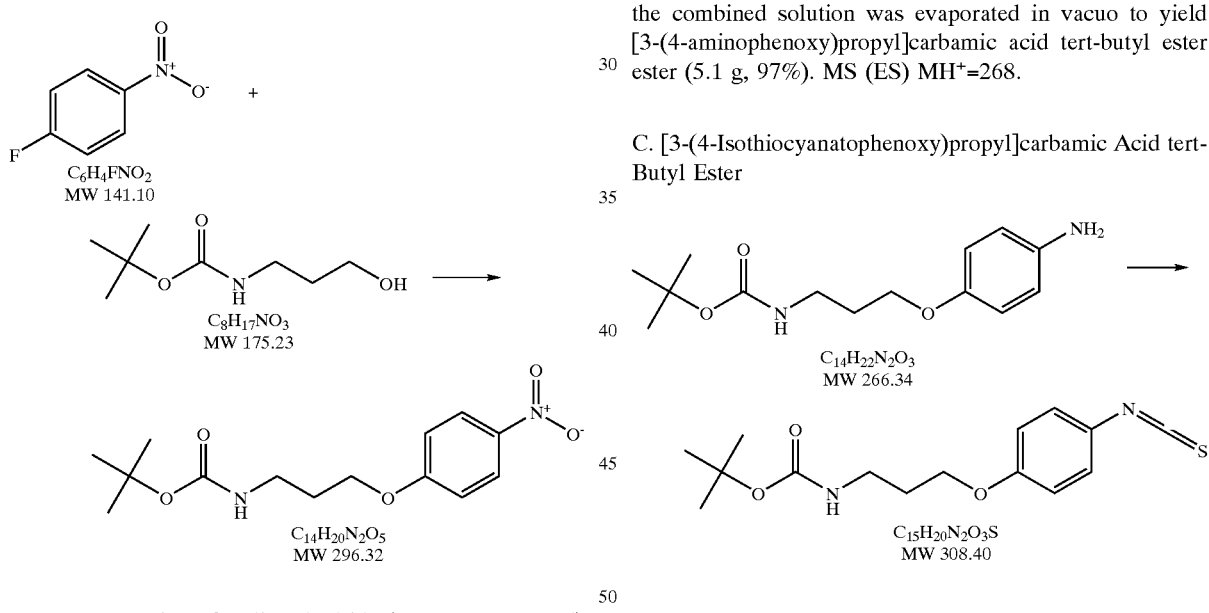

To a suspension of sodium hydride (2.48 g, 98.1 mmol) (Aldrich, 95%) in tetrahydrofuran (150 mL) was added a solution of 3-(Boc-amino)-1-propanol (8.1 g, 46.8 mmol) (Aldrich) in tetrahydrofuran (25 mL) at −10° C. After stirred for 15 minutes, the reaction was allowed to warm to room temperature and stirred for a further 30 minute. To this mixture was added a solution of 1-fluoro-4-nitro-benzene (6.92 g, 49.07 mmol) (Aldrich) and the reaction was stirred at room temperature for 2 hours. The resulting mixture was poured in cool aqueous ammonium chloride solution (100 mL). The aqueous layer was extracted with ethyl acetate (3×40 mL) and the combined organic extracts were washed with brine (3×30 mL), dried (Na$_2$SO$_4$) and evaporated in vacuo. The residue was purified on silica gel with 85:15 hexane/ethyl acetate to provide [3-(4-nitrophenoxy)propyl]carbamic acid tert-butyl ester (10.6 g, 73% yield) as light yellow solid. MS (ES) MH+=297.

B. [3-(4-Aminophenoxy)propyl]carbamic Acid tert-Butyl Ester

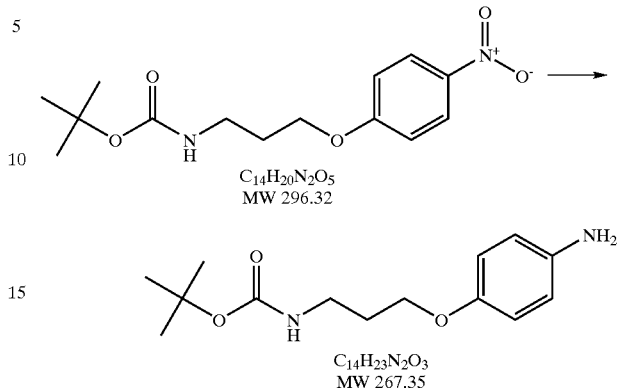

A solution of [3-(4-nitro-phenoxy)propyl]carbamic acid tert-butyl ester (5.8 g, from Step A above) in ethanol (150 mL) was treated with 10% Pd/C (250 mg) and stirred for 2 hours under 40 psi of hydrogen. The mixture was filtered through a celite pad. The pad was washed with ethanol and the combined solution was evaporated in vacuo to yield [3-(4-aminophenoxy)propyl]carbamic acid tert-butyl ester ester (5.1 g, 97%). MS (ES) MH+=268.

C. [3-(4-Isothiocyanatophenoxy)propyl]carbamic Acid tert-Butyl Ester

To a cooled (−15° C.) solution of 1,1-thiocarbonyidiimidazole (756 mg, 4.115 mmol) (Aldrich) in N,N-dimethylformamide (11 mL) was added dropwise a solution of [3-(4-aminophenoxy)propyl]carbamic acid tert-butyl ester (1.02 g, 3.84 mmol) (from Step B above) in N,N-dimethylformamide (11 mL) over 25 minute. After the addition was complete, the mixture was stirred at −15° C. for 20 minute and then at room temperature for 1 h. Ice-water was added and the mixture was extracted with ether. The ether layer was dried (MgSO$_4$), filtered, and evaporated. The residue was purified on silica gel with 85:15 hexane/ethyl acetate to give [3-(4-isothiocyanatophenoxy)propyl]-carbamic acid tert-butyl ester (1.07 g, 91% yield). HRMS, observed: 308.1197; Calcd for M+:308.1195.

Example 65

[4-Amino-2-[4-(2-dimethylamino-ethoxy)-phenylamino]-thiazol-5-yl]-(3-bromo-phenyl)-methanone

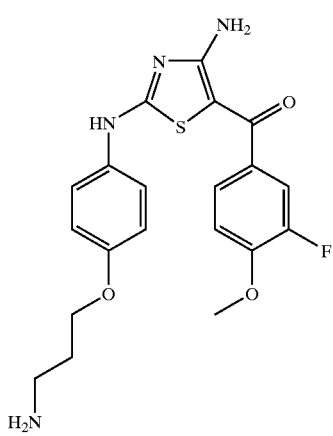

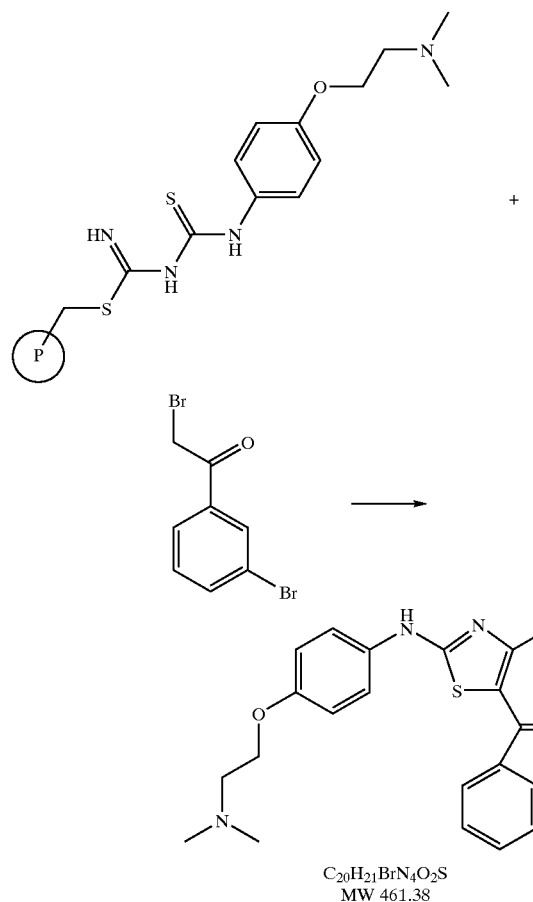

This compound was prepared from resin-bound thiourea of Example 25 and 2-bromo-1-(3-bromo-phenyl)-ethanone (Lancaster) by the procedure used in Example 36. MS (ES) MH$^+$=461.

Example 66

Ethyl-[3-(4-isothiocyanato-phenoxy)propyl] carbamic Acid tert-Butyl Ester

A. Ethyl-[3-(4-nitrophenoxy)propyl]carbamic Acid tert-Butyl Ester

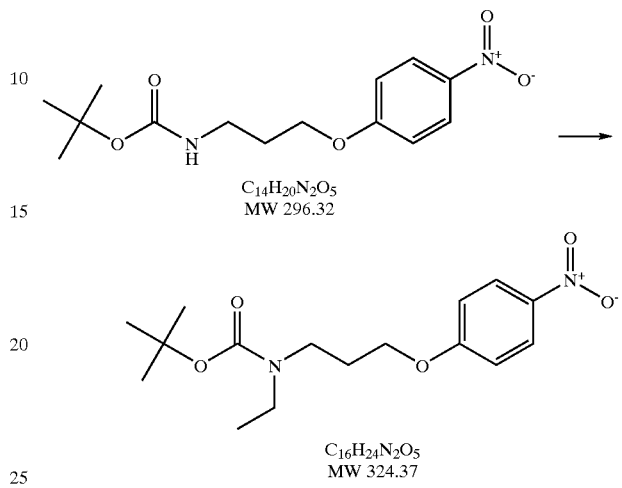

To a suspension of sodium hydride (477 mg, 18.88 mmol) (Aldrich, 95%) in tetrahydrofuran (25 mL) was added a solution of [3-(4-nitrophenoxy)propyl]-carbamic acid tert-butyl ester (3.0 g, 10.13 mmol) (from Example 64, Step A) in tetrahydrofuran (15 mL) at 0° C. Upon addition, the mixture was allowed to stir at room temperature for 30 minute, treated with iodoethane (3.76 g, 24.25 mmol) (Aldrich), and heated at 55° C. for one hour before it was quenched with aqueous ammonium chloride (20 mL). The resulting mixture was extracted with ethyl acetate (3×100 mL) and the combined organic extracts were washed with brine and dried (Na$_2$SO$_4$) and evaporated in vacuo. The residue was purified on silica gel with 75:25 hexane/ethyl acetate to give ethyl-[3-(4-nitrophenoxy) propyl]carbamic acid tert-butyl ester (3.15 g, 96%). MS (ES) MH$^+$=325.

B. [3-(4-Aminophenoxy)propyl]-ethyl-carbamic Acid tert-Butyl Ester

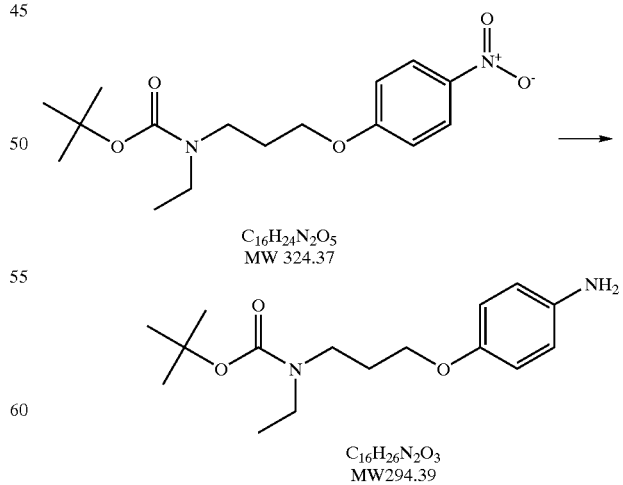

A solution of ethyl-[3-(4-nitrophenoxy)propyl]carbamic acid tert-butyl ester (2.9 g) (from step A above) in ethanol (70 mL) was treated with 10% Pd/C (442 mg) and stirred for 2 hours under 40 psi of hydrogen. The mixture was filtered through a celite pad. The pad was washed with ethanol and the combined solution was evaporated in vacuo to yield [3-(4-aminophenoxy)propyl]-ethyl-carbamic acid tert-butyl ester (2.63 g, 88%). HRMS, Observed: 317.1839; Calcd for M+Na: 317.1835

C. Ethyl-[3-(4-isothiocyanatophenoxy)propyl]carbamic Acid tert-Butyl Ester

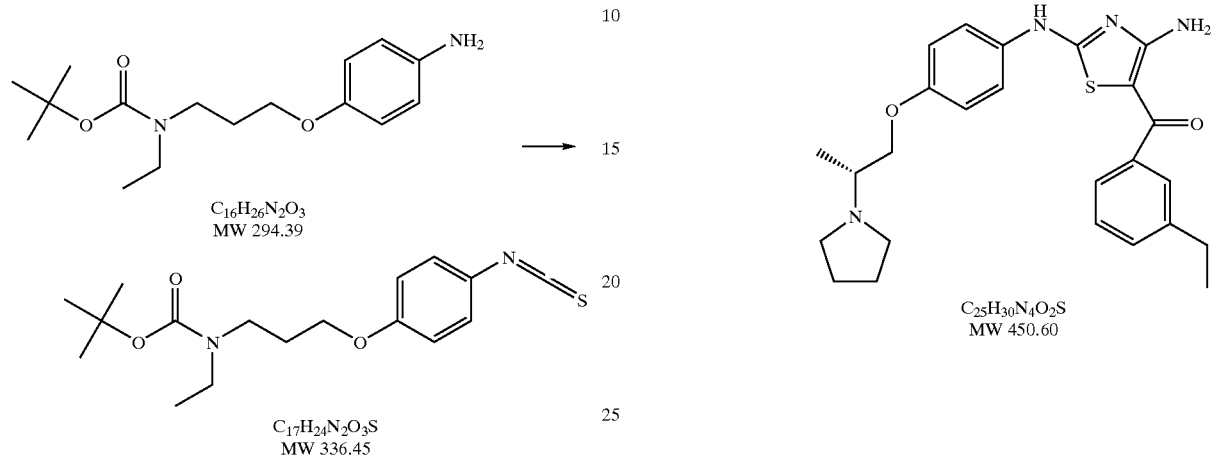

To a cooled (−20° C.) solution of 1,1-thiocarbonyldiimidazole (811 mg, 4.415 mmol) (Aldrich) in N,N-dimethylformamide (11 mL) was added dropwise a solution of [3-(4-aminophenoxy)propyl]-ethyl-carbamic acid tert-butyl ester (1.175 g, 3.99 mmol) (from Step B above) in N,N-dimethyl-formamide (11 mL) over 25 minute. After the addition was complete, the mixture was stirred at −20° C. for 20 minutes and then at room temperature for 1 hour. Ice-water was added and the mixture was extracted with ether. The ether layer was dried ($Na_2SO_4$), filtered, and evaporated. The residue was purified on silica gel with 85:15 hexane/ethyl acetate to give ethyl-[3-(4-isothiocyanatophenoxy)propyl]carbamic acid tert-butyl ester (1.24 g, 92% yield). HRMS, Observed: 336.1496; Calcd for $M^+$:336.1508.

Example 67

(R)-[4-Amino-2-[4-(2-pyrrolidin-1-yl-propoxy)-phenylamino]-thiazol-5-yl]-(3-ethyl-phenyl)-methanone

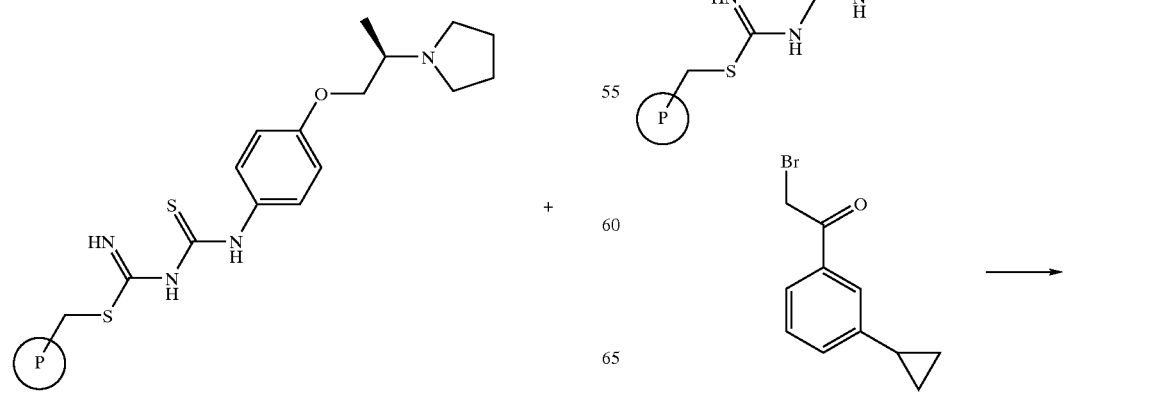

This compound was prepared from resin-bound thiourea of Example 29 and 2-bromo-1-(3-ethyl-phenyl)-ethanone (from Example 52A) by the procedure used in Example 36. MS (ES) $MH^+$=451.

Example 68

(R)-[4-Amino-2-[4-(2-pyrrolidin-1-yl-propoxy)-phenylamino]-thiazol-5-yl]-(3-cyclopropyl-phenyl)-methanone -continued

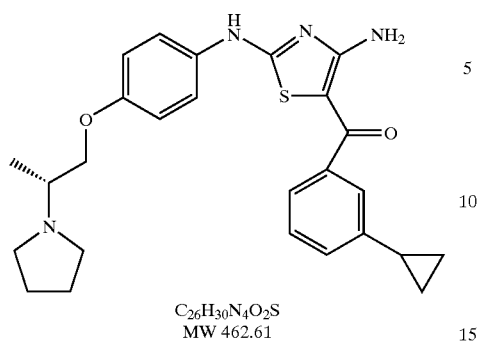

C₂₆H₃₀N₄O₂S
MW 462.61

This compound was prepared from resin-bound thiourea of Example 29 and 2-bromo-1-(3-cyclopropyl-phenyl)-ethanone (from Example 20C) by the procedure used in Example 36. MS (ES) MH$^+$=463.

Example 69

[4-Amino-2-[4-(2-dimethylamino-ethoxy)-phenylamino]-thiazol-5-yl]-(3-cyclopropyl-phenyl)-methanone

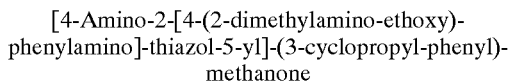

C₂₃H₂₆N₄O₂S
MW 422.55

This compound was prepared from resin-bound thiourea of Example 25 and 2-bromo-1-(3-cyclopropyl-phenyl)-ethanone (from Example 20C) by the procedure used in Example 36. MS (ES) MH$^+$=423.

Example 70

(R)-[4-Amino-2-[4-(2-dimethylamino-propoxy)-phenylamino]-thiazol-5-yl]-(3-cyclopropyl-phenyl)-methanone

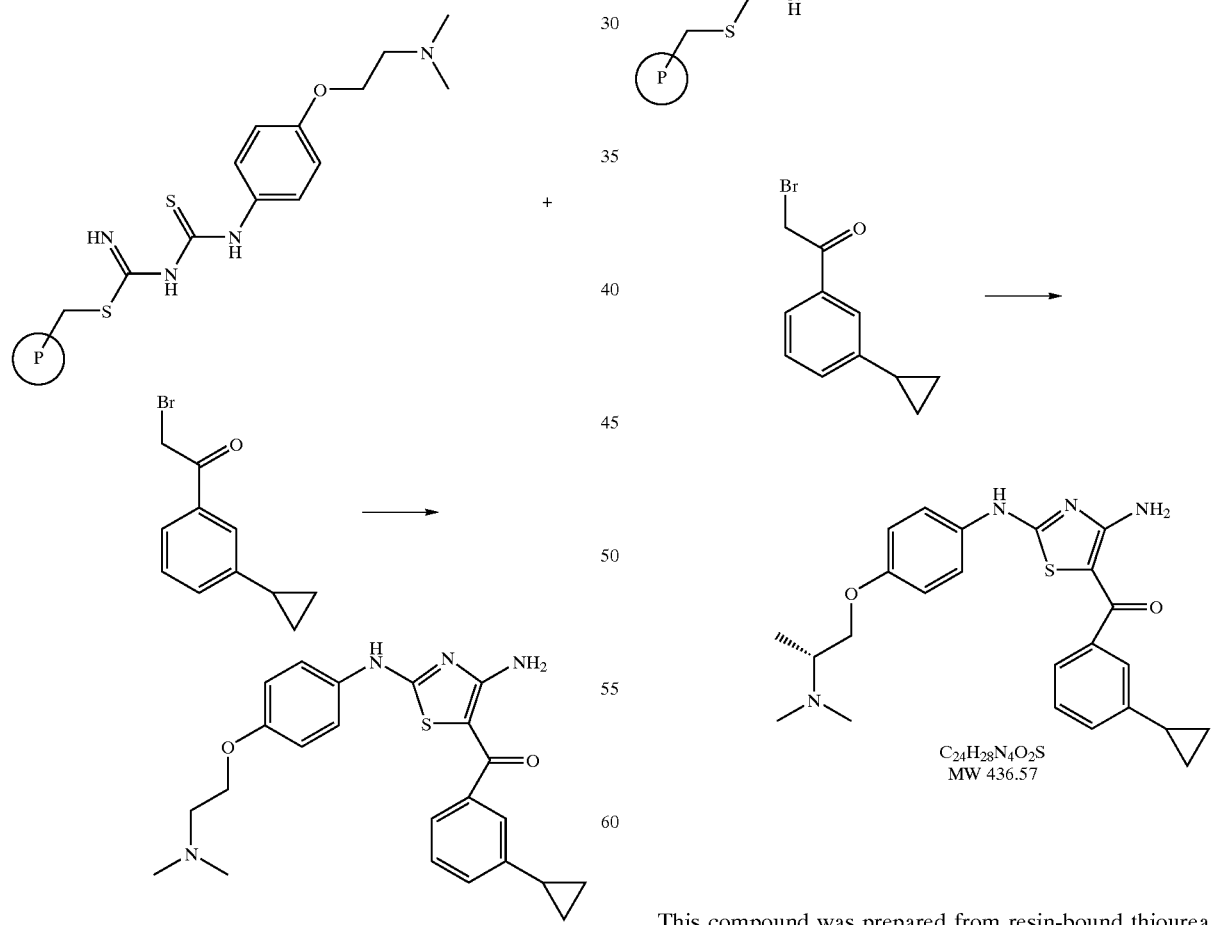

C₂₄H₂₈N₄O₂S
MW 436.57

This compound was prepared from resin-bound thiourea of Example 28 and 2-bromo-1-(3-cyclopropyl-phenyl)-ethanone (from Example 20C) by the procedure used in Example 36. MS (ES) MH$^+$=437.

Example 71

[4-Amino-2-[4-(2-dimethylamino-2-methyl-propoxy)-phenylamino]-thiazol-5-yl]-(3-cyclopropyl-phenyl)-methanone

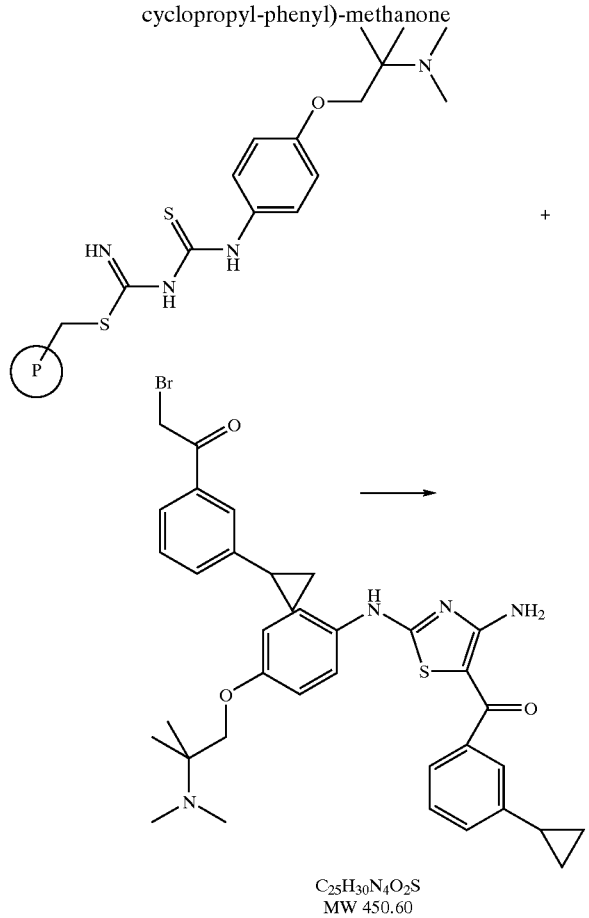

C$_{25}$H$_{30}$N$_4$O$_2$S
MW 450.60

This compound was prepared from resin-bound thiourea of Example 27 and 2-bromo-1-(3-cyclopropyl-phenyl)-ethanone (from Example 20C) by the procedure used in Example 36. MS (ES) MH$^+$=451.

Example 72

[4-Amino-2-[4-(2-pyrrolidin-1-yl-ethoxy)-phenylamino]-thiazol-5-yl]-(3-cyclopropyl-phenyl)-methanone

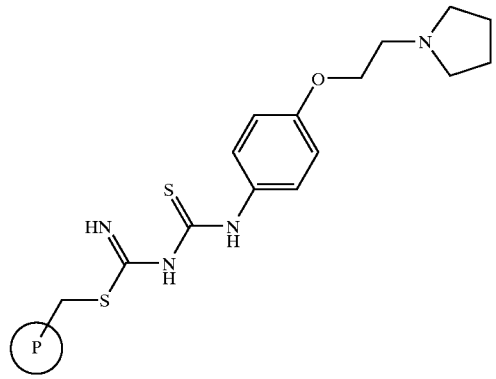

+

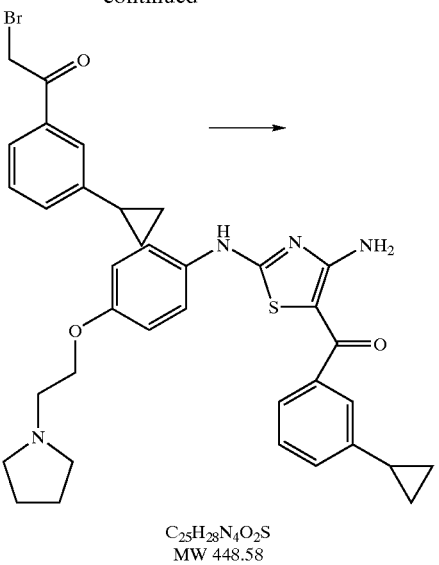

C$_{25}$H$_{28}$N$_4$O$_2$S
MW 448.58

This compound was prepared from resin-bound thiourea of Example 24 and 2-bromo-1-(3-cyclopropyl-phenyl)-ethanone (from Example 20C) by the procedure used in Example 36. MS (ES) MH$^+$=449.

Example 73

[4-Amino-2-[4-(2-dimethylamino-ethoxy)-phenylamino]-thiazol-5-yl]-(3-fluoro-4-methyl-phenyl)-methanone

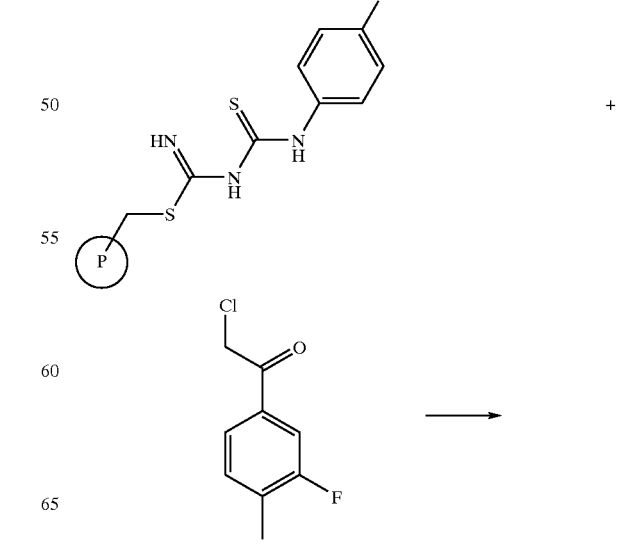

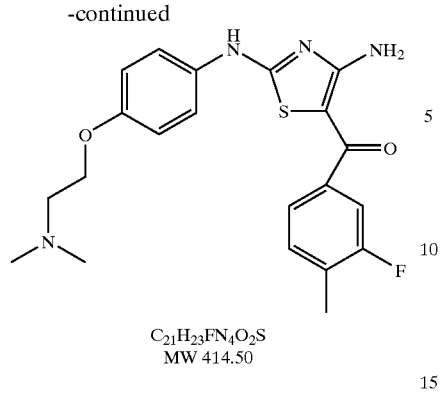

C₂₁H₂₃FN₄O₂S
MW 414.50

This compound was prepared from resin-bound thiourea of Example 25 and 2-chloro-1-(3-fluoro-4-methyl-phenyl)-ethanone (from Example 21) by the procedure used in Example 36. MS (ES) MH⁺=415.

Example 74

(R)-[4-Amino-2-[4-(2-dimethylamino-propoxy)-phenylamino]-thiazol-5-yl]-(3-fluoro-4-methyl-phenyl)-methanone This compound was prepared from resin-bound thiourea of Example 28 and 2-chloro-1-(3-fluoro-4-methyl-phenyl)-ethanone (from Example 21) by the procedure used in Example 36. MS (ES) MH⁺=429.

Example 75

[4-Amino-2-[4-(2-dimethylamino-2-methyl-propoxy)-phenylamino]-thiazol-5-yl]-(3-fluoro-4-methyl-phenyl)-methanone

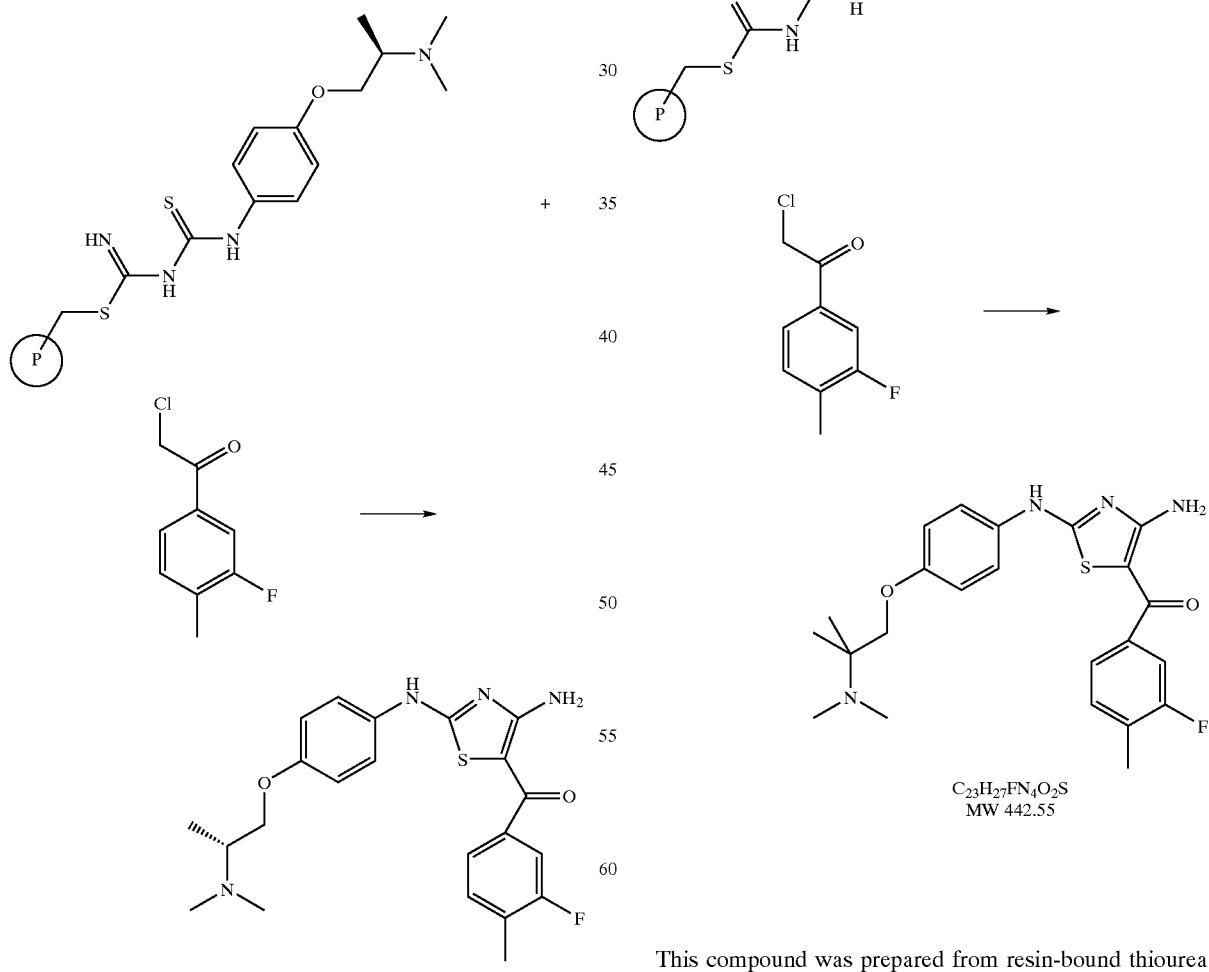

C₂₂H₂₅FN₄O₂S
MW 428.52

C₂₃H₂₇FN₄O₂S
MW 442.55

This compound was prepared from resin-bound thiourea of Example 27 and 2-chloro-1-(3-fluoro-4-methyl-phenyl)-ethanone (from Example 21) by the procedure used in Example 36. MS (ES) MH⁺=443.

Example 76

[4-Amino-2-[4-(2-pyrrolidin-1-yl-ethoxy)-phenylamino]-thiazol-5-yl]-(3-ethyl-4-fluoro-phenyl)-methanone

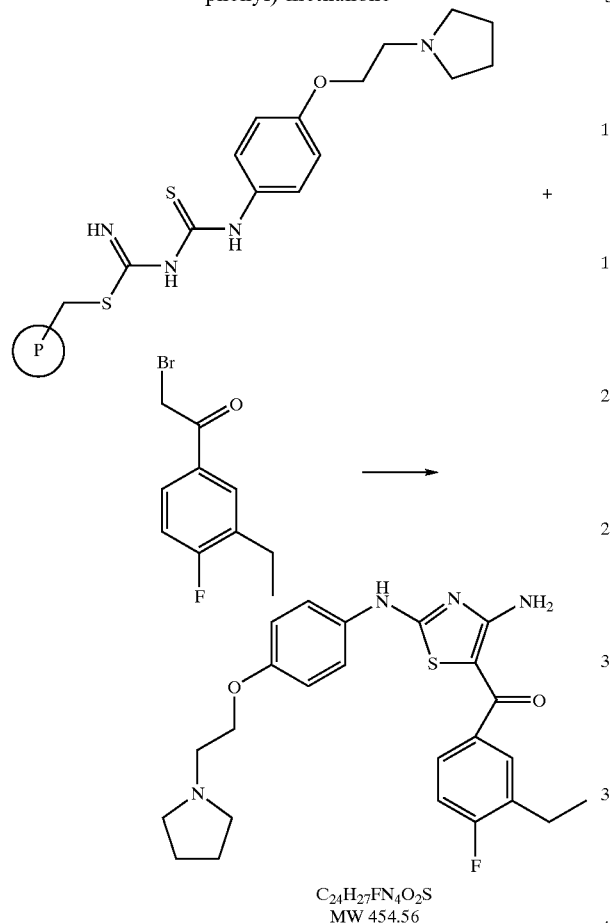

C$_{24}$H$_{27}$FN$_4$O$_2$S
MW 454.56

This compound was prepared from resin-bound thiourea of Example 24 and 2-bromo-1-(3-ethyl-4-fluoro-phenyl)-ethanone (from Example 22) by the procedure used in Example 36. MS (ES) MH$^+$=455.

Example 77

(R)-[4-Amino-2-[4-(2-dimethylamino-propoxy)-phenylamino]-thiazol-5-yl]-(3-ethyl-4-fluoro-phenyl)-methanone

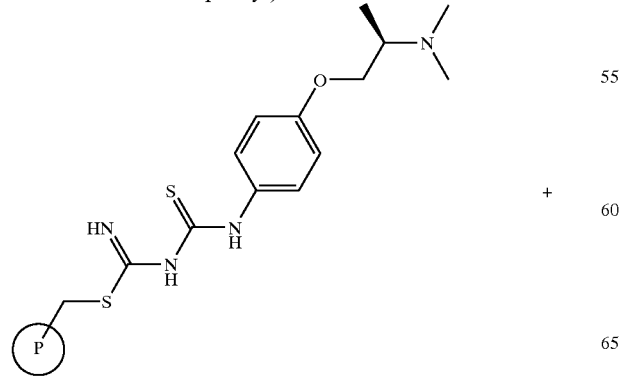

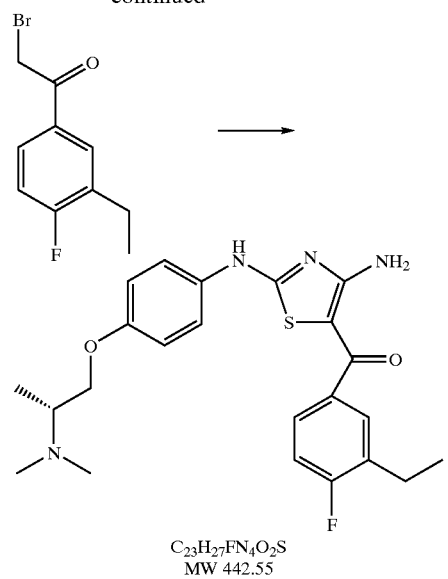

C$_{23}$H$_{27}$FN$_4$O$_2$S
MW 442.55

This compound was prepared from resin-bound thiourea of Example 28 and 2-bromo-1-(3-ethyl-4-fluoro-phenyl)-ethanone (from Example 22) by the procedure used in Example 36. MS (ES) MH$^+$=443.

Example 78

[4-Amino-2-[4-(1-ethyl-piperidin-3-yloxy)-phenylamino]-thiazol-5-yl]-m-tolyl-methanone

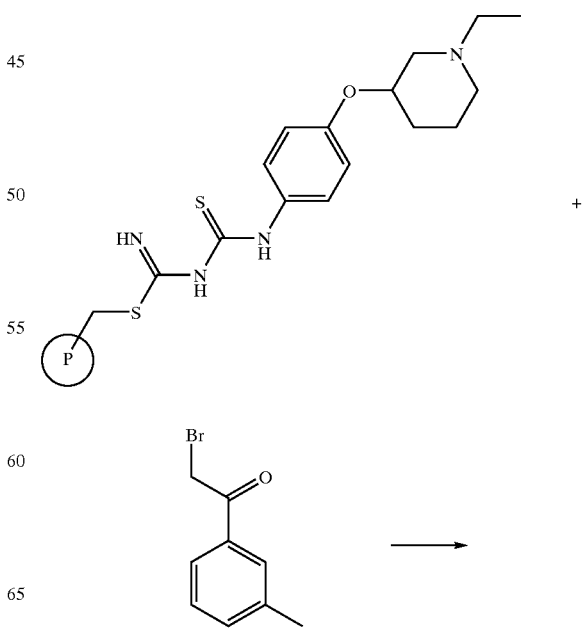

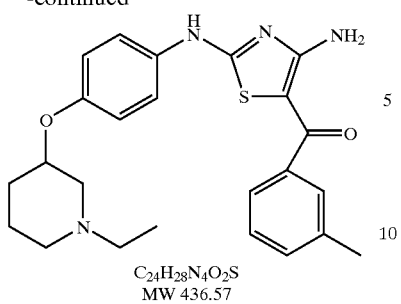

C₂₄H₂₈N₄O₂S
MW 436.57

This compound was prepared from resin-bound thiourea of Example 31 and 2-bromo-1-(3-methyl-phenyl)-ethanone by the procedure used in Example 36. MS (ES) MH⁺=437. The 2-bromo-1-(3-methyl-phenyl)-ethanone was prepared as described in Example 50.

Example 79

[4-Amino-2-[4-(1-ethyl-piperidin-3-yloxy)-phenylamino]-thiazol-5-yl]-(3-ethyl-phenyl)-methanone

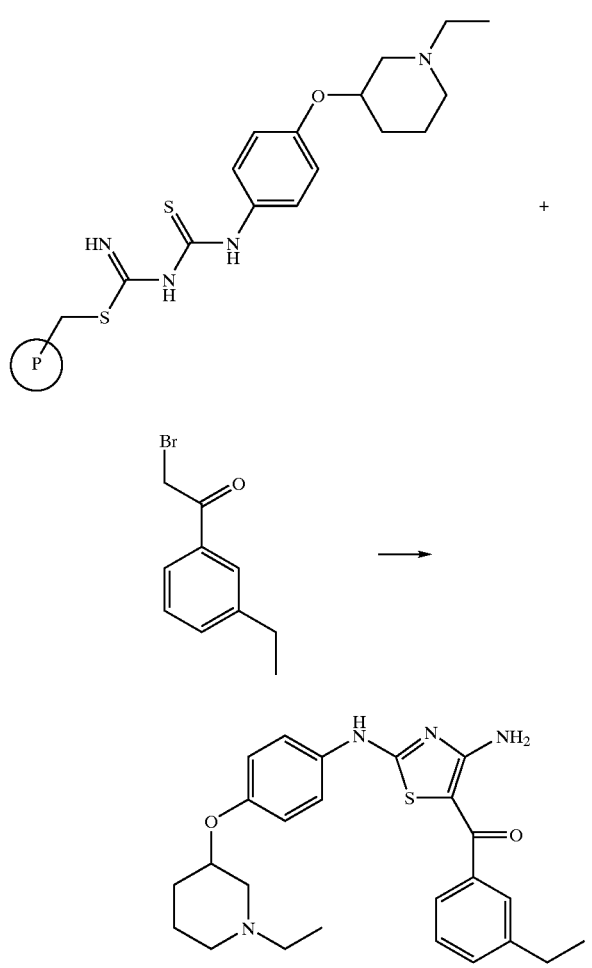

C₂₅H₃₀N₄O₂S
MW 450.60

This compound was prepared from resin-bound thiourea of Example 31 and 2-bromo-1-(3-ethyl-phenyl)-ethanone (from Example 52 step A) by the procedure used in Example 36. MS (ES) MH⁺=451.

Example 80

[4-Amino-2-[4-(1-ethyl-piperidin-3-yloxy)-phenylamino]-thiazol-5-yl]-(3-cyclopropyl-phenyl)-methanone

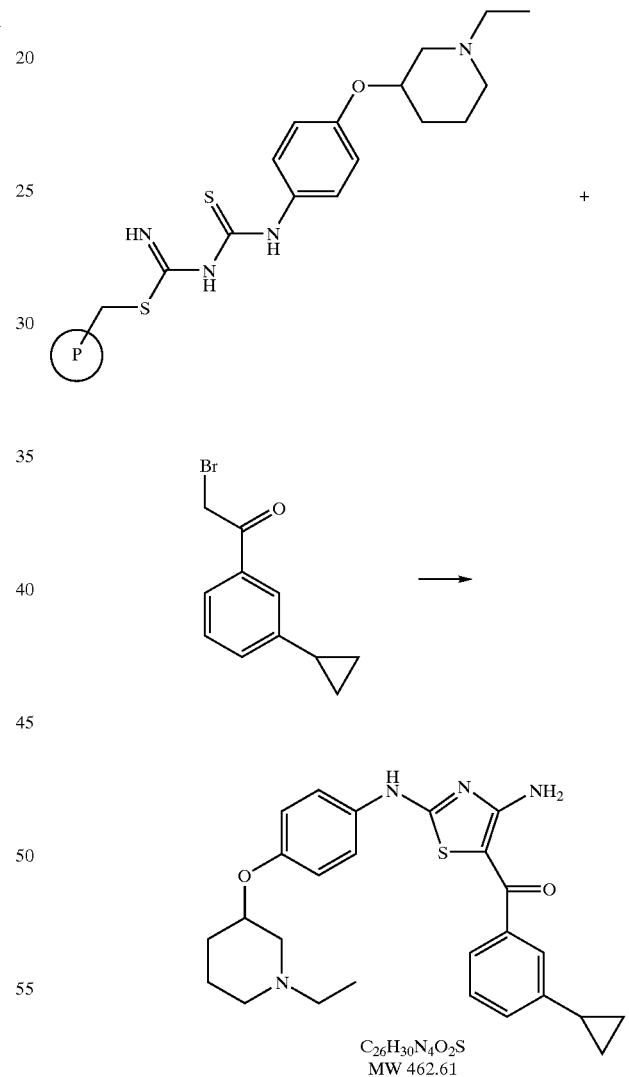

C₂₆H₃₀N₄O₂S
MW 462.61

This compound was prepared from resin-bound thiourea of Example 31 and 2-bromo-1-(3-cyclopropyl-phenyl)-ethanone (from Example 20C) by the procedure used in Example 36. MS (ES) MH⁺=463.

Example 81

[4-Amino-2-[4-(1-ethyl-piperidin-3-yloxy)-phenylamino]-thiazol-5-yl]-(3-ethyl-4-fluoro-phenyl)-methanone

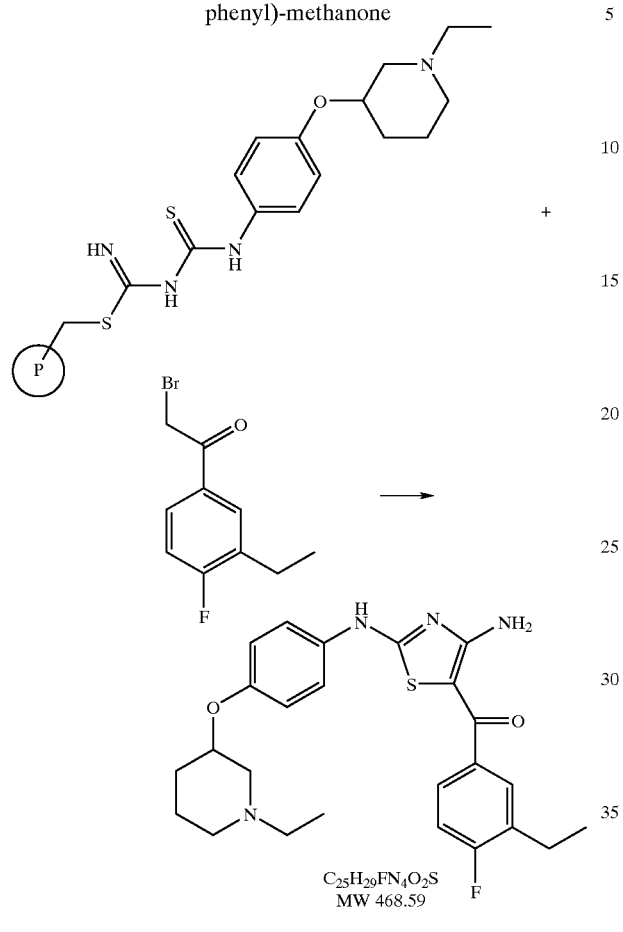

C$_{25}$H$_{29}$FN$_4$O$_2$S
MW 468.59

This compound was prepared from resin-bound thiourea of Example 31 and 2-bromo-1-(3-ethyl-4-fluoro-phenyl)-ethanone (from Example 22) by the procedure used in Example 36. MS (ES) MH$^+$=469.

Example 82

[4-Amino-2-[4-(1-ethyl-piperidin-3-yloxy)-phenylamino]-thiazol-5-yl]-(3-fluoro-4-hydroxy-phenyl)-methanone

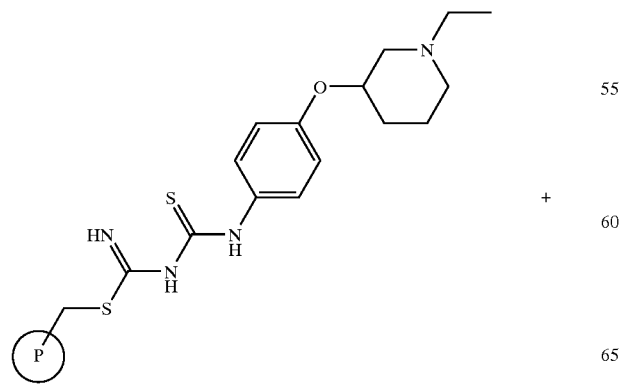

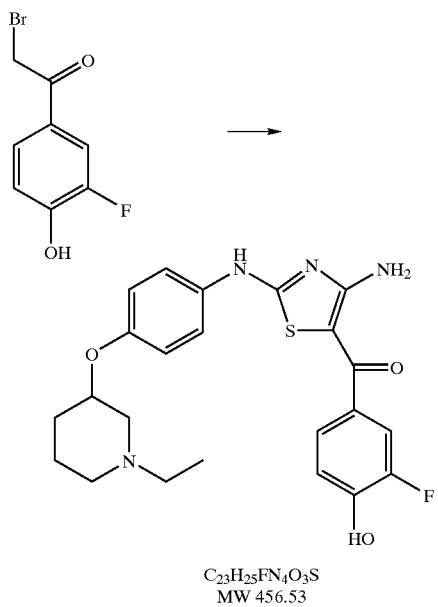

C$_{23}$H$_{25}$FN$_4$O$_3$S
MW 456.53

This compound was prepared from resin-bound thiourea of Example 31 and 2-bromo-1-(3-fluoro-4-hydroxy-phenyl)-ethanone (from Example 119) by the procedure used in Example 36. MS (ES) MH$^+$=457.

Example 83

[4-Amino-2-[4-(1-ethyl-pyrrolidin-3-yloxy)-phenylamino]-thiazol-5-yl]-m-tolyl-methanone

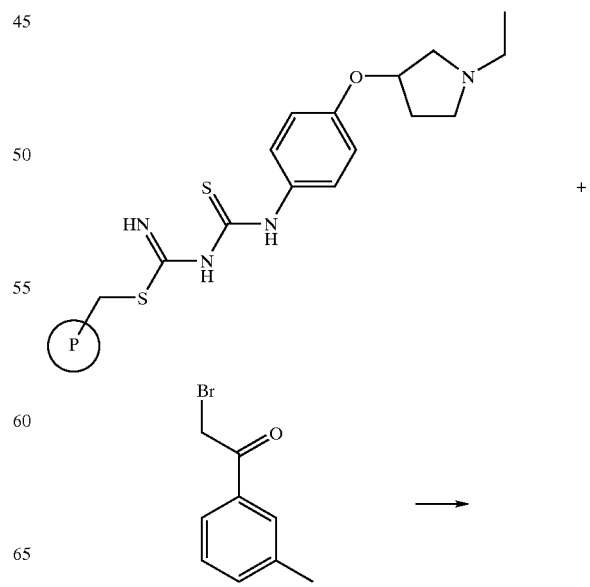

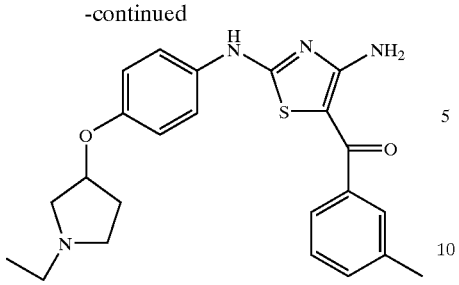

C₂₃H₂₆N₄O₂S
MW 422.55

This compound was prepared from resin-bound thiourea of Example 30 and 2-bromo-1-(3-methyl-phenyl)-ethanone by the procedure used in Example 36. MS (ES) MH$^+$=423. The 2-bromo-1-(3-methyl-phenyl)-ethanone was prepared as described in Example 50.

Example 84

[4-Amino-2-[4-(1-ethyl-pyrrolidin-3-yloxy)-phenylamino]-thiazol-5-yl]-(3-ethyl-phenyl)-methanone

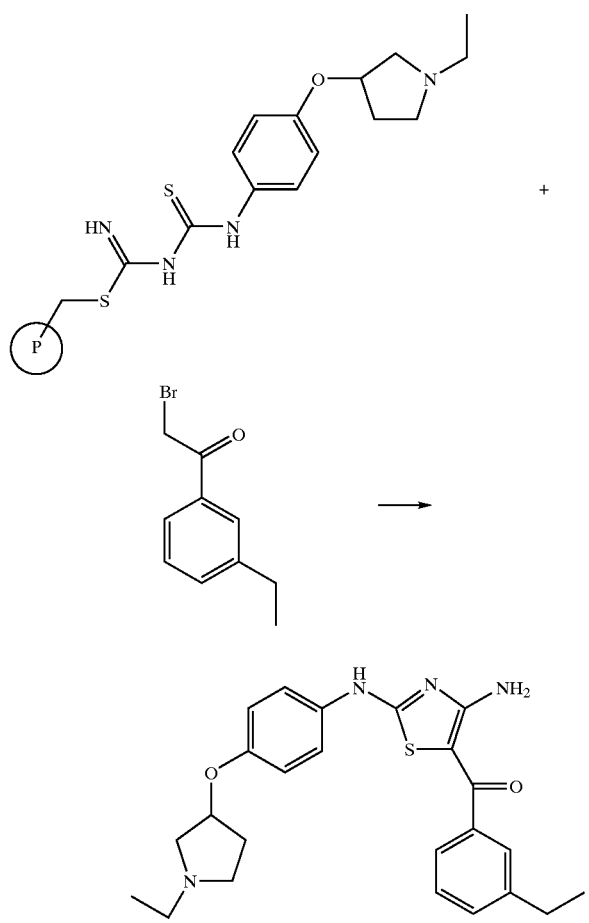

C₂₄H₂₈N₄O₂S
MW 436.57

This compound was prepared from resin-bound thiourea of Example 30 and 2-bromo-1-(3-ethyl-phenyl)-ethanone (from Example 52 step A) by the procedure used in Example 36. MS (ES) MH$^+$=437.

Example 85

[4-Amino-2-[4-(1-ethyl-pyrrolidin-3-yloxy)-phenylamino]-thiazol-5-yl]-(3-cyclopropyl-phenyl)-methanone

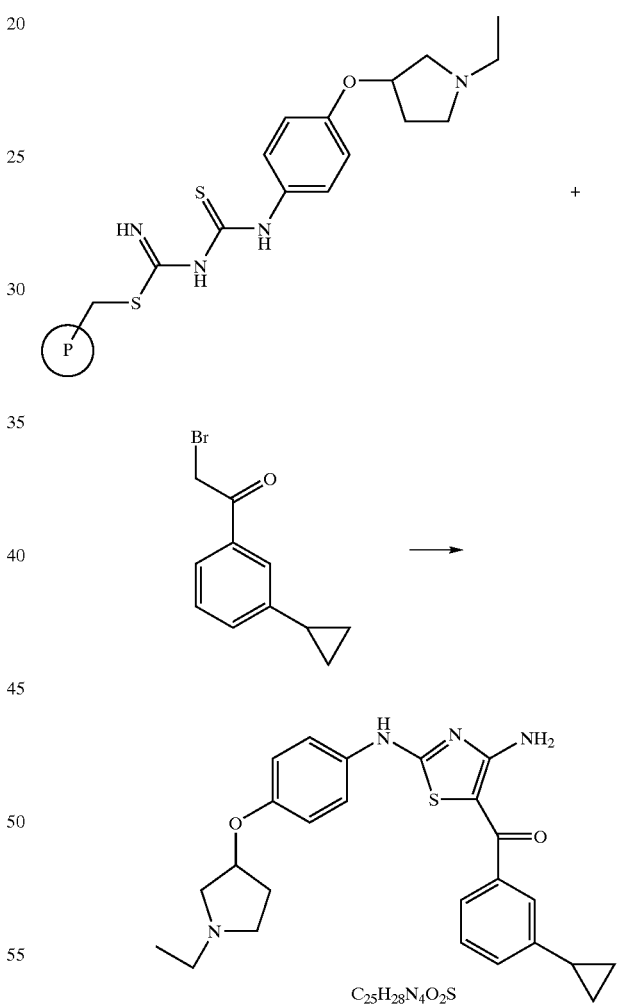

C₂₅H₂₈N₄O₂S
MW 448.58

This compound was prepared from resin-bound thiourea of Example 30 and 2-bromo-1-(3-cyclopropyl-phenyl)-ethanone (from Example 20C) by the procedure used in Example 36. MS (ES) MH$^+$=449.

Example 86

[4-Amino-2-[4-(1-ethyl-pyrrolidin-3-yloxy)-phenylamino]-thiazol-5-yl]-(3-fluoro-4-methyl-phenyl)-methanone

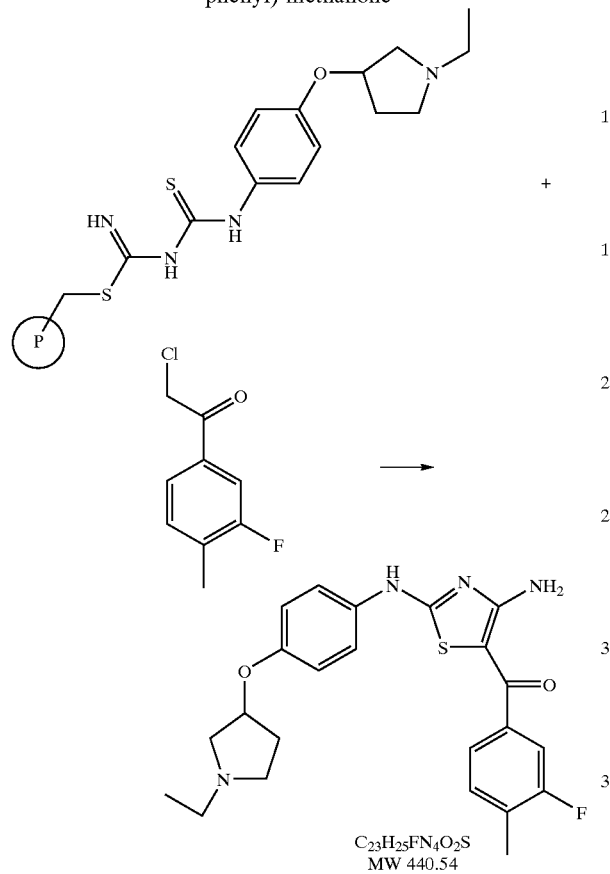

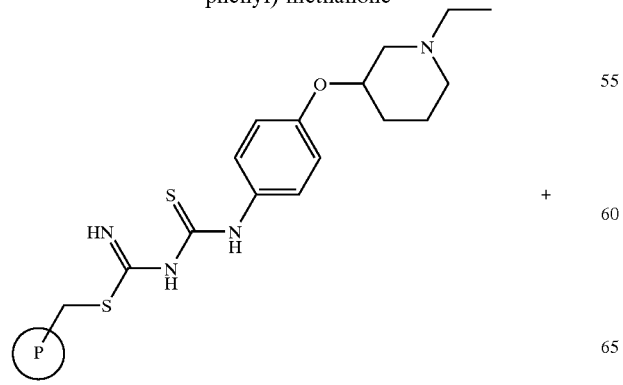

This compound was prepared from resin-bound thiourea of Example 30 and 2-chloro-1-(3-fluoro-4-methyl-phenyl)-ethanone (from Example 21) by the procedure used in Example 36. MS (ES) MH$^+$=441.

Example 87

[4-Amino-2-[4-(1-ethyl-piperidin-3-yloxy)-phenylamino]-thiazol-5-yl]-(3-fluoro-4-methyl-phenyl)-methanone

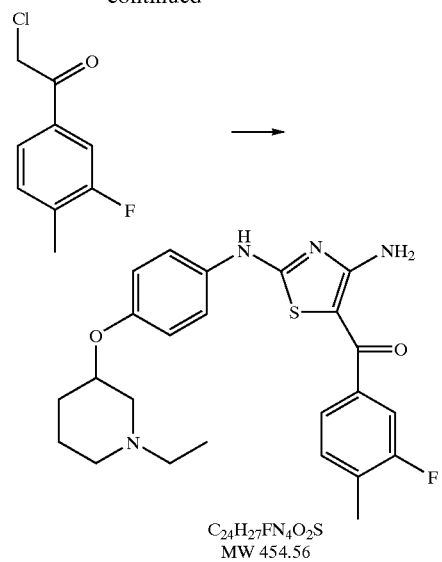

This compound was prepared from resin-bound thiourea of Example 31 and 2-chloro-1-(3-fluoro-4-methyl-phenyl)-ethanone (from Example 21) by the procedure used in Example 36. MS (ES) MH$^+$=455.

Example 88

[4-Amino-2-[4-(1-ethyl-piperidin-3-yloxy)-phenylamino]-thiazol-5-yl]-(4-hydroxy-3-propyl-phenyl)-methanone; Compound With Acetic Acid

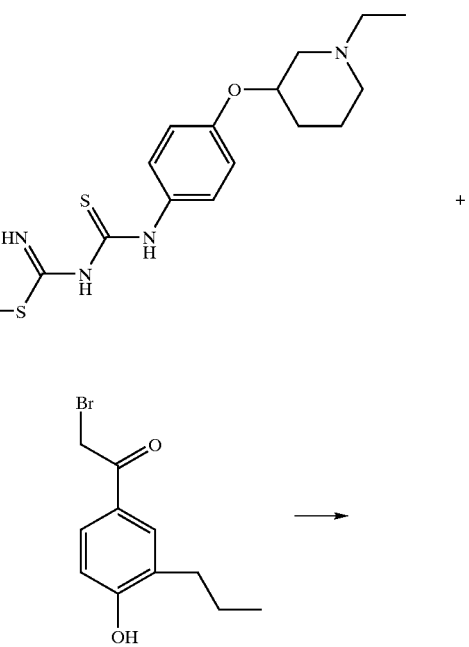

-continued

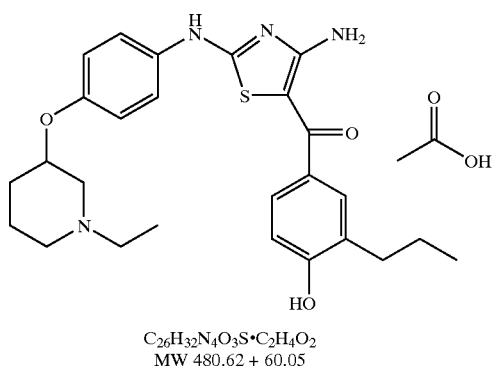

C<sub>26</sub>H<sub>32</sub>N<sub>4</sub>O<sub>3</sub>S•C<sub>2</sub>H<sub>4</sub>O<sub>2</sub>
MW 480.62 + 60.05

This compound was prepared from resin-bound thiourea of Example 31 (65 mg, 0.104 mmol, loading of resin, 1.6 mmol/g) and 2-bromo-1-(4-hydroxy-3-propyl-phenyl)-ethanone (of Example 23) (40.2 mg, 0.156 mmol) by the procedure used in Example 36. After the crude was obtained, it was purified by reverse phase HPLC as the acetic acid salt. 38.2 mg, 68%. MS (ES) MH$^+$=481.

Example 89

[4-Amino-2-[4-(1-ethyl-pyrrolidin-3-yloxy)-phenylamino]-thiazol-5-yl]-(4-hydroxy-3-propyl-phenyl)-methanone; Compound With Acetic Acid

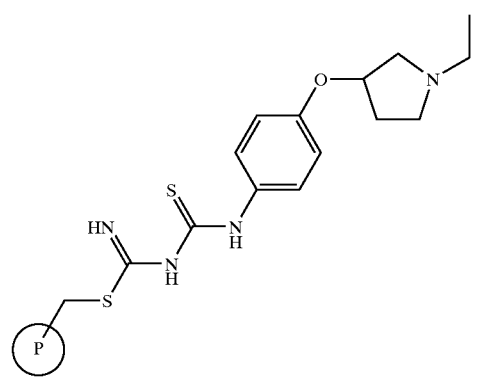

+

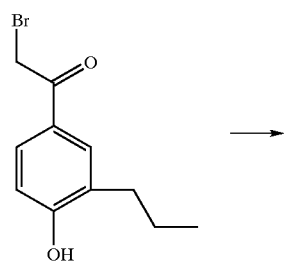

→

-continued

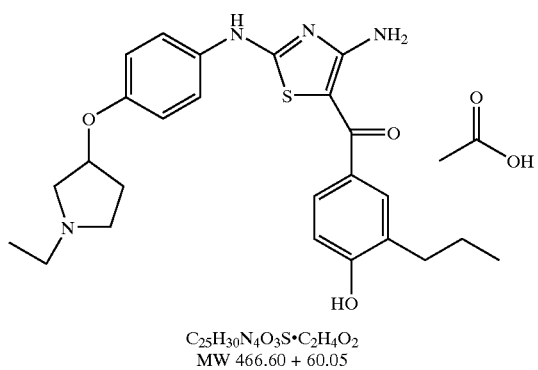

C<sub>25</sub>H<sub>30</sub>N<sub>4</sub>O<sub>3</sub>S•C<sub>2</sub>H<sub>4</sub>O<sub>2</sub>
MW 466.60 + 60.05

This compound was prepared from resin-bound thiourea of Example 30 (65 mg, 0.104 mmol, loading of resin, 1.6 mmol/g) and 2-bromo-1-(4-hydroxy-3-propyl-phenyl)-ethanone (40.2 mg, 0.1 56 mmol) (of Example 23) by the procedure used in Example 36. After the crude was obtained, it was purified by reverse phase HPLC as the acetic acid salt. 36 mg, 68% MS (ES) MH$^+$=467.

Example 90

[4-Amino-2-[4-(pyrrolidin-3-yloxy)-phenylamino]-thiazol-5-yl]-(4-hydroxy-3-propyl-phenyl)-methanone; Compound With Acetic Acid

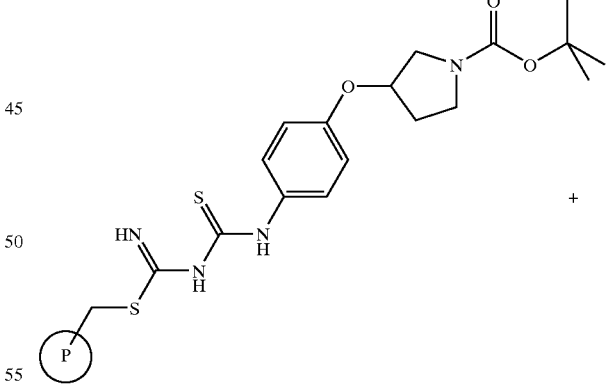

+

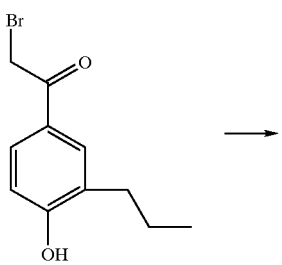

→

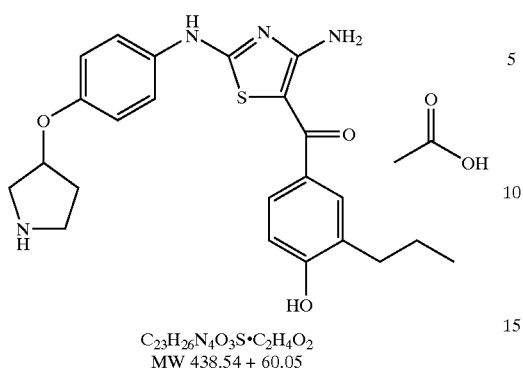

C₂₃H₂₆N₄O₃S•C₂H₄O₂
MW 438.54 + 60.05

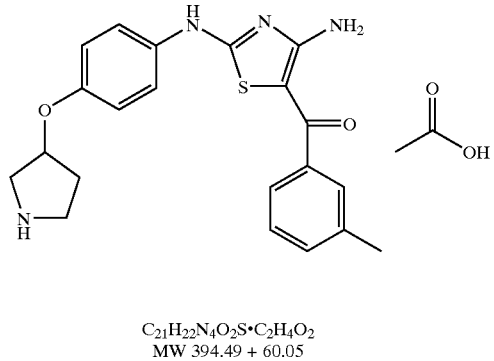

C₂₁H₂₂N₄O₂S•C₂H₄O₂
MW 394.49 + 60.05

This compound was prepared from resin-bound thiourea of Example 95 (65 mg, 0.104 mmol, loading of resin, 1.6 mmol/g) and 2-bromo-1-(4-hydroxy-3-propyl-phenyl)-ethanone (40.2 mg, 0.156 mmol) (of Example 23) by the procedure used in Example 45. The free base was treated with aqueous acetic acid and the mixture was lyophilized to give a yellow powder. 40 mg, 77% MS (ES) MH⁺=439.

This compound was prepared from resin-bound thiourea of Example 95 (65 mg, 0.104 mmol, loading of resin, 1.6 mmol/g) and 2-bromo-1-(3-methy-phenyl)-ethanone (31.2 mg, 0.156 mmol) by the procedure used in Example 45. The free base was treated with aqueous acetic acid and the mixture was lyophilized to give a yellow powder. 33 mg, 70% MS (ES) MH⁺=395. The 2-bromo-1-(3-methyl-phenyl)-ethanone was prepared as described in Example 50.

Example 91

[4-Amino-2-[4-(pyrrolidin-3-yloxy)-phenylamino]-thiazol-5-yl]-m-tolyl-methanone; Compound With Acetic Acid Example 92

[4-Amino-2-[4-(pyrrolidin-3-yloxy)-phenylamino]-thiazol-5-yl)-(3-ethyl-phenyl)-methanone; Compound With Acetic Acid

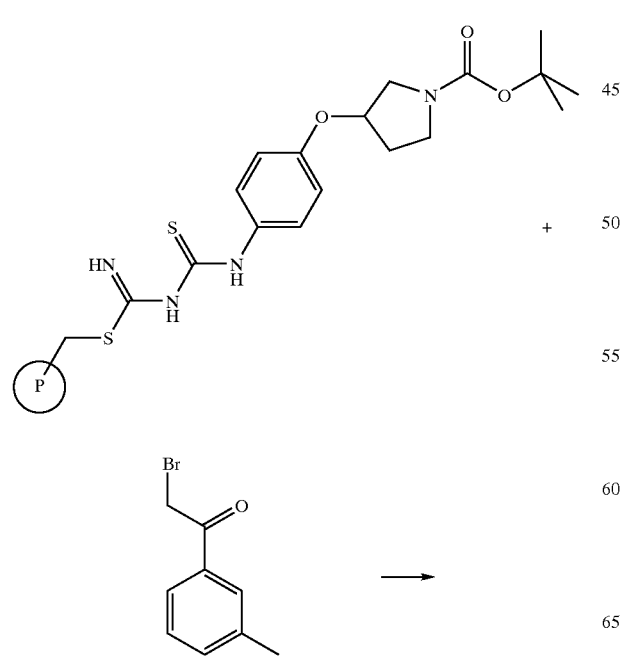

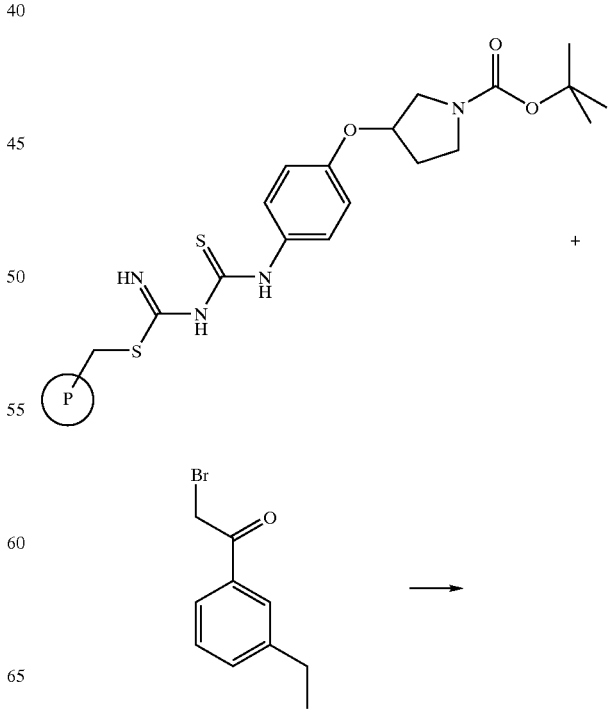

111
-continued

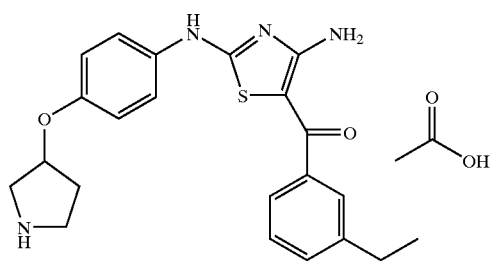

C$_{22}$H$_{24}$N$_4$O$_2$S•C$_2$H$_4$O$_2$
MW 408.52 + 60.05

This compound was prepared from resin-bound thiourea of Example 95 (65 mg, 0.104 mmol, loading of resin, 1.6 mmol/g) and 2-bromo-1-(3-ethyl-phenyl)-ethanone (35 mg, 0.156 mmol) (from Example 52 step A) by the procedure used in Example 45. The free base was treated with aqueous acetic acid and the mixture was lyophilized to give a yellow powder. 35 mg, 75% MS (ES) MH$^+$=409.

Example 93

[4-Amino-2-[4-(pyrrolidin-3-yloxy)-phenylamino]-thiazol-5-yl]-(3-cyclopropyl-phenyl)-methanone; Compound With Acetic Acid

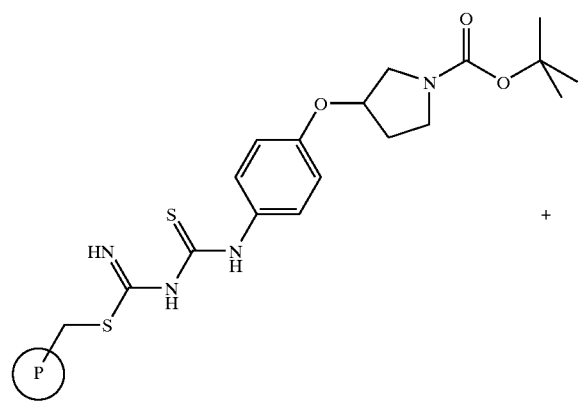

112
-continued

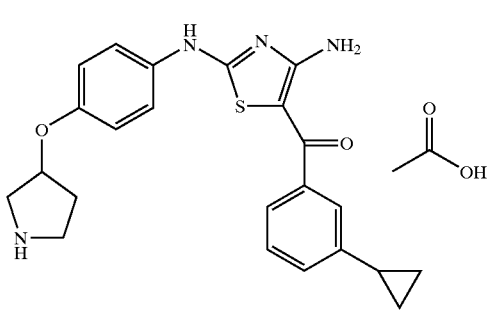

C$_{23}$H$_{24}$N$_4$O$_2$S•C$_2$H$_4$O$_2$
MW 420.53 + 60.05

This compound was prepared from resin-bound thiourea of Example 95 (65 mg, 0.104 mmol, loading of resin, 1.6 mmol/g) and 2-bromo-1-(3-cyclopropyl-phenyl)-ethanone (of Example 20C) (37 mg, 0.156 mmol) by the procedure used in Example 45. The free base was treated with aqueous acetic acid and the mixture was lyophilized to give a yellow powder. 37.3 mg, 80% MS (ES) MH$^+$=421.

Example 94

[4-Amino-2-[4-(pyrrolidin-3-yloxy)-phenylamino]-thiazol-5-yl]-(3-fluoro-4-methyl-phenyl)-methanone; Compound With Acetic Acid

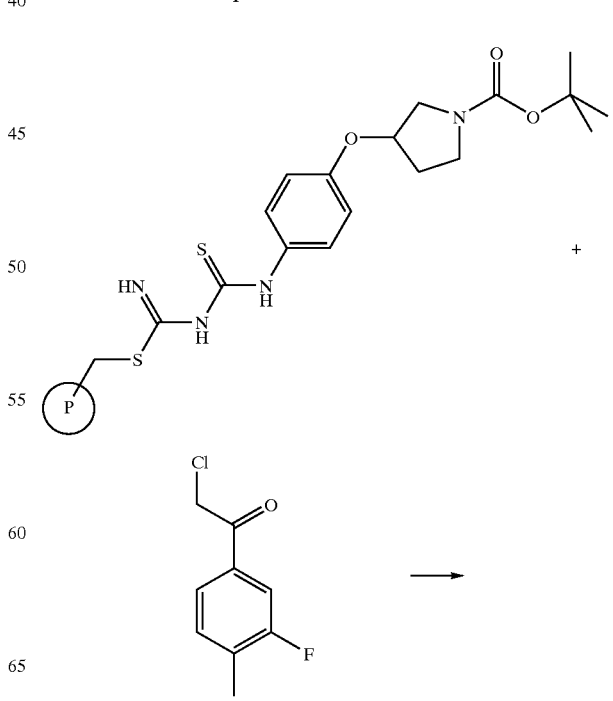

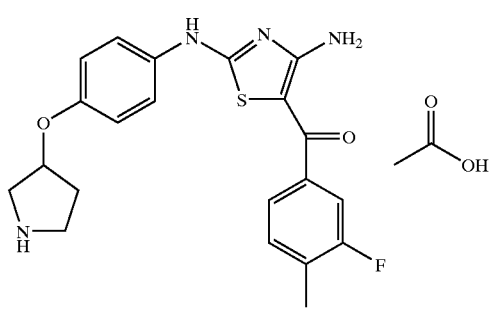

C₂₁H₂₁FN₄O₂S·C₂H₄O₂
MW 412.48 + 60.05

This compound was prepared from resin-bound thiourea of Example 95 (65 mg, 0.104 mmol, loading of resin, 1.6 mmol/g) and 2-chloro-1-(3-fluoro-4-methyl-phenyl)-ethanone (29 mg, 0.156 mmol) (from Example 21) by the procedure used in Example 45. The free base was treated with aqueous acetic acid and the mixture was lyophilized to give a yellow powder. 29 mg, 80% MS (ES) MH$^+$=413.

Example 95

Prepared as in Example 24 from the isothiocyanate prepared in Example 15.

Example 96

[4-Amino-2-[4-(pyrrolidin-3-yloxy)-phenylamino]-thiazol-5-yl]-(3-fluoro-4-methoxy-phenyl)-methanone

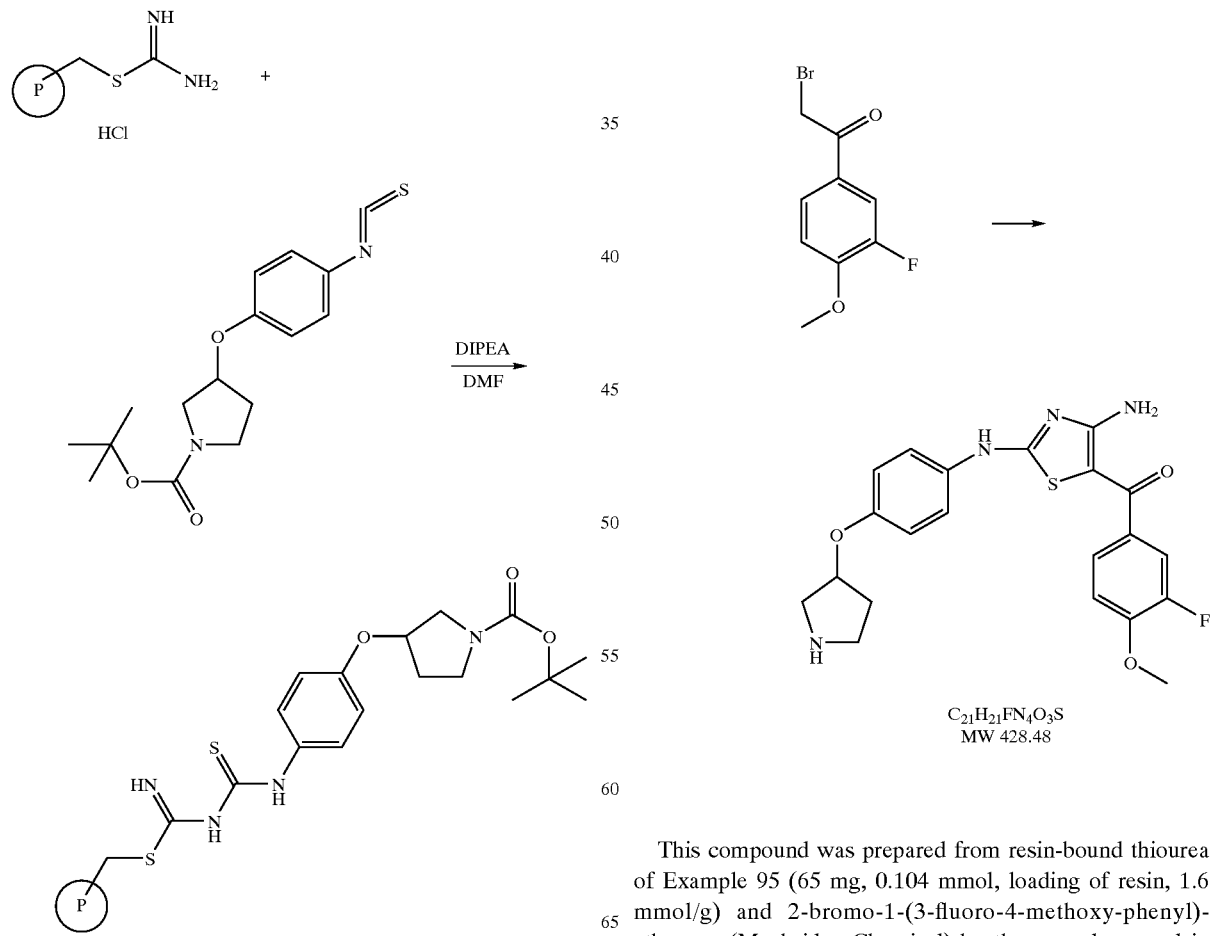

C₂₁H₂₁FN₄O₃S
MW 428.48

This compound was prepared from resin-bound thiourea of Example 95 (65 mg, 0.104 mmol, loading of resin, 1.6 mmol/g) and 2-bromo-1-(3-fluoro-4-methoxy-phenyl)-ethanone (Maybridge Chemical) by the procedure used in Example 45. MS (ES) MH$^+$=429.

Example 97

[4-Amino-2-[4-(piperidin-3-yloxy)-phenylamino]-thiazol-5-yl]-(3-fluoro-4-methoxy-phenyl)-methanone

Example 98

[4-Amino-2-[4-(piperidin-3-yloxy)-phenylamino]-thiazol-5-yl]-(3-ethyl-phenyl)-methanone

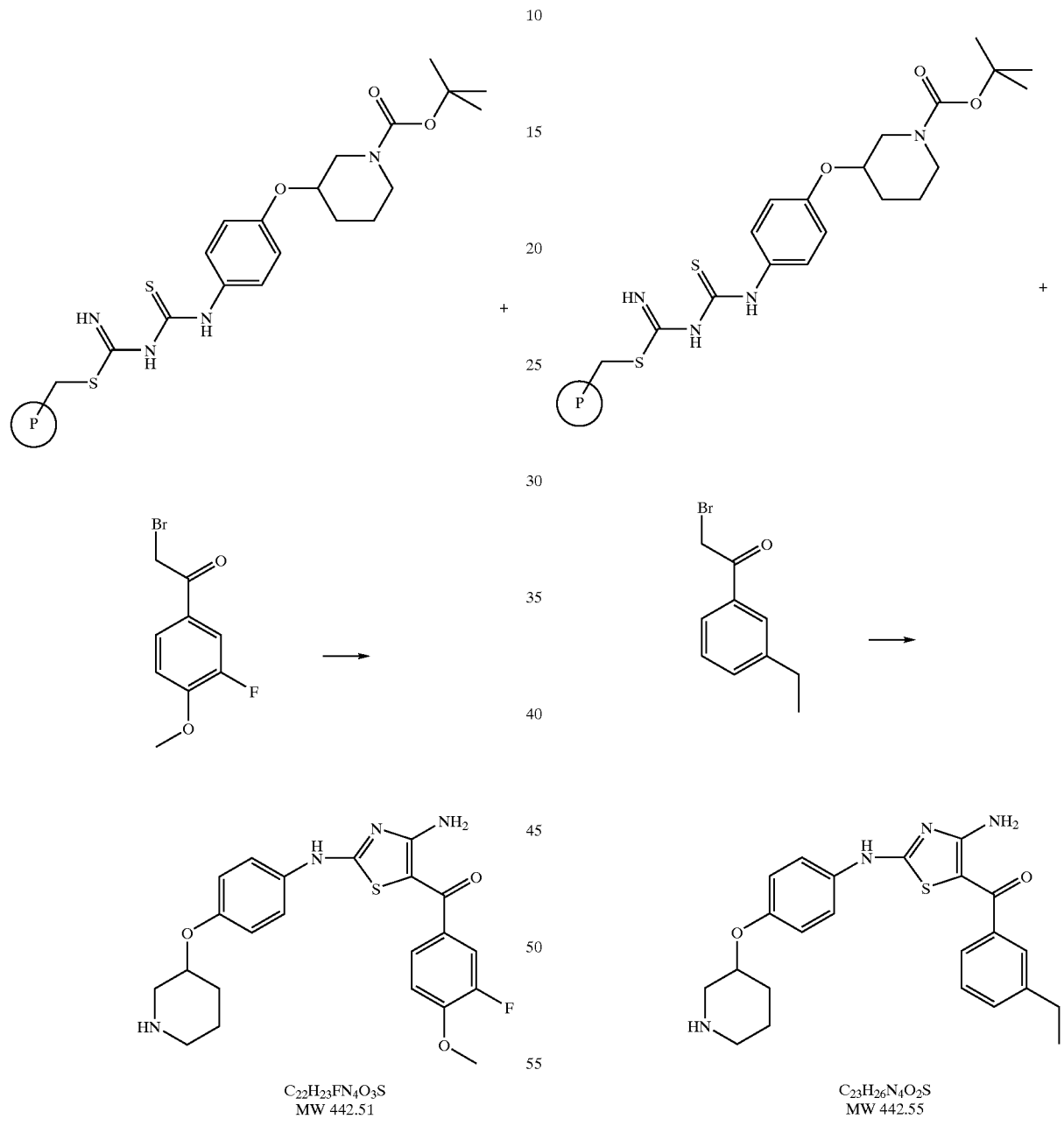

$C_{22}H_{23}FN_4O_3S$
MW 442.51

$C_{23}H_{26}N_4O_2S$
MW 442.55

This compound was prepared from resin-bound thiourea of Example 34 (65 mg, 0.104 mmol, loading of resin, 1.6 mmol/g) and 2-bromo-1-(3-fluoro-4-methoxy-phenyl)-ethanone (Maybridge Chemical) by the procedure used in Example 45. MS (ES) MH$^+$=443.

This compound was prepared from resin-bound thiourea of Example 34 (65 mg, 0.104 mmol, loading of resin, 1.6 mmol/g) and 2-bromo-1-(3-ethyl-phenyl)-ethanone (from Example 52 step A) by the procedure used in Example 45. MS (ES) MH$^+$=423.

Example 99

[4-Amino-2-[4-(piperidin-3-yloxy)-phenylamino]-thiazol-5-yl]-(4-hydroxy-3-propyl-phenyl)-methanone

Example 100

[4-Amino-2-(4-(2-ethylamino-ethoxy)-phenylamino]-thiazol-5-yl]-m-tolyl-methanone; Compound With Acetic Acid

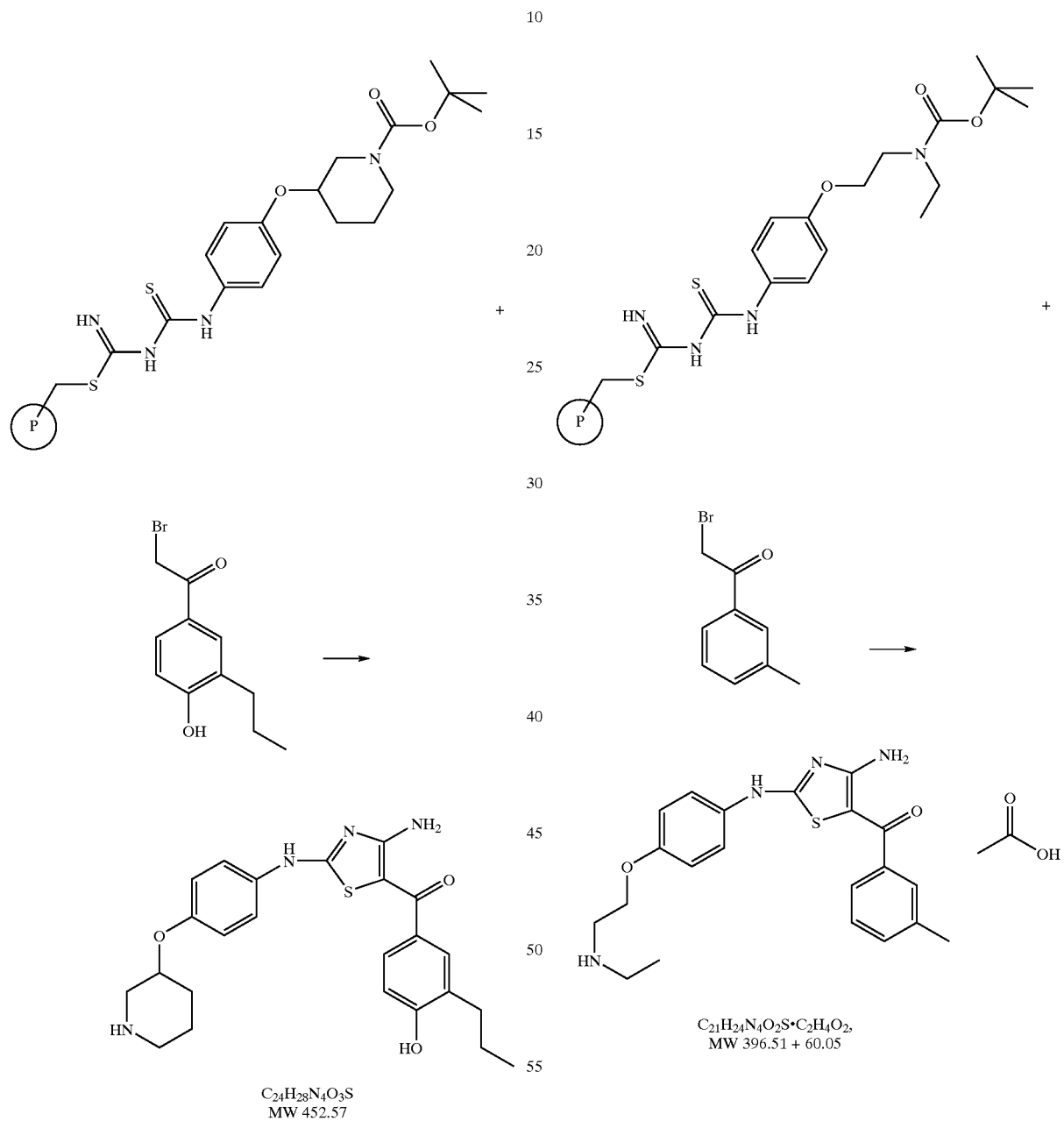

This compound was prepared from resin-bound thiourea of Example 34 (65 mg, 0.104 mmol, loading of resin, 1.6 mmol/g) and 2-bromo-1-(4-hydroxy-3-propyl-phenyl)-ethanone (of Example 23) by the procedure used in Example 45. MS (ES) MH$^+$=453.

This compound was prepared from resin-bound thiourea of Example 33 (65 mg, 0.104 mmol, loading of resin, 1.6 mmol/g) and 2-bromo-1-(3-methyl-phenyl)-ethanone by the procedure used in Example 45. The free base was treated with aqueous acetic acid and the mixture was lyophilized to give a yellow powder. MS (ES) MH$^+$=397. The 2-bromo-1-(3-methyl-phenyl)-ethanone was prepared as described in Example 50.

Example 101

[4-Amino-2-[4-(2-ethylamino-ethoxy)-phenylamino]-thiazol-5-yl]-(3-ethyl-phenyl)-methanone; Compound With Acetic Acid

Example 102

[4-Amino-2-[4-(2-ethylamino-ethoxy)-phenylamino]-thiazol-5-yl]-(3-cyclopropyl-phenyl)-methanone; Compound With Acetic Acid

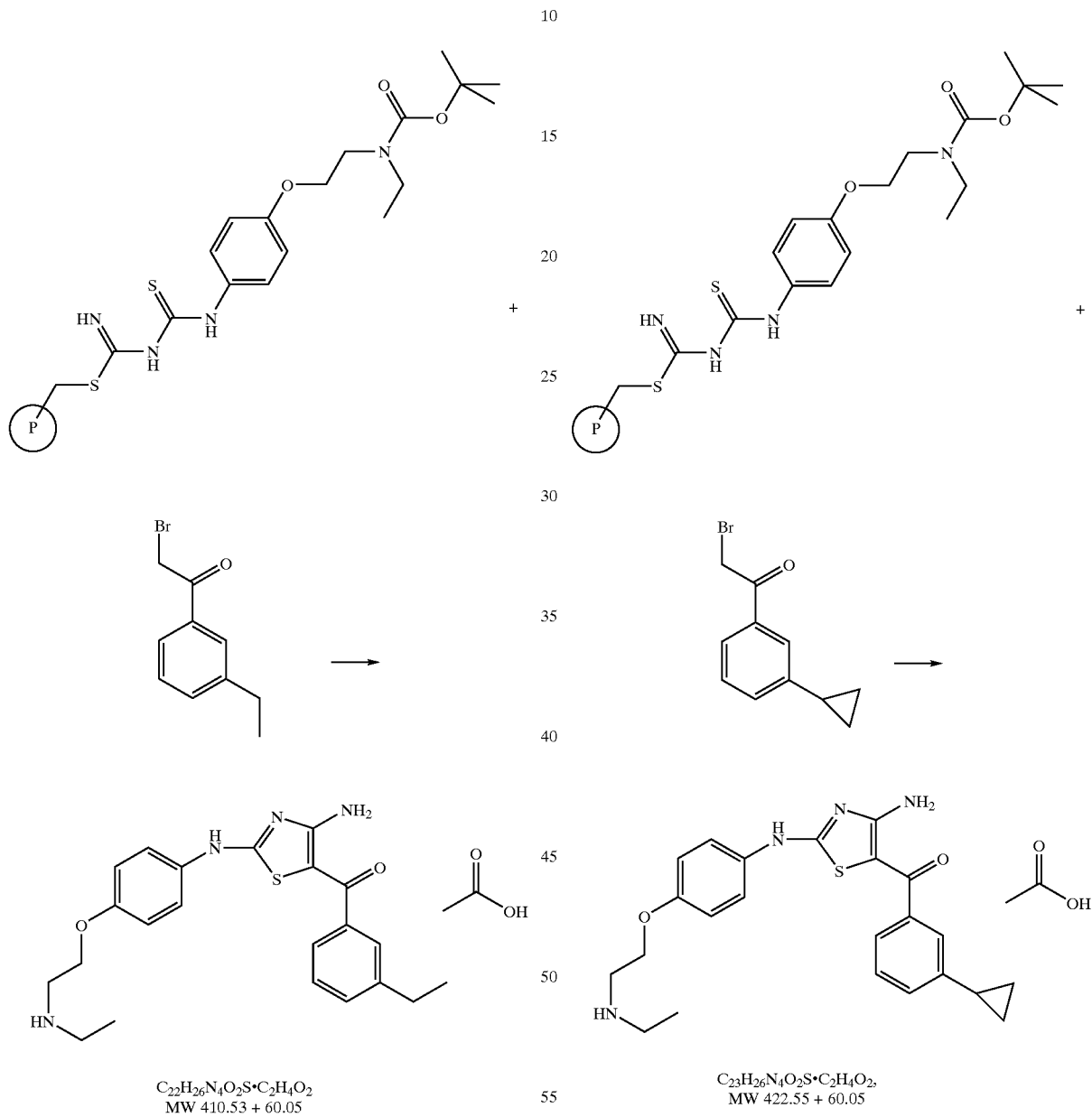

$C_{22}H_{26}N_4O_2S \cdot C_2H_4O_2$
MW 410.53 + 60.05

$C_{23}H_{26}N_4O_2S \cdot C_2H_4O_2$,
MW 422.55 + 60.05

This compound was prepared from resin-bound thiourea of Example 33 (65 mg, 0.104 mmol, loading of resin, 1.6 mmol/g) and 2-bromo-1-(3-ethyl-phenyl)-ethanone (from Example 52 step A) by the procedure used in Example 45. The free base was treated with aqueous acetic acid and the mixture was lyophilized to give a yellow powder. MS (ES) MH$^+$=411.

This compound was prepared from resin-bound thiourea of Example 33 (65 mg, 0.104 mmol, loading of resin, 1.6 mmol/g) and 2-bromo-1-(3-cyclopropyl-phenyl)-ethanone (of Example 20) by the procedure used in Example 45. The free base was treated with aqueous acetic acid and the mixture was lyophilized to give a yellow powder. MS (ES) MH$^+$=423.

Example 103

[4-Amino-2-[4-(2-ethylamino-ethoxy)-phenylamino]-thiazol-5-yl]-(3-fluoro-4-methyl-phenyl)-methanone; Compound With Acetic Acid

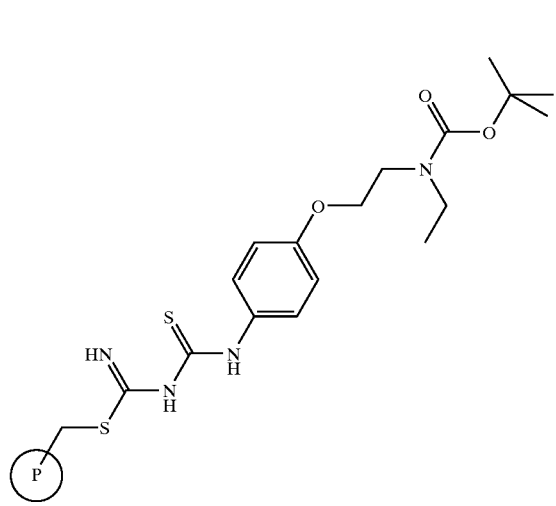

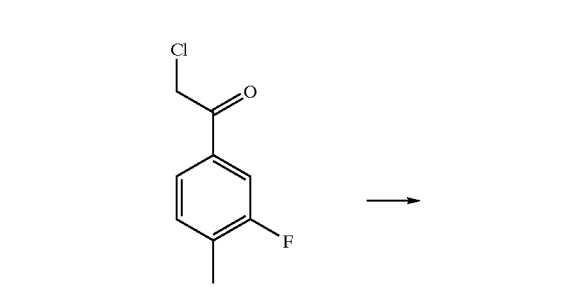

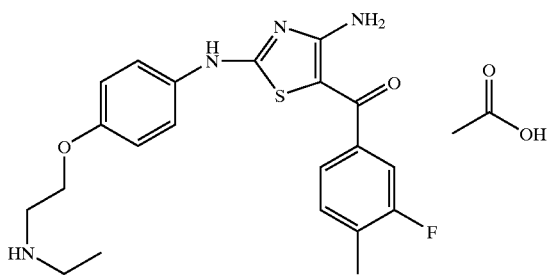

C$_{21}$H$_{23}$FN$_4$O$_2$S·C$_2$H$_4$O$_2$
MW 414.50 + 60.05

This compound was prepared from resin-bound thiourea of Example 33 (65 mg, 0.104 mmol, loading of resin, 1.6 mmol/g) and 2-chloro-1-(3-fluoro-4-methyl-phenyl)-ethanone (from Example 21) by the procedure used in Example 45. The free base was treated with aqueous acetic acid and the mixture was lyophilized to give a yellow powder. MS (ES) MH$^+$=415.

Example 104

[4-Amino-2-[4-(2-ethylamino-ethoxy)-phenylamino]-thiazol-5-yl]-(3-ethyl-4-fluoro-phenyl)-methanone; Compound With Acetic Acid

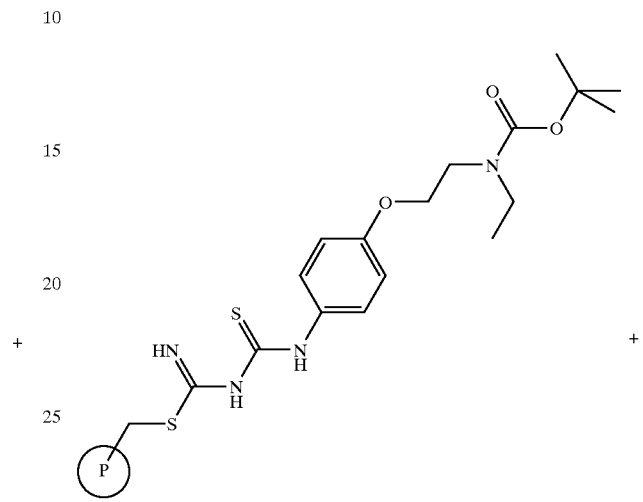

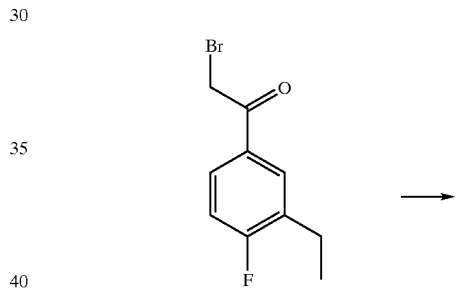

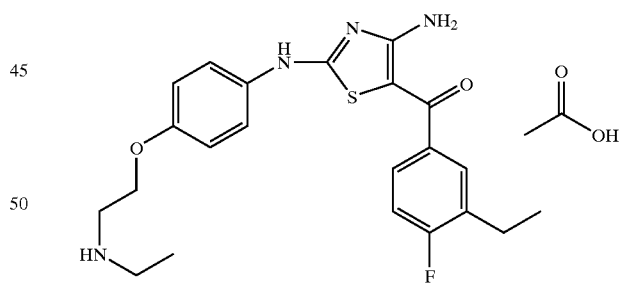

C$_{22}$H$_{25}$FN$_4$O$_2$S·C$_2$H$_4$O$_2$
MW 428.52 + 60.05

This compound was prepared from resin-bound thiourea of Example 33 (65 mg, 0.104 mmol, loading of resin, 1.6 mmol/g) and 2-bromo-1-(3-ethyl-4-phenyl)-ethanone (of Example 22) by the procedure used in Example 45. The free base was treated with aqueous acetic acid and the mixture was lyophilized to give a yellow powder. MS (ES) MH$^+$=429.

Example 105

[4-Amino-2-[4-(2-ethylamino-ethoxy)-phenylamino]-thiazol-5-yl]-(4-hydroxy-3-propyl-phenyl)-methanone; Compound With Acetic Acid

Example 106

[4-Amino-2-[4-(2-dimethylamino-ethoxy)-phenylamino]-thiazol-5-yl-](4-hydroxy-3-propyl-phenyl)-methanone; Compound With Acetic Acid

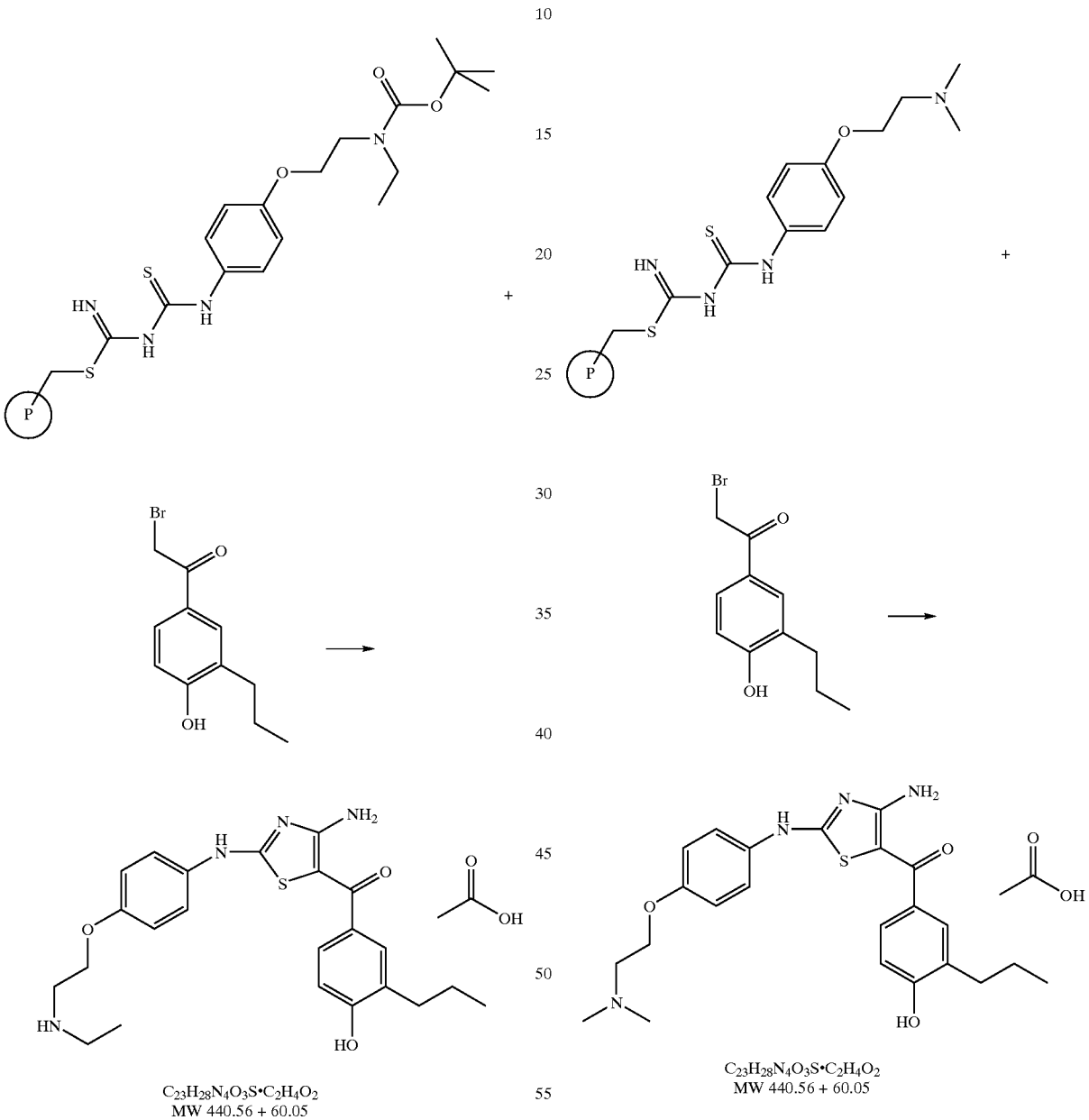

$C_{23}H_{28}N_4O_3S \cdot C_2H_4O_2$
MW 440.56 + 60.05

$C_{23}H_{28}N_4O_3S \cdot C_2H_4O_2$
MW 440.56 + 60.05

This compound was prepared from resin-bound thiourea of Example 33 (65 mg, 0.104 mmol, loading of resin, 1.6 mmol/g) and 2-bromo-1-(4-hydroxy-3-propyl-phenyl)-ethanone (of Example 23) by the procedure used in Example 45. The free base was treated with aqueous acetic acid and the mixture was lyophilized to give a yellow powder. MS (ES) MH$^+$=441.

This compound was prepared from resin-bound thiourea of Example 25 (65 mg, 0.104 mmol, loading of resin, 1.6 mmol/g) and 2-bromo-1-(4-hydroxy-3-propyl-phenyl)-ethanone (of Example 23) by the procedure used in Example 36. The free base was treated with aqueous acetic acid and the mixture was lyophilized to give a yellow powder. MS (ES) MH$^+$=441.

Example 107

(R)-[4-Amino-2-[4-(2-dimethylamino-propoxy)-phenylamino]-thiazol-5-yl]-(4-hydroxy-3-propyl-phenyl)-methanone; Compound With Acetic Acid

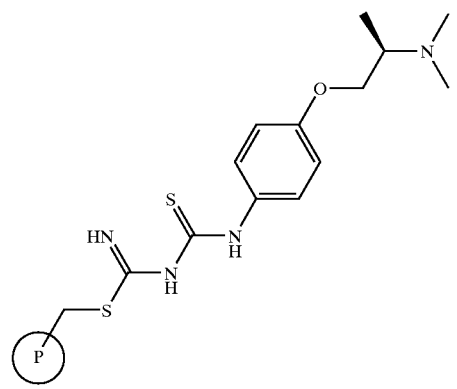

$C_{24}H_{30}N_4O_3S \cdot C_2H_4O_2$
MW 454.59 + 60.05

This compound was prepared from resin-bound thiourea of Example 28 (65 mg, 0.104 mmol, loading of resin, 1.6 mmol/g) and 2-bromo-1-(4-hydroxy-3-propyl-phenyl)-ethanone (of Example 23) by the procedure used in Example 36. The free base was treated with aqueous acetic acid and the mixture was lyophilized to give a yellow powder. MS (ES) $MH^+$=455.

Example 108

[4-Amino-2-[4-(2-dimethylamino-2-methyl-propoxy)-phenylamino]-thiazol-5-yl]-(4-hydroxy-3-propyl-phenyl)-methanone; Compound With Acetic Acid

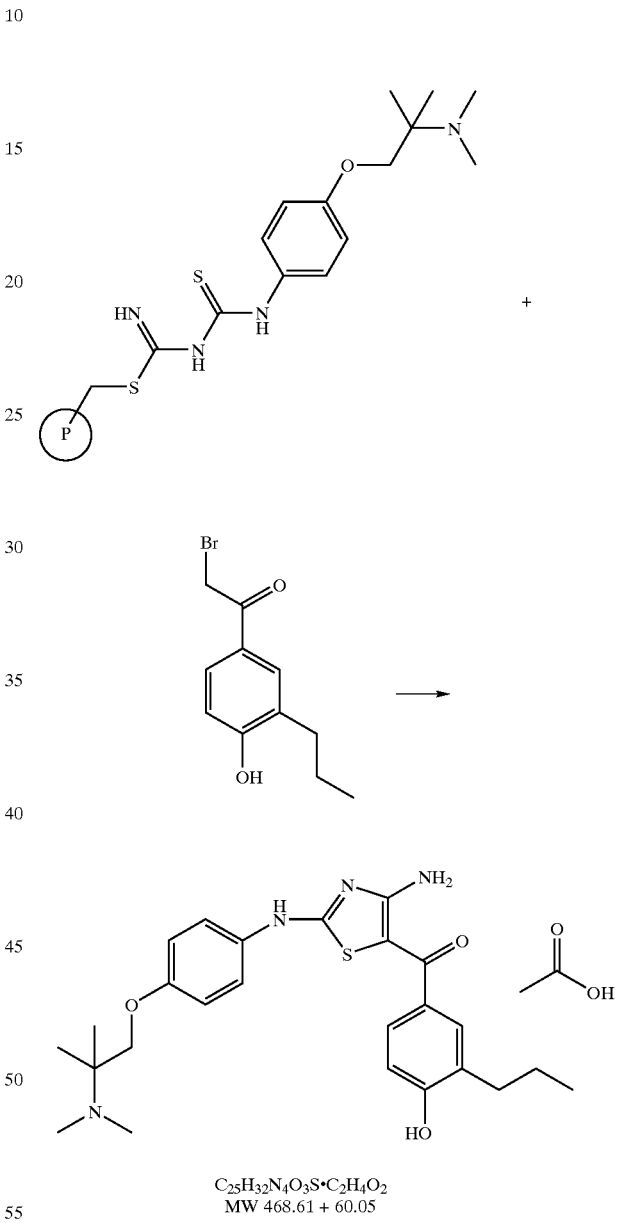

$C_{25}H_{32}N_4O_3S \cdot C_2H_4O_2$
MW 468.61 + 60.05

This compound was prepared from resin-bound thiourea of Example 27 (65 mg, 0.104 mmol, loading of resin, 1.6 mmol/g) and 2-bromo-1-(4-hydroxy-3-propyl-phenyl)-ethanone (of Example 23) by the procedure used in Example 36. The free base was treated with aqueous acetic acid and the mixture was lyophilized to give a yellow powder. MS (ES) $MH^+$=469.

Example 109

[4-Amino-2-[4-(2-pyrrolidin-1-yl-ethoxy)-phenylamino]-thiazol-5-yl]-(4-hydroxy-3-propyl-phenyl)-methanone; Compound With Acetic Acid

Example 110

(R)-[4-Amino-2-[4-(2-pyrrolidin-1-yl-propoxy)-phenylamino]-thiazol-5-yl]-(4-hydroxy-3-propyl-phenyl)-methanone; Compound With Acetic Acid

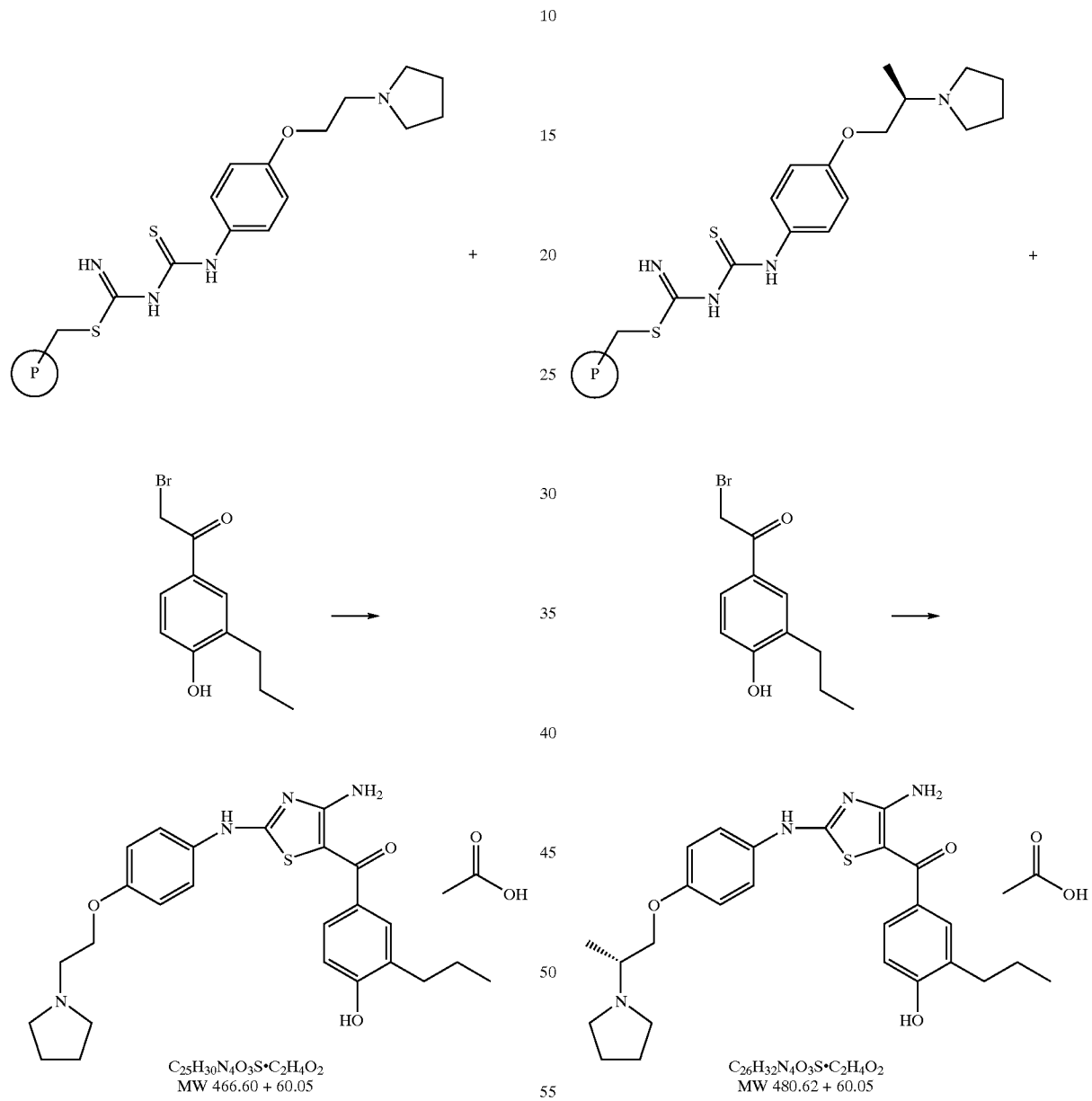

$C_{25}H_{30}N_4O_3S \cdot C_2H_4O_2$
MW 466.60 + 60.05

$C_{26}H_{32}N_4O_3S \cdot C_2H_4O_2$
MW 480.62 + 60.05

This compound was prepared from resin-bound thiourea of Example 24 (65 mg, 0.104 mmol, loading of resin, 1.6 mmol/g) and 2-bromo-1-(4-hydroxy-3-propyl-phenyl)-ethanone (of Example 23) by the procedure used in Example 36. The free base was treated with aqueous acetic acid and the mixture was lyophilized to give a yellow powder. MS (ES) MH$^+$=467.

This compound was prepared from resin-bound thiourea of Example 29 (65 mg, 0.104 mmol, loading of resin, 1.6 mmol/g) and 2-bromo-1-(4-hydroxy-3-propyl-phenyl)-ethanone (of Example 23) by the procedure used in Example 36. The free base was treated with aqueous acetic acid and the mixture was lyophilized to give a yellow powder. MS (ES) MH$^+$=481.

Example 111

(S)-[4-Amino-2-[4-(1-methyl-pyrrolidin-2-ylmethoxy)-phenylamino]-thiazol-5-yl]-m-tolyl-methanone

Example 112

(S)-[4-Amino-2-[4-(1-methyl-pyrrolidin-2-ylmethoxy)-phenylamino]-thiazol-5-yl]-(3-ethyl-phenyl)-methanone

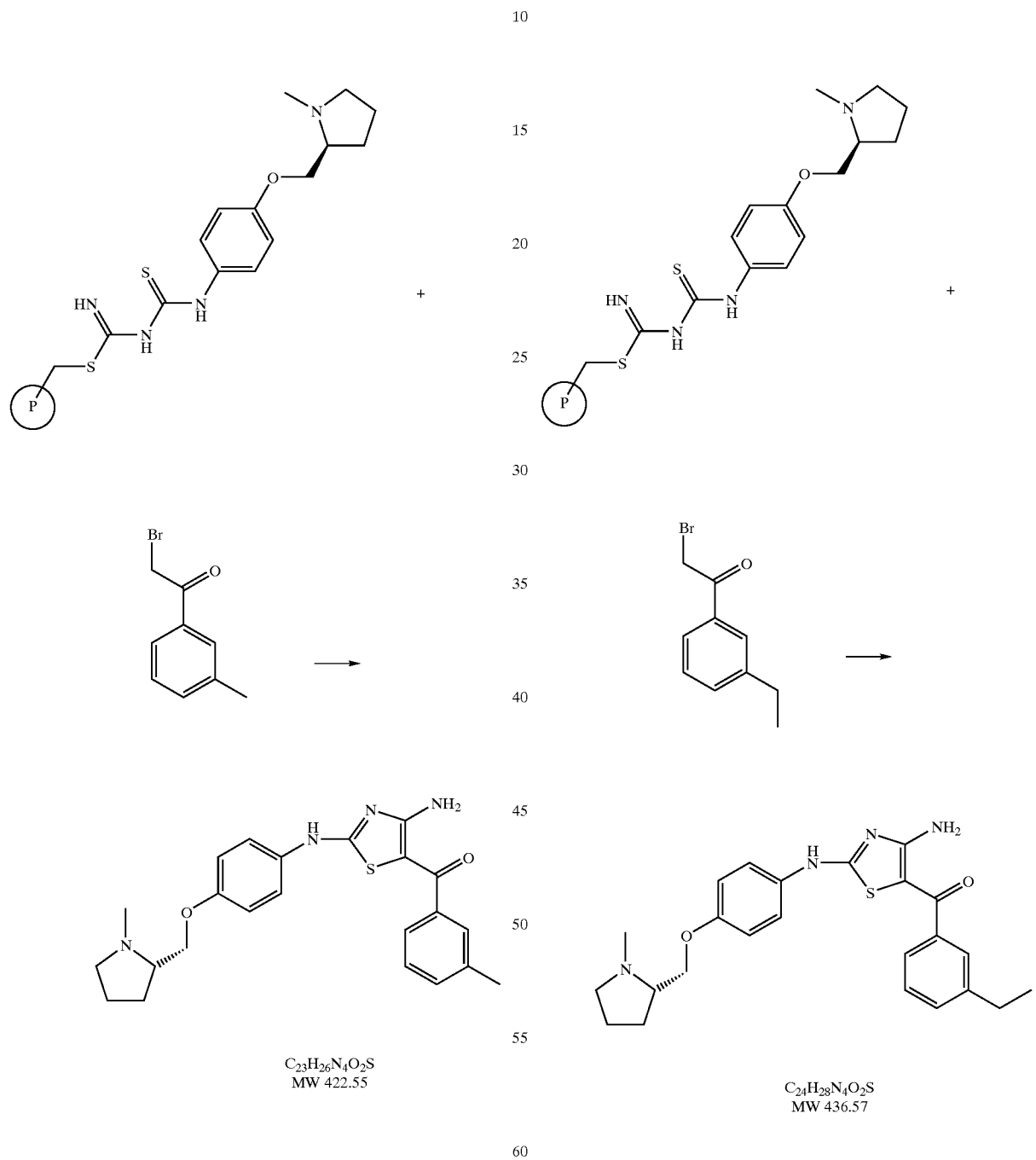

$C_{23}H_{26}N_4O_2S$
MW 422.55

$C_{24}H_{28}N_4O_2S$
MW 436.57

This compound was prepared from resin-bound thiourea of Example 32 and 2-bromo-1-(3-methyl-phenyl)-ethanone by the procedure used in Example 36. MS (ES) MH$^+$=423. The 2-bromo-1-(3-methyl-phenyl)-ethanone was prepared as described in Example 50.

This compound was prepared from resin-bound thiourea of Example 32 and 2-bromo-1-(3-ethyl-phenyl)-ethanone (from Example 52 step A) by the procedure used in Example 36. MS (ES) MH$^+$=437.

Example 113

(S)-[4-Amino-2-[4-(1-methyl-pyrrolidin-2-ylmethoxy)-phenylamino]-thiazol-5-yl]-(3-cyclopropyl-phenyl)-methanone

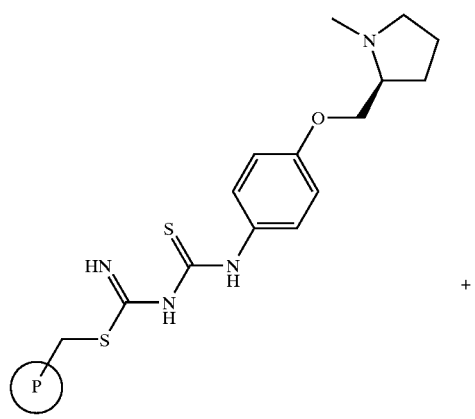

+

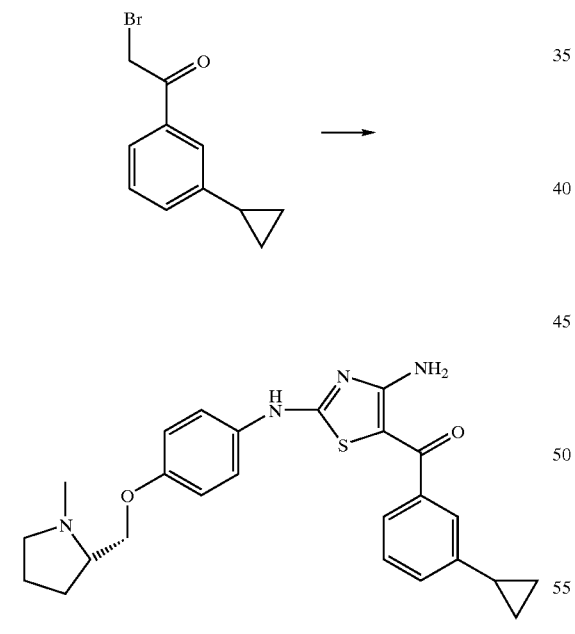

C$_{25}$H$_{28}$N$_4$O$_2$S
MW 448.58

This compound was prepared from resin-bound thiourea of Example 32 and 2-bromo-1-(3-cyclopropyl-phenyl)-ethanone (from Example 20C) by the procedure used in Example 36. MS (ES) MH$^+$=449.

Example 114

(S)-[4-Amino-2-[4-(1-methyl-pyrrolidin-2-ylmethoxy)-phenylamino]-thiazol-5-yl]-(3-fluoro-4-methyl-phenyl)-methanone

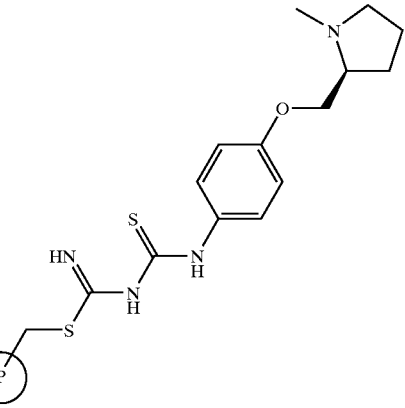

+

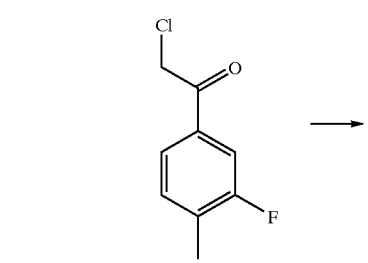

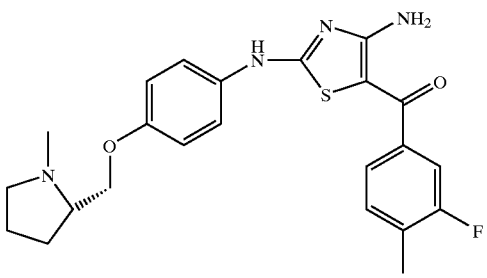

C$_{23}$H$_{25}$FN$_4$O$_2$S
MW 440.54

This compound was prepared from resin-bound thiourea of Example 32 and 2-chloro-1-(3-fluoro-4-methyl-phenyl)-ethanone (from example 21) by the procedure used in Example 36. MS (ES) MH$^+$=441.

Example 115

(S)-[4-Amino-2-[4-(1-methyl-pyrrolidin-2-ylmethoxy)-phenylamino]-thiazol-5-yl]-(4-hydroxy-3-propyl-phenyl)-methanone Acetate

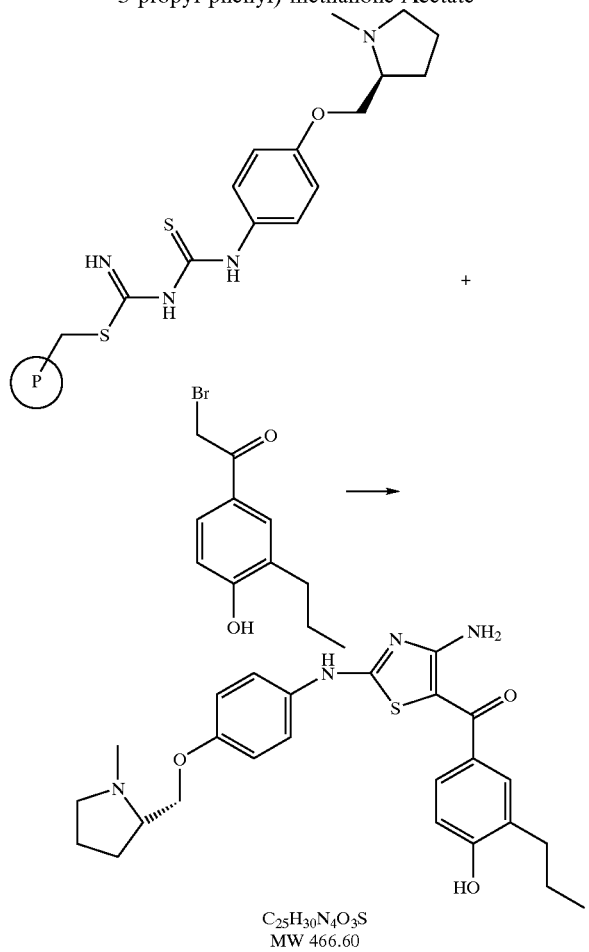

This compound was prepared from resin-bound thiourea of Example 32 and 2-bromo-1-(4-hydroxy-3-propyl-phenyl)-ethanone by the procedure used in Example 45. MS (ES) MH+=467.

Example 116

3-[4-[4-Amino-5-(3-fluoro-benzoyl)-thiazol-2-ylamino]-phenoxy]-azetidine-1-carboxylic Acid tert-Butyl Ester

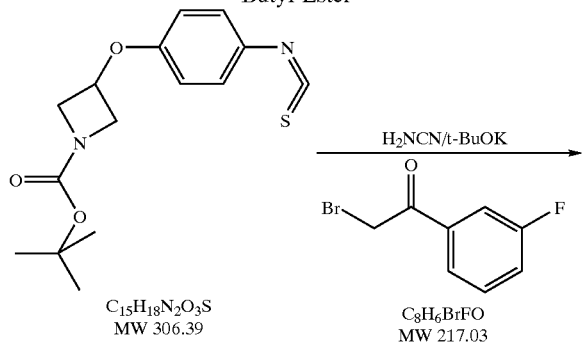

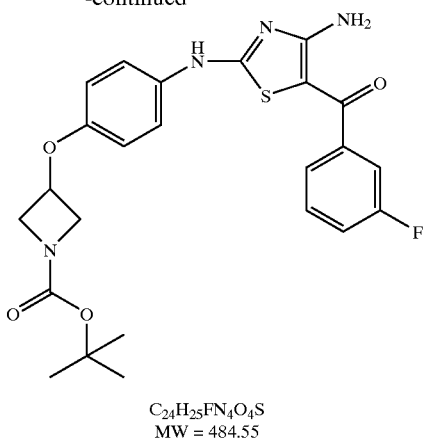

Cyanamide (46.2 mg, 1.1 mmol) was suspended in acetonitrile (5 mL). To the stirred suspension, potassium tert-butoxide (123 mg, 1.1 mmol) in 2 mL of tert-butanol was added followed by isothiocyanate (Example 19, 306 mg, 1 mmol). The mixture was stirred for 30 minutes at room temperature followed by the addition of 2-bromo-1-(3-fluoro-phenyl)-ethanone (TCI, 216 mg, 1 mmol). After being stirred for 2 hours at room temperature, the mixture was poured into water and the new mixture was extracted with ether. The extract was dried (Na₂SO₄) and concentrated to give the desired product as a yellow solid, 480 mg, 99%. MS (ES) MH+=485.

Example 117

[4-Amino-2-[4-(azetidin-3-yloxy)-phenylamino]-thiazol-5-yl]-(3-fluoro-phenyl)-methanone

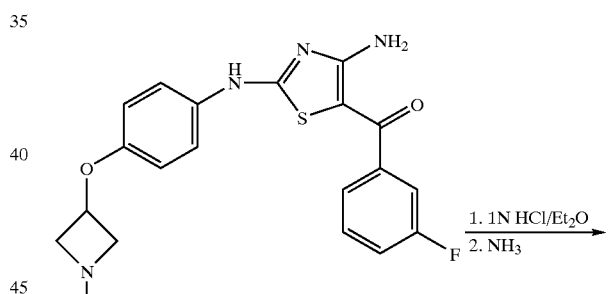

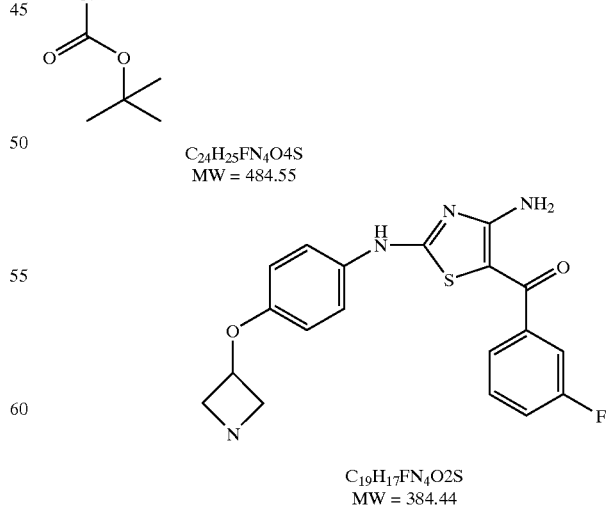

3-[4-[4-Amino-5-(3-fluoro-benzoyl)-thiazol-2-ylamino]-phenoxy]-azetidin-1-carboxylic acid tert-butyl ester (from Example 116, 160 mg, 0.33 mmol) was suspended in 1N HCl in diethyl ether and the mixture was stirred at room temperature overnight. The solid was filtered and passed through a C18 column eluting with aqueous ammonia in acetonitrile. The mixture was concentrated and the solid was filtered and dried to give a yellow solid. 110 mg, 87%. MS (ES) MH$^+$=385.

Example 118

[4-Amino-2-[4-(2-pyrrolidin-1-yl-ethoxy)-phenylamino]-thiazol-5-yl]-(3-fluoro-phenyl)-methanone; Compound With Acetic Acid

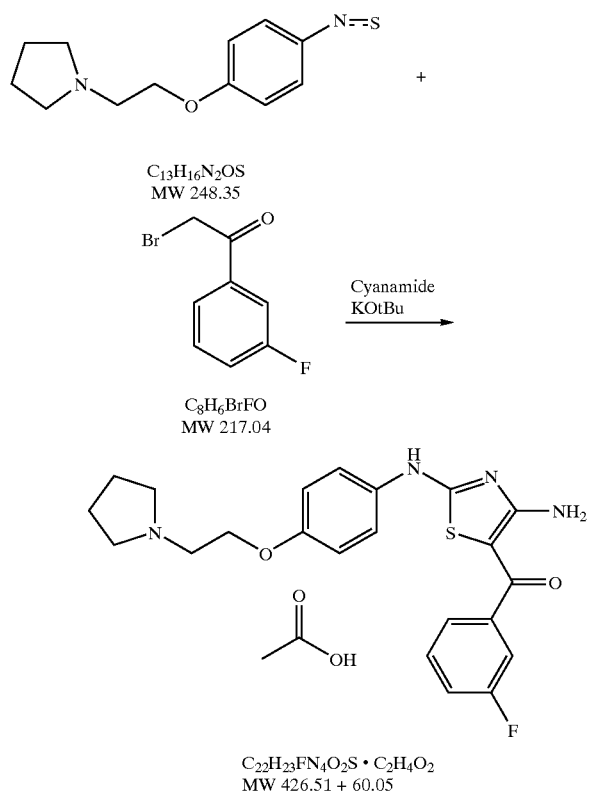

1-[2-(4-Isothiocyanato-phenoxy)-ethyl]-pyrrolidine (50 mg, 0.2 mmol) (from Example 5) and cyanamide (9.2 mg, 0.22 mmol) in acetonitrile (2 mL). Potassium t-butoxide solution (2 mL, 0.1M in tert-butanol, 0.2 mmol) was added and the solution stirred for 1 hour. 2-Bromo-1-(3-fluoro-phenyl)ethanone (44 mg, 2 mmol) (Maybridge Chemical.) was added and the solution was stirred at room temperature for 4 hours, poured into water, stirred for 1 hour, extracted with ethyl acetate, dried (Na$_2$SO$_4$) and concentrated to a solid. The crude product was purified by HPLC using a Waters Symmetry C-18 2×10 cm column with the following gradient: A (0.1% acetic acid in water), B (acetonitrile), A to B gradient (10 to 75% over 10 minutes), flow rate: 20 mL/minute. Mass spectrum (ES) MH$^+$=427.

Example 119

2-Bromo-1-(4-hydroxy-3-fluoro-phenyl)ethanone

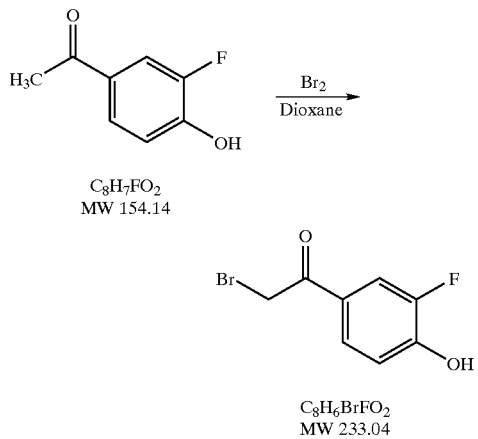

This compound was prepared from 1-(4-hydroxy-3-fluoro-phenyl)ethanone (Apin Chemicals Ltd.).

Example 120

[4-Amino-2-[4-(2-pyrrolidin-1-ylethoxy)-phenylamino]-thiazol-5-yl]-(3-fluoro-4-hydroxy-phenyl)-methanone; Compound With Acetic Acid

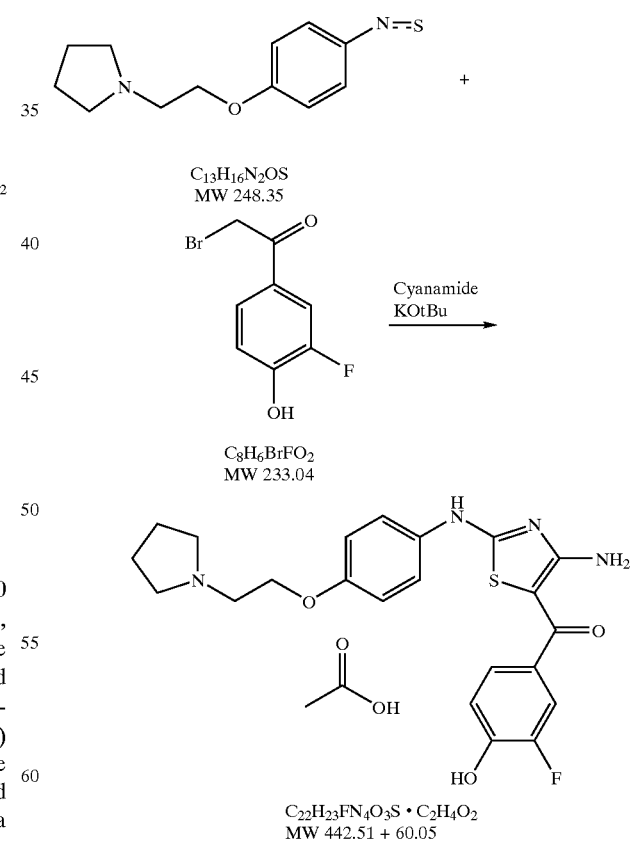

This compound was prepared from cyanamide and 1-[2-(4-isothiocyanato-phenoxy)-ethyl]-pyrrolidine (from Example 5) and 2-bromo-1-(3-fluoro-4-hydroxyphenyl)- ethanone (from Example 119) following the procedure used in Example 118. Mass spectrum (ES) MH⁺=453.

Example 121

[R]-[4-Amino-2-[4-(2-pyrrolidin-1-yl-propoxy)-phenylamino]-thiazol-5-yl]-(3-methoxy-phenyl)-methanone; Compound With Acetic Acid

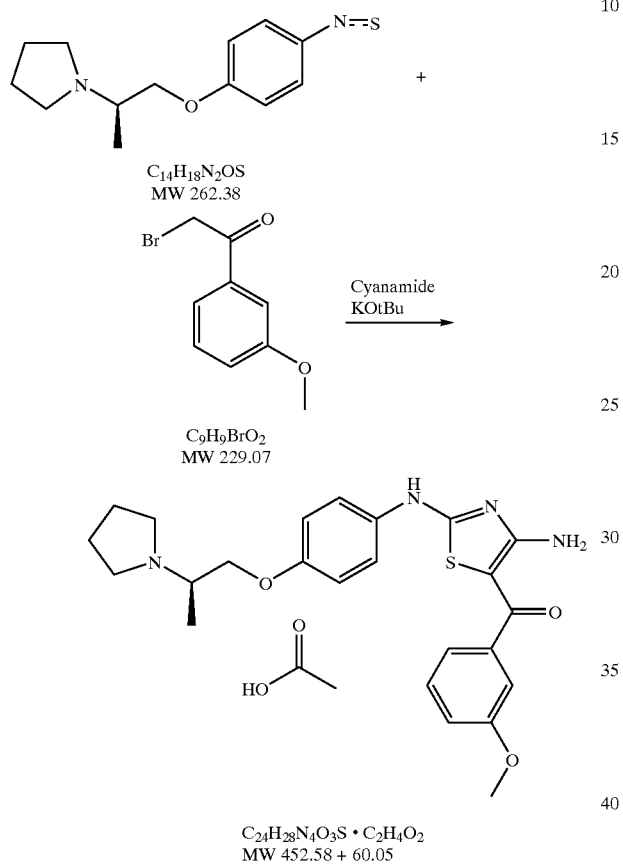

This compound was prepared from cyanamide, [R]-1-[2-(4-isothiocyanato-phenoxy)-1-methyl-ethyl)-pyrrolidine (of Example 11) and 2-bromo-1-(3-methoxyphenyl)ethanone (Aldrich) following the procedure used in Example 118. Mass spectrum (ES) MH⁺=453.

Example 122

Diethyl-[2-(4-isocyanato-phenoxy)-ethyl]-amine

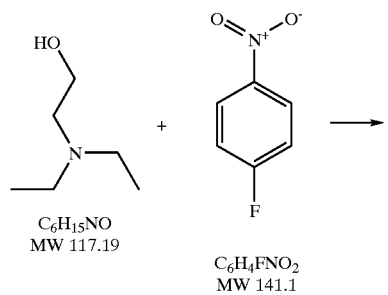

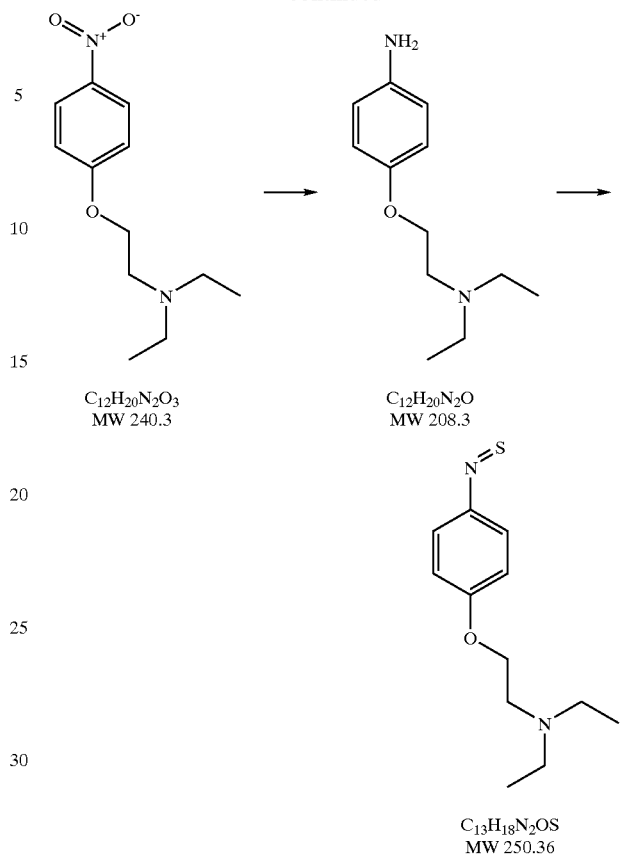

A. Diethyl-[2-(4-nitro-phenoxy)-ethyl]-amine

Sodium hydride (4.8 g, 50% in oil, 100 mmol) was added to a solution of 2-diethylamino-ethanol (11.7 g, 100 mmol) (Aldrich) in tetrahydrofuran (500 mL) and stirred for 15 minutes and then heated to 40° C. for an additional 15 minutes. The mixture was cooled to −10° C. and a solution of 1-fluoro-4-nitrobenzene (10 g, 70 mmol) in tetrahydrofuran (50 mL) was added dropwise and stirred at room temperature for 2 hours. The solvent was evaporated and the residue was dissolved in dichloromethane and washed twice with a 4:1 water/brine mixture. The dichloromethane was evaporated under vacuo and the residue chromatographed on silica gel using 1:1 hexane/ethyl acetate, ethyl acetate, then 20% methanol in dichloromethane. The product fractions were concentrated in vacuo, dissolved in ether, treated with activated charcoal, filtered through Celite™ and concentrated to give 9 g, (54%) of diethyl-[2-(4-nitro-phenoxy)-ethyl]-amine.

B. Diethyl-[2-(4-nitro-phenoxy)-ethyl]-amine

A solution of diethyl-[2-(4-nitro-phenoxy)-ethyl]-amine (6.8 g, 28.3 mmol) (from Step A above) and 200 mg of 10% palladium-on-carbon in ethanol (150 mL) was hydrogenated at 20 psi in a Parr shaker for 1 hour. The mixture was filtered through Celite™ and the solvent was evaporated to give 5.36 g, (90%) 4-(2-diethylamino-ethoxy)-phenylamine.

C. Diethyl-[2-(4-isocyanato-phenoxy)-ethyl]-amine

Thiocarbonyldiimidazole (4.56 g, 25.6 mmol) (Aldrich) was dissolved in N,N-dimethylformamide (25 mL) and the solution cooled to −15° C. A solution diethyl-[2-(4-nitro-phenoxy)-ethyl]-amine (5 g, 25.7 mmol) (from Step B above) in N,N-dimethylformamide (75 mL) was added dropwise and the mixture was then stirred at room temperature for 1 hour. The solution was cooled to 0° C. and poured into ice/water (1000 mL), stirred 30 minutes, and the precipitate was filtered off, washed with water and dried under high vacuum to give 4.95 g, (83%) diethyl-[2-(4-isocyanato-phenoxy)-ethyl]-amine. Mass spectrum (ES) MH$^+$=251.

Example 123

[4-Amino-2-[4-(2-diethylamino-ethoxy)-phenylamino]-thiazol-5-yl]-(3-fluoro-4-hydroxy-phenyl)-methanone

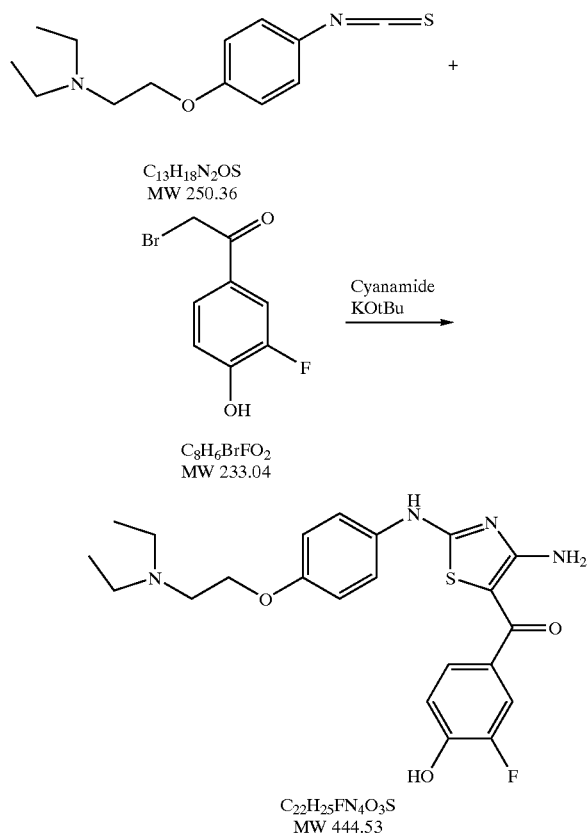

This compound was prepared from cyanamide, diethyl-[2-(4-isothiocyanato-phenoxy-ethyl]-amine (of Example 122) and 2-bromo-1-(3-fluoro-4-hydroxyphenyl)-ethanone (from Example 119) in a procedure similar to Example 118. Upon pouring the reaction into water and stirring, a precipitate formed which was filtered off and washed with water, then dried under vacuum to yield the product. Mass spectrum (ES) MH$^+$=445.

Example 124

2-Bromo-1-(3-fluoro-4-methoxyphenyl)ethanone

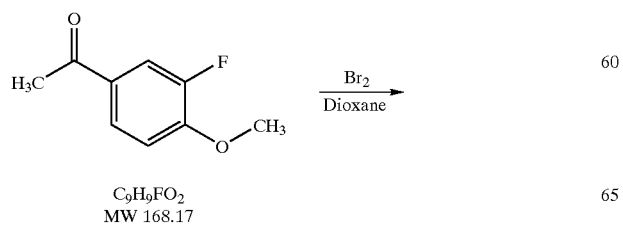

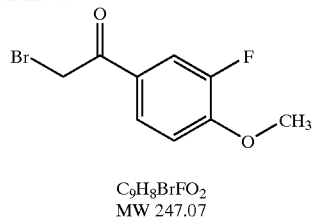

To a solution of 3'-fluoro-4'-methoxyacetophenone (1 g, 5.9 mmmol) (Aldrich) in dioxane (10 mL) was added dropwise a solution of bromine (1.13 g, 7.1 mmol) in dioxane (30 mL). After stirring for 10 minutes, the mixture was concentrated in vacuo and the residue was purified by flash chromatography, with 10:4 hexanes/dichloromethane as an eluant, to provide 2-bromo-1-(3-fluoro-4-methoxyphenyl)ethanone as a white powder (91,0 mg, 63% yield).

Example 125

[4-Amino-2-[4-(2-diethylamino-ethoxy)-phenylamino]-thiazol-5-yl]-(3-fluoro-4-methoxy-phenyl)-methanone

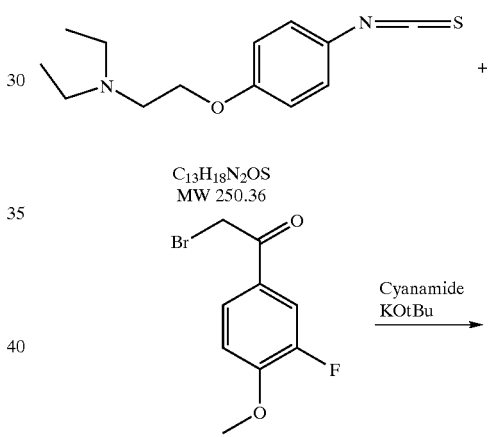

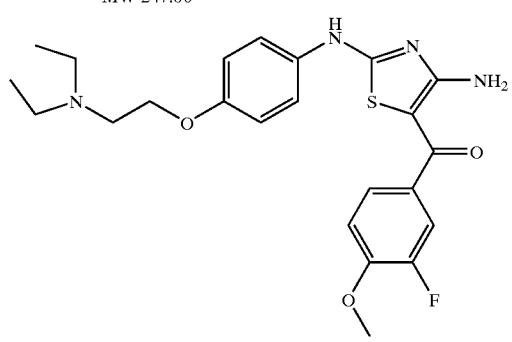

This compound was prepared from cyanamide, diethyl-[2-(4-isothiocyanato-phenoxy-ethyl]-amine (of Example 122) and 2-bromo-1-(3-fluoro-4-methoxyphenyl)-ethanone (of Example 124) following the procedure of Example 123. Mass spectrum (ES) MH$^+$=459.

Example 126

[4-Amino-2-[4-(2-diethylamino-ethoxy)-phenylamino]-thiazol-5-yl]-(3-methylsulfanyl-phenyl)-methanone

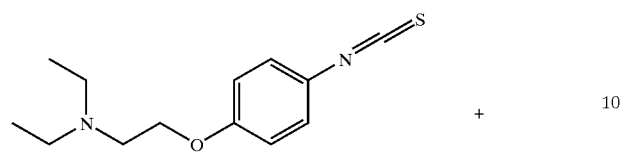

This compound was prepared from cyanamide, diethyl-[2-(4-isothiocyanato-phenoxy-ethyl]-amine of Example 122, and 2-bromo-1-(3-methylsulfanyl-phenyl)ethanone (which can be prepared by the procedure of Rogers, N. H., et. al., EP87953) following a procedure similar to Example 118. Extracting with dichloromethane and concentrating to a solid yielded the product. Mass spectrum (ES) MH$^+$=457.

Example 127

2-Bromo-1-(3-trifluoromethyl)-ethanone

To a stirred solution of 1-(3-trifluoromethyl-phenyl)-ethanone (6.15 g, 32.8 mmol) (Aldrich) in dioxane (20 mL) was added dropwise a solution of bromine (5.27 g, 32.9 mmol) in dioxane (60 mL). After addition, the mixture was stirred for 10 minutes, concentrated in vacuo, and the residue chromatographed on silica gel (4:1 hexane/dichloromethane) to provide 2-bromo-1-(3-trifluoromethyl)-ethanone.

Example 128

[4-Amino-2-[4-(2-pyrrolidin-1-yl-ethoxy)-phenylamino]-thiazol-5-yl]-(3-trifluoromethyl-phenyl)-methanone

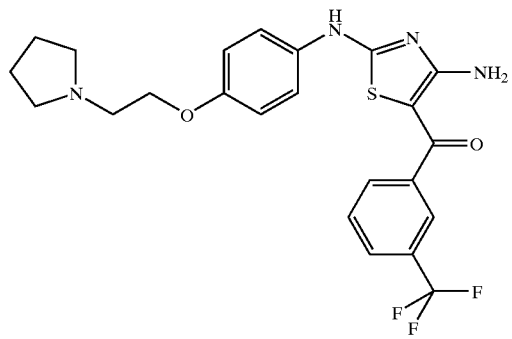

This compound was prepared from cyanamide, 1-[2-(isothiocyanato-phenoxy)-ethyl]-pyrrolidine of Example 118 and 2-bromo-1-(3-trifluoromethyl-phenyl)-ethanone of Example 127 following a procedure similar to Example 123. Mass spectrum (ES) MH$^+$=477.

Example 129

Ethyl-[2-(4-isothiocyanato-phenoxy)-ethyl]-carbamic Acid tert-Butyl Ester

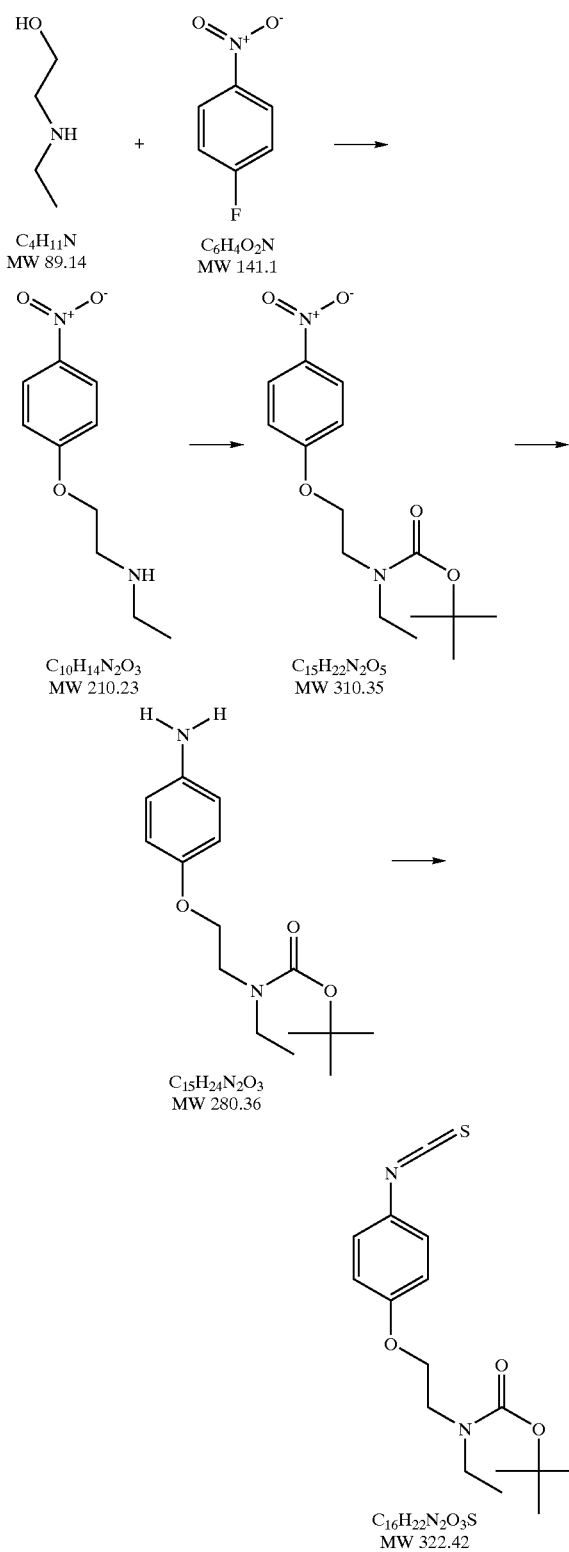

A. Ethyl-[2-(4-nitro-phenoxy)-ethyl]-amine 2-(Ethylamino)-ethanol (2.5 g, 24.2 mmol) (Aldrich) was added to a cooled (−5° C.) mixture of sodium hydride (50%, 580 mg, 24.2 mmol) in dimethyl-formamide (100 mL) and stirred for 10 minutes at 0° C., 30 minutes at room temperature, then 30 minutes at 45° C. After cooling to −1° C., 1-fluoro-4-nitrobenzene (4.1 g, 29 mmol) (Aldrich) was added and the mixture was stirred 20 minutes at −100° C. and for 90 minutes at room temperature. The resulting mixture was adjusted to pH 2 with 6N hydrochloric acid and the mixture extracted with ether (4×50 mL). The aqueous layer was adjusted to pH 9 with 3N sodium hydroxide and extracted with ethyl acetate (5×50 mL), dried ($Na_2SO_4$), concentrated in vacuo, and dried under high vacuum at 40° C. to give 2.2 g (41%) ethyl-[2-(4-nitro-phenoxy)-ethyl]-amine.

B. Ethyl-[2-(4-nitro-phenoxy)-ethyl]-carbamic Acid tert-Butyl Ester

To a solution of Ethyl-[2-(4-nitro-phenoxy)-ethyl]-amine (from step A above) (570 mg, 2.28 mmol) in dioxane was added diisopropylethylamine (327 mg, 2.53 mmol) and di-tert-butyl dicarbonate (503 mg, 2.28 mmol) (Fluka). The mixture was stirred overnight, poured into 600 mL of ice water, stirred for 1 hour, and the solids were filtered, washed with water and dried under vacuum to give 540 mg (68%) of ethyl-[2-(4-nitro-phenoxy)-ethyl]-carbamic acid tert-butyl ester.

C. [2-(4-Amino-phenoxy)-ethyl]-ethyl-carbamic Acid tert-Butyl Ester

A solution of ethyl-[2-(4-nitro-phenoxy)-ethyl]-carbamic acid tert-butyl ester (825 mg, 2.36 mmol) (from step B above) and 150 mg of 10% palladium-on-carbon in ethanol (25 mL) was hydrogenated at 20 psi in a Parr shaker for 1 hour. The mixture was filtered through Celite™ and the solvent was evaporated to give 750 mg (100%) [2-(4-amino-phenoxy)-ethyl]-ethyl-carbamic acid tert-butyl ester.

D. Ethyl-[2-(4-isothiocyanato-phenoxy)-ethyl]-carbamic Acid tert-Butyl Ester Thiocarbonyldiimidazole (438 mg, 2.46 mmol) (Aldrich) was dissolved in dimethylformamide (10 mL) and the solution was cooled to −15° C. A solution [2-(4-amino-phenoxy)-ethyl]-ethyl-carbamic acid tert-butyl ester (750 mg, 2.35 mmol) (from step C above) in dimethylformamide (25 mL) was added dropwise, stirred at room temperature for 90 minutes and poured into ice/water. After stirring 30 minutes the precipitate was filtered off, washed with water, and dried under high vacuum to give 453 mg (53%) of ethyl-[2-(4-isothiocyanato-phenoxy)-ethyl]-carbamic acid tert-butyl ester. Mass spectrum (ES) $MH^+=323$.

Example 130

[4-Amino-2-[4-(2-ethylamino-ethoxy)-phenylamino]-thiazol-5-yl]-(3-methoxy-phenyl)-methanone

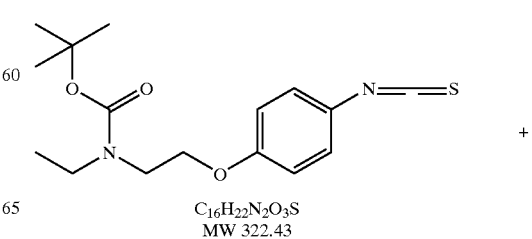

+

-continued

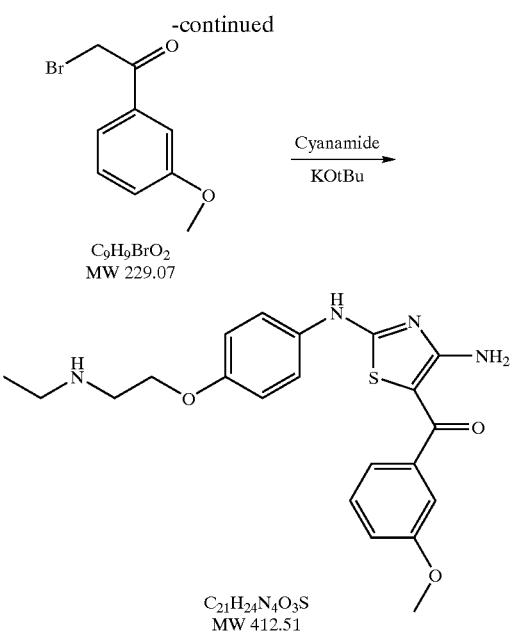

This compound was prepared from cyanamide, ethyl-[2-(4-isothiocyanato-phenoxy)-ethyl]-carbamic acid tert-butyl ester of Example 129D and 2-bromo-1-(3-methoxyphenyl)ethanone (Aldrich) following the procedure of Example 123. The protecting group was removed with 50% trifluoroacetic acid in dichloromethane, evaporated to a gum, taken into ethyl acetate, treated with 0.01N aqueous sodium hydroxide for 15 minutes and then washed with water. The ethyl acetate was dried (Na$_2$SO$_4$) and concentrated to a semi-solid which was triturated with ether to yield solid [4-amino-2-[4-(2-ethylamino-ethoxy)-phenylamino]-thiazol-5-yl]-(3-methoxy-phenyl)-methanone. Mass spectrum (ES) MH$^+$=413.

Example 131

[4-Amino-2-[4-(2-ethylamino-ethoxy)-phenylamino]-thiazol-5-yl]-(3-fluoro-phenyl)-methanone

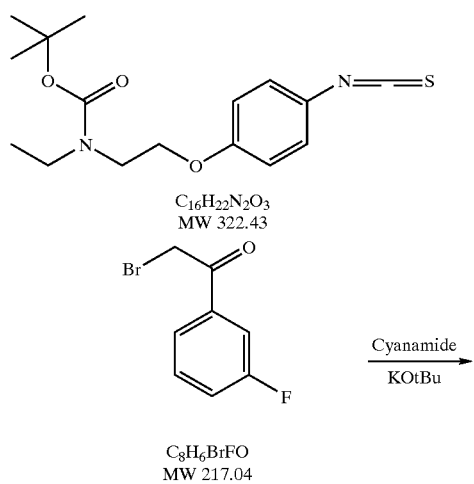

-continued

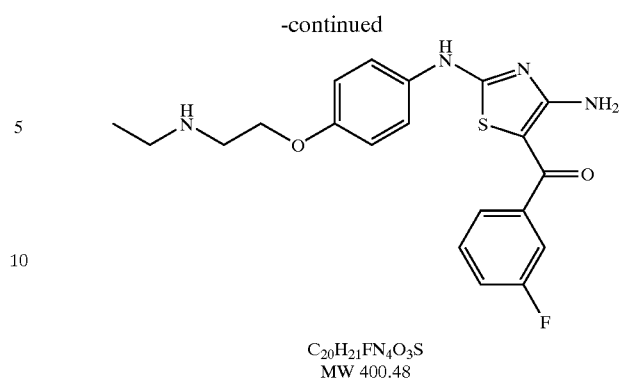

This compound was prepared from cyanamide, ethyl-[2-(4-isothiocyanato-phenoxy)-ethyl]-carbamic acid tert-butyl ester of Example 129D and 2-bromo-1-(3-fluorophenyl)ethanone (Maybridge Chemical) following a procedure similar to Example 123. Mass spectrum (ES) MH$^+$=401.

Example 132

1-(1,3-Benzodioxol-5-yl)-2-bromoethanone

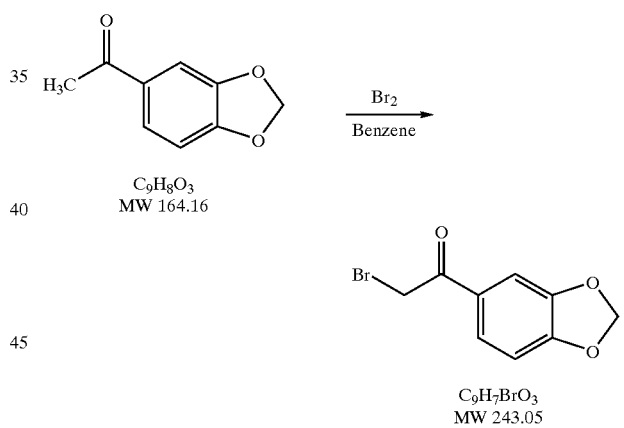

Eight drops of a solution of bromine (1.95 g, 12.2 mmol) in benzene (10 mL) were added to a solution of 1-(1,3-benzodioxol-5-yl)ethanone (2.00 g, 12.2 mmol) (Acros Organics) in benzene (40 mL) in a flask protected from light with aluminum foil. The solution was heated to reflux for 30 seconds, but it did not decolorize. The rest of the bromine solution was added in 1 mL aliquots and the solution was then allowed to stand for 2 h. Ethyl acetate (100 mL) was added, and the solution was washed with water and saturated sodium bicarbonate solution (100 mL each), dried (MgSO$_4$), filtered and evaporated to give a black liquid that solidified on standing. NMR indicated that it was a 1:3 mixture of 1-(1,3-benzodioxol-5-yl)-2,2-dibromoethanone and 1-(1,3-benzodioxol-5-yl)-2-bromoethanone. This material was used directly in subsequent steps without purification.

Example 133

[4-Amino-2-[4-(2-ethylamino-ethoxy)-phenylamino]-thiazol-5-yl]-benzo[1,3]dioxol-5-yl-methanone

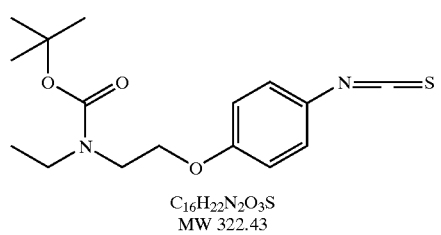

C₁₆H₂₂N₂O₃S
MW 322.43

+

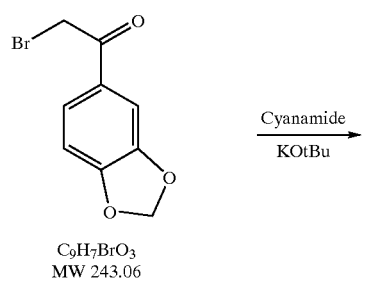

C₉H₇BrO₃
MW 243.06

→ Cyanamide / KOtBu →

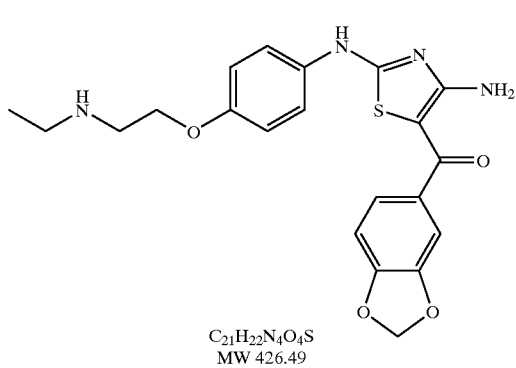

C₂₁H₂₂N₄O₄S
MW 426.49

This compound was prepared from cyanamide, ethyl-[2-(4-isothiocyanato-phenoxy)-ethyl]-carbamic acid tert-butyl ester of Example 129D and 1-benzo[1,3]dioxol-5-yl-2-bromoethanone (Example 132) following a procedure similar to Example 130. The crude product was purified by HPLC using a Waters Symmetry C-18 21.2×75 mm column with the following gradient: A (0.05% trifluoroacetic acid in water), B (0.035% trifluoroacetic acid in acetonitrile, A to B gradient (0 to 50% over 7 minutes) flow rate: 20 mL/minute. The recovered product was dissolved in ethyl acetate, washed with 0.05N aqueous sodium hydroxide, and then with water. The ethyl acetate was dried (Na₂SO₄), concentrated, and the resulting residue triturated with ether to yield the product. Mass spectrum (ES) MH⁺=427.

Example 134

[4-Amino-2-[4-(2-ethylamino-ethoxy)-phenylamino]-thiazol-5-yl]-(2,3-dihydro-benzo[1,4]dioxin-6-yl)-methanone

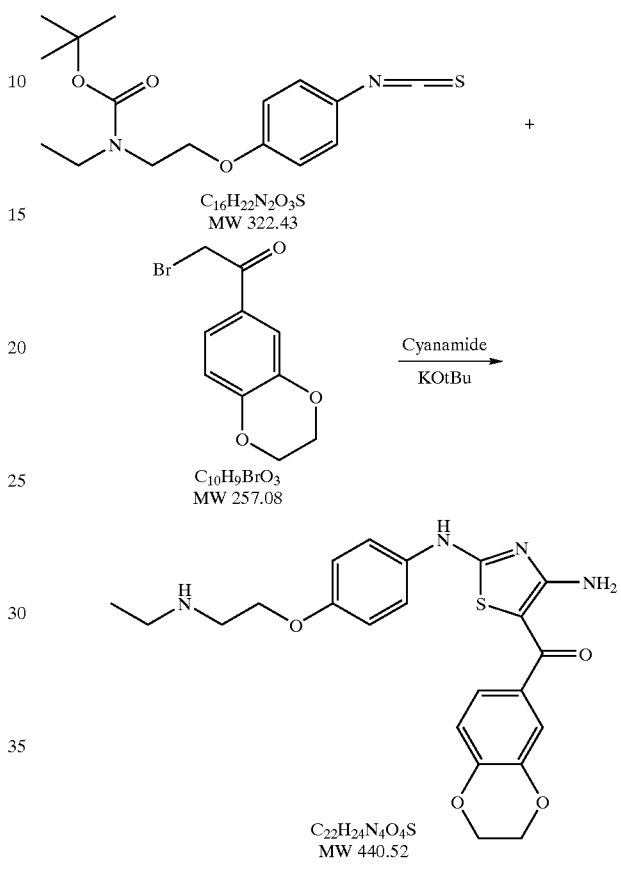

This compound was prepared from cyanamide, ethyl-[2-(4-isothiocyanato-phenoxy)-ethyl]-carbamic acid tert-butyl ester of Example 129D and 2-bromo-1-(2,3-dihydro-benzo[1,4]dioxin-6-yl)ethanone (Maybridge Chemical) following a procedure similar to Example 133. Mass spectrum (ES) MH⁺=441.

Example 135

Isopropyl-[2-(4-isothiocyanato-phenoxy)-ethyl]-carbamic Acid tert-Butyl Ester

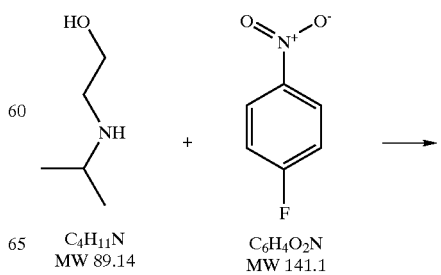

C₄H₁₁N
MW 89.14

C₆H₄O₂N
MW 141.1

→

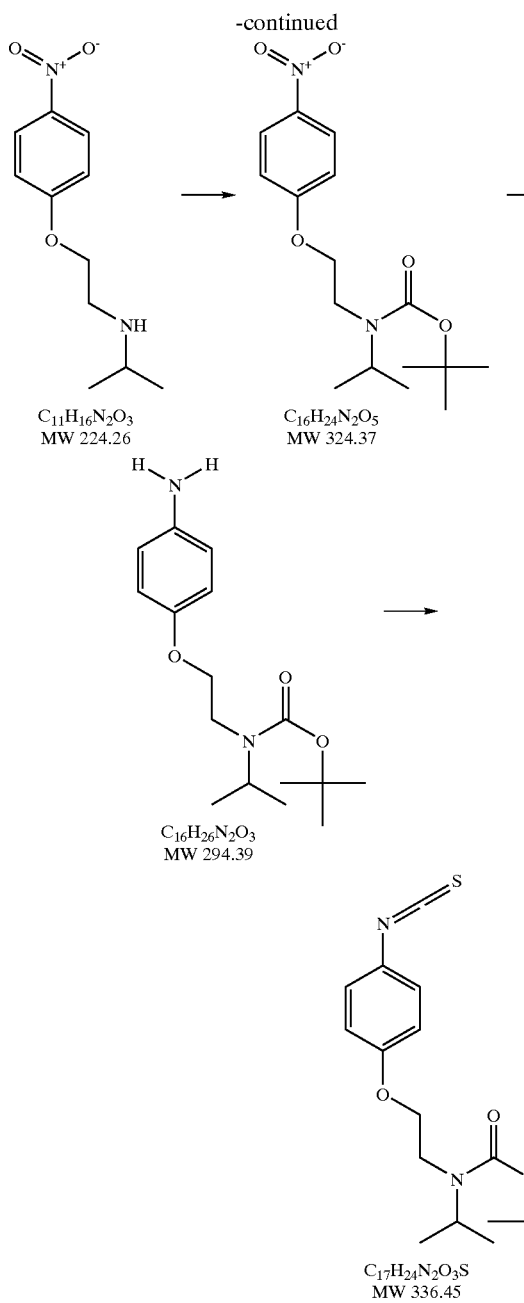

A. Isopropyl-[2-(4-nitro-phenoxy)-ethyl]-amine

2-Isopropylamino-ethanol (5 g, 48 mmol) (Fluka) was added to a cooled (−5° C.) mixture of sodium hydride (5 g, 48 mmol) in N,N-dimethylformamide (200 mL) and stirred for 10 minutes at 0° C., 30 minutes at room temperature, and then 30 minutes at 450° C. After cooling to −1° C., 1-fluoro-4-nitrobenzene (8.21 g, 57.6 mmol) (Aldrich) was added and stirred for 20 minutes at −10° C. and 90 minutes at room temperature. The reaction was adjusted to pH 2 with 6N hydrochloric acid and the mixture extracted with ether (4×100 mL). The aqueous layer was adjusted to pH 9 with 4N sodium hydroxide and extracted with ethyl acetate. (4×100 mL), dried (Na$_2$SO$_4$), filtered and the solution concentrated in vacuo and the residue was dried under high vacuum to give 6.14 g (57%) of isopropyl-[2-(4-nitro-phenoxy)-ethyl]-amine.

B. Isopropyl-[2-(4-nitro-penoxy)-ethyl]-carbamic Acid tert-Butyl Ester

To a solution of isopropyl-[2-(4-nitro-phenoxy)-ethyl]-amine (from step A above) (6.1 g, 27.4 mmol) in dioxane (50 mL) was added diisopropyl-ethylamine (3.89 g, 30.1 mmol) and di-tert-butyl dicarbonate (5.98 g, 27.4 mmol) (Fluka). The mixture was stirred for 3 hours at room temperature, poured into 1 L of ice/water, stirred for 90 minutes, and the solids collect by filtration, washed with water and dried under high vacuum to give 8.3 g (94%) of isopropyl-[2-(4-nitro-penoxy)-ethyl]-carbamic acid tert-butyl ester.

C. [2-(4-Amino-phenoxy)-ethyl]-isopropyl-carbamic Acid tert-Butyl Ester

A solution of isopropyl-[2-(4-nitro-penoxy)-ethyl]-carbamic acid tert-butyl ester (8.3 g, 25.58 mmol) (from step B above) and 600 mg of 10% palladium-on-carbon in ethanol (100 mL) was hydrogenated at 20 psi in a Parr shaker for 1 hour. The mixture was filtered through Celite™ and the solvent evaporated to give 7.46 g (99%) of [2-(4-amino-phenoxy)-ethyl]-isopropyl-carbamic acid tert-butyl ester.

D. Isopropyl-[2-(4-isothiocyanato-phenoxy)-ethyl]-carbamic Acid tert-Butyl Ester Thiocarbonyldiimidazole (3.64 g, 20.44 mmol) (Aldrich) was dissolved in N,N-dimethylformamide (3 mL) and the solution was cooled to −15° C. A solution [2-(4-amino-phenoxy)-ethyl]-isopropyl-carbamic acid tert-butyl ester (from step C above) in N,N-dimethylformamide (7 mL) was added dropwise and stirred at room temperature for 90 minutes. The mixture was poured into ice/water (1500 mL) and extracted with ether (4×250 mL). The ether was dried (Na$_2$SO$_4$) and concentrated in vacuo to give 6.5 g, (95%) isopropyl-[2-(4-isothiocyanato-phenoxy)-ethyl]-carbamic acid tert-butyl ester. Mass spectrum (ES) MH$^+$=367.

Example 136

[4-Amino-2-[4-(2-isopropylamino-ethoxy)-phenylamino]thiazol-5-yl]-(2,3-dihydro-benzo[1,4]dioxin-6-yl)-methanone

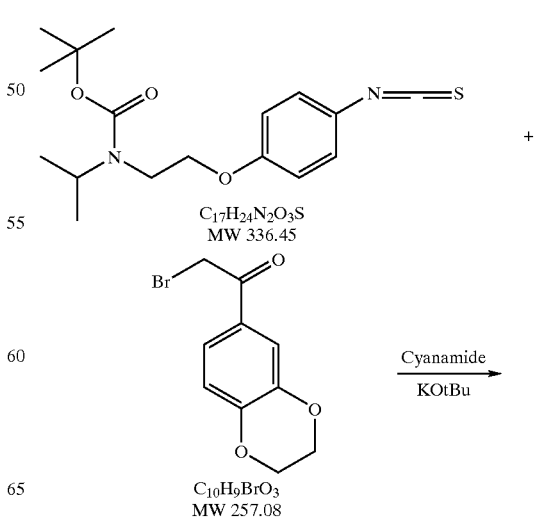

-continued

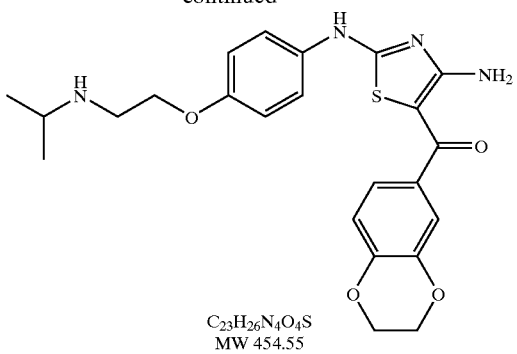

This compound was prepared from cyanamide, isopropyl-[2-(4-isothiocyanato-phenoxy)-ethyl]-carbamic acid tert-butyl ester of Example 135 and 2-bromo-1-(2,3-dihydro-benzo[1,4]dioxin-6-yl)ethanone (Maybridge Chemical) following a procedure similar to Example 130. Mass spectrum (ES) MH$^+$=455.

Example 137

[4-Amino-2-[4-(2-isopropylamino-ethoxy)-phenylamino]-thiazol-5-yl]-benzo[1,3]dioxol-5-yl-methanone

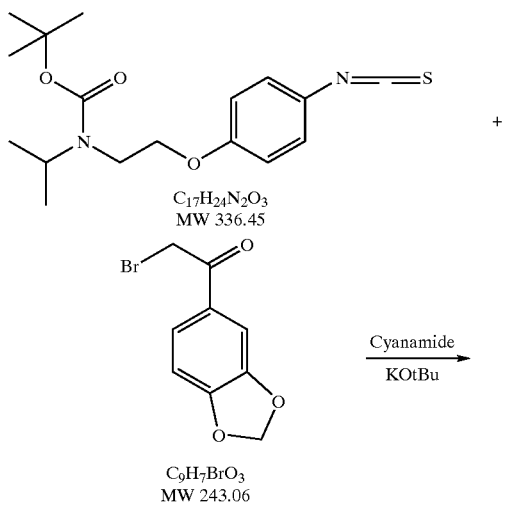

This compound was prepared from cyanamide, isopropyl-[2-(4-isothiocyanato-phenoxy)-ethyl]-carbamic acid tert-butyl ester of Example 135 and 1-benzo[1,3]dioxol-5-yl-2-bromo-ethanone (of Example 132) following a procedure similar to Example 130. Mass spectrum (ES) MH$^+$=441.

Example 138

2-Bromo-1-(3-methyl-2,3-dihydro-benzofuran-5-yl)-ethanone (33905-44)

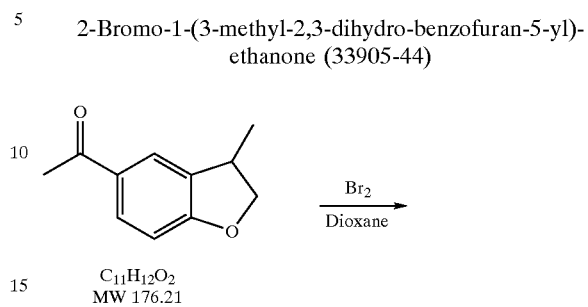

To a stirred solution of 1-[3-methyl-2,3-dihydro-benzofuran-5-yl]ethanone (1.4 g, 7.94 mmol) (Maybridge Chemical) in dioxane (10 mL) was added dropwise a solution of bromine (1.52 g, 9.5 mmol) in dioxane (30 mL). After stirring 15 minutes the mixture was concentrated in vacuo and the residue chromatographed on silica gel (2:1 hexane-dichloromethane) to provide 375 mg (19%) of 2-bromo-1-(3-methyl-2,3-dihydro-benzo-furan-5-yl)ethanone.

Example 139

[4-Amino-2-[4-(2-diethylamino-ethoxy)-phenylamino]-thiazol-5-yl]-(3-methyl-2,3-dihydro-benzofuran-5-yl)-methanone

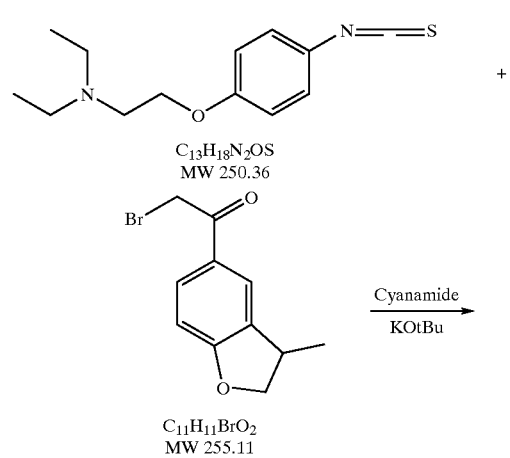

153

-continued

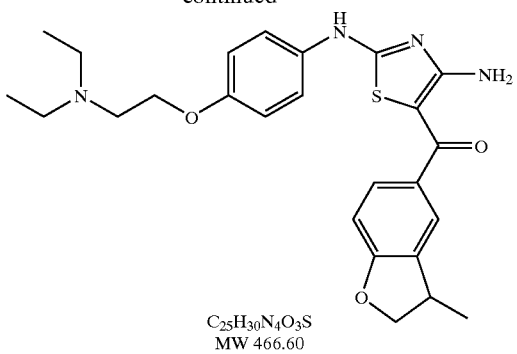

C<sub>25</sub>H<sub>30</sub>N<sub>4</sub>O<sub>3</sub>S
MW 466.60

This compound was prepared from cyanamide, diethyl-[2-(4-isothiocyanato-phenoxy-ethyl]-amine of Example 122 and 2-bromo-1-(3-methyl-2,3-dihydro-benzofuran-5-yl) ethanone of Example 138 following a procedure similar to Example 130. Mass spectrum (ES) MH$^+$=467.

Example 140

[4-Amino-2-[4-(2-pyrrolidin-1-yl-ethoxy)-phenylamino]-thiazol-5-yl]-(3-methyl-2,3-dihydro-benzofuran-5-yl)-methanone

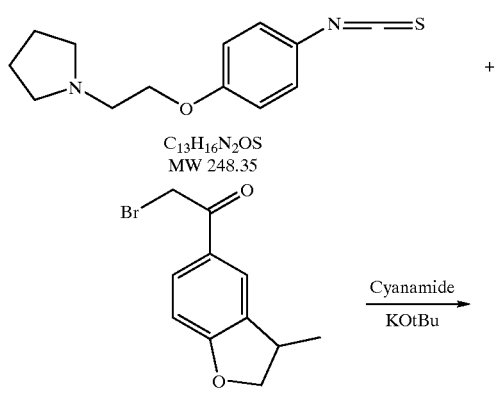

This compound was prepared from cyanamide, 1-[2-(4-Isothiocyanato-phenoxy)-ethyl]-pyrrolidine (from Example 5) and 2-bromo-1-(3-methyl-2,3-dihydro-benzofuran-5-yl) ethanone (from Example 138) following a procedure similar to Example 130. Mass spectrum (ES) MH$^+$=465.

154

Example 141

2-Bromo-1-(2,3-dihydro-benzofuran-5-yl)-ethanone

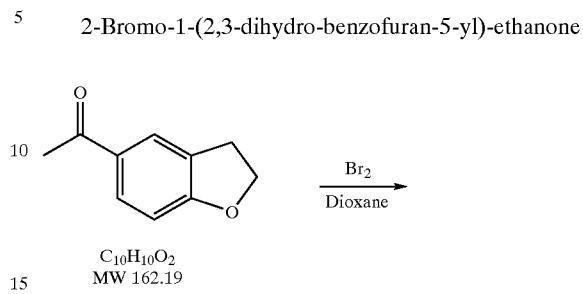

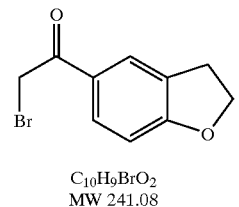

C<sub>10</sub>H<sub>9</sub>BrO<sub>2</sub>
MW 241.08

To a stirred solution of 1-(2,3-dihydro-benzofuran-5-yl)-ethanone (2.5 g, 15.4 mmol) (Lancaster) in dioxane (2 mL) was added dropwise a solution of bromine (2.96 g, 18.5 mmol) in dioxane (60 mL). After stirring 15 minute the mixture was concentrated in vacuo and the residue was purified by chromatography on silica gel (2:1 hexane-dichloromethane) to provide 1.41 g (38%) of 2-bromo-1-(2,3-dihydro-benzofuran-5-yl)-ethanone.

Example 142

[4-Amino-2-[4-(2-diethylamino-ethoxy)-phenylamino]-thiazol-5-yl]-(2,3-dihydro-benzofuran-5-yl)-methanone

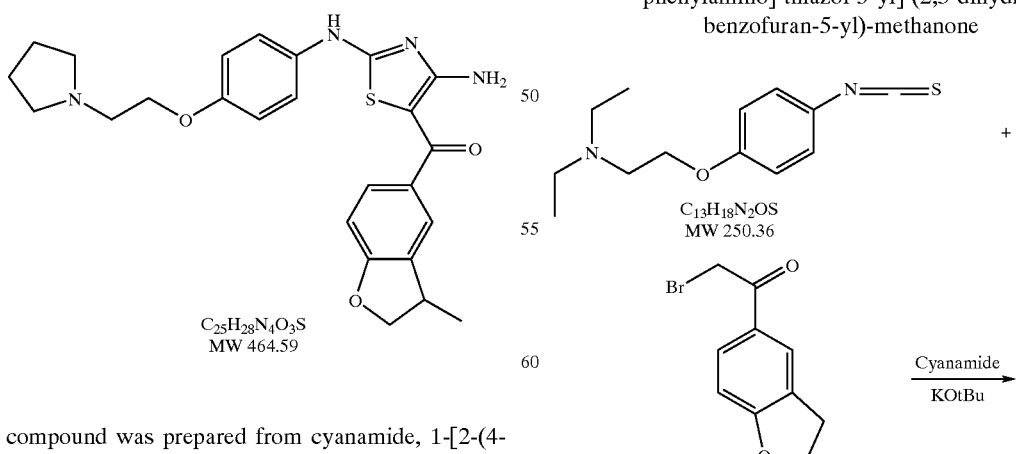

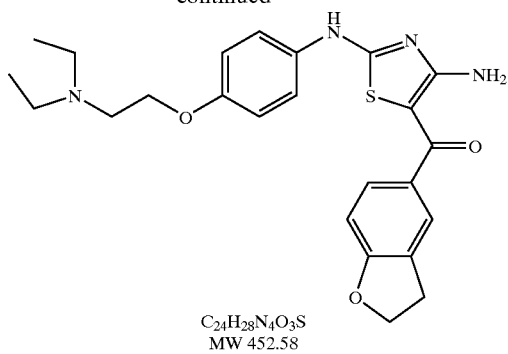

This compound was prepared from cyanamide, diethyl-[2-(4-isothiocyanato-phenoxy-ethyl]-amine of Example 122 and 2-bromo-1-(2,3-dihydro-benzofuran-5-yl)ethanone (from Example 141) following a procedure similar to Example 126. Mass spectrum (ES) MH$^+$=455.

Example 143

[4-Amino-2-[4-(2-ethylamino-ethoxy)-phenylamino]-thiazol-5-yl]-(2,3-dihydro-benzofuran-5-yl)-methanone

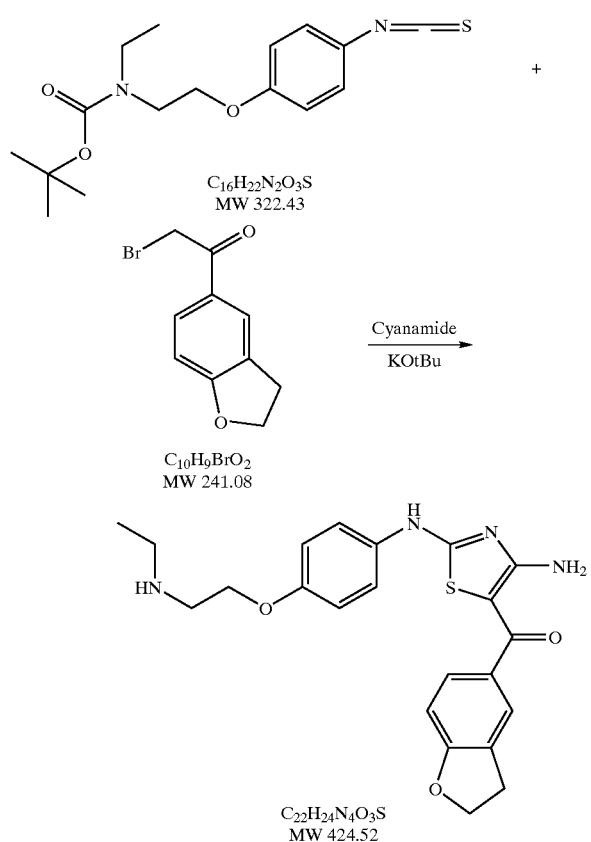

This compound was prepared from cyanamide, ethyl-[2-(4-isothiocyanato-phenoxy)-ethyl]-carbamic acid tert-butyl ester of Example 129 and 2-bromo-1-(2,3-dihydro-benzofuran-5-yl)ethanone (from Example 141) following a procedure similar to Example 132. Mass spectrum (ES) MH$^+$=425.

Example 144

[4-Amino-2-[4-(2-dimethylaminoethoxy)-phenylamino]-thiazol-5-yl]-(3-methoxy-phenyl)-methanone

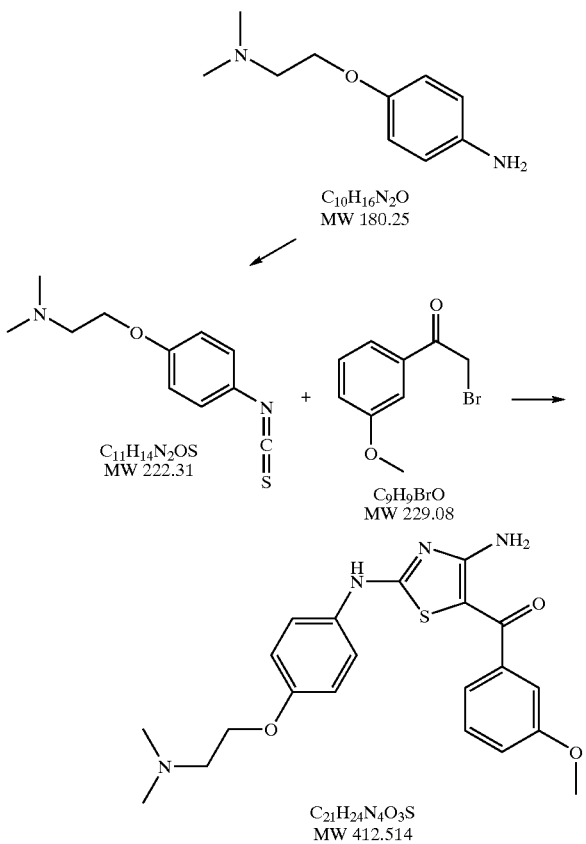

A. [2-(4-Isothiocyanato-phenoxy)-ethyl]-dimethylamine

A solution of 4-(2-dimethylamino-ethoxy)-phenylamine (Can. J. Chem., 62, 2015, (1984)) (4.5 g, 25 mmol) in dimethylformamide (20 mL) was added over about 20 minutes to a cold (−15° C.) solution of thiocarbonyldiimidizole (4.9 g, 27.5 mmol) in dimethylformamide (50 mL). The mixture was stirred cold for 30 minutes and then stirred at room temperature for one hour. The reaction mixture was poured into ice water, extracted with ether, and the organic solution washed in turn with water and brine. The dried (Na$_2$SO$_4$) solution was evaporated and the residue was dissolved in warm hexane, treated with activated charcoal, filtered and evaporated to give 4.7 g (85%) of [2-(4-isothiocyanato-phenoxy)-ethyl]-dimethylamine as a colorless oil. Mass spectrum (ES) MH$^+$=223.

B. [4-Amino-2-[4-(2-dimethylaminoethoxy)-phenylamino]-thiazol-5-yl]-(3-methoxy-phenyl)-methanone To a stirred mixture of [2-(4-isothiocyanato-phenoxy)-ethyl]-dimethylamine (0.6 g, 2.7 mmol) (from Step A) and cyanamide (0.123 g, 2.95 mmol) in acetonitrile (10 mL) and tert-butanol (10 mL), a solution of potassium tert-butoxide (2.7 mL, 1.0 M in tert-BuOH) was added. After 30 minutes at room temperature, 2-bromo-3'-methoxyacetophenone was added. The reaction mixture was stirred at room temperature for 1 hour and then refluxed for 1 hour. The chilled reaction mixture was diluted with ether and excess anhydrous hydrochloric acid/ether solution was added. The solids were filtered, washed with ether and then dissolved in dichloromethane/aqueous sodium bicarbonate. The dried ($Na_2SO_4$) organic solution was diluted with toluene (25 mL), concentrated, and refluxed to remove dichloromethane, The cooled mixture was diluted with hexane and filtered to give 0.47 g (42%) of [4-amino-2-[4-(2-dimethylaminoethoxy)-phenylamino]-thiazol-5-yl]-(3-methoxy-phenyl)-methanone as a yellow solid, mp 130° C. (dec). Mass spectrum (ES) $MH^+$=413.

Example 145

[4-Amino-2-[4-(2-diethylaminoethoxy)-phenylamino]-thiazol-5-yl]-(3-methoxy-phenyl)-methanone

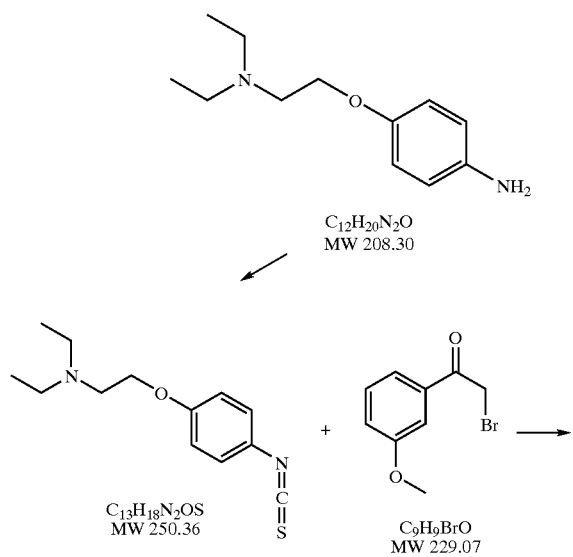

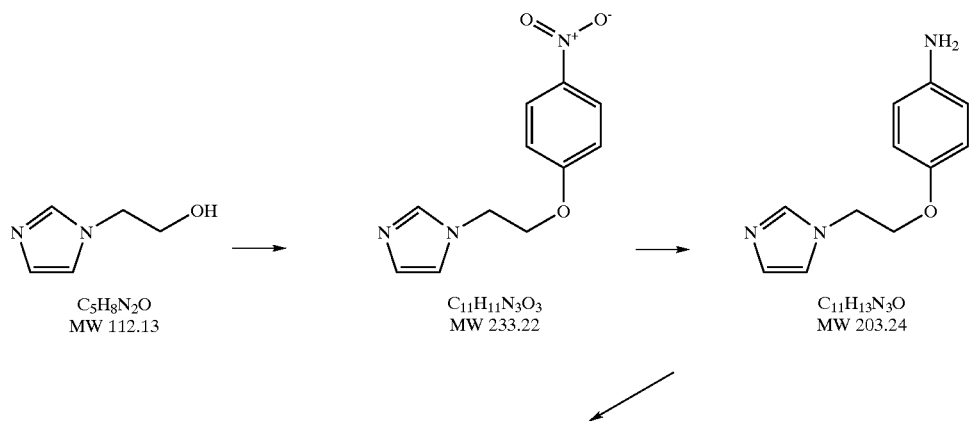

$C_{23}H_{28}N_4O_3S$
MW 440.57

In a similar manner to Example 143, 4-(2-diethylamino-ethoxy)-phenylamine (Chem. Ber., 72, 1333, (1939)) was converted to [2-(4-isothiocyanato-phenoxy)-ethyl]-diethylamine (Mass spectrum (ES) $MH^+$=251). The resulting isothio-cyanate was treated with 2-bromo-3'-methoxyacetophenone (Aldrich) to prepare [4-amino-2-[4-(2-diethylaminoethoxy)-phenylamino]-thiazol-5-yl]-(3-methoxy-phenyl)-methanone. After the addition of the reagents, stirring for 1 hour at room temperature and 15 minutes at reflux, the cooled reaction mixture was poured into aqueous sodium carbonate solution and extracted with ethyl acetate. The organic solution was dried ($Na_2SO_4$) evaporated and chromatographed on silica gel. The product was obtained by elution with methanol/triethyl-amine/dichloro-methane (2:2:96) and crystallized from dichloromethane/-ether/hexane to give 60% yield of [4-amino-2-[4-(2-diethylaminoethoxy)-phenylamino]-thiazol-5-yl]-(3-methoxy-phenyl)-methanone as a yellow solid, mp 118–123° C. Mass spectrum (ES) $MH^+$=441.

Example 146

[4-Amino-2-[4-(2-imidazol-1-yl-ethoxy)-phenylamino]-thiazol-5-yl]-(3-methoxy-phenyl)-methanone

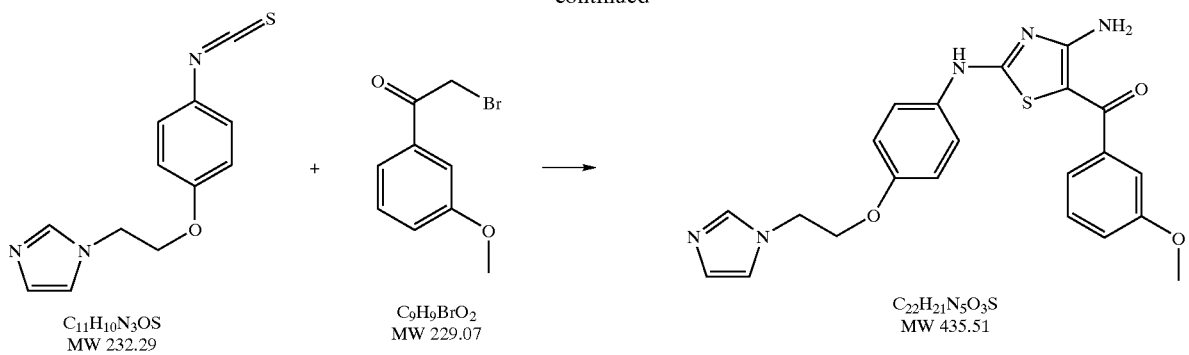

A. 1-[2-(4-Nitro-phenoxy)ethyl]-1H-imidazole

A stirred solution of 2-imidazol-1-yl-ethanol (J. Med. Chem., 39(10), 1991, (1996)) (3.9 g, 35 mmol) in dimethylformamide (75 mL) at 15° C. was treated portionwise with 60% sodium hydride (0.84 g, 35 mmol) and stirred at room temperature for 30 minutes. The mixture was rechilled and 4-fluoro-1-nitrobenzene (4.93 g, 35 mmol) added dropwise. The mixture was stirred cold for 30 minutes and heated at 35–40° C. for 30 minutes. A little water was added and the volatiles were removed on a pump. The residue was diluted with water, extracted with dichloromethane, washed with brine, dried ($Na_2SO_4$) and evaporated. Chromatography on silica gel and eluting with methanol/triethyl-amine/dichloromethane (2:2:96) and crystallization of the purified product from dichloromethane/ether gave 3.4 g (42%) of 1-[2-(4-nitro-phenoxy)ethyl]-1H-imidazole as a colorless solid, mp 55–57° C. Mass spectrum (LR-APCI) $MH^+$=234.

B. 4-(2-Imidazol-1-yl-ethoxy)-phenylamine

Hydrogenation of the nitro compound (Step A above) in ethanol with 10% palladium on carbon at 2 atmospheres pressure gave, after filtration, evaporation, and crystallization from dichloromethane/ether, 75% yield of 4-(2-imidazol-1-yl-ethoxy)-phenylamine as a light orange solid, mp 93–94° C. Mass spectrum (LR-APCI) $MH^+$=203.

C. 1-[2-(4-Isothiocyanato-phenoxy)-ethyl]-1H-imidazole

In a similar manner as described in Example 144, Step A, 4-(2-imidazol-1-yl-ethoxy)-phenylamine (from Step B above) was converted, in 81% yield, to 1-[2-(4-isothiocyanato-phenoxy)-ethyl]-1H-imidazole as a colorless solid, mp 81–83 (Mass spectrum (LR-APCI) $MH^+$=245).

D. [4-Amino-2-[4-(2-imidazol-1-yl-ethoxy)-phenylamino]thiazol-5-yl]-(3-methoxy-phenyl)-methanone In a similar manner as described in Example 144, Step B, 1-[2-(4-isothiocyanato-phenoxy)-ethyl]-1H-imidazole (from Step C above) and 2-bromo-3'-methoxy-acetophenone were used to prepare, in 61% yield, [4-amino-2-[4-(2-imidazol-1-yl-ethoxy)-phenylamino]thiazol-5-yl]-(3-methoxy-phenyl)-methanone, mp 185–190, after chromatography and crystallization from methanol/ethyl acetate. Mass spectrum (ES) $MH^+$=436.

Example 147

[4-Amino-2-[4-(3-amino-propoxy)-phenylamino]-thiazol-5-yl]-(3-fluoro-4-methoxy-phenyl)-methanone

A. (3-[4-[4-Amino-5-(3-fluoro-4-methoxy-benzoyl)-thiazol-2-ylamino]-phenoxy]-propyl)-carbamic Acid tert-Butyl Ester

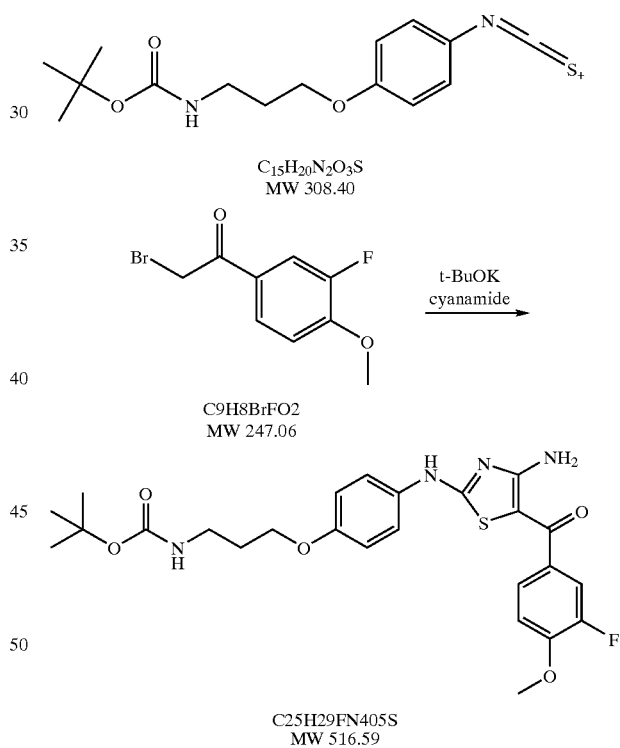

To a solution of cyanamide (23.2 mg, 0.546 mmol) (Aldrich) in acetonitrile (2.5 mL) and tert-butanol (2.5 mL) was added [3-(4-Isothiocyanatophenoxy)-propyl]carbamic acid tert-butyl ester (from Example 64; 156.9 mg, 0.508 mmol) followed by a solution of potassium tert-butoxide (0.56 mL, 1 M in tert-BUOH). After 30 minutes at room temperature, 2-bromo-1-(3-fluoro-4-methoxy-phenyl)ethan-1-one (125.8 mg, 0.509 mmol) (Maybridge Chemical) was added. The reaction mixture was stirred at room temperature for 1 hour and then heated at 75° C. for 2 hours. The resulting mixture was poured into water (10 mL). The product was collected by filtration, washed with diethyl ether and dried in vacuo to provide (3-[4-[4-Amino-5-(3-fluoro-4-methoxy-benzoyl)-thiazol-2-ylamino]-phenoxy]-propyl)-carbamic acid tert-butyl ester (260.1 mg, 99% yield). HRMS, Observed: 517.1921; Calcd for M+H$^+$ :517.1916.

B. [4-Amino-2-[4-(3-amino-propoxy)-phenylamino]-thiazol-5-yl]-(3-fluoro-4-methoxy-phenyl)-methanone

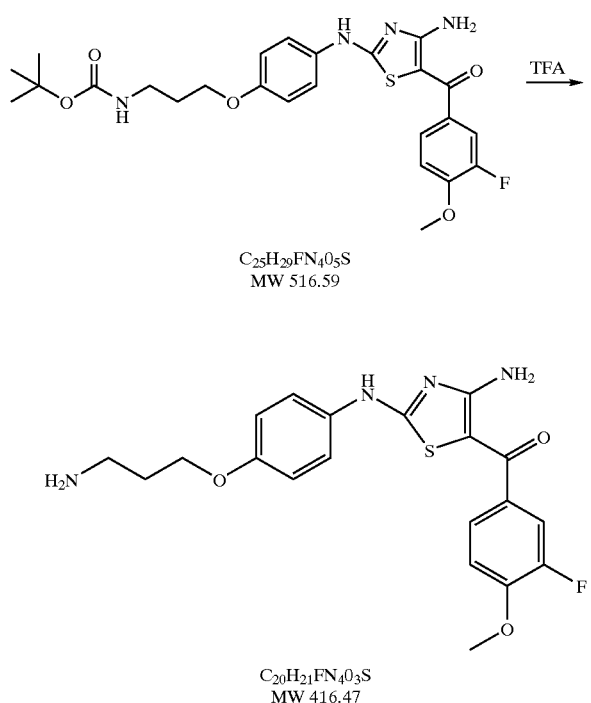

To a solution of (3-[4-[4-Amino-5-(3-fluoro-4-methoxy-benzoyl)-thiazol-2-ylamino]-phenoxy]-propyl)-carbamic acid tert-butyl ester (254 mg) (from Step A above) in dichloromethane (6 mL) at 0° C. was added trifluoroacetic acid (3 mL). After stirring for 1 hour, the mixture was concentrated and the residue was purified on HPLC to give [4-Amino-2-[4-(3-aminopropoxy)-phenylamino]-thiazol-5-yl]-(3-fluoro-4-methoxy-phenyl)-methanone (180.9 mg, 88% yield) as a light yellow solid. HRMS, Observed: 417.1394; Calcd for M+H$^+$: 417.1391.

Example 148

[4-Amino-2-[4-(3-ethylamino-propoxy)-phenylamino]-thiazol-5-yl]-(3-fluoro-4-methoxy-phenyl)methanone A. (3-[4-[4-Amino-5-(3-fluoro-4-methoxy-benzoyl)-thiazol-2-ylamino]-phenoxy]-propyl)-ethyl-carbamic Acid tert-Butyl Ester

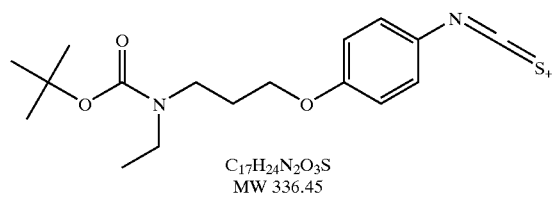

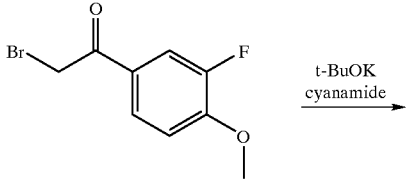

To a solution of cyanamide (21.2 mg, 0.499 mmol) (Aldrich) in acetonitrile (2.5 mL) and tert-butanol (2.5 mL) was added ethyl-[3-(4-isothiocyanato-phenoxy)propyl] carbamic acid tert-butyl ester (153.8 mg, 0.4571 mmol from Example 66, step C) followed by a solution of potassium tert-butoxide (0.50 mL, 1 M in tert-butanol) (Aldrich). After 30 minutes at room temperature, 2-bromo-1-(3-fluoro-4-methoxyphenyl)ethan-1-one (112.5 mg, 0.4553 mmol) (Maybridge Chemical) was added. The reaction mixture was stirred at room temperature for 1 hour and then heated at 75° C. for 2 hours. The resulting mixture was poured into water (10 mL). The product was collected by filtration, washed with diethyl ether and dried in vacuo to provide (3-[4-[4-Amino-5-(3-fluoro-4-methoxy-benzoyl)-thiazol-2-ylamino]-phenoxy]-propyl)-ethyl-carbamic acid tert-butyl ester (245.1.6 mg, 99% yield). HRMS, observed: 545.2230; Calcd for M+H: 545.2229.

B. [4-Amino-2-[4-(3-ethylamino-propoxy)-phenylamino]-thiazol-5-yl]-(3-fluoro-4-methoxy-phenyl)-methanone

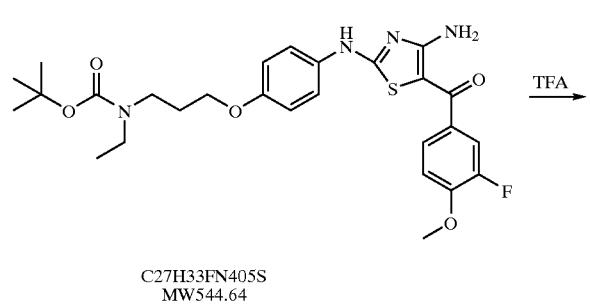

-continued

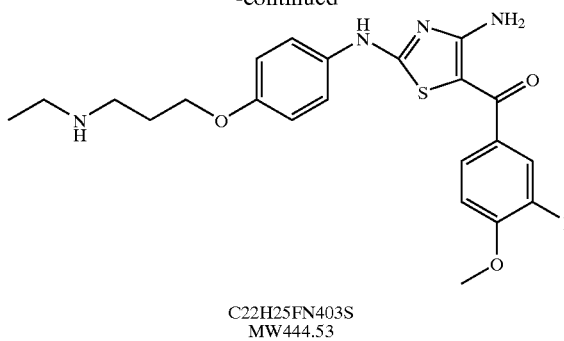

C22H25FN4O3S
MW444.53

To a solution of (3-[4-[4-Amino-5-(3-fluoro-4-methoxybenzoyl)-thiazol-2-ylamino]-phenoxy]-propyl)-ethyl-carbamic acid tert-butyl ester (220.5 mg) (from Step A above) in dichloromethane (6 mL) at 0° C. was added trifluoroacetic acid (3 mL). After stirring for 1 hour, the mixture was concentrated and the residue was purified on HPLC to [4-Amino-2-[4-(3-ethylamino-propoxy)-phenylamino]-thiazol-5-yl]-(3-fluoro-4-methoxyphenyl)-methanone (159.8 mg, 89% yield) as a light yellow solid. HRMS, observed: 445.1707; Calcd for M+H: 445.1704.

Example 149

Antiproliferative Activity

The antiproliferative activity of the compounds of the invention is demonstrated below. These activities indicate that the compounds of the present invention are useful in treating cancer, in particular solid tumors such as breast and colon tumors.

Kinase Assays

To determine inhibition of Cdk4, Cdk2 and Cdk1 activity, kinase assays were conducted using FlashPlate™ assays (NEN™-Life Science Products). FlashPlate assays were performed using recombinant human cyclin B-CDK1, human cyclin E-CDK2 or human cyclin D1-CDK4 complexes. GST-cyclinE (GST-cycE), CDK2, GST-cyclinB (GST-cycB), CDK1, GST-CDK4 and cyclin D1 (cycD1) cDNA clones in baculovirus vectors were provided by Dr. W. Harper at the Baylor College of Medicine, Houston, Tex. Proteins were co-expressed in High Five™ insect cells and the complex was purified on glutathione Sepharose resin (Pharmacia, Piscataway, N.J.) as previously described (Harper, J. W. et al. Cell 1993, 75, 805–816). A 6×-Histidine tagged truncated form of retinoblastoma (Rb) protein (amino acid 386–928) was used as the substrate for the cycD1-CDK4, cycB-CDK1 and the cycE-CDK2 assays (the expression plasmid was provided by Dr. Veronica Sullivan, Department of Molecular Virology, Roche Research Centre, Welwyn Garden City, United Kingdom). The Rb protein is a natural substrate for phosphorylation by CDK4, CDK2 and CDK1 (see Herwig and Strauss Eur. J. Biochem. Vol. 246 (1997) pp. 581–601 and the references cited therein).

The expression of the 62 Kd protein was under the control of an IPTG inducible promoter in an M15 E. coli strain. Cells were lysed by sonication and purification was carried out by binding lysates at pH 8.0 to a Ni-chelated agarose column pretreated with 1 mM imidazole. The resin was then washed several times with incrementally decreasing pH buffers to pH 6.0, and eluted with 500 mM imidazole. Eluted protein was dialysed against 20 mM HEPES pH 7.5, 30% glycerol, 200 mM NaCl, and 1 mM DTT. Purified Rb fusion protein stocks were quantitated for protein concentration, aliquoted, and stored at −70° C.

For all three kinase assays reported herein, 96-well Flash-Plates were coated with Rb protein at 10 μg/ml, using 100 μl per well. Plates were incubated at 4° C. overnight or at room temperature for 3 hours on a shaker. To control for nonspecific phosphorylation, one row of wells was coated with 100 μl/well coating buffer (20 mM HEPES, 0.2 M NaCl). Plates were then washed twice with wash buffer (0.01% Tween 20 in phosphate-buffered saline). Compounds to be tested ("test compounds") were added to the wells at 5×final concentration. Reactions were initiated by immediate addition of 40 μl reaction mix (25 mM HEPES, 20 mM $MgCl_2$, 0.002% Tween 20, 2 mM DTT, 1 μM ATP, 4 nM $^{33}$P-ATP) and a sufficient amount of enzyme to give counts that were at least 10-fold above background. Plates were incubated at room temperature on a shaker for 30 minutes. Plates were washed four times with the wash buffer, sealed, and counted on the TopCount scintillation counter (Packard Instrument Co., Downers Grove, Ill.]. The percent inhibition of Rb phosphorylation, which is a measure of the inhibition of CDK activity, was determined according to the following formula:

$$100 \times \frac{1 - \text{test compound} - \text{nonspecific}}{\text{total} - \text{nonspecific}}$$

where "test compound" refers to the average counts per minute of the test duplicates, "nonspecific" refers to the average counts per minute when no CyclinD/Cdk4, etc., was added, and "total" refers to the average counts per minute when no compound was added. The $IC_{50}$ value is the concentration of test compound that reduces by 50% the protein-kinase induced incorporation of the radiolabel under the test conditions described.

The results of the foregoing in vitro experiments (the $IC_{50}$ values) are summarized in Table I below.

Cell Based Assays (Tetrazolium Dye Proliferation Assay)("MTT Assay")

Proliferation was evaluated by the tetrazolium dye assay according to the procedure of Denizot and Lang (Denizot, F. and Lang, R. J Immunol Methods 1986, 89, 271–277). The cell line used was HCT116, a colorectal carcinoma cell line obtained from the American Type Cell Culture Collection (ATCC; Rockville, Md.). The cells were grown in McCoy's 5A medium supplemented with 10% FCS and L-glutamine.

Cells were plated at the appropriate seeding density to give logarithmic growth over the course of the assay in a 96-well tissue culture plate. Plates were incubated overnight at 37° C. in a humidified incubator with 5% $CO_2$. The next day, test compounds were serially diluted to four times the final concentration in the appropriate medium containing 1.2% DMSO. One-fourth final volume of each dilution was added in duplicate to the plates containing cells. The same volume of 1.2% DMSO in medium was added to a row of "control wells" such that the final concentration of DMSO in each well was 0.3%. Wells to which no cells were added served as the "blank." Wells to which no inhibitor was added served as "no inhibitor control." The plates were) returned to the incubator, and at set time points (determined by their growth curves) plates were analyzed as described below.

3-(4,5-dimethylthiazole-2-yl)-2,5-diphenyl-2H-tetrazolium bromide (thiazolyl blue; MTT; Sigma) was added to each well to yield a final concentration of 1 mg/ml.

Plates were returned to the incubator for 2.5–3 hours at 37° C. The MTT-containing medium was removed and the resulting formazan metabolite was solubilized in 100% ethanol with shaking for 15 minutes at room temperature. Absorbance readings were taken in a microtiter plate reader (Dynatech and Molecular Devices plate readers were used interchangeably) at a wavelength of 570 nm with a 650 nm reference. Percent inhibition (% INH) is calculated by subtracting the absorbance of the blank well from all wells, then subtracting the ratio of the average absorbance of each test duplicate (SAVE) by the average of the controls (CAVE) from 1.00. The final number is then multiplied by 100 (% INH=$(1.00-S_{AVE}/C_{AVE})\times100$). The concentration at which 50% inhibition of cell proliferation is obtained (the $IC_{50}$) is determined from the linear regression of a plot of the logarithm of the concentration versus percent inhibition. The $IC_{50}$ values are also shown in Table I below.

TABLE I

This table summarizes the $IC_{50}$s of compounds according to the invention in CDK4, CDK2, and CDK1 kinase assays, and also the $IC_{50}$s in a cell-based ("MTT") assay.

| Example Number | Structure | CDK1 $IC_{50}$ (μM) | CDK2 $IC_{50}$ (μM) | CDK4 $IC_{50}$ (μM) | MTT $IC_{50}$ (μM) |
|---|---|---|---|---|---|
| 6 | 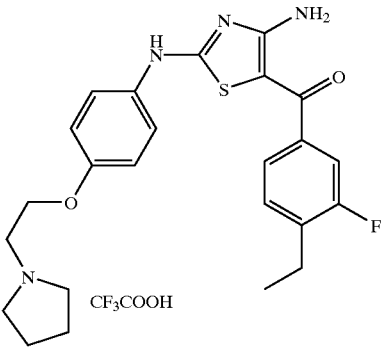 | 1.134 | 3.170 | 0.043 | 3.70 |
| 36 | 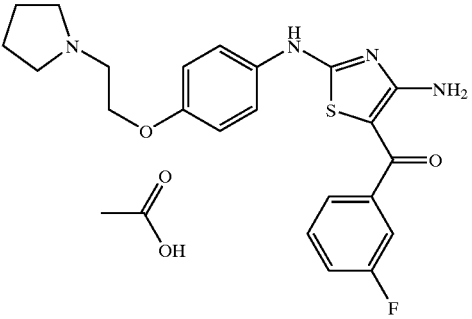 | 0.338 | 0.800 | 0.027 | 0.477 |
| 37 | 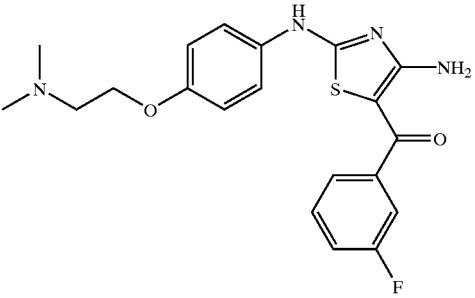 | 0.126 | 0.892 | 0.032 | 0.52 |

TABLE I-continued

This table summarizes the IC$_{50}$s of compounds according to the invention in CDK4, CDK2, and CDK1 kinase assays, and also the IC$_{50}$s in a cell-based ("MTT") assay.

| Example Number | Structure | CDK1 IC$_{50}$ ($\mu$M) | CDK2 IC$_{50}$ ($\mu$M) | CDK4 IC$_{50}$ ($\mu$M) | MTT IC$_{50}$ ($\mu$M) |
|---|---|---|---|---|---|
| 38 | 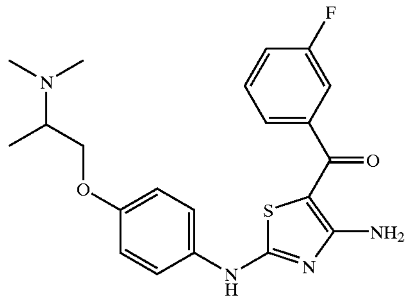 | 0.576 | 1.384 | 0.097 | 0.436 |
| 39 | 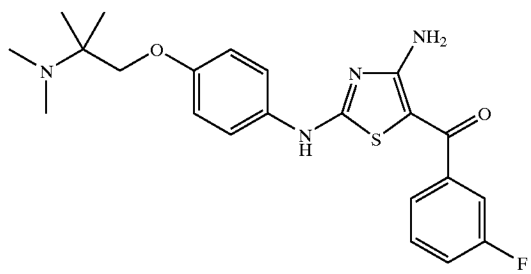 | 0.613 | 0.850 | 0.092 | |
| 40 | Chiral | 0.581 | 1.006 | 0.087 | 0.346 |
| 41 | Chiral | 0.435 | 1.036 | 0.063 | 0.669 |
| 47 | 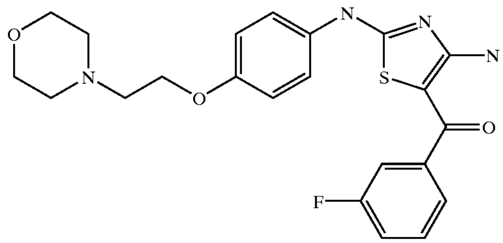 | 0.196 | 1.079 | 0.073 | |

TABLE I-continued

This table summarizes the IC$_{50}$s of compounds according to the invention in CDK4, CDK2, and CDK1 kinase assays, and also the IC$_{50}$s in a cell-based ("MTT") assay.

| Example Number | Structure | CDK1 IC$_{50}$ ($\mu$M) | CDK2 IC$_{50}$ ($\mu$M) | CDK4 IC$_{50}$ ($\mu$M) | MTT IC$_{50}$ ($\mu$M) |
|---|---|---|---|---|---|
| 48 | 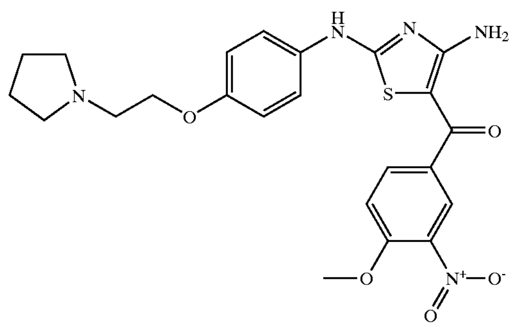 | 1.555 | 3.163 | 0.085 | |
| 49 | 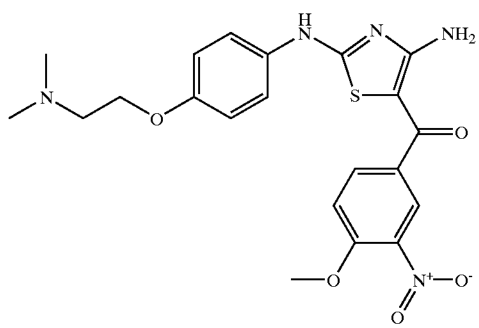 | 2.389 | 4.299 | 0.088 | |
| 50 | 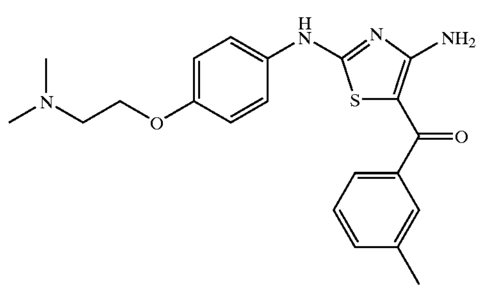 | 1.697 | 3.356 | 0.060 | 1.04 |
| 51 | 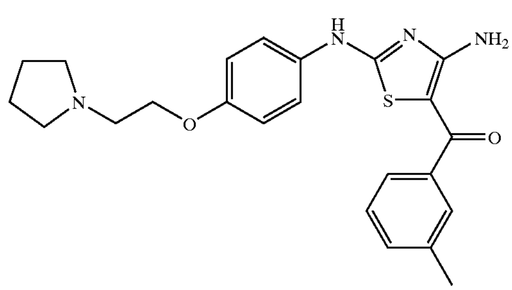 | 1.060 | 2.926 | 0.053 | 0.614 |

TABLE I-continued

This table summarizes the IC$_{50}$s of compounds according to the invention in CDK4, CDK2, and CDK1 kinase assays, and also the IC$_{50}$s in a cell-based ("MTT") assay.

| Example Number | Structure | CDK1 IC$_{50}$ ($\mu$M) | CDK2 IC$_{50}$ ($\mu$M) | CDK4 IC$_{50}$ ($\mu$M) | MTT IC$_{50}$ ($\mu$M) |
|---|---|---|---|---|---|
| 52 | 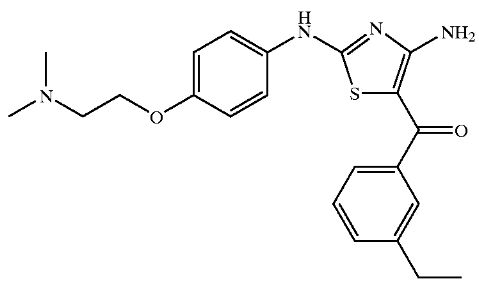 | 3.229 | 1.213 | 0.027 | 0.526 |
| 53 | 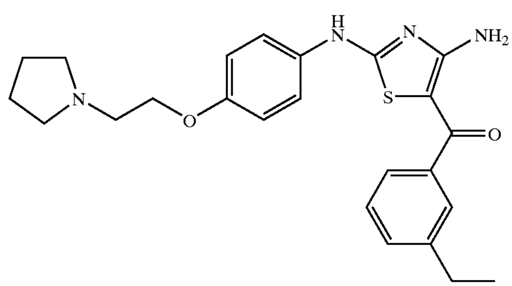 | 2.993 | 0.930 | 0.022 | 0.402 |
| 54 | 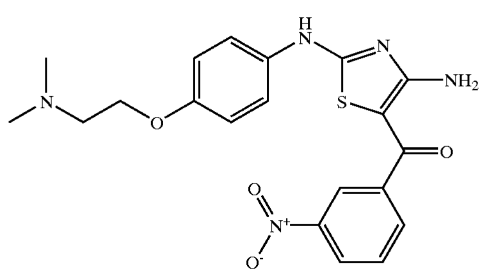 | 0.381 | 1.244 | 0.036 | 1.637 |
| 55 | 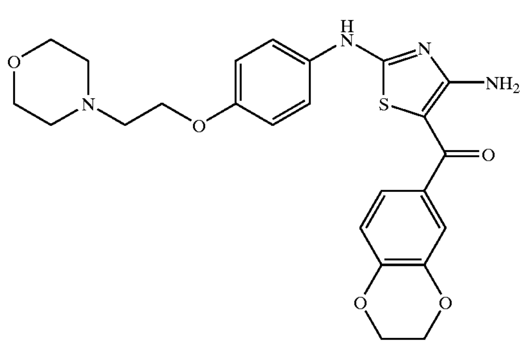 | 0.610 | 3.196 | 0.085 | |

TABLE I-continued

This table summarizes the IC$_{50}$s of compounds according to the invention in CDK4, CDK2, and CDK1 kinase assays, and also the IC$_{50}$s in a cell-based ("MTT") assay.

| Example Number | Structure | CDK1 IC$_{50}$ ($\mu$M) | CDK2 IC$_{50}$ ($\mu$M) | CDK4 IC$_{50}$ ($\mu$M) | MTT IC$_{50}$ ($\mu$M) |
|---|---|---|---|---|---|
| 56 | 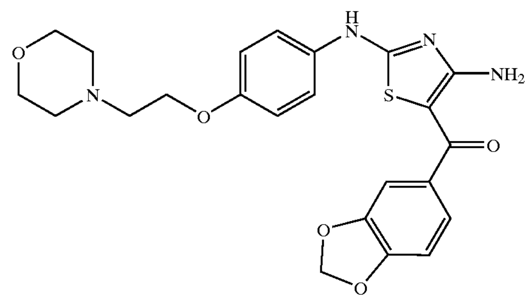 | 0.155 | 3.019 | 0.029 | |
| 57 | 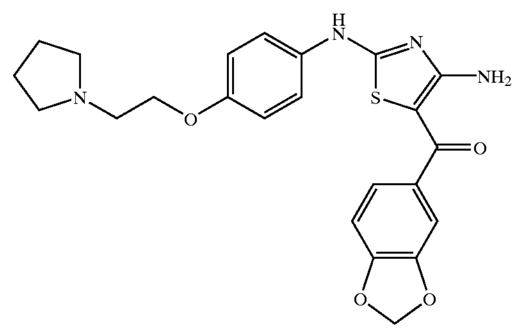 | 0.376 | 4.894 | 0.066 | 2.92 |
| 58 | 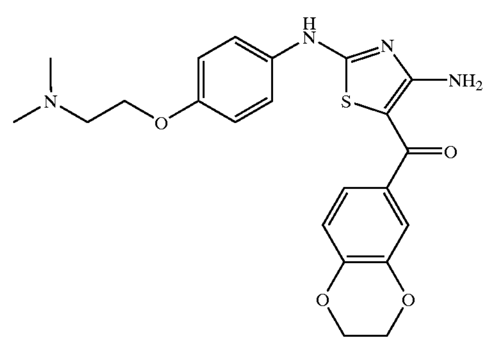 | 0.884 | 10.0 | 0.043 | 3.7 |
| 59 | 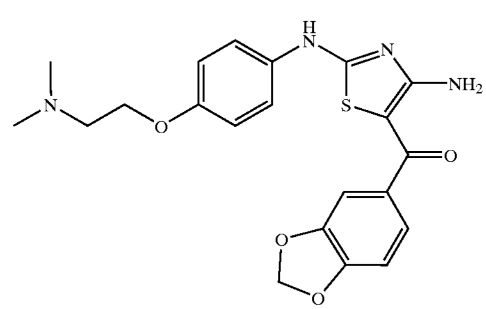 | 0.434 | 5.60 | 0.063 | |

TABLE I-continued

This table summarizes the IC$_{50}$s of compounds according to the invention in CDK4, CDK2, and CDK1 kinase assays, and also the IC$_{50}$s in a cell-based ("MTT") assay.

| Example Number | Structure | CDK1 IC$_{50}$ ($\mu$M) | CDK2 IC$_{50}$ ($\mu$M) | CDK4 IC$_{50}$ ($\mu$M) | MTT IC$_{50}$ ($\mu$M) |
|---|---|---|---|---|---|
| 60 | 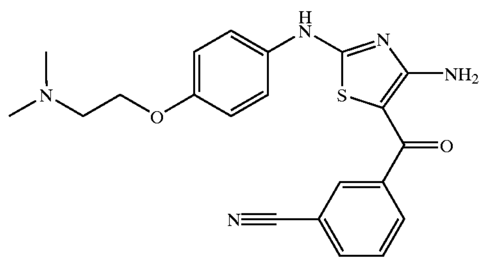 | 0.847 | 1.705 | 0.079 | |
| 61 | 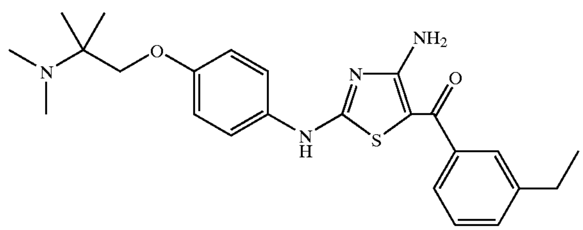 | 1.215 | 1.557 | 0.046 | 0.954 |
| 62 | 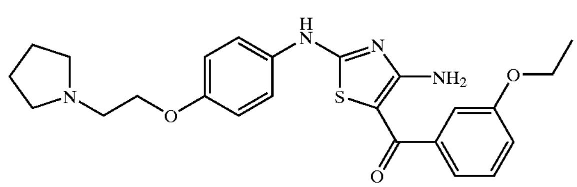 | 1.806 | 4.445 | 0.033 | 1.296 |
| 63 | 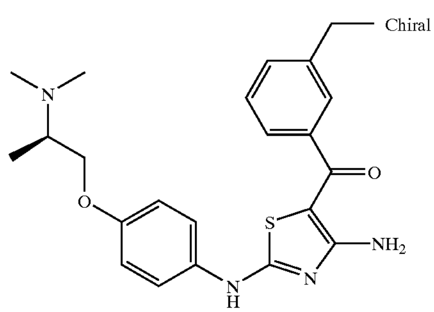 | 2.572 | 1.899 | 0.080 | 0.623 |
| 65 | 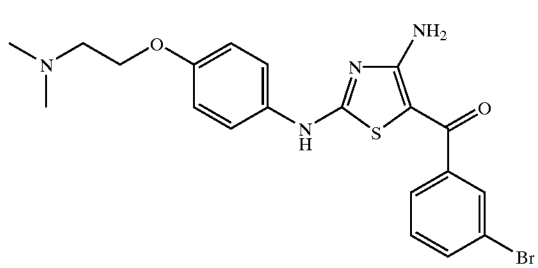 | 1.071 | 1.688 | 0.085 | 3.243 |

TABLE I-continued
This table summarizes the IC$_{50}$s of compounds according to the invention in CDK4, CDK2, and CDK1 kinase assays, and also the IC$_{50}$s in a cell-based ("MTT") assay.
| Example Number | Structure | CDK1 IC$_{50}$ ($\mu$M) | CDK2 IC$_{50}$ ($\mu$M) | CDK4 IC$_{50}$ ($\mu$M) | MTT IC$_{50}$ ($\mu$M) |
|---|---|---|---|---|---|
| 67 | 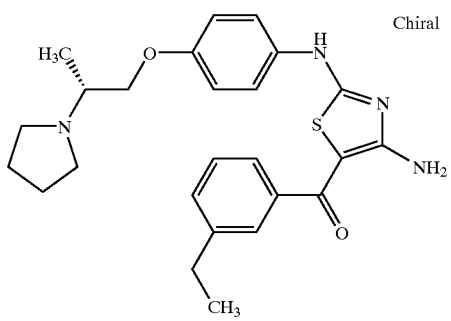 Chiral | 2.759 | 1.483 | 0.070 | 0.846 |
| 68 | 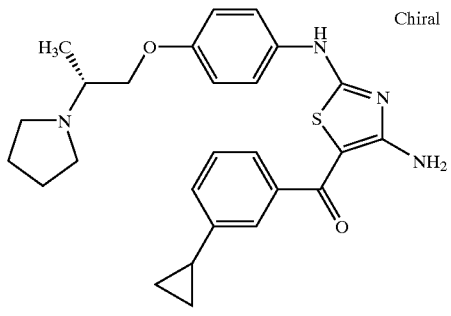 Chiral | 2.070 | 4.537 | 0.051 | 1.208 |
| 69 | 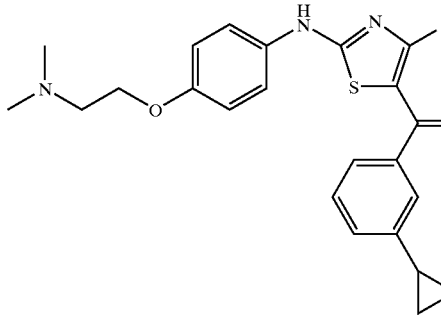 | 1.783 | 2.886 | 0.040 | 1.054 |
| 70 | 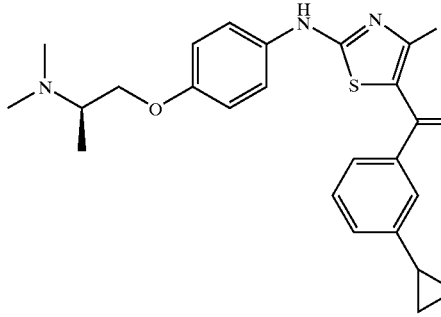 Chiral | 2.956 | 3.139 | 0.038 | 1.93 |

TABLE I-continued
This table summarizes the IC$_{50}$s of compounds according to the invention in CDK4, CDK2, and CDK1 kinase assays, and also the IC$_{50}$s in a cell-based ("MTT") assay.
| Example Number | Structure | CDK1 IC$_{50}$ ($\mu$M) | CDK2 IC$_{50}$ ($\mu$M) | CDK4 IC$_{50}$ ($\mu$M) | MTT IC$_{50}$ ($\mu$M) |
|---|---|---|---|---|---|
| 71 | 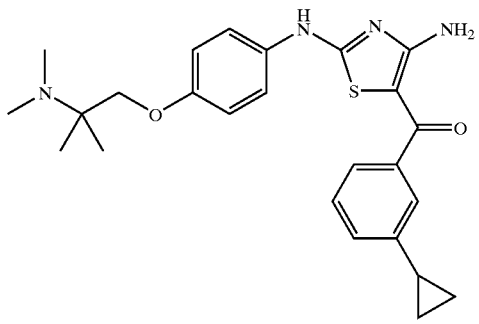 | 3.865 | 2.113 | 0.039 | 2.36 |
| 72 | 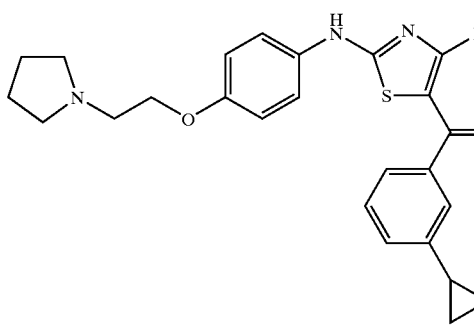 | 1.982 | 1.179 | 0.037 | 1.379 |
| 73 | 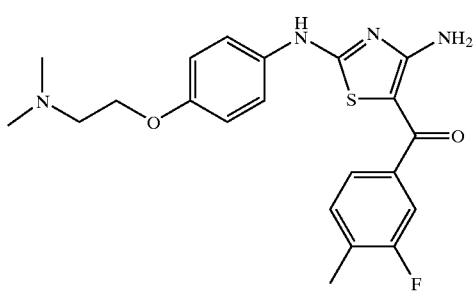 | 1.172 | 5.988 | 0.101 | |
| 74 | 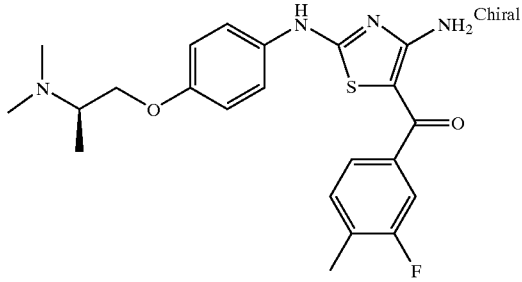 | 0.869 | 5.131 | 0.092 | |

TABLE I-continued

This table summarizes the IC$_{50}$s of compounds according to the invention in CDK4, CDK2, and CDK1 kinase assays, and also the IC$_{50}$s in a cell-based ("MTT") assay.

| Example Number | Structure | CDK1 IC$_{50}$ ($\mu$M) | CDK2 IC$_{50}$ ($\mu$M) | CDK4 IC$_{50}$ ($\mu$M) | MTT IC$_{50}$ ($\mu$M) |
|---|---|---|---|---|---|
| 75 | 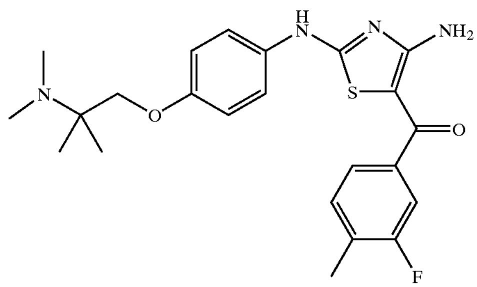 | 0.578 | 4.241 | 0.097 | |
| 76 | 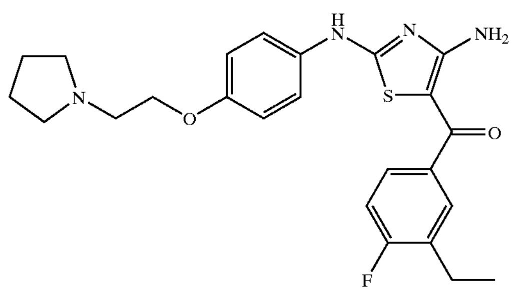 | 3.894 | 10.00 | 0.063 | 3.686 |
| 77 | Chiral | 7.801 | 10.00 | 0.080 | 4.40 |
| 100 | 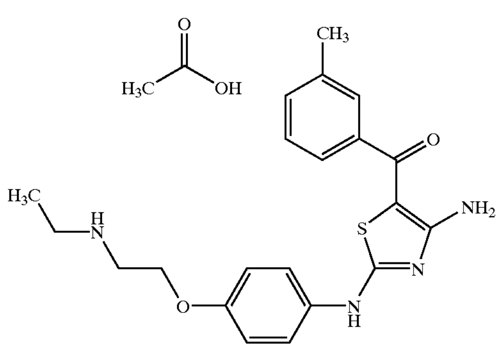 | 0.731 | 1.233 | 0.043 | 0.880 |

TABLE I-continued
This table summarizes the IC$_{50}$s of compounds according to the invention in CDK4, CDK2, and CDK1 kinase assays, and also the IC$_{50}$s in a cell-based ("MTT") assay.
| Example Number | Structure | CDK1 IC$_{50}$ ($\mu$M) | CDK2 IC$_{50}$ ($\mu$M) | CDK4 IC$_{50}$ ($\mu$M) | MTT IC$_{50}$ ($\mu$M) |
|---|---|---|---|---|---|
| 101 | 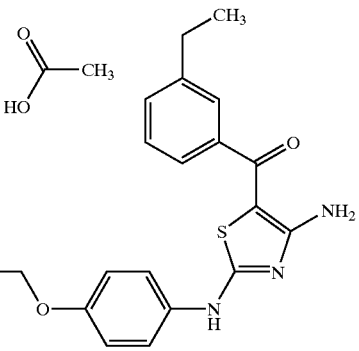 | 0.660 | 1.114 | 0.021 | 0.685 |
| 102 | 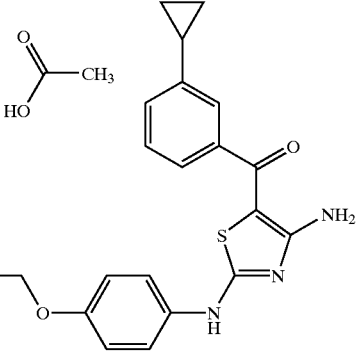 | 0.883 | 1.694 | 0.026 | 0.738 |
| 103 | 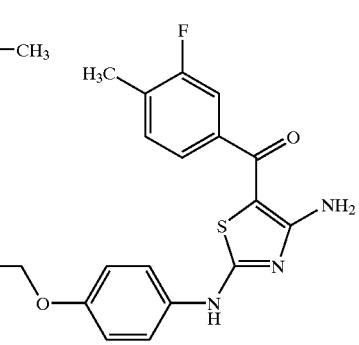 | 0.432 | 1.762 | 0.041 | 1.429 |
| 104 | 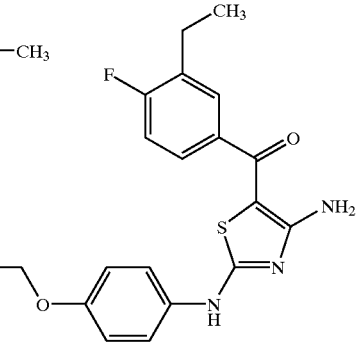 | 3.509 | 3.307 | 0.052 | 2.452 |

TABLE I-continued

This table summarizes the IC$_{50}$s of compounds according to the invention in CDK4, CDK2, and CDK1 kinase assays, and also the IC$_{50}$s in a cell-based ("MTT") assay.

| Example Number | Structure | CDK1 IC$_{50}$ (µM) | CDK2 IC$_{50}$ (µM) | CDK4 IC$_{50}$ (µM) | MTT IC$_{50}$ (µM) |
| --- | --- | --- | --- | --- | --- |
| 105 | 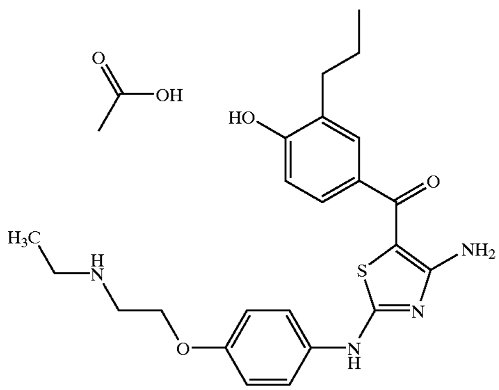 | 0.112 | 0.176 | 0.018 | 0.390 |
| 106 | 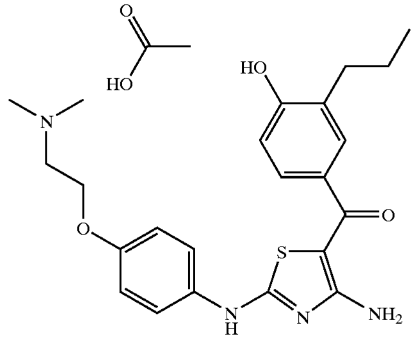 | 0.344 | 0.272 | 0.017 | |
| 107 | 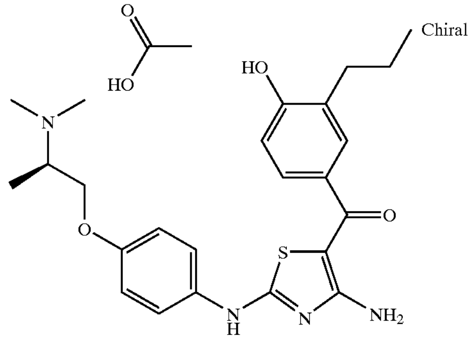 | 0.240 | 0.213 | 0.026 | 0.491 |
| 108 | 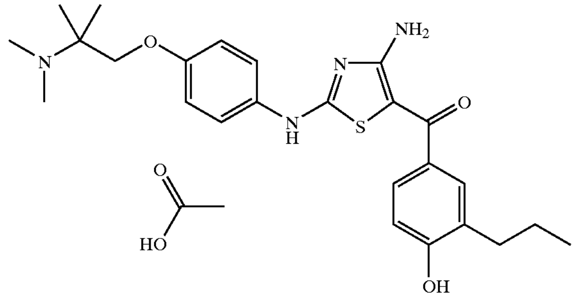 | 0.291 | 0.295 | 0.026 | 0.518 |

TABLE I-continued

This table summarizes the IC$_{50}$s of compounds according to the invention in CDK4, CDK2, and CDK1 kinase assays, and also the IC$_{50}$s in a cell-based ("MTT") assay.

| Example Number | Structure | CDK1 IC$_{50}$ ($\mu$M) | CDK2 IC$_{50}$ ($\mu$M) | CDK4 IC$_{50}$ ($\mu$M) | MTT IC$_{50}$ ($\mu$M) |
|---|---|---|---|---|---|
| 109 | 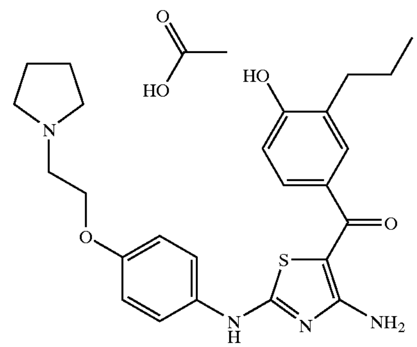 | 0.151 | 0.207 | 0.014 | 0.229 |
| 110 | 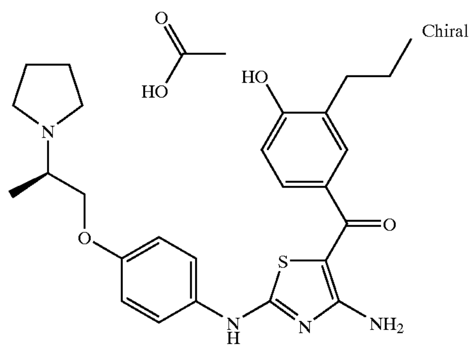 | 0.177 | 0.182 | 0.023 | 0.291 |
| 118 | 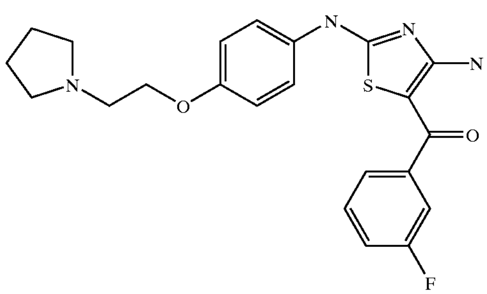 | 0.248 | 0.889 | 0.062 | 0.517 |
| 120 | 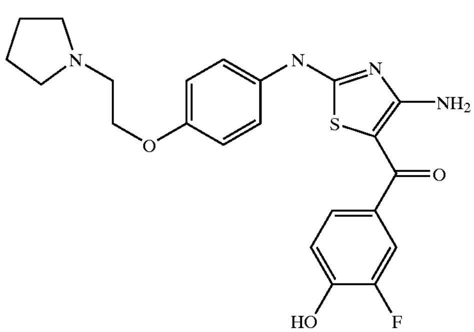 | 0.422 | 0.781 | 0.038 | 1.629 |

TABLE I-continued

This table summarizes the IC$_{50}$s of compounds according to the invention in CDK4, CDK2, and CDK1 kinase assays, and also the IC$_{50}$s in a cell-based ("MTT") assay.

| Example Number | Structure | CDK1 IC$_{50}$ ($\mu$M) | CDK2 IC$_{50}$ ($\mu$M) | CDK4 IC$_{50}$ ($\mu$M) | MTT IC$_{50}$ ($\mu$M) |
|---|---|---|---|---|---|
| 121 | 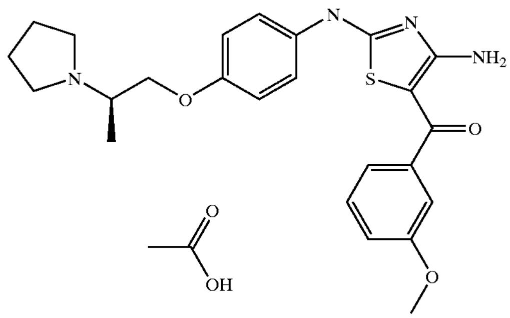 | 1.793 | 4.909 | 0.060 | 1.06 |
| 123 | 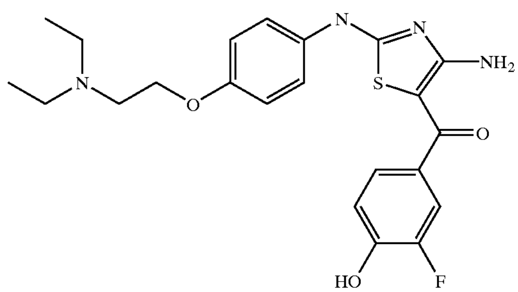 | 0.422 | 1.655 | 0.036 | 1.870 |
| 125 | 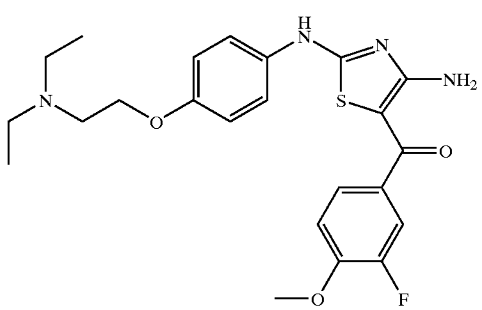 | 2.177 | 6.791 | 0.032 | 2.223 |
| 126 | 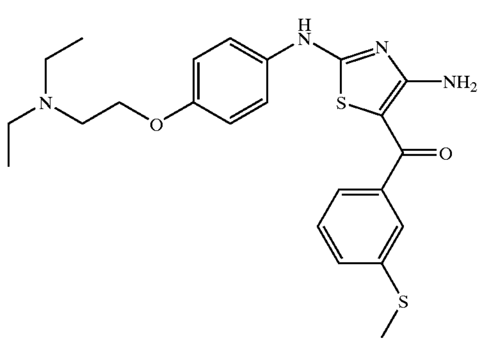 | 1.649 | 6.069 | 0.047 | 3.966 |
| 128 | 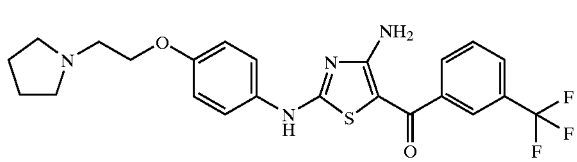 | 2.053 | 1.307 | 0.065 | 4.593 |

TABLE I-continued

This table summarizes the IC$_{50}$s of compounds according to the invention in CDK4, CDK2, and CDK1 kinase assays, and also the IC$_{50}$s in a cell-based ("MTT") assay.

| Example Number | Structure | CDK1 IC$_{50}$ ($\mu$M) | CDK2 IC$_{50}$ ($\mu$M) | CDK4 IC$_{50}$ ($\mu$M) | MTT IC$_{50}$ ($\mu$M) |
|---|---|---|---|---|---|
| 130 | 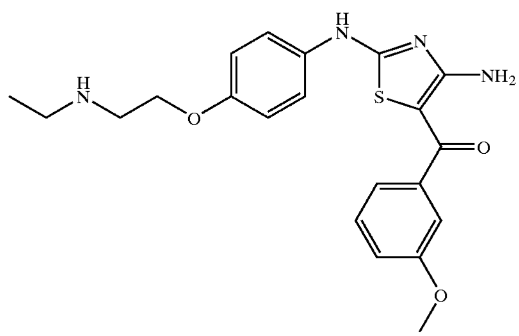 | 0.784 | 3.330 | 0.048 | 1.390 |
| 131 | 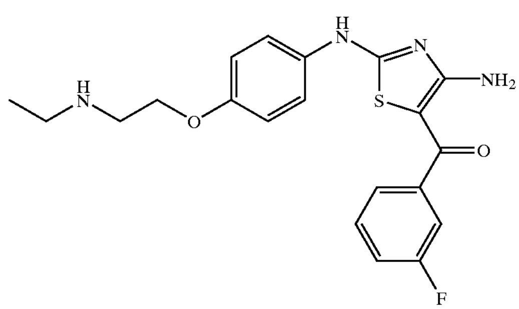 | 0.298 | 0.892 | 0.52 | 0.693 |
| 133 | 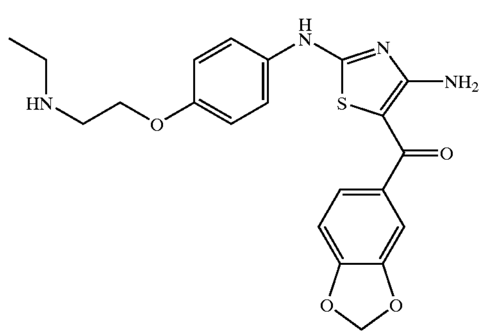 | 0.338 | 3.170 | 0.029 | 3.000 |
| 134 | 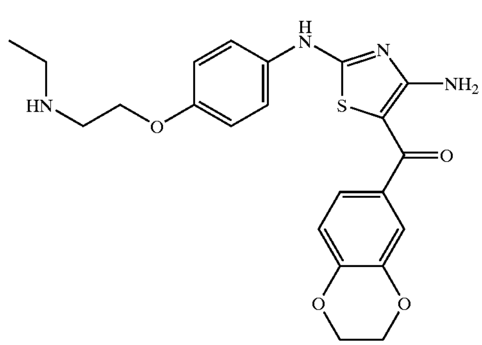 | 1.935 | 10.0 | 0.044 | 7.29 |

TABLE I-continued

This table summarizes the IC$_{50}$s of compounds according to the invention in CDK4, CDK2, and CDK1 kinase assays, and also the IC$_{50}$s in a cell-based ("MTT") assay.

| Example Number | Structure | CDK1 IC$_{50}$ ($\mu$M) | CDK2 IC$_{50}$ ($\mu$M) | CDK4 IC$_{50}$ ($\mu$M) | MTT IC$_{50}$ ($\mu$M) |
|---|---|---|---|---|---|
| 136 | 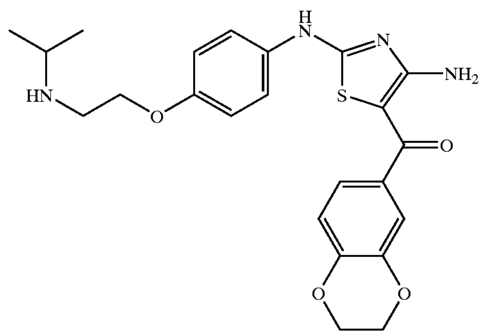 | 1.757 | 10.0 | 0.045 | 5.09 |
| 137 | 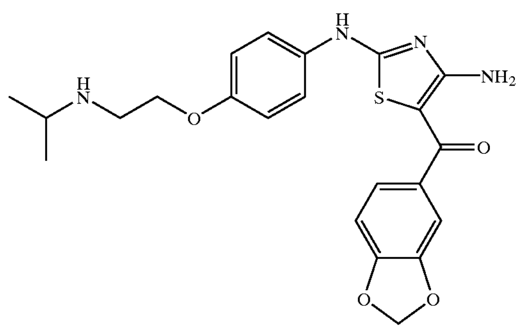 | 0.457 | 2.752 | 0.019 | 1.73 |
| 139 | 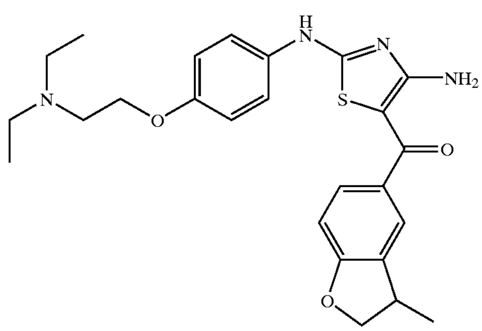 | 10.0 | 10.0 | 0.070 | |
| 140 | 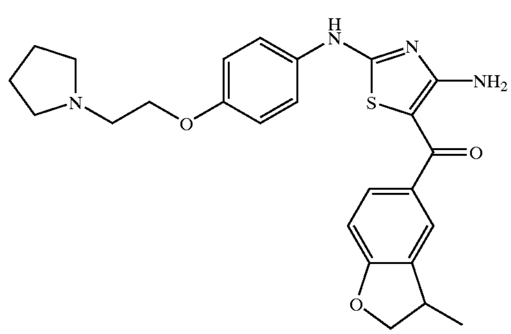 | 10.0 | 10.0 | 0.063 | 4.629 |

TABLE I-continued

This table summarizes the IC$_{50}$s of compounds according to the invention in CDK4, CDK2, and CDK1 kinase assays, and also the IC$_{50}$s in a cell-based ("MTT") assay.

| Example Number | Structure | CDK1 IC$_{50}$ ($\mu$M) | CDK2 IC$_{50}$ ($\mu$M) | CDK4 IC$_{50}$ ($\mu$M) | MTT IC$_{50}$ ($\mu$M) |
|---|---|---|---|---|---|
| 142 | [structure] | 6.428 | 10.0 | 0.100 | |
| 143 | [structure] | 2.362 | 3.016 | 0.091 | |
| 144 | [structure] | 2.49 | 4.54 | 0.087 | |
| 145 | [structure] | 0.219 | 0.900 | 0.041 | |

TABLE I-continued

This table summarizes the IC$_{50}$s of compounds according to the invention in CDK4, CDK2, and CDK1 kinase assays, and also the IC$_{50}$s in a cell-based ("MTT") assay.

| Example Number | Structure | CDK1 IC$_{50}$ ($\mu$M) | CDK2 IC$_{50}$ ($\mu$M) | CDK4 IC$_{50}$ ($\mu$M) | MTT IC$_{50}$ ($\mu$M) |
|---|---|---|---|---|---|
| 146 | 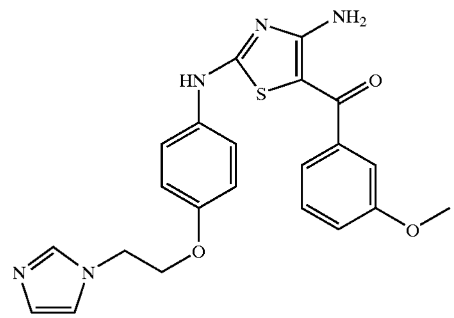 | 0.600 | 0.814 | 0.067 | 4.186 |
| 147 | 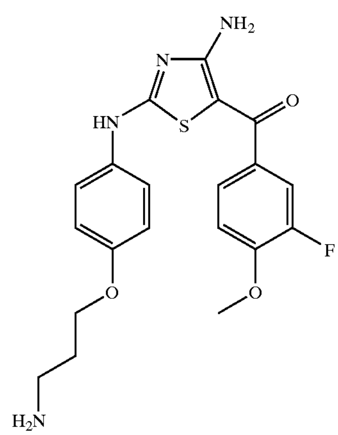 | 0.578 | 1.733 | 0.097 | |
| 148 | 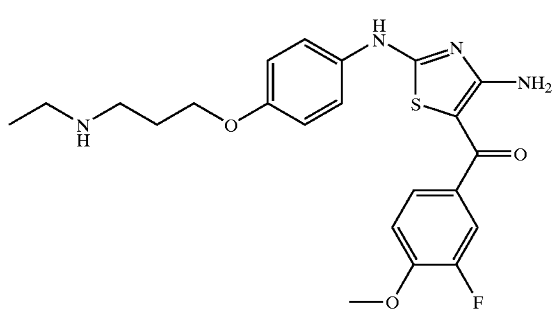 | 0.519 | 1.908 | 0.067 | |
| 3 | 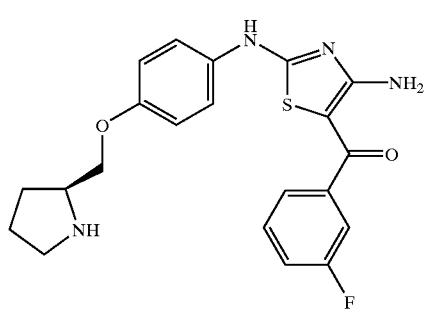 | 0.440 | 1.168 | 0.038 | |

TABLE I-continued

This table summarizes the IC$_{50}$s of compounds according to the invention in CDK4, CDK2, and CDK1 kinase assays, and also the IC$_{50}$s in a cell-based ("MTT") assay.

| Example Number | Structure | CDK1 IC$_{50}$ (μM) | CDK2 IC$_{50}$ (μM) | CDK4 IC$_{50}$ (μM) | MTT IC$_{50}$ (μM) |
|---|---|---|---|---|---|
| 44 | 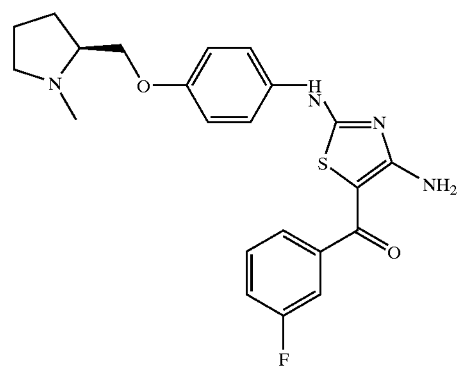 | 0.594 | 1.270 | 0.065 | 0.390 |
| 111 | 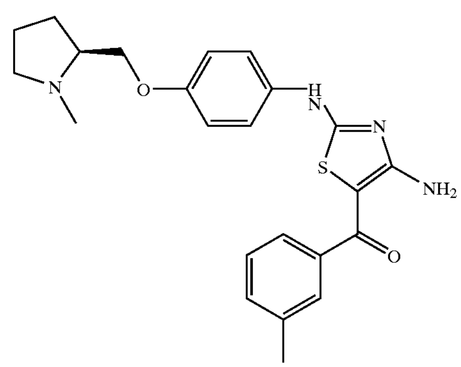 | 1.558 | 2.992 | 0.086 | |
| 112 | 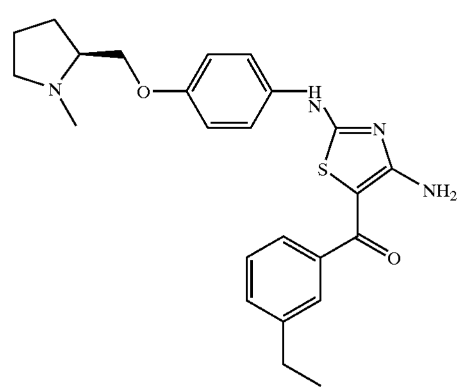 | 1.892 | 2.315 | 0.042 | 0.419 |
| 113 | 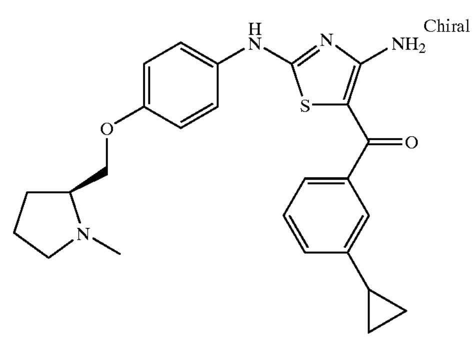 | 3.903 | 3.342 | 0.062 | 1.068 |

TABLE I-continued

This table summarizes the IC$_{50}$s of compounds according to the invention in CDK4, CDK2, and CDK1 kinase assays, and also the IC$_{50}$s in a cell-based ("MTT") assay.

| Example Number | Structure | CDK1 IC$_{50}$ ($\mu$M) | CDK2 IC$_{50}$ ($\mu$M) | CDK4 IC$_{50}$ ($\mu$M) | MTT IC$_{50}$ ($\mu$M) |
|---|---|---|---|---|---|
| 114 | 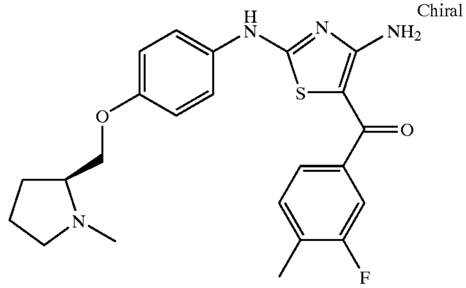 | 0.850 | 5.033 | 0.063 | 2.068 |
| 115 | 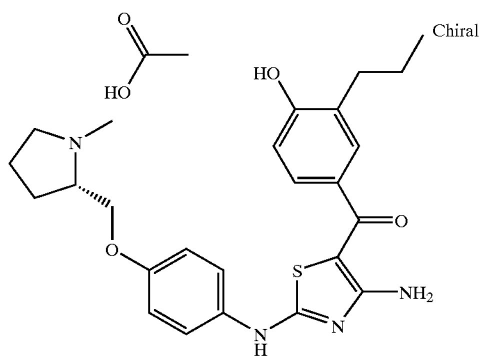 | 0.357 | 0.267 | 0.027 | 0.169 |
| 42 | 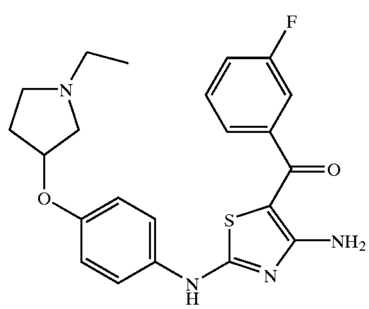 | 0.298 | 0.496 | 0.057 | 0.859 |
| 43 | 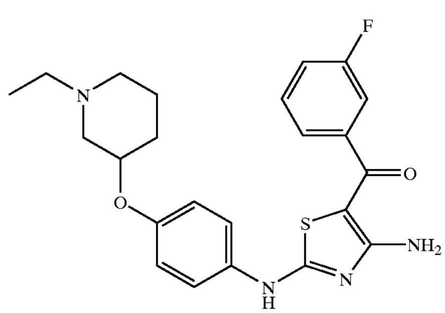 | 0.700 | 1.148 | 0.059 | 0.760 |

TABLE I-continued

This table summarizes the IC$_{50}$s of compounds according to the invention in CDK4, CDK2, and CDK1 kinase assays, and also the IC$_{50}$s in a cell-based ("MTT") assay.

| Example Number | Structure | CDK1 IC$_{50}$ (μM) | CDK2 IC$_{50}$ (μM) | CDK4 IC$_{50}$ (μM) | MTT IC$_{50}$ (μM) |
|---|---|---|---|---|---|
| 45 | 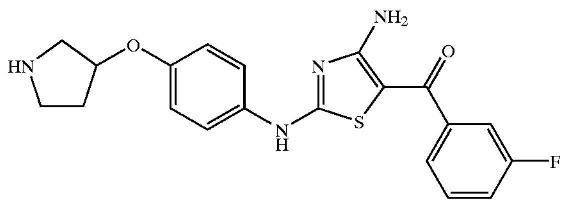 | 0.158 | 0.589 | 0.039 | 1.240 |
| 46 | 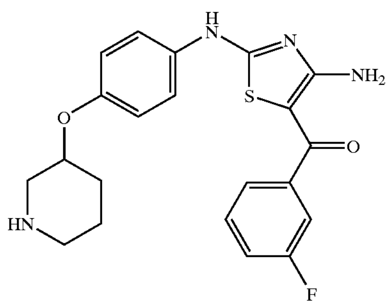 | 0.416 | 1.137 | 0.065 | |
| 78 | 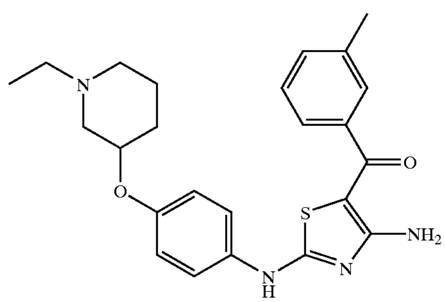 | 0.806 | 1.084 | 0.041 | 1.507 |
| 79 | 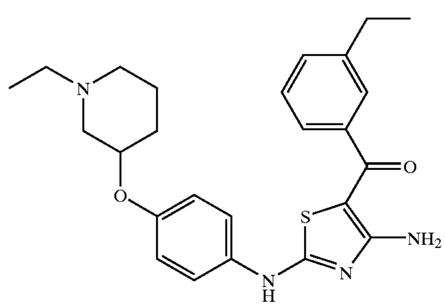 | 1.077 | 1.169 | 0.023 | 1.469 |
| 80 | 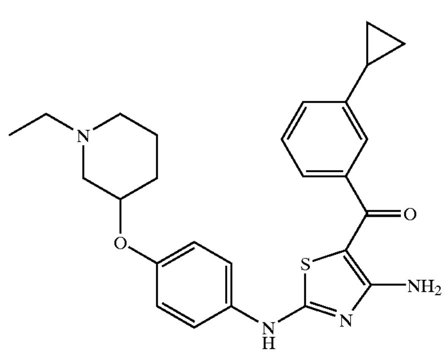 | 1.841 | 2.282 | 0.019 | 1.718 |

TABLE I-continued

This table summarizes the IC$_{50}$s of compounds according to the invention in CDK4, CDK2, and CDK1 kinase assays, and also the IC$_{50}$s in a cell-based ("MTT") assay.

| Example Number | Structure | CDK1 IC$_{50}$ ($\mu$M) | CDK2 IC$_{50}$ ($\mu$M) | CDK4 IC$_{50}$ ($\mu$M) | MTT IC$_{50}$ ($\mu$M) |
|---|---|---|---|---|---|
| 81 | 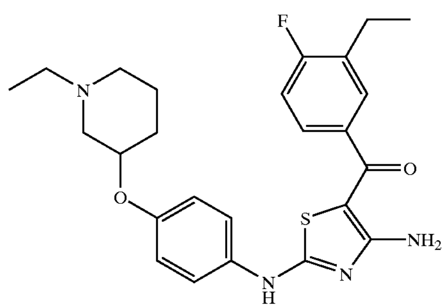 | 10.0 | 6.400 | 0.055 | 4.237 |
| 82 | 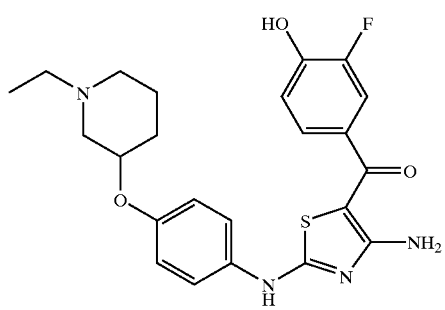 | 1.021 | 1.497 | 0.071 | |
| 83 | 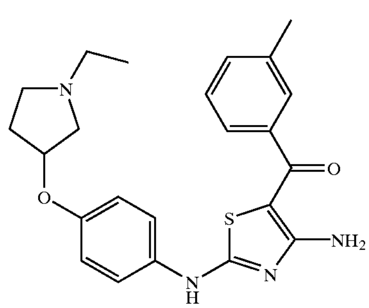 | 0.980 | 0.499 | 0.049 | 1.563 |
| 84 | 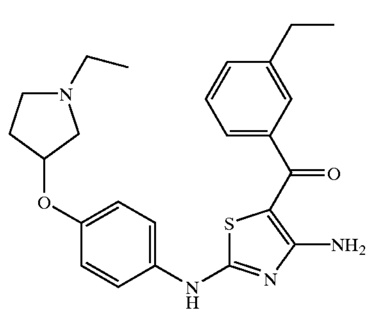 | 0.655 | 0.278 | 0.046 | 1.511 |

TABLE I-continued

This table summarizes the IC$_{50}$s of compounds according to the invention in CDK4, CDK2, and CDK1 kinase assays, and also the IC$_{50}$s in a cell-based ("MTT") assay.

| Example Number | Structure | CDK1 IC$_{50}$ ($\mu$M) | CDK2 IC$_{50}$ ($\mu$M) | CDK4 IC$_{50}$ ($\mu$M) | MTT IC$_{50}$ ($\mu$M) |
|---|---|---|---|---|---|
| 85 | 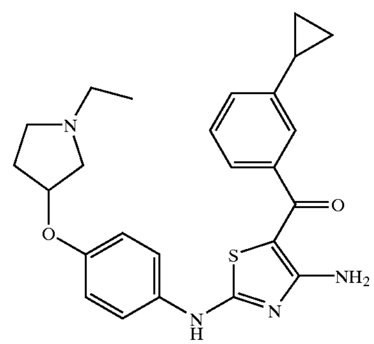 | 1.075 | 0.887 | 0.051 | 2.006 |
| 86 | 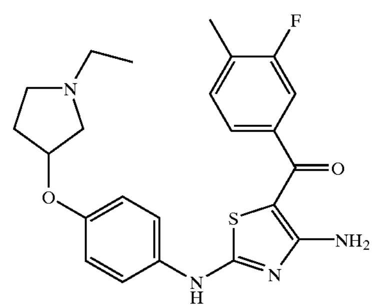 | 0.977 | 1.644 | 0.097 | |
| 87 | 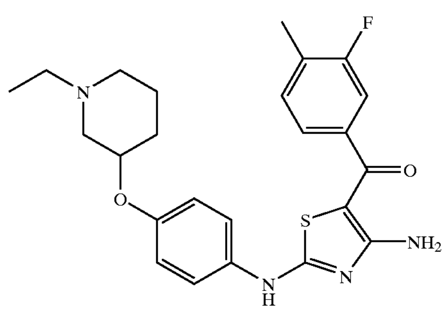 | 0.451 | 0.957 | 0.074 | |
| 88 | 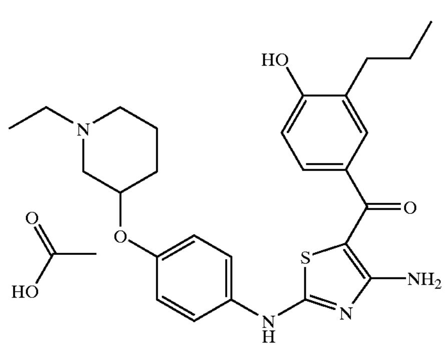 | 0.241 | 0.234 | 0.039 | 0.280 |

TABLE I-continued

This table summarizes the IC$_{50}$s of compounds according to the invention in CDK4, CDK2, and CDK1 kinase assays, and also the IC$_{50}$s in a cell-based ("MTT") assay.

| Example Number | Structure | CDK1 IC$_{50}$ ($\mu$M) | CDK2 IC$_{50}$ ($\mu$M) | CDK4 IC$_{50}$ ($\mu$M) | MTT IC$_{50}$ ($\mu$M) |
|---|---|---|---|---|---|
| 89 | 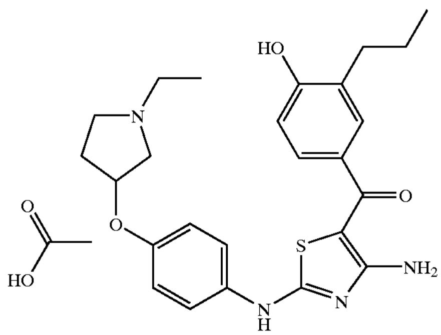 | 0.261 | 0.175 | 0.019 | 0.327 |
| 90 | 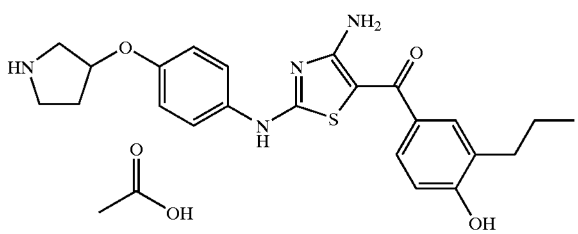 | 0.228 | 0.130 | 0.043 | |
| 91 | 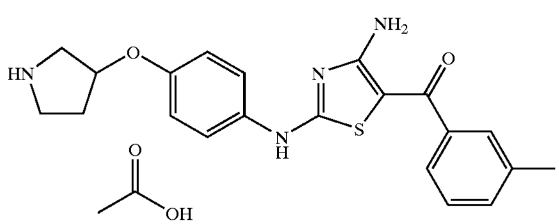 | 0.471 | 0.817 | 0.067 | |
| 92 | 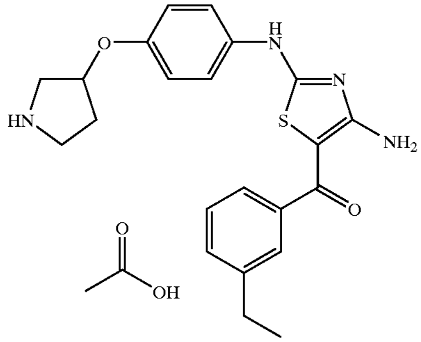 | 0.538 | 0.495 | 0.051 | 1.567 |
| 93 | 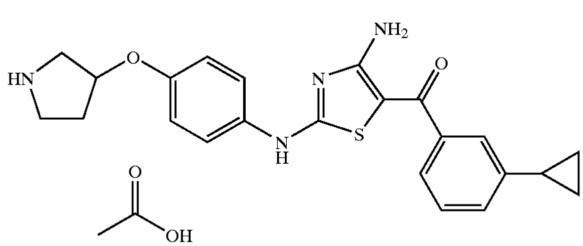 | 0.859 | 1.198 | 0.042 | 2.024 |

TABLE I-continued

This table summarizes the $IC_{50}$s of compounds according to the invention in CDK4, CDK2, and CDK1 kinase assays, and also the $IC_{50}$s in a cell-based ("MTT") assay.

| Example Number | Structure | CDK1 $IC_{50}$ (μM) | CDK2 $IC_{50}$ (μM) | CDK4 $IC_{50}$ (μM) | MTT $IC_{50}$ (μM) |
|---|---|---|---|---|---|
| 94 | 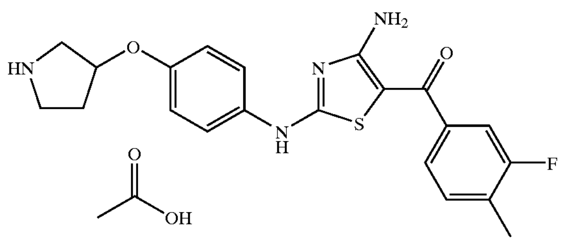 | 0.682 | 2.036 | 0.086 | |
| 96 | 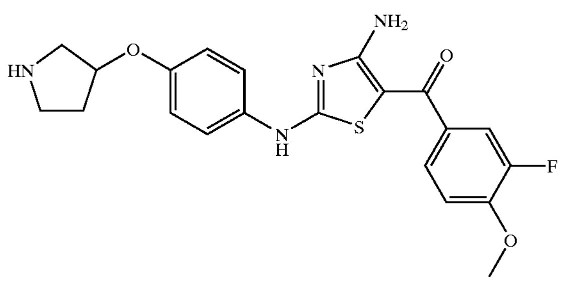 | 0.668 | 1.438 | 0.039 | 3.290 |
| 97 | 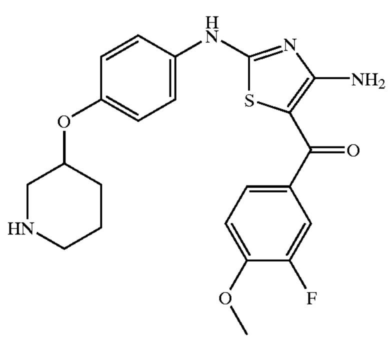 | 1.718 | 3.739 | 0.096 | |
| 98 | 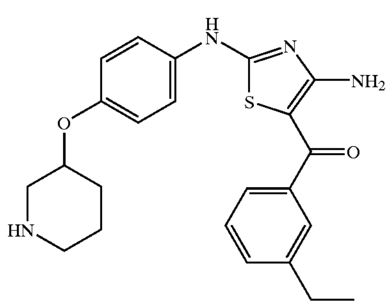 | 0.523 | 1.227 | 0.034 | |

TABLE I-continued

This table summarizes the IC$_{50}$s of compounds according to the invention in CDK4, CDK2, and CDK1 kinase assays, and also the IC$_{50}$s in a cell-based ("MTT") assay.

| Example Number | Structure | CDK1 IC$_{50}$ ($\mu$M) | CDK2 IC$_{50}$ ($\mu$M) | CDK4 IC$_{50}$ ($\mu$M) | MTT IC$_{50}$ ($\mu$M) |
|---|---|---|---|---|---|
| 99 | (structure) | 0.174 | 0.158 | 0.038 | |

Example 150

Tablet Formulation

| Item | Ingredients | Mg/Tablet | | | | | |
|---|---|---|---|---|---|---|---|
| 1 | Compound A* | 5 | 25 | 100 | 250 | 500 | 750 |
| 2 | Anhydrous Lactose | 103 | 83 | 35 | 19 | 38 | 57 |
| 3 | Croscarmellose Sodium | 6 | 6 | 8 | 16 | 32 | 48 |
| 4 | Povidone K30 | 5 | 5 | 6 | 12 | 24 | 36 |
| 5 | Magnesium Stearate | 1 | 1 | 1 | 3 | 6 | 9 |
| | Total Weight | 120 | 120 | 150 | 300 | 600 | 900 |

*Compound A represents a compound of the invention.

Manufacturing Procedure:
1. Mix Items 1, 2 and 3 in a suitable mixer for 15 minutes.
2. Granulate the powder mix from Step 1 with 20% Povidone K30 Solution (Item 4).
3. Dry the granulation from Step 2 at 50° C.
4. Pass the granulation from Step 3 through a suitable milling equipment.
5. Add the Item 5 to the milled granulation Step 4 and mix for 3 minutes.
6. Compress the granulation from Step 5 on a suitable press.

Example 151

Capsule Formulation

| Item | Ingredients | mg/Capsule | | | | |
|---|---|---|---|---|---|---|
| 1 | Compound A* | 5 | 25 | 100 | 250 | 500 |
| 2 | Anhydrous Lactose | 159 | 123 | 148 | — | — |
| 3 | Corn Starch | 25 | 35 | 40 | 35 | 70 |
| 4 | Talc | 10 | 15 | 10 | 12 | 24 |
| 5 | Magnesium Stearate | 1 | 2 | 2 | 3 | 6 |
| | Total Fill Weight | 200 | 200 | 300 | 300 | 600 |

*Compound A represents a compound of the invention.

Manufacturing Procedure:
1. Mix Items 1, 2 and 3 in a suitable mixer for 15 minutes.
2. Add Items 4 & 5 and mix for 3 minutes.
3. Fill into a suitable capsule.

Example 152

Injection Solution/Emulsion Preparation

| Item | Ingredient | mg/mL |
|---|---|---|
| 1 | Compound A* | 1 mg |
| 2 | PEG 400 | 10–50 mg |
| 3 | Lecithin | 20–50 mg |
| 4 | Soy Oil | 1–5 mg |
| 5 | Glycerol | 8–12 mg |
| 6 | Water q.s. | 1 mL |

*Compound A represents a compound of the invention.

Manufacturing Procedure:
1. Dissolve item 1 in item 2.
2. Add items 3, 4 and 5 to item 6 and mix until dispersed, then homogenize.
3. Add the solution from step 1 to the mixture from step 2 and homogenize until the dispersion is translucent.
4. Sterile filter through a 0.2 $\mu$m filter and fill into vials.

Example 153

Injection Solution/Emulsion Preparation

| Item | Ingredient | mg/mL |
|---|---|---|
| 1 | Compound A* | 1 mg |
| 2 | Glycofurol | 10–50 mg |
| 3 | Lecithin | 20–50 mg |
| 4 | Soy Oil | 1–5 mg |
| 5 | Glycerol | 8–12 mg |
| 6 | Water | q.s. 1 mL |

*Compound A represents a compound of the invention.

Manufacturing Procedure:
1. Dissolve item 1 in item 2.
2. Add items 3, 4 and 5 to item 6 and mix until dispersed, then homogenize.

3. Add the solution from step 1 to the mixture from step 2 and homogenize until the dispersion is translucent.
4. Sterile filter through a 0.2 μm filter and fill into vials.

While the invention has been illustrated by reference to specific and preferred embodiments, those skilled in the art will understand that variations and modifications may be made through routine experimentation and practice of the invention. Thus, the invention is intended not to be limited by the foregoing description, but to be defined by the appended claims and their equivalents.

What is claimed is:

1. A compound of formula

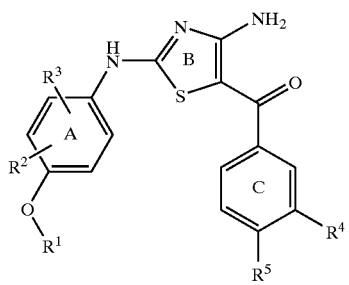

I wherein,

O—$R^1$ represents a group selected from

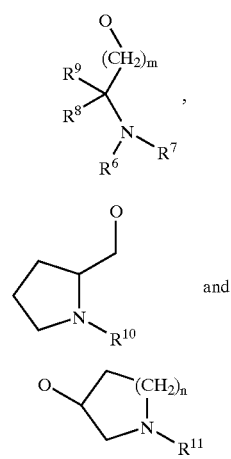

II

III and

IV $R^2$ and $R^3$ are independently selected from the group consisting of
H,
lower alkyl, and
halogen;

$R^4$ is selected from the group consisting of
lower alkyl,
lower alkyl-cycloalkyl,
cycloalkyl,
O-lower alkyl,
halogen,
$NO_2$,
S-lower alkyl
$CF_3$, and
CN;

$R^5$ is selected from the group consisting of
H,
O-lower alkyl,
lower alkyl,
halogen, and
OH, or alternatively, $R^4$ and $R^5$ together with the two carbon atoms and bond between them from the benzene ring (C) to which $R^4$ and $R^5$ are attached can form a ring having 5–7 atoms, said 5–7 atom ring optionally including one or two heteroatoms and being optionally substituted by $C_1$–$C_4$-alkyl;

$R^6$ and $R^7$ are each independently selected from the group consisting of
H,
lower alkyl,
lower alkyl substituted by OH, and
$COOR^{12}$, or, alternatively, the group —$NR^6R^7$ can be a ring having 5–7 atoms, said ring optionally including one or two additional heteroatoms and being optionally substituted by lower alkyl;

$R^8$ and $R^9$ are each independently selected from the group consisting of
H, and
lower alkyl;

$R^{10}$ is selected from the group consisting of
H,
lower alkyl,
lower alkyl substituted by OH, and
$COOR^{12}$;

$R^{11}$ is selected from the group consisting of
H,
lower alkyl, and
lower alkyl substituted by OH; and
$COOR^{12}$;

$R^{12}$ is lower alkyl;

m is 1 or 2;

n is 0, 1 or 2;

provided that when m is 2 and $R^4$ is F, $R^5$ is not H, and provided further that when m is 2 and $R^4$ is lower alkyl, $R^5$ is not OH;

or a pharmaceutically acceptable salt or ester thereof.

2. The compound of claim 1 wherein $R^2$ is lower alkyl.

3. The compound of claim 2 wherein $R^2$ is methyl.

4. The compound of claim 1 wherein $R^2$ is halogen.

5. The compound of claim 4 wherein $R^2$ is F.

6. The compound of claim 1 wherein $R^3$ is H.

7. The compound of claim 1 wherein $R^4$ is halogen.

8. The compound of claim 1 wherein $R^4$ is F.

9. The compound of claim 1 wherein $R^4$ is lower alkyl.

10. The compound of claim 9 wherein $R^4$ is methyl.

11. The compound of claim 1 wherein $R^5$ is halogen or H.

12. The compound of claim 11 where in $R^5$ is F.

13. A compound of formula

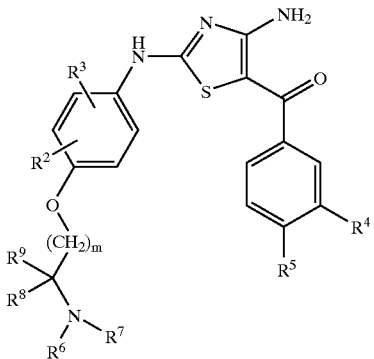

Ia wherein,
R$^2$ and R$^3$ are independently selected from the group consisting of
H,
lower alkyl, and
halogen;
R$^4$ is selected from the group consisting of
lower alkyl,
lower alkyl-cycloalkyl,
cycloalkyl,
O-lower alkyl,
halogen,
NO$_2$,
S-lower alkyl,
CF$_3$, and
CN;
R$^5$ is selected from the group consisting of
H,
O-lower alkyl,
lower alkyl,
halogen, and
OH,
or alternatively, R$^4$ and R$^5$ together with the two carbon atoms and bond between them from the benzene ring (C) to which R$^4$ and R$^5$ are attached can form a ring having 5–7 atoms, said 5–7 atom ring optionally including one or two heteroatoms and being optionally substituted by C$_1$–C$_4$-alkyl;
R$^6$ and R$^7$ are each independently selected from the group consisting of
H,
lower alkyl,
lower alkyl substituted by OH, and
or, alternatively, the group —NR$^6$R$^7$ can be a ring having 5–7 atoms, said ring optionally including one or two additional heteroatoms; and being optionally substituted by lower alkyl; and
R$^8$ and R$^9$ are each independently selected from the group consisting of
H, and
lower alkyl; and
m is 1 or 2;
provided that when m is 2 and R$^4$ is F, R$^5$ is not H, and provided further that when m is 2 and R$^4$ is lower alkyl, R$^5$ is not OH;
or a pharmaceutically acceptable salt or ester thereof.

14. The compound of claim 13 wherein R$^2$ is lower alkyl or halogen.

15. The compound of claim 14 wherein R$^2$ is methyl or F.

16. The compound of claim 13 wherein R$^3$ is H.

17. The compound of claim 13 wherein R$^4$ is halogen or lower alkyl.

18. The compound of claim 17 wherein R$^4$ is F or methyl.

19. The compound of claim 13 wherein R$^5$ is halogen or H.

20. The compound of claim 19 where in R$^5$ is F.

21. The compound of claim 13 wherein R$^8$ and R$^9$ are each independently selected from H and lower alkyl.

22. The compound of claim 21 wherein R$^8$ and R$^9$ are each independently selected from H and methyl.

23. The compound of claim 13 wherein m is 1.

24. The compound of formula Ia selected from the group
[4-Amino-2-[4-(2-pyrrolidin-1-yl-ethoxy)-phenylamino]-thiazol-5-yl]-(4-ethyl-3-fluoro-phenyl)-methanone; compound with trifluoroacetic acid;
[4-Amino-2-[4-(2-pyrrolidin-1-yl-ethoxy)-phenylamino]-thiazol-5-yl]-(3-fluoro-phenyl)-methanone;
[4-Amino-2-[4-(2-dimethylamino-ethoxy)-phenylamino]-thiazol-5-yl]-(3-fluoro-phenyl)-methanone;
[4-Amino-2-[4-(2-dimethylamino-propoxy)-phenylamino]-thiazol-5-yl]-(3-fluoro-phenyl)-methanone;
[4-Amino-2-[4-(2-dimethylamino-2-methyl-propoxy)-phenylamino]-thiazol-5-yl]-(3-fluoro-phenyl)-methanone;
(R)-[4-Amino-2-[4-(2-dimethylamino-propoxy)-phenylamino]-thiazol-5-yl]-(3-fluoro-phenyl)-methanone;
(R)-[4-Amino-2-[4-(2-pyrrolidin-1-yl-propoxy)-phenylamino]-thiazol-5-yl]-(3-fluoro-phenyl)-methanone;
[4-Amino-2-[4-(2-morpholin-4-yl-ethoxy)-phenylamino]-thiazol-5-yl]-(3-fluoro-phenyl)-methanone;
[4-Amino-2-[4-(2-pyrrolidin-1-yl-ethoxy)-phenylamino]-thiazol-5-yl]-(4-methoxy-3-nitro-phenyl)-methanone; and
[4-Amino-2-[4-(2-dimethylamino-ethoxy)-phenylamino]-thiazol-5-yl]-(4-methoxy-3-nitro-phenyl)-methanone.

25. The compound of formula Ia selected from the group
[4-Amino-2-[4-(2-dimethylamino-ethoxy)-phenylamino]-thiazol-5-yl]-m-tolyl-methanone;
[4-Amino-2-[4-(2-pyrrolidin-1-yl-ethoxy)-phenylamino]-thiazol-5-yl]-m-tolyl-methanone;
[4-Amino-2-[4-(2-dimethylamino-ethoxy)-phenylamino]-thiazol-5-yl]-(3-ethyl-phenyl)-methanone;
[4-Amino-2-[4-(2-pyrrolidin-1-yl-ethoxy)-phenylamino]-thiazol-5-yl]-(3-ethyl-phenyl)-methanone;
[4-Amino-2-[4-(2-dimethylamino-ethoxy)-phenylamino]-thiazol-5-yl]-(3-nitro-phenyl)-methanone;
[4-Amino-2-[4-(2-morpholin-4-yl-ethoxy)-phenylamino]-thiazol-5-yl]-(2,3-dihydro-benzo[1,4]dioxin-6-yl)-methanone;
[4-Amino-2-[4-(2-morpholin-4-yl-ethoxy)-phenylamino]-thiazol-5-yl]-benzo[1,3]dioxol-5-yl-methanone;
[4-Amino-2-[4-(2-pyrrolidin-1-yl-ethoxy)-phenylamino]-thiazol-5-yl]-benzo[1,3]dioxol-5-yl-methanone;

[4-Amino-2-[4-(2-dimethylamino-ethoxy)-phenylamino]-thiazol-5-yl]-(2,3-dihydro-benzo[1,4]dioxin-6-yl)-methanone; and

[4-Amino-2-[4-(2-dimethylamino-ethoxy)-phenylamino]-thiazol-5-yl]-benzo[1,3]dioxol-5-yl-methanone.

26. The compound of formula Ia selected from the group
3-[4-Amino-2-[4-(2-dimethylamino-ethoxy)-phenylamino]-thiazole-5-carbonyl]-benzonitrile;

[4-Amino-2-[4-(2-dimethylamino-2-methyl-propoxy)-phenylamino]-thiazol-5-yl]-(3-ethyl-phenyl)-methanone;

[4-Amino-2-[4-(2-pyrrolidin-1-yl-ethoxy)-phenylamino]-thiazol-5-yl]-(3-ethoxy-phenyl)-methanone;

(R)-[4-Amino-2-[4-(2-dimethylamino-propoxy)-phenylamino]-thiazol-5-yl]-(3-ethyl-phenyl)-methanone;

[4-Amino-2-[4-(2-dimethylamino-ethoxy)-phenylamino]-thiazol-5-yl]-(3-bromo-phenyl)-methanone;

(R)-[4-Amino-2-[4-(2-pyrrolidin-1-yl-propoxy)-phenylamino]-thiazol-5-yl]-(3-ethyl-phenyl)-methanone;

(R)-[4-Amino-2-[4-(2-pyrrolidin-1-yl-propoxy)-phenylamino]-thiazol-5-yl]-(3-cyclopropyl-phenyl)-methanone;

[4-Amino-2-[4-(2-dimethylamino-ethoxy)-phenylamino]-thiazol-5-yl]-(3-cyclopropyl-phenyl)-methanone;

(R)-[4-Amino-2-[4-(2-dimethylamino-propoxy)-phenylamino]-thiazol-5-yl]-(3-cyclopropyl-phenyl)-methanone; and

[4-Amino-2-[4-(2-dimethylamino-2-methyl-propoxy)-phenylamino]-thiazol-5-yl]-(3-cyclopropyl-phenyl)-methanone.

27. The compound of formula Ia selected from the group
[4-Amino-2-[4-(2-pyrrolidin-1-yl-ethoxy)-phenylamino]-thiazol-5-yl]-(3-cyclopropyl-phenyl)-methanone;

[4-Amino-2-[4-(2-dimethylamino-ethoxy)-phenylamino]-thiazol-5-yl]-(3-fluoro-4-methyl-phenyl)-methanone;

(R)-[4-Amino-2-[4-(2-dimethylamino-propoxy)-phenylamino]-thiazol-5-yl]-(3-fluoro-4-methyl-phenyl)-methanone;

[4-Amino-2-[4-(2-dimethylamino-2-methyl-propoxy)-phenylamino]-thiazol-5-yl]-(3-fluoro-4-methyl-phenyl)-methanone;

[4-Amino-2-[4-(2-pyrrolidin-1-yl-ethoxy)-phenylamino]-thiazol-5-yl]-(3-ethyl-4-fluoro-phenyl)-methanone;

(R)-[4-Amino-2-[4-(2-dimethylamino-propoxy)-phenylamino]-thiazol-5-yl]-(3-ethyl-4-fluoro-phenyl)-methanone;

[4-Amino-2-[4-(2-ethylamino-ethoxy)-phenylamino]thiazol-5-yl]-m-tolyl-methanone; compound with acetic acid;

[4-Amino-2-[4-(2-ethylamino-ethoxy)-phenylamino]-thiazol-5-yl]-(3-ethyl-phenyl)-methanone; compound with acetic acid;

[4-Amino-2-[4-(2-ethylamino-ethoxy)-phenylamino]-thiazol-5-yl]-(3-cyclopropyl-phenyl)-methanone; compound with acetic acid; and

[4-Amino-2-[4-(2-ethylamino-ethoxy)-phenylamino]-thiazol-5-yl]-(3-fluoro-4-methyl-phenyl)-methanone; compound with acetic acid.

28. The compound of formula Ia selected from the group
[4-Amino-2-[4-(2-ethylaminoethoxy)-phenylamino]-thiazol-5-yl]-(3-ethyl-4-fluoro-phenyl)-methanone; compound with acetic acid;

[4-Amino-2-[4-(2-ethylamino-ethoxy)-phenylamino]-thiazol-5-yl]-(4-hydroxy-3-propyl-phenyl)-methanone; compound with acetic acid;

[4-Amino-2-[4-(2-dimethylaminoethoxy)-phenylamino]-thiazol-5-yl]-(4-hydroxy-3-propyl-phenyl)-methanone; compound with acetic acid;

(R)-[4-Amino-2-[4-(2-dimethylamino-propoxy)-phenylamino]-thiazol-5-yl]-(4-hydroxy-3-propyl-phenyl)-methanone; compound with acetic acid;

[4-Amino-2-[4-(2-dimethylamino-2-methyl-propoxy)-phenylamino]-thiazol-5-yl]-(4-hydroxy-3-propyl-phenyl)-methanone; compound with acetic acid;

[4-Amino-2-[4-(2-pyrrolidin-1-yl-ethoxy)-phenylamino]-thiazol-5-yl]-(4-hydroxy-3-propyl-phenyl)-methanone; compound with acetic acid;

(R)-[4-Amino-2-[4-(2-pyrrolidin-1-yl-propoxy)-phenylamino]-thiazol-5-yl]-(4-hydroxy-3-propyl-phenyl)-methanone; compound with acetic acid;

[4-Amino-2-[4-(2-pyrrolidin-1-yl-ethoxy)-phenylamino]-thiazol-5-yl]-(3-fluoro-phenyl)-methanone; compound with acetic acid;

[4-Amino-2-[4-(2-pyrrolidin-1-yl-ethoxy)-phenylamino]-thiazol-5-yl]-(3-fluoro-4-hydroxy-phenyl)-methanone; compound with acetic acid; and

[R]-[4-Amino-2-[4-(2-pyrrolidin-1-yl-propoxy)-phenylamino]-thiazol-5-yl]-(3-methoxy-phenyl)-methanone; compound with acetic acid.

29. The compound of formula Ia selected from the group
[4-Amino-2-[4-(2-diethylamino-ethoxy)-phenylamino]-thiazol-5-yl]-(3-fluoro-4-hydroxy-phenyl)-methanone;

[4-Amino-2-[4-(2-diethylamino-ethoxy)-phenylamino]-thiazol-5-yl]-(3-fluoro-4-methoxy-phenyl)-methanone;

[4-Amino-2-[4-(2-diethylamino-ethoxy)-phenylamino]-thiazol-5-yl]-(3-methylsulfanyl-phenyl)-methanone;

[4-Amino-2-[4-(2-pyrrolidin-1-yl-ethoxy)-phenylamino]-thiazol-5-yl]-(3-trifluoromethyl-phenyl)-methanone;

[4-Amino-2-[4-(2-ethylamino-ethoxy)-phenylamino]-thiazol-5-yl]-(3-methoxy-phenyl)-methanone;

[4-Amino-2-[4-(2-ethylamino-ethoxy)-phenylamino]-thiazol-5-yl]-(3-fluoro-phenyl)-methanone;

[4-Amino-2-[4-(2-ethylamino-ethoxy)-phenylamino]-thiazol-5-yl]-benzo[1,3]dioxol-5-yl-methanone;

[4-Amino-2-[4-(2-ethylamino-ethoxy)-phenylamino]-thiazol-5-yl]-(2,3-dihydro-benzo[1,4]dioxin-6-yl)-methanone;

[4-Amino-2-[4-(2-isopropylamino-ethoxy)-phenylamino]-thiazol-5-yl]-(2,3-dihydro-benzo[1,4]dioxin-6-yl)-methanone; and

[4-Amino-2-[4-(2-isopropylamino-ethoxy)-phenylamino]-thiazol-5-yl]-benzo[1,3]dioxol-5-yl-methanone.

30. The compound of formula Ia selected from the group
[4-Amino-2-[4-(2-diethylamino-ethoxy)-phenylamino]-thiazol-5-yl]-(3-methyl-2,3-dihydro-benzofuran-5-yl)-methanone;

[4-Amino-2-[4-(2-pyrrolidin-1-yl-ethoxy)-phenylamino]-thiazol-5-yl]-(3-methyl-2,3-dihydro-benzofuran-5-yl)-methanone;

[4-Amino-2-[4-(2-diethylamino-ethoxy)-phenylamino]-thiazol-5-yl]-(2,3-dihydro-benzofuran-5-yl)-methanone;

[4-Amino-2-[4-(2-ethylamino-ethoxy)-phenylamino]-thiazol-5-yl]-(2,3-dihydro-benzofuran-5-yl)-methanone;

[4-Amino-2-[4-(2-dimethylaminoethoxy)-phenylamino]-thiazol-5-yl]-(3-methoxy-phenyl)-methanone;

[4-Amino-2-[4-(2-diethylaminoethoxy)-phenylamino]-thiazol-5-yl]-(3-methoxy-phenyl)-methanone; and

[4-Amino-2-[4-(2-imidazol-1-yl-ethoxy)-phenylamino]-thiazol-5-yl]-(3-methoxy-phenyl)-methanone.

31. The compound of claim 13 wherein m is 2.

32. The compound of claim 31 which is selected from the group consisting of

[4-Amino-2-[4-(3-amino-propoxy)-phenylamino]-thiazol-5-yl]-(3-fluoro-4-methoxy-phenyl)-methanone; and

[4-Amino-2-[4-(3-ethylamino-propoxy)-phenylamino]-thiazol-5-yl]-(3-fluoro-4-methoxy-phenyl)methanone.

33. A compound of formula

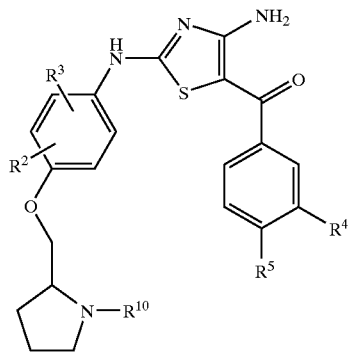

Ib wherein
$R^2$ and $R^3$ are independently selected from the group consisting of
H,
lower alkyl, and
halogen;
$R^4$ is selected from the group consisting of
lower alkyl,
lower alkyl-cycloalkyl,
cycloalkyl,
O-lower alkyl,
halogen,
$NO_2$,
S-lower alkyl
$CF_3$, and
CN;
$R^5$ is selected from the group consisting of
H,
O-lower alkyl,
lower alkyl,
halogen, and
OH,
or alternatively, $R^4$ and $R^5$ together with the two carbon atoms and bond between them from the benzene ring (C) to which $R^4$ and $R^5$ are attached can form a ring having 5–7 atoms, said 5–7 atom ring optionally including one or two heteroatoms and being optionally substituted by $C_1$–$C_4$-alkyl;
$R^{10}$ is selected from the group consisting of
H,
lower alkyl,
lower alkyl substituted by OH, and
$COOR^{12}$; and
$R^{12}$ is lower alkyl;
or a pharmaceutically acceptable salt or ester thereof.

34. The compound of claim 33 wherein $R^2$ is lower alkyl or halogen.

35. The compound of claim 34 wherein $R^2$ is methyl or F.

36. The compound of claim 33 wherein $R^3$ is H.

37. The compound of claim 33 wherein $R^4$ is halogen or lower alkyl.

38. The compound of claim 37 wherein $R^4$ is F or methyl.

39. The compound of claim 33 wherein $R^5$ is halogen or H.

40. The compound of claim 39 where in $R^5$ is F.

41. The compound of claim 33 wherein $R^{10}$ is lower alkyl or H.

42. The compound of claim 41 wherein $R^{10}$ is methyl.

43. The compound of claim 33 which is selected from the group consisting of

[4-Amino-2-[4-(pyrrolidin-2-ylmethoxy)-phenylamino]-thiazol-5-yl]-(3-fluoro-phenyl)-methanone;

(S)-[4-Amino-2-[4-(1-methyl-pyrrolidin-2-ylmethoxy)-phenylamino]-thiazol-5-yl]-(3-fluoro-phenyl)-methanone;

(S)-[4-Amino-2-[4-(1-methyl-pyrrolidin-2-ylmethoxy)-phenylamino]-thiazol-5-yl]-m-tolyl-methanone;

(S)-[4-Amino-2-[4-(1-methyl-pyrrolidin-2-ylmethoxy)-phenylamino]-thiazol-5-yl]-(3-ethyl-phenyl)-methanone;

(S)-[4-Amino-2-[4-(1-methyl-pyrrolidin-2-ylmethoxy)-phenylamino]-thiazol-5-yl]-(3-cyclopropyl-phenyl)-methanone;

(S)-[4-Amino-2-[4-(1-methyl-pyrrolidin-2-ylmethoxy)-phenylamino]-thiazol-5-yl]-(3-fluoro-4-methyl-phenyl)-methanone; and (S)-[4-Amino-2-[4-(1-methyl-pyrrolidin-2-ylmethoxy)-phenylamino]-thiazol-5-yl]-(4-hydroxy-3-propyl-phenyl)-methanone acetate.

44. A compound of formula

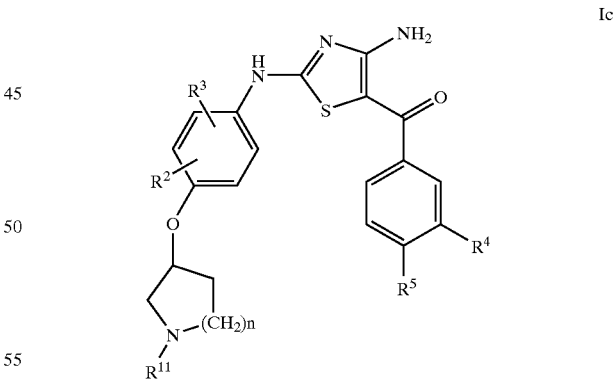

Ic wherein
$R^2$ and $R^3$ are independently selected from the group consisting of
H,
lower alkyl, and
halogen;
$R^4$ is selected from the group consisting of
lower alkyl,
lower alkyl-cycloalkyl,
cycloalkyl, O-lower alkyl,
halogen,
$NO_2$,
S-lower alkyl
$CF_3$, and
CN;
$R^5$ is selected from the group consisting of
H,
O-lower alkyl,
lower alkyl,
halogen, and
OH,
or alternatively, $R^4$ and $R^5$ together with the two carbon atoms and bond between them from the benzene ring (C) to which $R^4$ and $R^5$ are attached can form a ring having 5–7 atoms, said 5–7 atom ring optionally including one or two heteroatoms and being optionally substituted by $C_1$–$C_4$-alkyl;
$R^{11}$ is selected from the group consisting of
H,
lower alkyl, and
lower alkyl substituted by OH; and
$COOR^{12}$;
$R^{12}$ is lower alkyl; and
n is 0, 1 or 2;
or a pharmaceutically acceptable salt or ester thereof.

45. The compound of claim 44 wherein $R^2$ is lower alkyl or halogen.
46. The compound of claim 45 wherein $R^2$ is methyl or F.
47. The compound of claim 44 wherein $R^3$ is H.
48. The compound of claim 44 wherein $R^4$ is halogen or lower alkyl.
49. The compound of claim 48 wherein $R^4$ is F or methyl.
50. The compound of claim 44 wherein $R^5$ is halogen or H.
51. The compound of claim 50 where in $R^5$ is F.
52. The compound of claim 44 wherein $R^{11}$ is lower alkyl or H.
53. The compound of claim 52 wherein $R^{11}$ is ethyl.
54. The compound of claim 44 wherein $R^{12}$ is methyl.
55. The compound of claim 44 wherein n is 1 or 2.
56. The compound of claim 44 wherein n is 1.
57. The compound of claim 44 which is selected from the group consisting of
    [4-Amino-2-[4-(1-ethyl-pyrrolidin-3-yloxy)-phenylamino]-thiazol-5-yl]-(3-fluoro-phenyl)-methanone;
    [4-Amino-2-[4-(1-ethyl-piperidin-3-yloxy)-phenylamino]-thiazol-5-yl]-(3-fluoro-phenyl)-methanone;
    [4-Amino-2-[4-(pyrrolidin-3-yloxy)-phenylamino]-thiazol-5-yl]-(3-fluoro-phenyl)-methanone;
    [4-Amino-2-[4-(piperidin-3-yloxy)-phenylamino]-thiazol-5-yl]-(3-fluoro-phenyl)-methanone;
    [4-Amino-2-[4-(1-ethyl-piperidin-3-yloxy)-phenylamino]-thiazol-5-yl]-m-tolyl-methanone;
    [4-Amino-2-[4-(1-ethyl-piperidin-3-yloxy)-phenylamino]-thiazol-5-yl]-(3-ethyl-phenyl)-methanone;
    [4-Amino-2-[4-(1-ethyl-piperidin-3-yloxy)-phenylamino]-thiazol-5-yl]-(3-cyclopropyl-phenyl)-methanone;
    [4-Amino-2-[4-(1-ethyl-piperidin-3-yloxy)-phenylamino]-thiazol-5-yl]-(3-ethyl-4-fluoro-phenyl)-methanone;
    [4-Amino-2-[4-(1-ethyl-piperidin-3-yloxy)-phenylamino]-thiazol-5-yl]-(3-fluoro-4-hydroxy-phenyl)-methanone; and
    [4-Amino-2-[4-(1-ethyl-pyrrolidin-3-yloxy)-phenylamino]-thiazol-5-yl]-m-tolyl-methanone.
58. The compound of claim 44 which is selected from the group consisting of
    [4-Amino-2-[4-(1-ethyl-pyrrolidin-3-yloxy)-phenylamino]-thiazol-5-yl]-(3-ethyl-phenyl)-methanone;
    [4-Amino-2-[4-(1-ethyl-pyrrolidin-3-yloxy)-phenylamino]-thiazol-5-yl]-(3-cyclopropyl-phenyl)-methanone;
    [4-Amino-2-[4-(1-ethyl-pyrrolidin-3-yloxy)-phenylamino]-thiazol-5-yl]-(3-fluoro-4-methyl-phenyl)-methanone;
    [4-Amino-2-[4-(1-ethyl-piperidin-3-yloxy)-phenylamino]-thiazol-5-yl]-(3-fluoro-4-methyl-phenyl)-methanone;
    [4-Amino-2-[4-(1-ethyl-piperidin-3-yloxy)-phenylamino]-thiazol-5-yl]-(4-hydroxy-3-propyl-phenyl)-methanone; compound with acetic acid;
    [4-Amino-2-[4-(1-ethyl-pyrrolidin-3-yloxy)-phenylamino]-thiazol-5-yl]-(4-hydroxy-3-propyl-phenyl)-methanone; compound with acetic acid;
    [4-Amino-2-[4-(pyrrolidin-3-yloxy)-phenylamino]-thiazol-5-yl]-(4-hydroxy-3-propyl-phenyl)-methanone; compound with acetic acid;
    [4-Amino-2-[4-(pyrrolidin-3-yloxy)-phenylamino]-thiazol-5-yl]-m-tolyl-methanone; compound with acetic acid;
    [4-Amino-2-[4-(pyrrolidin-3-yloxy)-phenylamino]-thiazol-5-yl]-(3-ethyl-phenyl)-methanone; compound with acetic acid; and
    [4-Amino-2-[4-(pyrrolidin-3-yloxy)-phenylamino]-thiazol-5-yl]-(3-cyclopropyl-phenyl)-methanone; compound with acetic acid.
59. The compound of claim 44 which is selected from the group consisting of
    [4-Amino-2-[4-(pyrrolidin-3-yloxy)-phenylamino]-thiazol-5-yl]-(3-fluoro-4-methyl-phenyl)-methanone; compound with acetic acid;
    [4-Amino-2-[4-(pyrrolidin-3-yloxy)-phenylamino]-thiazol-5-yl]-(3-fluoro-4-methoxy-phenyl)-methanone;
    [4-Amino-2-[4-(piperidin-3-yloxy)-phenylamino]-thiazol-5-yl]-(3-fluoro-4-methoxy-phenyl)-methanone;
    [4-Amino-2-[4-(piperidin-3-yloxy)-phenylamino]-thiazol-5-yl]-(3-ethyl-phenyl)-methanone;
    [4-Amino-2-[4-(piperidin-3-yloxy)-phenylamino]-thiazol-5-yl]-(4-hydroxy-3-propyl-phenyl)-methanone;
    3-[4-[4-Amino-5-(3-fluoro-benzoyl)-thiazol-2-ylamino]-phenoxy]-azetidine-1-carboxylic acid tert-butyl ester; and
    [4-Amino-2-[4-(azetidin-3-yloxy)-phenylamino]-thiazol-5-yl]-(3-fluoro-phenyl)-methanone.
60. The compound of claim 1 wherein $R^4$ is F and $R^5$ is O-methyl.
61. A pharmaceutical composition comprising as an active ingredient an effective amount of a compound of claim 1 and a pharmaceutically acceptable carrier or excipient.
62. The pharmaceutical composition of claim 61 which is suitable for parenteral administration.
63. A method for treating a solid breast or colon, tumor comprising administering to a subject in need thereof a therapeutically effective amount of a compound according to claim 1.

* * * * *

UNITED STATES PATENT AND TRADEMARK OFFICE
CERTIFICATE OF CORRECTION

PATENT NO. : 6,818,663 B2
DATED : November 16, 2004
INVENTOR(S) : Xin-Jie Chu et al.

It is certified that error appears in the above-identified patent and that said Letters Patent is hereby corrected as shown below:

Title page,
Item [73], Assignee, reads "Hoffmann-La Roches, Nutley, NY (US)." should read
-- Hoffmann-La Roche Inc., Nutley, NJ (US) --.
Item [74], *Attorney, Agent, or Firm*, "George W. Johnston; Patricia S. Rocha-Tramaioni." should read -- George W. Johnston; Patricia S. Rocha-Tramaloni --.

Column 217,
Line 52, "lower alkyl substituted by OH, and" should read -- lower alkyl substituted by OH, and $COOR^{12}$, --.

Signed and Sealed this

Twenty-first Day of June, 2005

JON W. DUDAS
*Director of the United States Patent and Trademark Office*